(12) United States Patent
Torjek et al.

(10) Patent No.: US 10,017,781 B2
(45) Date of Patent: Jul. 10, 2018

(54) RHIZOMANIA-RESISTANT GENE

(71) Applicant: KWS SAAT SE, Einbeck (DE)

(72) Inventors: Otto Torjek, Einbeck (DE); Dietrich Borchardt, Einbeck (DE); Wolfgang Mechelke, Einbeck (DE); Jens Christoph Lein, Gottingen (DE)

(73) Assignee: KWS SAAT SE, Einbeck (DE)

( * ) Notice: Subject to any disclaimer, the term of this patent is extended or adjusted under 35 U.S.C. 154(b) by 0 days.

(21) Appl. No.: 14/899,416

(22) PCT Filed: Jun. 6, 2014

(86) PCT No.: PCT/DE2014/000310
§ 371 (c)(1),
(2) Date: Dec. 17, 2015

(87) PCT Pub. No.: WO2014/202044
PCT Pub. Date: Dec. 24, 2014

(65) Prior Publication Data
US 2016/0152999 A1  Jun. 2, 2016

(30) Foreign Application Priority Data
Jun. 17, 2013 (DE) .................. 10 2013 010 026

(51) Int. Cl.
C12N 15/82 (2006.01)
C07K 14/415 (2006.01)
C12Q 1/6895 (2018.01)

(52) U.S. Cl.
CPC ........ *C12N 15/8283* (2013.01); *C07K 14/415* (2013.01); *C12Q 1/6895* (2013.01); *C12Q 2600/13* (2013.01); *C12Q 2600/156* (2013.01)

(58) Field of Classification Search
None
See application file for complete search history.

(56) References Cited

FOREIGN PATENT DOCUMENTS

| DE | 69220028 T2 | 9/1997 |
|---|---|---|
| EP | 0552393 A1 | 7/1993 |
| WO | 00/29592 A2 | 5/2000 |
| WO | 2006/128444 A2 | 12/2006 |
| WO | 2007/147395 A2 | 12/2007 |
| WO | 2013/050024 A2 | 4/2013 |
| WO | 2013/091612 A2 | 6/2013 |
| WO | 2013/127379 A1 | 9/2013 |

OTHER PUBLICATIONS

Amiri, et al., "A new RAPD marker for beet necrotic yellow vein virus resistance gene in Beta vulgaris", Biologia Plantarum 53(1): 112-119, 2009.

Butorina, et al., "Molecular genetic investigation of sugar beet (L.)", Russian Journal of Genetics 47(10): 1141-1150, 2011.
Clark, et al., "Characteristics of the Microplate Method of Enzyme-Linked Immunosorbent Assay for the Detection of Plant Viruses", J. Gen. Virol. 34: 475-483, 1977.
Depicker, et al., "Nopaline Synthase: Transcript Mapping and DNA Sequence", Journal of Molecular and Applied Genetics 1(6): 561-573, 1982.
Esser K Kryptogamen 1: Cyanobakterien Algen Pilze Flechten Praktikum and Lehrbuch, Springer Publishing House, Berlin, Heidelberg, 3rd Ed., pp. 255-256, 2000.
Gidner, et al., "QTL mapping of BNYVV resistance from the WB4' source in sugar beet", Genome 48(2): 279-285, 2005.
Grimmer, et al., "An anchored linkage map for sugar beet based on AFLP, SNP and RAPD markers and QTL mapping of a new source of resistance to Beet necrotic yellow vein virus", Theoretical and Applied Genetics; International Journal of Plant Breeding Researh 114(7): 1151-1160, 2007.
International Search Report, dated Nov. 3, 2014, issued in corresponding International Application No. PCT/DE2014/000310.
Larson, et al., "Proteome changes in sugar beet in response to Beet necrotic yellow vein virus", Physiological and Molecular Plant Pathology 72: 62-72, 2008.
Lein, et al., "Resistance gene analogues are clustered on chromosome 3 of sugar beet and consegregate with QTL for rhizomania resistance", Genome 50(1): 61-71, 2006.
Lindsey, et al., "Transformation of Sugarbeet (Beta vulgaris) by Agrobacterium tumefaciens", Journal of Experimental Botany 41(226): 529-536, 1990.
Martin, et al., "Understanding the functions of plant disease resistance proteins", Annu. Rev. Plant Biol. 54: 23-61, 2003.
Mechelke, Probleme in der Rizomainiaresistenzzachtüng, Vorträge für Pflanzenzüchtung, Resiustenzzüchtung bei Zuckerrüben, Gesellschaft für Pflanzenzüchtung, pp. 113-123, 1997.
Odell, et al., "Identification of DNA sequences required for activity of the cauliflower mosaic virus 35S promoter", Nature 313: 810-812, 1985.
Pavli, et al., "Achievements and prospects in breeding for rhizomania resistance in sugar beet", Field Crops Research 122(3): 165-172, 2011.
Rushton, et al., "Interaction of elicitor-induced DNA-binding proteins with elicitor response elements in the promoters of parsley PR1 genes", The EMBO Journal 15(20: 5690-5700, 1996.
Sambrook, et al., "Analysis of Genomic DNA by Southern Hybridization", Analysis and Cloning of Eukaryotic Genomic DNA, Molecular Cloning, Laboratory Manual, Cold Spring Harbor Laboratory Press, 2001.
Schmidlin, et al., "Identification of differentially expressed root genes upon rhizomania disease", Molecular -Plant Pathology 9(6): 741-751, 2008.

(Continued)

*Primary Examiner* — Medina A Ibrahim
(74) *Attorney, Agent, or Firm* — Troutman Sanders LLP

(57) ABSTRACT

The present invention provides a new nucleic acid molecule which encodes a polypeptide that is able to convey a resistance to a pathogen, in particular to "Beet Necrotic Yellow Vein Virus" in a plant, in particular a plant of the *Beta* genus, in which the polypeptide is expressed, and also a preferred nucleic acid molecule encoding the RZ-3 gene of *Beta maritima*, derivatives and homologues thereof. Further aspects of the invention include vectors, transgenic plant cells, transgenic plants, methods for production thereof, and methods for identifying a resistance-conveying nucleic acid molecule.

24 Claims, 36 Drawing Sheets

(56) References Cited

OTHER PUBLICATIONS

Figure 4:
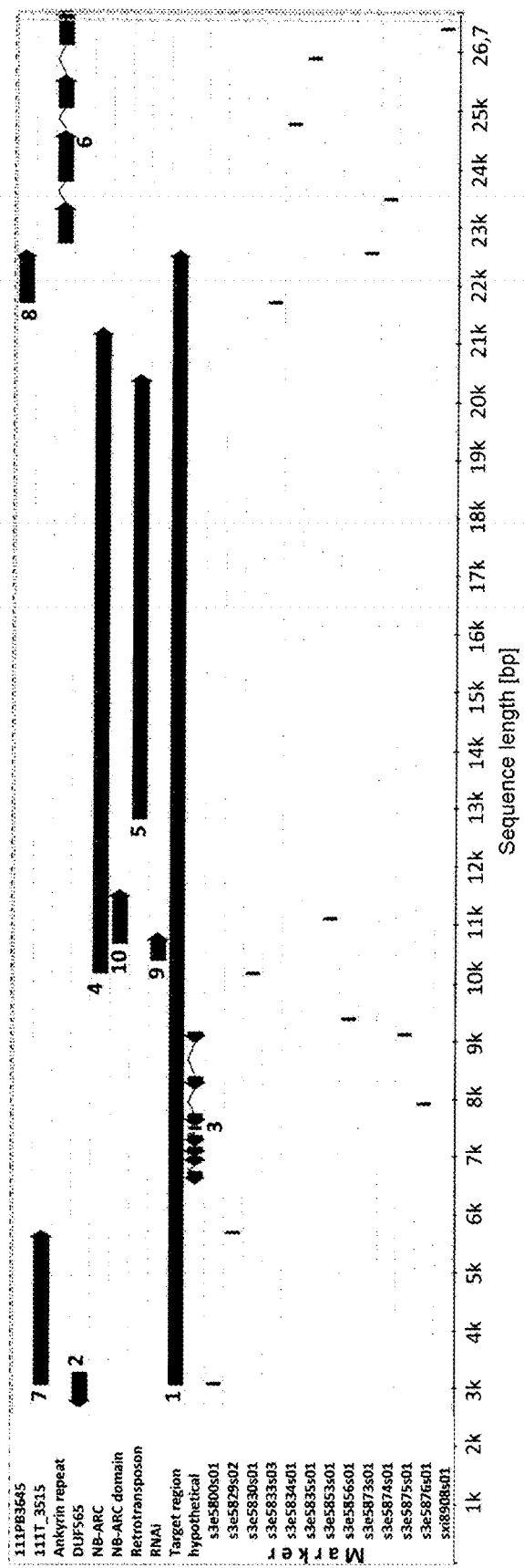

Scholten, et al., "Inheritance of resistance to beet necrotic yellow vein virus in Beta vulgaris conferred by a second gene for resistance", Theor. Appl. Genet. 99: 740-746, 1999.

Sohi, et al., "Evidence for Presence of Types A and B of Beet Necrotic Yellow Vein Virus (BNYVV) in Iran", Virus Genes 29(3): 353-258, 2004.

Tian, et al., "The absence of TIR-type resistance gene analogues in the sugar beet (*Beta vulgaris* L.) genome", Journal of Molecular Evolution 58(1): 40-53, 2004.

Van Ooijen, et al., "Structure-function analysis of the NB-ARC domain of plant disease resistance proteins", Journal of Experimental Botany 59(6): 1383-1397, 2008.

Capistrano, G. et al., "Fine Mapping of the Rhizomania Resistance Gene Rz2 in *Beta vulgaris* ssp. maritima" Christian-Albrects-Universitaet zu Kiel website, Mar. 14, 2017 available at https://www.plantbreeding.uni-kiel.de/de/forschung/fine-mapping-of-the-rhizornania-resistance-gene-rz2-in-beta-vulgaris-ssp.-maritima.

GenBank Accession No. DQ907612.1, "Beta vulgaris clone cZR-7(f) NBS-LRR type resistance protein mRNA, complete cds", Aug. 18, 2006.

Meulernans, M. et al., "Interactions Between Major Genes, and Influence of the Genetic Background in the Expression of Rhizornania Resistance" Session Genetics and Germplasm Enhancement, First Joint IIRB-ASSBT Congress, Feb. 26, 2003 to Mar. 1, 2003, San Antonio, TX, USA.

Ni, W. et al., "Construction of a Plant Transformation-ready Expression cDNA Library for Thellungiella halophila Using Recombination Cloning" Journal of Integrative Plant Biology, 2007, 49(9): 1313-1319.

SES Vanderhave, "Tandem Technology Observations" Technical Bulletin, Aug. 8, 2007.

Thiel, H. et al.. "Identification of Beet necrotic yellow vein virus P25 Pathogenicity Factor-Interacting Sugar Beet Proteins That Represent Putative Virus Targets or Components of Plant Resistance" MPMI, 2009, 22(8):999-1010.

Tian, Y. et al., "The absence of TIR-type resistance gene analogues in the sugar beet (*Beta vulgaris* L.) genome" J. Mol. Evol., 2004, 58(1):40-53.

Chu, C.G. et al., "A Novel Retrotransposon Inserted in the Dominant Vrn-B1 Allele Confers Spring Growth Habit in etraploid Wheat (*Triticum turgidum* L.)." G3 (Bethesda), Dec. 2011, 1(7):637-645.

Sesvanderhave, Third Party Observation Pursuant to Art. 115 EPC concerning European Patent Application EP14750139.9, corresponding to WO 2014/202044, dated Jun. 13, 2017, 8 pages.

FIG 1A

```
                              1                                                         70
consensus-sensitive    (1)    CAAATCTTCTGGCATCAATGGCGGTGTTGCCGTTCATCAWTTAACATCAATGGAGGTAAGAGTCATGTT
resistant sequence     (1)    CAAATCTTCTGGCATCAATGGCGGTGTTGCCGTTCATCAATTTAACATCAATGGAGGTAAGAGTCATGTT
                              71                                                        140
consensus-sensitive    (71)   TTTTCAACAATATAAAACTTATA                TGATTTTCTGTTTTTCCCC
resistant sequence     (71)   TTTTCAACAATATAAAACTTATACTTCC

FIG 1 B

```
                                                                                             630
consensus-sensitiv   (461)  NNNNNNNNNNNNNNNNNNNNNNNNNNNNNNNNNGATGGAAGGTTAGAGYYCTAAAGATAGAAAGTTGAAAATCTAAMT
resistente-sequenz   (561)  ---------------------------------GATGGAAGTTAGAGTTCTAAAGATAGAAAGTTGAAAATCTAAAT
                                                                                             700
consensus-sensitiv   (531)  ATAAATCATTGACAAATTTATTAAGGGTGAGAAACAAGGGTGTTTTCTTCAAATATGAAGCAAAATTTTC
resistente-sequenz   (606)  ATAAATCATTGACAAATTTATTAAGGGTGAGAAACAAGGGTGTTTTCTTCAAATATGAAGCAAAATTTTC
                                                                                             770
consensus-sensitiv   (601)  AAAATAAANNNNNNNNNNNNNNNNNNNNNNNN-----------------------------------------
resistente-sequenz   (676)  AAAATAAATAACTTCCTCCGTTTCTAAATAGTGCAACATTTGCATATAAT

FIG 1C

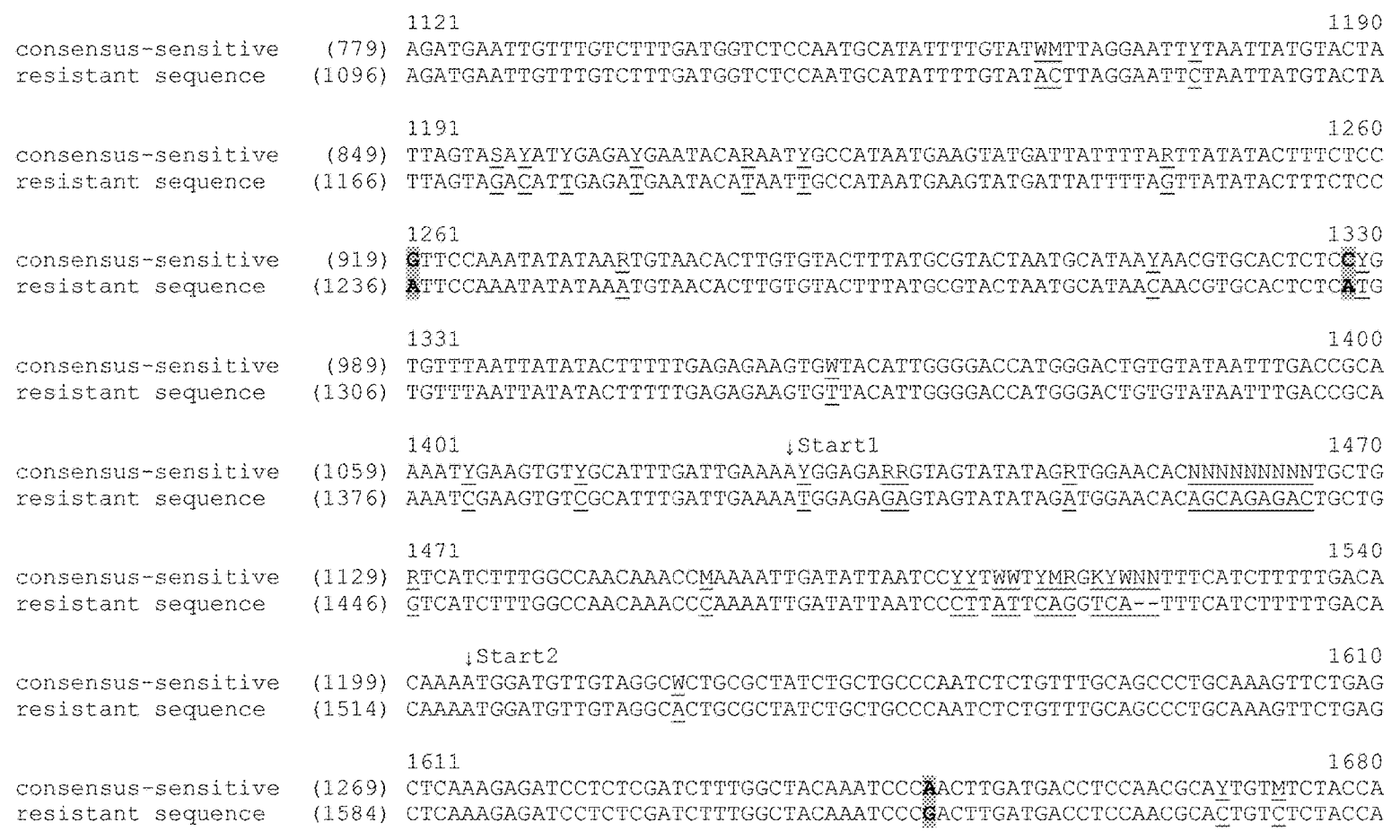

```
consensus-sensitive  (779)  AGATGAATTGTTGTCTTTGATGGTCTCCAATGCATATTTTGTATWMTTAGGAATTYTAATTATGTACTA  1190
resistant sequence  (1096) AGATGAATTGTTGTCTTTGATGGTCTCCAATGCATATTTTGTATACTTAGGAATTCTAATTATGTACTA consensus-sensitive  (849)  TTAGTASAYATYGAGAYGAATACARAATYGCCATAATGAAGTATGATTATTTARTTATATACTTTCTCC  1260
resistant sequence  (1166) TTAGTA

FIG 1D

```
                           1681                                                              1750
consensus-sensitive (1339) TCAAYGCTGTATTCCGTGATGCTGAGACCAAACAGGAGCTCACTCATGAAGCACARCATTGGCTCGAGGA
resistant sequence  (1654) TCAACGCTGTATTCCGTGATGCTGAGACCAAACAGGAGCTCACTCATGAAGCACAGCATTGGCTCGAGGA 1751                                                              1820
consensus-sensitive (1409) ACTCAAGGATGCTGTCTTTGAAGCAGATGATCTGTTCGACGAGTTTGTCACTCTTGCCGAGCAGAAGCAA
resistant sequence  (1724) ACTCAAGGATGCTGTCTTTGAAGCAGATGATCTGTTCGACGAGTTTGTCACTCTTGCCGAGCAGAAGCAA 1821                                                              1890
consensus-sensitive (1479) CTTGTAGAGGCTGGTGGCAGTCTTTCCAAAAAGATGCGCCAATTCTTTTCTGATTCCAACCCCCTTGGCA
resistant sequence  (1794) CTTGTAGAGGCTGGTGGCAGTCTTTCCAAAAAGATGCGCCAATTCTTTTCTGATTCCAACCCCCTTGGCA 1891                                                              1960
consensus-sensitive (1549) TYGCTTATARGATGTCACRAGGGGTTAAGAAGATCAAGAAGAAGTTGGATGYTATYGCTTACAATCATCA
resistant sequence  (1864) TTGCTTATAGGATGTCACGAGGGGTTAAGAAGATCAAGAAGAAGTTGGATGCTATCGCTTACAATCATCA 1961                                                              2030
consensus-sensitive (1619) ATTTAGCTTTAAGATTGATCTTGAGCCTATRAAAGAGAGAGAAGGCTCGAGACTGGTTCTGTCGTGAACGCA
resistant sequence  (1934) ATTTAGCTTTAAGATTGATCTTGAGCCTATGAAAGAGAGAGAAGGCTAGAGACTGGTTCTGTCGTGAACGCA 2031                                                              2100
consensus-sensitive (1689) GGTGATATCATTGGAAGAGAGGATGACTTGGAGAAGATCGTAGGTTTGTTKCTTGATTCTAACATCCAGC
resistant sequence  (2004) GGTGATATCATTGGAAGAGAGAGACGACTTGGAGAAGATTGTAGGTTTGTTGCTTGATTCTAACATCCAAC 2101                                                              2170
consensus-sensitive (1759) GTGATGTGTCTTTCCTTACKATWGTGGGAATGGGAGGGTTGGGTAAAACTGCTCTTGCCCAACTCGTGTA
resistant sequence  (2074) GTGATGTGTCTTTCCTTACTATTGTGGGAATGGGAGGGTTGGGTAAAACTGCTCTTGCCCAACTCGTGTA 2171                                                              2240
consensus-sensitive (1829) CAATGATCCAAGGGTCAGAACTGCTTTTCCATTGAGATGTTGGAATTGTNNCTCTGATCAAGATCAAAAK
resistant sequence  (2144) CAATGATCCAAGGGTCAGAACTGCTTTTCCATTGAGATGTTGGAATTGTGTCTGATCAAGATCAAAAG
```

FIG 1 E

```
consensus-sensitive  (1899)  2241                                                                    2310
                             MAACTAGATGTGAAAGAAATTTGGGTAAGAATTCTGTCTACAGCTACTGGTAAGAATCAYRAGGGTTCAA
resistant sequence   (2214)  CAACTAGATGTGAAAGAAATTTTGGGTAAGAATTCTGGCTACAGCTACTGGTAAGAATC

FIG 1F

```
consensus-sensitive   (2459)  2801 TCAKGAGATGCTTTAGTTATTGTGCARTGTTTCCAAAGGATTTCCTTATAGGGAAGAAGACGTTGATAAA 2870
resistant sequence    (2773)       TTAAGAGATGCTTTAGTTATTGTGCAGTGTTTCCAAAGGATTTCCTTATAGGGAAGCAGACGCTGATAAA consensus-sensitive   (2529)  2871 CCTTTGGATGGCACAAGGTTATATTGTTCCATTAGACAAAGATCAAAGCATAGATGAYGCTAGTGAGGAA 2940
resistant sequence    (2843)       CCTCTGGATGGCACAAGGTTATATTGTTCCGTTAGACAAAGATCAAAGCATAGATGATGCTAGTGAGGAA consensus-sensitive   (2599)  2941 TACATATCA

FIG 1G

```
                              3361                                                          3430
consensus-sensitive  (3019)  CTTCCAACTCAATTGCYAAACTATATAATCTRCAAACCTTACAATTGAAGGGTTGCAAGAGATTGGAAG
resistant sequence   (3333)  CTTCCAACTCAATTGCTAAACTATATAATCTACAAACCTTACAATTGAAGGGTTGCAAGAGATTGGAAG 3431                                                          3500
consensus-sensitive  (3089)  GGTTAYCAAAACATTTGAGCAGGCTGGTTAAGCTTCAAACTTTRGATATAAATGGTTGCA

FIG 1H

```
consensus-sensitive  (3579)  TTTWTCTTTYTGATTGTGGGGAAYYGGAGWRCCTTCCATGCMTGGGAAACTTGGWTYDTCTRAAMGTYCTC  3990
resistant sequence   (3893)  TTTTCTTTCTGATTGTGGGGAAACTTGGGAAACCTTCCATGCCTGGGAAACTTGGATCATCTAAAAGTCCTC consensus-sensitive  (3649)  CGRCTTTCGCATTTGGCRAAATTGGAGTAYATTGRAGAAGATAGCWCATCAGCTMWTTTCAGKTKTAGGC  4060
resistant sequence   (3963)  CGACTTTCGCATTTGGCAAAATTGGAGTACATTGGAGAAGATAGCTCATCAGCTAATTTCAGGTGTAGGC consensus-sensitive  (3719)  CTGGACCCRGAAAGTGCAGGACTATCATTATACTTCCCCTCCCTTGAACKCCTTGAGTTGAAGCRTTTGYR  4130
resistant sequence   (4033)  CTGGACCCAGAAAGTG

FIG 1 I

```
                             4481                                                                  4550
consensus-sensitive  (4103)  CTATGGAGGCTTTTAGGTGTCTCACTCATATGACAATAAAAAACGACAGGTAGAGAGTTTGGGAGAAGT
resistant sequence   (4453)  CTATGGAGGCTTTTAGGTGTCTCACTCATATGACAATAAAAAACGACAGGTAGAGAGTTTGGGAGAAGT 4551                                                                  4620
consensus-sensitive  (4173)  TGGGAGGTGTTTCGGAGCTRCTCATCTTCTTTGCGATCCTTGAATATCACAGGTTGCTCCAACTTAAGA
resistant sequence   (4523)  TGGGAGGTGTTTCGGAGCTGCTCATCTTCTTTGCGATCCTTGAATATCACAGGTTGCTCCAACTTAAGA 4621                                                                  4690
consensus-sensitive  (4243)  AGTGTTTCTGGAGGGCTGGAGCATCTCACTRCTTTGGAGATKTTAGAAATATACGACACCCATAAGCTGA
resistant sequence   (4593)  AGTGTTTCTGGAGGGCTGGAGCATCTCACTGCTTTGGAGATGTTAGAAATATACGACACCCATAAGCTGA 4691                                                                  4760
consensus-sensitive  (4313)  GTCTWTCAGAAGACCCAGAAGGTGTTGTGCCATGGAAATCCCTTCATCACTCCCTCAGCTACTTGMAAT
resistant sequence   (4663)  GTCTATCAGAAGACCCAGAAGGTGTTGTGCCATGGAAATCCCTTCATCACTCCCTCAGCTACTTGCAAT 4761                                                                  4830
consensus-sensitive  (4383)  GATGAATCTCCCWCAGCTGGTCAACCTGCCTGATTCGATGCAGTTCTTGGYCCCTCCAACCTTTCA
resistant sequence   (4733)  GATGAATCTCCCACAGCTGGTCAACCTGCCTGATTCGATGCAGTTCTTGGCCCCTCCAACCTTTCA 4831                                                                  4900
consensus-sensitive  (4453)  ATGTGCATTGCATAAACTGAATCAGTGCCAGATTGGATGCCCMGACTCACTTCYCTCAGGAAGCTTA
resistant sequence   (4803)  ATGTGCATTGCATAAACTGAATCAGTGCCAGATTGGATGCCCAGACTCACTTCTCTCAGGAAGCTTA 4901                                                                  4970
consensus-sensitive  (4523)  TGGTTTCATTCTGTTCCGCACATCTGGAGAGAAGATGYCAAAATCCAACTGGGGTGGACTGGCCTAACAT
resistant sequence   (4873)  TGGTTTCATTCTGTTCCGCACATCTGGAGAGAAGATGCCAAAATCCAACTGGGGTGGACTGGCCTAACAT 4971                                                              5037
consensus-sensitive  (4593)  TCAACACATCCCCTSCATTGATGTCACCTCTAGCCTCCTAAGTTTTTAGTGTTGCCGTATGAATAG
resistant sequence   (4943)  TCAACACATCCCCTCCATTGATGTCACCTCTAGCCTCCTAAGTTTTTAGTGTTGCCGTATGAATAG
```

FIG 2 A

```
                   1                                                                          70
Res. sequence  (1) MDVVGTALSAAQSLFAALQSSELKEILSIFGYKS█LDDLQRTVSTINAVFRDAETKQELTHEAQHWLEEL
Sen. sequence  (1) MDVVGTALSAAQSLFAALQSSELKEILSIFGYKSQLDDLQRTVSTINAVFRDAETKQELTHEAQHWLEEL
Sen. sequence2 (1) MDVVGTALSAAQSLFAALQSSELKEILSIFGYKSQLDDLQRTVSTINAVFRDAETKQELTHEAQHWLEEL
Sen. sequence3 (1) MDVVGTALSAAQSLFAALQSSELKEILSIFGYKSQLDDLQRTVSTINAVFRDAETKQELTHEAQHWLEEL
Sen. sequence4 (1) MDVVGTALSAAQSLFAALQSSELKEILSIFGYKSQLDDLQRTVSTINAVFRDAETKQELTHEAQHWLEEL
Sen. sequence5 (1) MDVVGTALSAAQSLFAALQSSELKEILSIFGYKSQLDDLQRTVSTINAVFRDAETKQELTHEAQHWLEEL
Sen. sequence6 (1) MDVVGTALSAAQSLFAALQSSELKEILSIFGYKSQLDDLQRTVSTINAVFRDAETKQELTHEAQHWLEEL
Sen. sequence7 (1) ---------------------------------------STINAVFRDAETKQELTHEAQHWLEEL
Sen. sequence8 (1) MDVVGTALSAAQSLFAALQSSELKEILSIFGYKSQLDDLQRTVSTINAVFRDAETKQELTHEAQHWLEEL
Sen. sequence9 (1) MDVVGTALSAAQSLFAALQSSELKEILSIFGYKSQLDDLQRTVSTINAVFRDAETKQELTHEAQHWLEEL
Sen. sequence10(1) MDVVGTALSAAQSLFAALQSSELKEILSIFGYKSQLDDLQRTVSTINAVFRDAETKQELTHEAQHWLEEL
Sen. sequence11(1) MDVVGTALSAAQSLFAALQSSELKEILSIFGYKSQLDDLQRTVSTINAVFRDAETKQELTHEAQHWLEEL
Sen. sequence12(1) MDVVGTALSAAQSLFAALQSSELKEILSIFGYKSQLDDLQRTVSTINAVFRDAETKQELTHEAQHWLEEL
Sen. sequence13(1) ---------------------------------------STINAVFRDAETKQELTHEAQHWLEEL
Sen. sequence14(1) MDVVGTALSAAQSLFAALQSSELKEILSIFGYKSQLDDLQRTVSTINAVFRDAETKQELTHEAQHWLEEL
Sen. sequence15(1) MDVVGTALSAAQSLFAALQSSELKEILSIFGYKSQLDDLQRTVSTINAVFRDAETKQELTHEAQHWLEEL
Sen. sequence16(1) MDVVGTALSAAQSLFAALQSSELKEILSIFGYKSQLDDLQRTVSTINAVFRDAETKQELTHEAQHWLEEL
Sen. sequence17(1) MDVVGTALSAAQSLFAALQSSELKEILSIFGYKSQLDDLQRTVSTINAVFRDAETKQELTHEAQHWLEEL
Sen. sequence18(1) MDVVGTALSAAQSLFAALQSSELKEILSIFGYKSQLDDLQRTVSTINAVFRDAETKQELTHEAQHWLEEL
Sen. sequence19(1) MDVVGTALSAAQSLFAALQSSELKEILSIFGYKSQLDDLQRTVSTINAVFRDAETKQELTHEAQHWLEEL
Sen. sequence20(1) MDVVGTALSAAQSLFAALQSSELKEILSIFGYKSQLDDLQRTVSTINAVFRDAETKQELTHEAQHWLEEL
Sen. sequence21(1) MDVVGSALSAAQSLFAALQSSELKEILSIFGYKSQLDDLQRIVSTINAVFRDAETKQELTHEAQHWLEEL
Sen. sequence22(1) MDVVGSALSAAQSLFAALQSSELKEILSIFGYKSQLDDLQRIVSTINAVFRDAETKQELTHEAQHWLEEL
```

FIG 2 B

```
                      71                                                                          140
Res. sequence     KDAVFEADDLFDEFVTLAEQKQLVEAGGSLSKKMRQFFSDSNPLGIAYRMSRGVKKIKKKLDAIAYNHQF
Sen. sequence1   (71) KDAVFEADDLFDEFVTLAEQKQLVEAGGSLSKKMRQFFSDSNPLGIAYRMSRGVKKIKKKLDAIAYNHQF
Sen. sequence2   (71) KDAVFEADDLFDEFVTLAEQKQLVEAGGSLSKKMRQFFSDSNPLGIAYRMSRGVKKIKKKLDAIAYNHQF
Sen. sequence3   (71) KDAVFEADDLFDEFVTLAEQKQLVEAGGSLSKKMRQFFSDSNPLGIAYRMSRGVKKIKKKLDAIAYNHQF
Sen. sequence4   (71) KDAVFEADDLFDEFVTLAEQKQLVEAGGSLSKKMRQFFSDSNPLGIAYRMSRGVKKIKKKLDAIAYNHQF
Sen. sequence5   (71) KDAVFEADDLFDEFVTLAEQKQLVEAGGSLSKKMRQFFSDSNPLGIAYRMSRGVKKIKKKLDAIAYNHQF
Sen. sequence6   (71) KDAVFEADDLFDEFVTLAEQKQLVEAGGSLSKKMRQFFSDSNPLGIAYRMSRGVKKIKKKLDAIAYNHQF
Sen. sequence7   (28) KDAVFEADDLFDEFVTLAEQKQLVEAGGSLSKKMRQFFSDSNPLGIAYRMSRGVKKIKKKLDAIAYNHQF
Sen. sequence8   (71) KDAVFEADDLFDEFVTLAEQKQLVEAGGSLSKKMRQFFSDSNPLGIAYRMSRGVKKIKKKLDAIAYNHQF
Sen. sequence9   (71) KDAVFEADDLFDEFVTLAEQKQLVEAGGSLSKKMRQFFSDSNPLGIAYRMSRGVKKIKKKLDAIAYNHQF
Sen. sequence10  (71) KDAVFEADDLFDEFVTLAEQKQLVEAGGSLSKKMRQFFSDSNPLGIAYRMSRGVKKIKKKLDAIAYNHQF
Sen. sequence11  (71) KDAVFEADDLFDEFVTLAEQKQLVEAGGSLSKKMRQFFSDSNPLGIAYRMSRGVKKIKKKLDAIAYNHQF
Sen. sequence12  (71) KDAVFEADDLFDEFVTLAEQKQLVEAGGSLSKKMRQFFSDSNPLGIAYRMSRGVKKIKKKLDAIAYNHQF
Sen. sequence13  (28) KDAVFEADDLFDEFVTLAEQKQLVEAGGSLSKKMRQFFSDSNPLGIAYRMSRGVKKIKKKLDAIAYNHQF
Sen. sequence14  (71) KDAVFEADDLFDEFVTLAEQKQLVEAGGSLSKKMRQFFSDSNPLGIAYRMSRGVKKIKKKLDAIAYNHQF
Sen. sequence15  (71) KDAVFEADDLFDEFVTLAEQKQLVEAGGSLSKKMRQFFSDSNPLGIAYRMSRGVKKIKKKLDAIAYNHQF
Sen. sequence16  (71) KDAVFEADDLFDEFVTLAEQKQLVEAGGSLSKKMRQFFSDSNPLGIAYRMSRGVKKIKKKLDAIAYNHQF
Sen. sequence17  (71) KDAVFEADDLFDEFVTLAEQKQLVEAGGSLSKKMRQFFSDSNPLGIAYRMSRGVKKIKKKLDAIAYNHQF
Sen. sequence18  (71) KDAVFEADDLFDEFVTLAEQKQLVEAGGSLSKKMRQFFSDSNPLGIAYRMSRGLKKIKKKLDAIAYNHQF
Sen. sequence19  (71) KDAVFEADDLFDEFVTLAEQKQLVEAGGSLSKKMRQFFSDSNPLGIAYRMSRGVKKIKKKLDAIAYNHQF
Sen. sequence20  (71) KDAVFEADDLFDEFVTLAEQKQLVEAGGSLSKKMRQFFSDSNPLGIAYKMSRGVKKIKKKLDVIAYNHQF
Sen. sequence21  (71) KDAVFEADDLFDEFVTLAEQKQLVEAGGSLSKKMRQFFSDSNPLGIAYKMSQGVKKIKKKLDVIAYNHQF
Sen. sequence22  (71) KDAVFEADDLFDEFVTLAEQKQLVEAGGSLSKKMRQFFSDSNPLGIAYKMSQGVKKIKKKLDVIAYNHQF
```

FIG 2 C

```
                    141                                                                           210
Res. sequence  (141) SFKIDLEPIKERRLETGSVVNAGDIIGREDDLEKIVGLLLLDSNIQRDVSFLTIVGMGGLGKTALAQLVYN
Sen. sequence1 (141) SFKIDLEPIKERRLETGSVVNAGDIIGREDDLEKIVGLLLLDSNIQRDVSFLTIVGMGGLGKTALAQLVYN
Sen. sequence2 (141) SFKIDLEPIKERRLETGSVVNAGDIIGREDDLEKIVGLLLLDSNIQRDVSFLTIVGMGGLGKTALAQLVYN
Sen. sequence3 (141) SFKIDLEPIKERRLETGSVVNAGDIIGREDDLEKIVGLLLLDSNIQRDVSFLTIVGMGGLGKTALAQLVYN
Sen. sequence4 (141) SFKIDLEPIKERRLETGSVVNAGDIIGREDDLEKIVGLLLLDSNIQRDVSFLTIVGMGGLGKTALAQLVYN
Sen. sequence5 (141) SFKIDLEPIKERRLETGSVVNAGDIIGREDDLEKIVGLLLLDSNIQRDVSFLTIVGMGGLGKTALAQLVYN
Sen. sequence6 (141) SFKIDLEPIKERRLETGSVVNAGDIIGREDDLEKIVGLLLLDSNIQRDVSFLTIVGMGGLGKTALAQLVYN
Sen. sequence7  (98) SFKIDLEPIKERRLETGSVVNAGDIIGREDDLEKIVGLLLLDSNIQRDVSFLTIVGMGGLGKTALAQLVYN
Sen. sequence8 (141) SFKIDLEPIKERRLETGSVVNAGDIIGREDDLEKIVGLLLLDSNIQRDVSFLTIVGMGGLGKTALAQLVYN
Sen. sequence9 (141) SFKIDLEPIKERRLETGSVVNAGDIIGREDDLEKIVGLLLLDSNIQRDVSFLTIVGMGGLGKTALAQLVYN
Sen. sequence10 (141) SFKIDLEPIKERRLETGSVVNAGDIIGREDDLEKIVGLLLLDSNIQRDVSFLTIVGMGGLGKTALAQLVYN
Sen. sequence11 (141) SFKIDLEPIKERRLETGSVVNAGDIIGREDDLEKIVGLLLLDSNIQRDVSFLTIVGMGGLGKTALAQLVYN
Sen. sequence12 (141) SFKIDLEPIKERRLETGSVVNAGDIIGREDDLEKIVGLLLLDSNIQRDVSFLTIVGMGGLGKTALAQLVYN
Sen. sequence13  (98) SFKIDLEPIKERRLETGSVVNAGDIIGREDDLEKIVGLLLLDSNIQRDVSFLTIVGMGGLGKTALAQLVYN
Sen. sequence14 (141) SFKIDLEPIKERRLETGSVVNAGDIIGREDDLEKIVGLLLLDSNIQRDVSFLTIVGMGGLGKTALAQLVYN
Sen. sequence15 (141) SFKIDLEPIKERRLETGSVVNAGDIIGREDDLEKIVGLLLLDSNIQRDVSFLTIVGMGGLGKTALAQLVYN
Sen. sequence16 (141) SFKIDLEPIKERRLETGSVVNAGDIIGREDDLEKIVGLLLLDSNIQRDVSFLTIVGMGGLGKTALAQLVYN
Sen. sequence17 (141) SFKIDLEPIKERRLETGSVVNAGDIIGREDDLEKIVGLLLLDSNIQRDVSFLTIVGMGGLGKTALAQLVYN
Sen. sequence18 (141) SFKIDLEPIKERRLETGSVVNAGDIIGREDDLEKIVGLLLLDSNIQRDMSFLTIVGMGGLGKTALAQLVYN
Sen. sequence19 (141) SFKIDLEPIKERRLETGSVVNAGDIIGREDDLEKIVGLLLLDSNIQRDVSFLTIVGMGGLGKTALAQLVYN
Sen. sequence20 (141) SFKIDLEPIKERRLETGSVVNAGDIIGREDDLEKIVGLFLLDSNIQRDVSFLTIVGMGGLGKTALAQLVYN
Sen. sequence21 (141) SFKIDLEPIKERRLETGSVVNAGDIIGREDDLEKIVGLFLLDSNIQRDVSFLTIVGMGGLGKTALAQLVYN
Sen. sequence22 (141) SFKIDLEPIKERRLETGSVVNAGDIIGREDDLEKIVGLLLLDSNIQRDVSFLTIVGMGGLGKTALAQLVYN
```

FIG 2 D

```
                      211                                                              280
Res. sequence   (211) DPRVRTAFPLRCWNCVSDQDQKLDVKEILGKILSTATGKNHEGSTMDQVQTQLREQLCGKRYLLVLDDV
Sen. sequence1  (211) DPRVRTAFPLRCWNCVSDQDQKKLDVKEILGKILSTATGKNHEGSTMDHVQTQLREQLCGKRYLLVLDDV
Sen. sequence2  (211) DPRVRTAFPLRCWNCVSDQDQKKLDVKEILGKILSTATGKNHEGSTMDHVQTQLQEQLCGKRYLLVLDDV
Sen. sequence3  (211) DPRVRTAFPLRCWNCVSDQDQKKLDVKEILGKILSTATGKNHEGSTMDHVQTQLQEQLCGKRYLLVLDDV
Sen. sequence4  (211) DPRVRTAFPLRCWNCVSDQDQKKLDVKEILGKILSTATGKNHEGSTMDHVQTQLQEQLCGKRYLLVLDDV
Sen. sequence5  (211) DPRVRTAFPLRCWNCVSDQDQKKLDVKEILGKILSTATGKNHEGSTMDHVQTQLQEQLCGKRYLLVLDDV
Sen. sequence6  (211) DPRVRTAFPLRCWNCVSDQDQKKLDVKEILGKILSTATGKNHEGSTMDHVQTQLREQLCGKRYLLVLDDV
Sen. sequence7  (168) DPRVRTAFPLRCWNCL*-----------------------------------------------------
Sen. sequence8  (211) DPRVRTAFPLRCWNCVSDQDQKKLDVKEILGKILSTATGKNHEGSTMDHVQTQLQEQLCGKRYLLVLDDV
Sen. sequence9  (211) DPRVRTAFPLRCWNCVSDQDQKKLDVKEILGKILSTATGKNHEGSTMDHVQTQLQEQLCGKRYLLVLDDV
Sen. sequence10 (211) DPRVRTAFPLRCWNCVSDQDQKKLDVKEILGKILSTATGKNHEGSTMDHVQTQLREQLCGKRYLLVLDDV
Sen. sequence11 (211) DPRVRTAFPLRCWNCVSDQDQKKLDVKEILGKILSTATGKNHEGSTMDHVQTQLREQLCGKRYLLVLDDV
Sen. sequence12 (211) DPRVRTAFPLRCWNCVSDQDQKKLDVKEILGKILSTATGKNHEGSTMDHVQTQLREQLCGKRYLLVLDDV
Sen. sequence13 (168) DPRVRTAFPLRCWNCL*-----------------------------------------------------
Sen. sequence14 (211) DPRVRTAFPLRCWNCVSDQDQKKLDVKEILGKILSTATGKNHEGSTMDHVQTQLREQLCGKRYLLVLDDV
Sen. sequence15 (211) DPRVRTAFPLRCWNCVSDQDQKKLDVKEILGKILSTATGKNHEGSTMDHVQTQLREQLCGKRYLLVLDDV
Sen. sequence16 (211) DPRVRTAFPLRCWNCVSDQDQKKLDVKEILGKILSTATGKNHEGSTMDHVQTQLREQLCGKRYLLVLDDV
Sen. sequence17 (211) DPRVRTAFPLRCWNCVSDQDQKKLDVKEILGKILSTATGKNHEGSTMDHVQTQLQEQLCGKRYLLVLDDV
Sen. sequence18 (211) DPRVRTAFPLRCWNCVFDQDQKQLDVKEILGKILSTATGKNHEGSTMDQVQTQLRE-LCGKRYLLVLDDV
Sen. sequence19 (211) DPRVRTAFPLRCWNCVSDQDQKKLDVKEILGKILSTATGKNHEGSTMDHVQTQLREQLCGKRYLLVLDDV
Sen. sequence20 (211) DPRVRTAFPLRCWNCVSDQDQKKLDVKEILGKILSTATGKNHEGSTMDHVQTQLREQLCGKRYLLVLDDV
Sen. sequence21 (211) DPRVRTAFPLRCWNCVSDQDQNQLDVKEILGKILSTATGKNHKGSTMDQVQTQLREQLCGKRYLLVLDDV
Sen. sequence22 (211) DPRVRTAFPLRCWNCVSDQDQNQLDVKEILGKILSTATGKNHKGSTMDQVQTQLREQLCGKRYLLVLDDV
```

FIG 2 E

```
                    281                                                                                          350
Res. sequence       WNENPNQLRDLVEFFMGGQRGNWIVVTTRSHETARIIRDGPLHKLQGLSEENSWRLFVRWTFGSVQ   KFP
Sen. sequence1  (281) WNENPNQLRYLVEFFMGGQRGNWIVVTTRSHETARIIRDGPLHKLQGLSEENSWRLFVRWTFGSVQPKFP
Sen. sequence2  (281) WNENPNQLRXXXXFMGGQRGNWIVVTTRSHETTRIIRDGPLHKLQGLSEENSWRLFVRWTFGSVQPKFP
Sen. sequence3  (281) WNENPNQLRDLGKFFMGGQRGNWIVVTTRSHETTRIIRDGPLHKLQGLSEENSWRLFVRWTFGSVQPKFP
Sen. sequence4  (281) WNENPNQLRDXVEFFMGGQRGNWIVVTTRSHETTRIIRDGPLHKLQGLSEENSWRLFVRWTFGSVQPKFP
Sen. sequence5  (281) WN

FIG 2 F

```
                  351                                                                     420
Res. sequence   (351) NDF█MIARDIVDKCARNPLAIRVVGSLLCGQDKSKWLSFHEI█L█NIRKSHNDIMPILNLSYHHLEPPI█
Sen. sequence1  (351) NDFVMIARDIVDKCARNPLAIRVVGSLLCGQDKSKWLSFHEICLANIRKSHNDIMPILNLSYHHLEPPIR
Sen. sequence2  (351) NDFVMIARDIVDKCARNPLAIRVVGSLLCGQDKSKWLSFHEICLANIRKSHNDIMLILNLSYHHLEPPIR
Sen. sequence3  (351) NDFVMIARDIVDKCARNPLAIRVVGSLLCGQDKSKWLSFHEICLANIRKSHNDIMLILNLSYHHLEPPIR
Sen. sequence4  (351) NDFVMIARDIVDKCARNPLAIRVVGSLLCGQDKSKWLSFHEICLANIRKSHNDIMLILNLSYHHLEPPIR
Sen. sequence5  (351) NDFVMIARDIVDKCARNPLAIRVVGSLLCGQDKSKWLSFHEICLANIRKSHNDIMLILNLSYHHLEPPIR
Sen. sequence6  (351) NDFVMIARDIVDKCARNPLAIRVVGSLLCGQDKSKWLSFHEICLANIRKSHNDIMLILNLSYHHLEPPIR
Sen. sequence8  (351) NDFVMIARDIVDKCARNPLAIRVVGSLLCGQDKSKWLSFHEICLANIRKSHNDIMLILNLSYHHLEPPIR
Sen. sequence9  (351) NDFVMIARDIVDKCARNPLAIRVVGSLLCGQDKSKWLSFHEICLANIRKSHNDIMPILNLSYHHLEPPIR
Sen. sequence10 (351) NDFVMIARDIVDKCARNPLAIRVVGSLLCGQDKSKWLSFHEICLANIRKSHNDIMPILNLSYHHLEPPIR
Sen. sequence11 (351) NDFVMIARDIVDKCARNPLAIRVVGSLLCGQDKSKWLSFHEICLANIRKSHNDIMLILNLSYHHLEPPIR
Sen. sequence12 (351) NDFVMIARDIVDKCARNPLAIRVVGSLLCGQDKSKWLSFHEICLANIRKSHNDIMLILNLSYHHLEPPIR
Sen. sequence14 (351) NDFVMIARDIVDKCARNPLAIRVVGSLLCGQDKSKWLSFHEICLANIRKSHNDIMPILNLSYHHLEPPIR
Sen. sequence15 (351) NDFVMIARDIVDKCARNPLAIRVVGSLLCGQDKSKWLSFHEICLANIRKSHNDIMPILNLSYHHLEPPIR
Sen. sequence16 (351) NDFVMIARDIVDKCARNPLAIRVVGSLLCGQDKSKWLSFHEICLANIRKSHNDIMPILNLSYHHLEPPIR
Sen. sequence17 (351) NDFVMIARDIVDKCARNPLAIRVVGSLLCGQDKSKWLSFHEICLANIRKSHNDIMLILNLSYHHLEPPIR
Sen. sequence18 (350) NDFVMIARDIVDKCARNPLAIRVVGSLLCGQDKSKWLSFHEICLANIRKSHNDIMPILNLSYHHLEPPIR
Sen. sequence19 (351) NDFVMIARDIVDKCARNPLAIRVVGSLLCGQDKSKWLSFHEICLANIRKSHNDIMPILNLSYHHLEPPIR
Sen. sequence20 (351) NDFVMIARDIVDKCARNPLAIRVVGSLLCGQDKSKWLSFHEICLANIRKSHNDIMPILNLSYHHLEPPIR
Sen. sequence21 (333) XXXXXXXXXXXXXXXXXXXXXXXXXXXXXXXXXXXXXXXXXXXXXXXXXXXXXXXXXXXXXXXXXXXXXX
Sen. sequence22 (351) XXXXXXXXDKCARNPLAIRVVGSLLCGQDKSKWLSFHEXCLANIRKSHNDIMPILNLSYHHLEPPIR
```

FIG 2 G

```
                    421                                                                   490
Res. sequence   (421) RCFSYCAMFPKDFLIGKTLINLWMAQGYIVPLDKDQSIDDASEEYISILLIRCFFENIGEKDGVIKIH
Sen. sequence1  (421) RCFSYCAMFPKDFLIGKKTLINLWMAQGYIVPLDKDQSIDDASEEYISILLQRCFFENIGTEKDYVIKIH
Sen. sequence2  (421) RCFSYCAMFPKDFLIGKKTLINLWMAQGYIVPLDKDQSIDDASEEYISILLQRCFFENIGTEKDYVIKIH
Sen. sequence3  (421) RCFSYCAMFPKDFLIGKKTLINLWMAQGYIVPLDKDQSIDDASEEYISILLQRCFFENIGTEKDYVIKIH
Sen. sequence4  (421) RCFSYCAMFPKDFLIGKKTLINLWMAQGYIVPLDKDQSIDDASEEYISILLQRCFFENIGTEKDYVIKIH
Sen. sequence5  (421) RCFSYCAMFPKDFLIGKKTLINLWMAQGYIVPLDKDQSIDDASEEYISILLQRCFFENIGTEKDYVIKIH
Sen. sequence6  (421) RCFSYCAMFPKDFLIGKKTLINLWMAQGYIVPLDKDQSIDDASEEYISILLQRCFFENIGTEKDYVIKIH
Sen. sequence8  (421) RCFSYCAMFPKDFLIGKKTLINLWMAQGYIVPLDKDQSIDDASEEYISILLQRCFFENIGTEKDYVIKIH
Sen. sequence9  (421) RCFSYCAMFPKDFLIGKKTLINLWMAQGYIVPLDKDQSIDDASEEYISILLQRCFFENIGTEKDYVIKIH
Sen. sequence10 (421) RCFSYCAMFPKDFLIGKKTLINLWMAQGYIVPLDKDQSIDDASEEYISILLQRCFFENIGTEKDYVIKIH
Sen. sequence11 (421) RCFSYCAMFPKDFLIGKKTLINLWMAQGYIVPLDKDQSIDDASEEYISILLQRCFFENIGTEKDYVIKIH
Sen. sequence12 (421) RCFSYCAMFPKDFLIGKKTLINLWMAQGYIVPLDKDQSIDDASEEYISILLQRCFFENIGTEKDYVIKIH
Sen. sequence14 (421) RCFSYCAMFPKDFLIGKKTLINLWMAQGYIVPLDKDQSIDDASEEYISILLQRCFFENIGTEKDYVIKIH
Sen. sequence15 (421) RCFSYCAMFPKDFLIGKKTLINLWMAQGYIVPLDKDQSIDDASEEYISILLQRCFFENIGTEKDYVIKIH
Sen. sequence16 (421) RCFSYCAMFPKDFLIGKKTLINLWMAQGYIVPLDKDQSIDDASEEYISILLQRCFFENIGTEKDYVIKIH
Sen. sequence17 (421) RCFSYCAMFPKDFLIGKKTLINLWMAQGYIVPLDKDQSIDDASEEYISILLQRCFFENIGTEKDYVIKIH
Sen. sequence18 (420) RCFSYCVVFPKDFLIGKKTLINLWMAQGYIVPLDKDQSIDDASEEYISILLQRCFFENIGTEKDYVIKIH
Sen. sequence19 (421) RCFSYCAMFPKDFLIGKKTLINLWMAQGYIVPLDKDQSIDDASEEYISILLQRCFFENIGTEKDDVIKIH
Sen. sequence20 (421) RCFSYCAMFPKDFLIGKKTLINLWMAQGYIVPLDKXXXXXXXXXXXXXXXXXXXXXXXXXXXXXXXXXXXX
Sen. sequence21 (378) XXXXXXXXXXXXXXXXXXXXXXXXXXXXXXXXXXXXXXXXXXXXXXXXXXXXXXXXXXXXXXXXXXXXXX
Sen. sequence22 (421) RCFSYCAVFPKDFLIGKKTLINLWMAQGYIVPLDKDQSIDDASEEYISILXQRCFFENIGTEKDDVIKIH
```

FIG 2 H

```
                    491                                                                                           560
Res. sequence   (491) DLMHDIAQNVMGKELCTTKNISGSLDKNVRHLSLARTSFARYSFNATHIRSYF■AGYWCQDAEINQFSVE
Sen. sequence1  (491) DLMHDIAQNVMGKELCTTKNISGSLDKNVRHLSLARTSFARYSFNATHIRSYFYAGYWCQDAEINQFSVE
Sen. sequence2  (491) DLMHDIAQNVMGKELCTTKNISGSLDKNVRHLSLARTSFARYSFNATHIRSYFYAGYWCQDAEIXQFSVE
Sen. sequence3  (491) DLMHDIAQNVMGKELCTTKNISGSLDKNVRHLSLARTSFARYSFNATHIRSYFYAGYWCQDAEINQFSVE
Sen. sequence4  (491) DLMHDIAQNVMGKELCTTKNISGSLDKNVRHLSLARTSFARYSFNATHIRSYFYAGYWCQDAEINQFSVE
Sen. sequence5  (491) DLMHDIAQNVMGKELCTTKNISGSLDKNVRHLSLARTSFARYSFNATHIRSYFXAGYWCQDAEINQFSVE
Sen. sequence6  (491) DLMHDIAQNVMGKELCTTKNISGSLDKNVRHLSLARTSFARYSFNATHIRSYFYAGYWCQDAEINQFSVE
Sen. sequence8  (491) DLMHDIAQNVMGKELCTTKNISGSLDKNVRHLSLARTSFARYSFNATHIRSYFYAGYWCQDAEINQFSVE
Sen. sequence9  (491) DLMHDIAQNVMGKELCTTKNISGSLDKNVRHLSLARTSFARYSFNATHIRSYFYAGYWCQDAEINQFSVE
Sen. sequence10 (491) DLMHDIAQNVMGKELCTTKNISGSLDKNVRHLSLARTSFARYSFNATHIRSYFYAGYWCQDAEINQFSVE
Sen. sequence11 (491) DLMHDIAQNVMGKELCTTKNISGSLDKNVRHLSLARTSFARYSFNATHIRSYFYAGYWCQDAEINQFSVE
Sen. sequence12 (491) DLMHDIAQNVMGKELCTTKNISGSLDKNVRHLSLARTSFARYSFNATHIRSYFYAGYWCQDAEINQFSVE
Sen. sequence14 (491) DLMHDIAQNVMGKELCTTKNISGSLDKNVRHLSLARTSFARYSFNATHIRSYFYAGYWCQDAEINQFSVE
Sen. sequence15 (491) DLMHDIAQNVMGKELCTTKNISGSLDKNVRHLSLARTSFARYSFNATHIRSYFYAGYWCQDAEINQFSVE
Sen. sequence16 (491) DLMHDIAQNVMGKELCTTKNISGSLDKNVRHLSLARTSFARYSFNATHIRSYFYAGYWCQDAEINQFSVE
Sen. sequence17 (491) DLMHDIAQNVMGKELCTTKNISGSLDKNVRHLSLARTSFARYSFNATHIRSYFYAGYWCQDAEINQFSVE
Sen. sequence18 (490) DLMHDIAQNVMGKELCTTKNISGSLDKNVRHLSLARTSFARYSFNATHIRSYFYAGYWCQNAEINQFSVE
Sen. sequence19 (491) DLMHDIAQNVMGKELCTTKNISGSLDKNVRHLSLARTSFARYSFNATHIRSYFYAGYWCQDAEINQFSVE
Sen. sequence20 (491) DLMHDIAQNVMGKELCTTKNISGSLDKNVRHLSLARTSFARYSFNATHIRSYFYAGYWCQDAEINQFSVE
Sen. sequence21 (448) XXXXXXXXXXXXXXXXXXXXXXXXXXXXXXXXXXXXXXXXXXXXXXXXXXXXXAGYWCQESEINQFSVE
Sen. sequence22 (491) DLMHDIAQNVMGKELCTTKNISGSLDKNVRHLSLXXXXXXXXXXXXXXXXXXXXXXXXXXXXXXXXXXXX
```

FIG 2 I

```
                          561                                                                           630
Res. sequence       (561) ALVPNCLXXLRAXDLAWSKIKSLPDSIGGLLHLRYLDLSYNEDLEVLPNSIAKLYNLQTLQLKGCKRLEGL
Sen. sequence1      (561) ALVPNCLCLRALDLAWSKIKSVPDSIGGLLHLRYLDLSYNEDLEVLPNSIAKLYNLQTLQLKGCKRLEGL
Sen. sequence2      (561) ALVPNCLCLRALDLAWSKIKSVPDSIGGLLHLRYLDLSYNEDLEVLPNSIAKLYNLQTLQLKGCKRLEGL
Sen. sequence3      (561) ALVPNCLCLRALDLAWSKIKSVPDSIGGLLHLRYLDLSYNEDLEVLPNSIAKLYNLQTLQLKGCKRLEGL
Sen. sequence4      (561) ALVPNCLCLRALDLAWSKIKSVPDSIGGLLHLRYLDLSYNEDLEVLPNSIAKLYNLQTLQLKGCKRLEGL
Sen. sequence5      (561) ALVPNCLCLRALDLAWSKIKSVPDSIGGLLHLRYLDLSYNEDLEVLPNSIAKLYNLQTLQLKGCKRLEGL
Sen. sequence6      (561) ALVPNCLCLRALDLAWSKIKSVPDSIGGLLHLRYLDLSYNEDLEVLPNSIAKLYNLQTLQLKGCKRLEGL
Sen. sequence8      (561) ALVPNCLCLRALDLAWSKIKSVPDSIGGLLHLRYLDLSYNEDLEVLPNSIAKLYNLQTLQLKGCKRLEGL
Sen. sequence9      (561) ALVPNCLCLRALDLAWSKIKSVPDSIGGLLHLRYLDLSYNEDLEVLPNSIAKLYNLQTLQLKGCKRLEGL
Sen. sequence10     (561) ALVPNCLCLRALDLAWSKIKSVPDSIGGLLHLRYLDLSYNEDLEVLPNSIAKLYNLQTLQLKGCKRLEGL
Sen. sequence11     (561) ALVPNCLCLRALDLAWSKIKSVPDSIGGLLHLRYLDLSYNEDLEVLPNSIAKLYNLQTLQLKGCKRLEGL
Sen. sequence12     (561) ALVPNCLCLRALDLAWSKIKSVPDSIGGLLHLRYLDLSYNEDLEVLPNSIAKLYNLQTLQLKGCKRLEGL
Sen. sequence14     (561) ALVPNCLCLRALDLAWSKIKSVPDSIGGLLHLRYLDLSYNEDLEVLPNSIAKLYNLQTLQLKGCKRLEGL
Sen. sequence15     (561) ALVPNCLCLRALDLAWSKIKSVPDSIGGLLHLRYLDLSYNEDLEVLPNSIAKLYNLQTLQLKGCKRLEGL
Sen. sequence16     (561) ALVPNCLCLRALDLAWSKIKSVPDSIGGLLHLRYLDLSYNEDLEVLPNSIAKLYNLQTLQLKGCKRLEGL
Sen. sequence17     (561) ALVPNCLCLRALDLAWSKIKSVPDSIGGLLHLRYIDLSYNEDLEVLPNSIAKLYNLQTLQLKGCKRLEGL
Sen. sequence18     (560) ALVPNCLCLRALDLAWSKIKSVPDSIGGLLHLRYLDLSYNEDLEVLPNSIAKLYNLQTLQLKGCKRLEGL
Sen. sequence19     (561) ALVPNCLCLRALDLAWSKIKSVPDSIGGLLHLRYLDLSYNEDLEVLPNSIAKLYNLQTLQLKGCKRLEGL
Sen. sequence20     (561) ALVPNCLCLRALDLAWSKIKSVPDSIGGLLHLRYLDLSYNEDLEVLPNSIAKLYNLQTLQLKGCKRLEGL
Sen. sequence21     (504) ALVPNCLCLRALDLAWSKIKSLPDSIGGLLHLRYLDLSYNEDLEVLPNSIAKLYNLQTLQLKGCKRLEGL
Sen. sequence22     (533) XXXXNCLCLRALDLAWSKIKSLPDSIGGLLHLRYLDLSYNEDLEVLPNSIAKLYNLQTLQLKGCKRLEGL
```

FIG 2 J

```
                        631                                                                                             700
Res. sequence   (631)   PKHLSRLVKLQTLDIGCNNVTYMPKGMGKMTCLHTLSKFIVGGEGSCSSWKQFDGLEDLKALNNLKGH
Sen. sequence1  (631)   PKHLSRLVKLQTLDIYGCNNVTYMPKGMGKMTCLHTLSKFIVGGEGSCSSWKQWFDGQEDLKALNNLKGH
Sen. sequence2  (631)   PKHLSRLVKLQTLDIYGCNNVTYMPKGMGKMTCLHTLSKFIVGGEGSCSSWKQWFDGQEDLKALNNLKGH
Sen. sequence3  (631)   PKHLSRLVKLQTLDIYGCNNVTYMPKGMGKMTCLHTLSKFIVGGEGSCSSWKQWFDGQEDLKALNNLKGH
Sen. sequence4  (631)   PKHLSRLVKLQTLDIYGCNNVTYMPKGMGKMTCLHTLSKFIVGGEGSCSSWKQWFDGQEDLKALNNLKGH
Sen. sequence5  (631)   PKHLSRLVKLQTLDIYGCNNVTYMPKGMGKMTCLHTLSKFIVGGEGSCSSWKQWFDGQEDLKALNNLKGH
Sen. sequence6  (631)   PKHLSRLVKLQTLDIYGCNNVTYMPKGMGKMTCLHTLSKFIVGGEGSCSSWKQWFDGQEDLKALNNLKGH
Sen. sequence8  (631)   PKHLSRLVKLQTLDIYGCNNVTYMPKGMGKMTCLHTLSKFIVGGEGSCSSWKQWFDGQEDLKALNNLKGH
Sen. sequence9  (631)   PKHLSRLVKLQTLDIYGCNNVTYMPKGMGKMTCLHTLSKFIVGGEGSCSSWKQWFDGQEDLKALNNLKGH
Sen. sequence10 (631)   PKHLSRLVKLQTLDIYGCNNVTYMPKGMGKMTCLHTLSKFIVGGEGSCSSWKQWFDGQEDLKALNNLKGH
Sen. sequence11 (631)   PKHLSRLVKLQTLDIYGCNNVTYMPKGMGKMTCLHTLSKFIVGGEGSCSSWKQWFDGQEDLKALNNLKGH
Sen. sequence12 (631)   PKHLSRLVKLQTLDIYGCNNVTYMPKGMGKMTCLHTLSKFIVGGEGSCSSWKQWFDGQEDLKALNNLKGH
Sen. sequence14 (631)   PKHLSRLVKLQTLDIYGCNNVTYMPKGMGKMTCLHTLSKFIVGGEGSCSSWKQWFDGQEDLKALNNLKGH
Sen. sequence15 (631)   PKHLSRLVKLQTLDIYGCNNVTYMPKGMGKMTCLHTLSKFIVGGEGSCSSWKQWFDGQEDLKALNNLKGH
Sen. sequence16 (631)   PKHLSRLVKLQTLDIYGCNNVTYMPKGMGKMTCLHTLSKFIVGGEGSCSSWKQWFDGQEDLKALNNLKGH
Sen. sequence17 (631)   PKHLSRLVKLQTLDIYGCNNVTYMPKGMGKMTCLHTLSKFIVGGEGSCSSWKQWFDGQEDLKALNNLKGH
Sen. sequence18 (630)   PKHLSRLVKLQTLDIYGCNNVTYMPKGMGKMTCLHTLSKFIVGGEGSCSSWKQWFDGLEDLKALNNLKGH
Sen. sequence19 (631)   PKHLSRLVKLQTLDIYGCNNVTYMPKGMGKMTCLHTLSKFIVGGEGSCSSWKQWFDGQEDLKALNNLKGH
Sen. sequence20 (631)   PKHLSRLVKLQTLDIYGCNNVTYMPKGMGKMTCLHTLSKFIVGGEGSCSSWKQWFDGQEDLKALNNLKGH
Sen. sequence21 (574)   PKHLSRLVKLQTLDIYGCNNVTYMPKGMGKMTCLHTLSKFIVGGEGSCSSWKKRFDGLEDLKALNNLKGH
Sen. sequence22 (599)   PKHLSRLVKLQTLDIYGCNNVTYMPKGMGKMTCLHTLSKFIVGGEGSCSSWKKRFDGLEDLKALNNLKGH
```

FIG 2 K

```
                           701                                                                            770
Res. sequence     (701)    LEIQIRWPENTTDAVKEDVKREGLYLNHKEHLNHIVVDFRCEEGGGRMDDEEARRLMEELRPHPYLENLA
Sen. sequence1    (701)    LEIQIRWPENTTDAVKEDVKREGLYLNHKEHLNHIVVDFRCEEGGGRMDDEEARRLMEELRPHPYLENLA
Sen. sequence2    (701)    LEIQIRWPENTTDAVKEDVKREGLYLNHKEHLNHIVVD---------------------------------
Sen. sequence3    (701)    LEIQIRWPENTTDAVKEDVKREGLYLNHKEHLNHIVVD---------------------------------
Sen. sequence4    (701)    LEIQIRWPENTTDAVKEDVKREGLYLNHKEHLNHIVVD---------------------------------
Sen. sequence5    (701)    LEIQIRWPENTTDAVKEDVKREGLYLNHKEHLNH-------------------------------------
Sen. sequence6    (701)    LEIQIRWPENTTDAVKEDVKREGLYLN--------------------------------------------
Sen. sequence8    (701)    LEIQIRWPENTTDAVKEDVKREGLYLNH-------------------------------------------
Sen. sequence9    (701)    LEIQIRWPENTTDAVKEDVKREGLYLNH-------------------------------------------
Sen. sequence10   (701)    LEIQIRWPENTTDAVKEDVKREGLYLNHKEHLNHIVVDFRCEEGGGRMDDEEARRLMEELRPHPYLENLA
Sen. sequence11   (701)    LEIQIRWPENTTDAVKEDVKREGLYLNHKEHLNHIVVD---------------------------------
Sen. sequence12   (701)    LEIQIRWPENTTDAVKEDVKREGLYLNHKEHLNHIVVD---------------------------------
Sen. sequence14   (701)    LEIQIRWPENTTDAVKEDVKREGLYLNHKEHLNHIVVD---------------------------------
Sen. sequence15   (701)    LEIQIRWPENTTDAVKEDVKREGLYLNHKEHLNHIVVD---------------------------------
Sen. sequence16   (701)    LEIQIRWPENTTDAVKEDVKREGLYLNHKEHLNHIVVD---------------------------------
Sen. sequence17   (701)    LEIQIRWPENTTDAVKEDVKREGLYLNHKEHLNHIVVD---------------------------------
Sen. sequence18   (700)    LEIQIRWPENTTDVVKEDVKREGLYLNHKEHLNHIVVD---------------------------------
Sen. sequence19   (701)    LEIQIRWPENTTDAVKEDVKREGLYLNHKEHLNHIVVD---------------------------------
Sen. sequence20   (701)    LEIQIRWPENTTDAVKEDVKREGLYLNHKEHLNHIVVD---------------------------------
Sen. sequence21   (644)    LEIQIRWPENTTDAVKEDVKREGLYLNH-------------------------------------------
Sen. sequence22   (669)    LEIQIRWPENTTDAVKEDVKREGLYLNHKEHLNHIVVD---------------------------------
```

FIG 2 L

```
                        771                                                           840
Res. sequence     (771) VKAYYGVKMPGWATLLPNLTELFLSDCGELENLPCLGNLDHLKVLRLSHLAKLEYIEEDSSSANFRCRPG
Sen. sequence1    (771) VKAYYGAKMPGWATLLPNLTELYLSDCGESECLPCMGNLDCLKVLRLSHLAKLEYIEEDSTSANFSFRPG
Sen. sequence10   (771) VKAYYGAKMPGWATLLPNLTELYLSDCGESECLPCMGNLDCLKVLRLSHLAKLEYIEEDSTSANFSFRPG 841                                                           910
Res. sequence     (841) PESAGLSLYFPSLERLELELKRLCKLKGWRRGEGLGDDHQPFNESSS>Ret.Ins<NTQVQLQLCLPQLKSLRIERCPLLT
Sen. sequence1    (841) PESAGLSLYFPSLELLELELKRLHKLKGWRRREGLGDDHQPFNESSS>Ret.Ins<------------------------
Sen. sequence10   (841) PESAGLSLYFPSLELLELELKRLHKLKGWRRREGLGDDHQPFNESSS>Ret.Ins<------------------------

911                                                           980
Res. sequence     (911) FMPLCPKTEKLHLVVENERLRIVHAKRDENFYAPLHSSSSDPENPRNTIPIPMFREVYINNVAWLNSLPM 981                                                          1050
Res. sequence     (981) EAFRCLTHMTIKNDEVESLGEVGEVFRSCSSSLRSLNITGCSNLRSVSGGLEHLTALEMLEIYDTHKLSL 1051                                                          1120
Res. sequence    (1051) SEDPEGVVPWKSLHHSLYLQIMNLPQLVNLPDSMQFLAALRTLSIVHCTKLQSVPDWMPRLTSLRKLMV 1121                      1163
Res. sequence    (1121) SFCSAHLERRCQNPTGVDWPNIQHIPSIDVTSSLPKFLVLPYE
```

FIG 3 A

```
                                                                                      70
Res. sequence    (1)
Sen. sequence1   (1) MERVVYRWNTAETAGHLWPTNPKLILIPYSALQSSELKEILSIFGYKSLDDLQRTVSTINAVFRDAETKQELTHEAQHWLEEL
Sen. sequence2   (1) MERVVYRWN----TAGHLWPTNQKLILIPY-ALQSSELKEILSIFGYKSQLDDLQRTVSTINAVFRDAETKQELTHEAQHWLEEL
Sen. sequence3   (1) MERVVYRWNTAETAGHLWPTNPKLILIPYSALQSSELKEILSIFGYKSQLDDLQRTVSTINAVFRDAETKQELTHEAQHWLEEL
Sen. sequence4   (1) MERVVYRWNTAETAGHLWPTNPKLILIPYSALQSSELKEILSIFGYKSQLDDLQRTVSTINAVFRDAETKQELTHEAQHWLEEL
Sen. sequence5   (1) MERVVYRWNTAETAGHLWPTNPKLILIPYSALQSSELKEILSIFGYKSQLDDLQRTVSTINAVFRDAETKQELTHEAQHWLEEL
Sen. sequence6   (1) MERVVYRWNTAETAGHLWPTNPKLILIPYSALQSSELKEILSIFGYKSQLDDLQRTVSTINAVFRDAETKQELTHEAQHWLEEL
Sen. sequence7   (1) MERVVYRWN----TAGHLWPTNQKLILIPYSALQSSELKEILSIFGYKSQLDDLQRTVSTINAVFRDAETKQELTHEAQHWLEEL
Sen. sequence8   (1) ------------------------------------------------------STINAVFRDAETKQELTHEAQHWLEEL
Sen. sequence9   (1) MERVVYRWNTAETAGHLWPTNPKLILIPYSALQSSELKEILSIFGYKSQLDDLQRTVSTINAVFRDAETKQELTHEAQHWLEEL
Sen. sequence10  (1) MERVVYRWNTAETAGHLWPTNPKLILIPYSALQSSELKEILSIFGYKSQLDDLQRTVSTINAVFRDAETKQELTHEAQHWLEEL
Sen. sequence11  (1) MERVVYRWN----TAGHLWPTNQKLILIPY-ALQSSELKEILSIFGYKSQLDDLQRTVSTINAVFRDAETKQELTHEAQHWLEEL
Sen. sequence12  (1) MERVVYRWN----TAGHLWPTNQKLILIPYSALQSSELKEILSIFGYKSQLDDLQRTVSTINAVFRDAETKQELTHEAQHWLEEL
Sen. sequence13  (1) MERVVYRWN----TAGHLWPTNQKLILIPYSALQSSELKEILSIFGYKSQLDDLQRTVSTINAVFRDAETKQELTHEAQHWLEEL
Sen. sequence14  (1) ------------------------------------------------------STINAVFRDAETKQELTHEAQHWLEEL
Sen. sequence15  (1) MERVVYRWN----TAGHLWPTNQKLILIPYSALQSSELKEILSIFGYKSQLDDLQRTVSTINAVFRDAETKQELTHEAQHWLEEL
Sen. sequence16  (1) MERVVYRWN----TAGHLWPTNQKLILIPYSALQSSELKEILSIFGYKSQLDDLQRTVSTINAVFRDAETKQELTHEAQHWLEEL
Sen. sequence17  (1) MERVVYRWN----TAGHLWPTNQKLILIPYSALQSSELKEILSIFGYKSQLDDLQRTVSTINAVFRDAETKQELTHEAQHWLEEL
Sen. sequence18  (1) MERVVYRWNTAETAGHLWPTNPKLILIPYSALQSSELKEILSIFGYKSQLDDLQRTVSTINAVFRDAETKQELTHEAQHWLEEL
Sen. sequence19  (1) MERVVYRWN----TAGHLWPTNQKLILIPYSALQSSELKEILSIFGYKSQLDDLQRTVSTINAVFRDAETKQELTHEAQHWLEEL
Sen. sequence20  (1) MERVVYRWN----TAGHLWPTNQKLILIPYSALQSSELKEILSIFGYKSQLDDLQRTVSTINAVFRDAETKQELTHEAQHWLEEL
Sen. sequence21  (1) ---------------------------ALQSSELKEILSIFGYKSQLDDLQRTVSTINAVFRDAETKQELTHEAQHWLEEL
Sen. sequence22  (1) ---------------------------ALQSSELKEILSIFGYKSQLDDLQRIVSTINAVFRDAETKQELTHEAQHWLEEL
```

FIG 3 B

FIG 3 C

```
                        141                                                                210
Res. sequence   (141) SFKIDLEPKERRLETGSVVNAGDIIGREDDLEKIVGLLLLDSNIQRDVSFLTIVGMGGLGKTALAQLVYN
Sen. sequence1  (141) SFKIDLEPIKERRLETGSVVNAGDIIGREDDLEKIVGLLLLDSNIQRDVSFLTIVGMGGLGKTALAQLVYN
Sen. sequence2  (141) SFKIDLEPIKERRLETGSVVNAGDIIGREDDLEKIVGLLLLDSNIQRDVSFLTIVGMGGLGKTALAQLVYN
Sen. sequence3  (141) SFKIDLEPIKERRLETGSVVNAGDIIGREDDLEKIVGLLLLDSNIQRDVSFLTIVGMGGLGKTALAQLVYN
Sen. sequence4  (141) SFKIDLEPIKERRLETGSVVNAGDIIGREDDLEKIVGLLLLDSNIQRDVSFLTIVGMGGLGKTALAQLVYN
Sen. sequence5  (141) SFKIDLEPIKERRLETGSVVNAGDIIGREDDLEKIVGLLLLDSNIQRDVSFLTIVGMGGLGKTALAQLVYN
Sen. sequence6  (141) SFKIDLEPIKERRLETGSVVNAGDIIGREDDLEKIVGLLLLDSNIQRDVSFLTIVGMGGLGKTALAQLVYN
Sen. sequence7   (98) SFKIDLEPIKERRLETGSVVNAGDIIGREDDLEKIVGLLLLDSNIQRDVSFLTIVGMGGLGKTALAQLVYN
Sen. sequence8  (141) SFKIDLEPIKERRLETGSVVNAGDIIGREDDLEKIVGLLLLDSNIQRDVSFLTIVGMGGLGKTALAQLVYN
Sen. sequence9  (141) SFKIDLEPIKERRLETGSVVNAGDIIGREDDLEKIVGLLLLDSNIQRDVSFLTIVGMGGLGKTALAQLVYN
Sen. sequence10 (141) SFKIDLEPIKERRLETGSVVNAGDIIGREDDLEKIVGLLLLDSNIQRDVSFLTIVGMGGLGKTALAQLVYN
Sen. sequence11 (141) SFKIDLEPIKERRLETGSVVNAGDIIGREDDLEKIVGLLLLDSNIQRDVSFLTIVGMGGLGKTALAQLVYN
Sen. sequence12 (141) SFKIDLEPIKERRLETGSVVNAGDIIGREDDLEKIVGLLLLDSNIQRDVSFLTIVGMGGLGKTALAQLVYN
Sen. sequence13  (98) SFKIDLEPIKERRLETGSVVNAGDIIGREDDLEKIVGLLLLDSNIQRDVSFLTIVGMGGLGKTALAQLVYN
Sen. sequence14 (141) SFKIDLEPIKERRLETGSVVNAGDIIGREDDLEKIVGLLLLDSNIQRDVSFLTIVGMGGLGKTALAQLVYN
Sen. sequence15 (141) SFKIDLEPIKERRLETGSVVNAGDIIGREDDLEKIVGLLLLDSNIQRDVSFLTIVGMGGLGKTALAQLVYN
Sen. sequence16 (141) SFKIDLEPIKERRLETGSVVNAGDIIGREDDLEKIVGLLLLDSNIQRDVSFLTIVGMGGLGKTALAQLVYN
Sen. sequence17 (141) SFKIDLEPIKERRLETGSVVNAGDIIGREDDLEKIVGLLLLDSNIQRDMSFLTIVGMGGLGKTALAQLVYN
Sen. sequence18 (141) SFKIDLEPIKERRLETGSVVNAGDIIGREDDLEKIVGLLLLDSNIQRDVSFLTIVGMGGLGKTALAQLVYN
Sen. sequence19 (141) SFKIDLEPIKERRLETGSVVNAGDIIGREDDLEKIVGLLLLDSNIQRDVSFLTIVGMGGLGKTALAQLVYN
Sen. sequence20 (141) SFKIDLEPIKERRLETGSVVNAGDIIGREDDLEKIVGLLLLDSNIQRDVSFLTIVGMGGLGKTALAQLVYN
Sen. sequence21 (141) SFKIDLEPIKERRLETGSVVNAGDIIGREDDLEKIVGLFLLDSNIQRDVSFLTIVGMGGLGKTALAQLVYN
Sen. sequence22 (141) SFKIDLEPIKERRLETGSVVNAGDIIGREDDLEKIVGLFLLDSNIQRDVSFLTIVGMGGLGKTALAQLVYN
```

FIG 3 D

```
                    211                                                                    280
Res. sequence  (211) DPRVRTAFPLRCWNCVSDQDQKQLDVKEILGKILSTATGKNHEGSTMDQVQTQLREQLCGKRYLLVLDDV
Sen. sequence1 (211) DPRVRTAFPLRCWNCVSDQDQDQKKLDVKEILGKILSTATGKNHEGSTMDHVQTQLREQLCGKRYLLVLDDV
Sen. sequence2 (211) DPRVRTAFPLRCWNCVSDQDQDQKKLDVKEILGKILSTATGKNHEGSTMDHVQTQLREQLCGKRYLLVLDDV
Sen. sequence3 (211) DPRVRTAFPLRCWNCVSDQDQKKLDVKEILGKILSTATGKNHEGSTMDHVQTQLQEQLCGKRYLLVLDDV
Sen. sequence4 (211) DPRVRTAFPLRCWNCVSDQDQKKLDVKEILGKILSTATGKNHEGSTMDHVQTQLQEQLCGKRYLLVLDDV
Sen. sequence5 (211) DPRVRTAFPLRCWNCVSDQDQKKLDVKEILGKILSTATGKNHEGSTMDHVQTQLQEQLCGKRYLLVLDDV
Sen. sequence6 (211) DPRVRTAFPLRCWNCVSDQDQKKLDVKEILGKILSTATGKNHEGSTMDHVQTQLQEQLCGKRYLLVLDDV
Sen. sequence7 (168) DPRVRTAFPLRCWNCL*-----------------------------------------------------
Sen. sequence8 (211) DPRVRTAFPLRCWNCVSDQDQKKLDVKEILGKILSTATGKNHEGSTMDHVQTQLQEQLCGKRYLLVLDDV
Sen. sequence9 (211) DPRVRTAFPLRCWNCVSDQDQKKLDVKEILGKILSTATGKNHEGSTMDHVQTQLREQLCGKRYLLVLDDV
Sen. sequence10 (211) DPRVRTAFPLRCWNCVSDQDQKKLDVKEILGKILSTATGKNHEGSTMDHVQTQLREQLCGKRYLLVLDDV
Sen. sequence11 (211) DPRVRTAFPLRCWNCVSDQDQKKLDVKEILGKILSTATGKNHEGSTMDHVQTQLREQLCGKRYLLVLDDV
Sen. sequence12 (211) DPRVRTAFPLRCWNCVSDQDQKKLDVKEILGKILSTATGKNHEGSTMDHVQTQLREQLCGKRYLLVLDDV
Sen. sequence13 (168) DPRVRTAFPLRCWNCL*-----------------------------------------------------
Sen. sequence14 (211) DPRVRTAFPLRCWNCVSDQDQKKLDVKEILGKILSTATGKNHEGSTMDHVQTQLREQLCGKRYLLVLDDV
Sen. sequence15 (211) DPRVRTAFPLRCWNCVSDQDQKKLDVKEILGKILSTATGKNHEGSTMDHVQTQLREQLCGKRYLLVLDDV
Sen. sequence16 (211) DPRVRTAFPLRCWNCVSDQDQKKLDVKEILGKILSTATGKNHEGSTMDHVQTQLREQLCGKRYLLVLDDV
Sen. sequence17 (211) DPRVRTAFPLRCWNCVSDQDQKKLDVKEILGKILSTATGKNHEGSTMDHVQTQLQEQLCGKRYLLVLDDV
Sen. sequence18 (211) DPRVRTAFPLRCWNCVEDQDQDQKKLDVKEILGKILSTATGKNHEGSTMDQVQTQLRE-LCGKRYLLVLDDV
Sen. sequence19 (211) DPRVRTAFPLRCWNCVSDQDQDQKKLDVKEILGKILSTATGKNHEGSTMDHVQTQLREQLCGKRYLLVLDDV
Sen. sequence20 (211) DPRVRTAFPLRCWNCVSDQDQNQLDVKEILGKILSTATGKNHKGSTMDHVQTQLREQLCGKRYLLVLDDV
Sen. sequence21 (211) DPRVRTAFPLRCWNCVSDQDQNQLDVKEILGKILSTATGKNHEGSTMDHVQTQLREQLCGKRYLLVLDDV
Sen. sequence22 (211) DPRVRTAFPLRCWNCVSDQDQNQLDVKEILGKILSTATGKNHKGSTMDQVQTQLREQLCGKRYLLVLDDV
```

FIG 3 E

```
                        281                                                                  350
Res. sequence    (281)  WNENPNQLRDLVEFFMGGRSRNWIVVTTRSHETARIIRDGPLHKLQGLSEENSWRLFVRWTFGSVQAKFP
Sen. sequence1   (281)  WNENPNQLRYLVEFFMGGQRGNWIVVTTRSHETARIIRDGPLHKLQGLSEENSWRLFVRWTFGSVQPKFP
Sen. sequence2   (281)  WNENPNQLRXXXXFFMGGQRGNWIVVTTRSHETTRIIRDGPLHKLQGLSEENSWRLFVRWTFGSVQPKFP
Sen. sequence3   (281)  WNENPNQLRDLGKFFMGGQRGNWIVVTTRSHETTRIIRDGPLHKLQGLSEENSWRLFVRWTFGSVQPKFP
Sen. sequence4   (281)  WNENPNQLRDXVEFFMGGQRGNWIVVTTRSHETTRIIRDGPLHKLQGLSEENSWRLFVRWTFGSVQPKFP
Sen. sequence5   (281)  WNENPNQLXXXXXFFMGGQRGNWIVVTTRSHETTRIIRDGPLHKLQGLSEENSWRLFVRWTFGSVQPKFP
Sen. sequence6   (281)  WNENPNQLRIXVEFFMGGQRGNWIVVTTRSHETARIIRDGPLHKLQGLSEENSWRLFVRWTFGSVQPKFP
Sen. sequence7   (184)  ----------------------------------------------------------------------
Sen. sequence8   (281)  WNENPNQLRXXXXFFMGGQRGNWIVVTTRSHETTRIIRDGPLHKLQGLSEENSWRLFVRWTFGSVQPKFP
Sen. sequence9   (281)  WNENPNQLRDXVEFFMGGQRGNWIVVTTRSHETTRIIRDGPLHKLQGLSEENSWRLFVRWTFGSVQPKFP
Sen. sequence10  (281)  WNENPNQLRYLVEFFMGGQRGNWIVVTTRSHETARIIRDGPLHKLQGLSEENSWRLFVRWTFGSVQPKFP
Sen. sequence11  (281)  WNENPNQLRYLVEFFMGGQRGNWIVVTTRSHETARIIRDGPLHKLQGLSEENSWRLFVRWTFGSVQPKFP
Sen. sequence12  (281)  WNENPNQLXXXXXFFMGGQRGNWIVVTTRSHETARIIRDGPLHKLQGLSEENSWRLFVRWTFGSVQPKFP
Sen. sequence14  (281)  WNENPNQLRILVEFFMGGQRGNWIVVTTRSHETARIIRDGPLHKLQGLSEENSWRLFVRWTFGSVQPKFP
Sen. sequence15  (281)  WNENPNQLRXXXXFFMGGQRGNWIVVTTRSHETARIIRDGPLHKLQGLSEENSWRLFVRWTFGSVQPKFP
Sen. sequence16  (281)  WNENPNQLRXXVEFFMGGQRGNWIVVTTRSHETARIIRDGPLHKLQGLSEENSWRLFVRWTFGSVQPKFP
Sen. sequence17  (281)  WNENPNQLRDLVEFFMGGQRGNWIVVTTRSHETTRIIRDGPLHKLQGLSEENSWRLFVRWTFGSVQPKFP
Sen. sequence18  (280)  WNENPNQLRDLVEFFMGGQRGNWIVVTTRSHETARIIRDGPLHKLQGLSEENSWRLFVRWTFGSVQPKFP
Sen. sequence19  (281)  WNENPNQLRILVEFFMXXXXXXXXXXXXXXXXXXXXXXXXXXXXXXXXQGLSEENSWRLFVRWTFGSVQPKFP
Sen. sequence20  (281)  WNENPNQLRDLVEFFMGGQRGNWIVVTTRSHETARIIRDGPLHKLQGLSEENSWRLFVRWTFGSVQPKFP
Sen. sequence21  (281)  WNENPNQLRDLVEFFMGXXXXXXXXXXXXXXXXXXXXXXXXXXXXXXXXXXXXXXXXXXXXXXXXXXXXX
Sen. sequence22  (281)  WNENPNQLRXXXXXXXXXXXXXXXXXXXXXXXXXXXXXXXXXXXXXXXXXXXXXXXXXXXXXXXXXXXXX
```

FIG 3 F

```
                        351                                                                              420
Res. sequence    (351)  NDFVMIARDIVDKCARNPLAIRVVGSLLCGQDKSKWLSFHEILXNIRKSHNDIMPILNLSYHHLEPPIX
Sen. sequence1   (351)  NDFVMIARDIVDKCARNPLAIRVVGSLLCGQDKSKWLSFHEICLANIRKSHNDIMPILNLSYHHLEPPIR
Sen. sequence2   (351)  NDFVMIARDIVDKCARNPLAIRVVGSLLCGQDKSKWLSFHEICLANIRKSHNDIMLILNLSYHHLEPPIR
Sen. sequence3   (351)  NDFVMIARDIVDKCARNPLAIRVVGSLLCGQDKSKWLSFHEICLANIRKSHNDIMLILNLSYHHLEPPIR
Sen. sequence4   (351)  NDFVMIARDIVDKCARNPLAIRVVGSLLCGQDKSKWLSFHEICLANIRKSHNDIMLILNLSYHHLEPPIR
Sen. sequence5   (351)  NDFVMIARDIVDKCARNPLAIRVVGSLLCGQDKSKWLSFHEICLANIRKSHNDIMLILNLSYHHLEPPIR
Sen. sequence6   (351)  NDFVMIARDIVDKCARNPLAIRVVGSLLCGQDKSKWLSFHEICLANIRKSHNDIMLILNLSYHHLEPPIR
Sen. sequence8   (351)  NDFVMIARDIVDKCARNPLAIRVVGSLLCGQDKSKWLSFHEICLANIRKSHNDIMLILNLSYHHLEPPIR
Sen. sequence9   (351)  NDFVMIARDIVDKCARNPLAIRVVGSLLCGQDKSKWLSFHEICLANIRKSHNDIMLILNLSYHHLEPPIR
Sen. sequence10  (351)  NDFVMIARDIVDKCARNPLAIRVVGSLLCGQDKSKWLSFHEICLANIRKSHNDIMPILNLSYHHLEPPIR
Sen. sequence11  (351)  NDFVMIARDIVDKCARNPLAIRVVGSLLCGQDKSKWLSFHEICLANIRKSHNDIMPILNLSYHHLEPPIR
Sen. sequence12  (351)  NDFVMIARDIVDKCARNPLAIRVVGSLLCGQDKSKWLSFHEICLANIRKSHNDIMPILNLSYHHLEPPIR
Sen. sequence14  (351)  NDFVMIARDIVDKCARNPLAIRVVGSLLCGQDKSKWLSFHEICLANIRKSHNDIMPILNLSYHHLEPPIR
Sen. sequence15  (351)  NDFVMIARDIVDKCARNPLAIRVVGSLLCGQDKSKWLSFHEICLANIRKSHNDIMPILNLSYHHLEPPIR
Sen. sequence16  (351)  NDFVMIARDIVDKCARNPLAIRVVGSLLCGQDKSKWLSFHEICLANIRKSHNDIMLILNLSYHHLEPPIR
Sen. sequence17  (351)  NDFVMIARDIVDKCARNPLAIRVVGSLLCGQDKSKWLSFHEICLANIRKSHNDIMLILNLSYHHLEPPIR
Sen. sequence18  (350)  NDFVMIARDIVDKCARNPLAIRVVGSLLCGQDKSKWLSFHEICLANIRKSHNDIMPILNLSYHHLEPPIR
Sen. sequence19  (351)  NDFVMIARDIVDKCARNPLAIRVVGSLLCGQDKSKWLSFHEICLANIRKSHNDIMPILNLSYHHLEPPIR
Sen. sequence20  (351)  XXXXXXXXXXXXXXXXXXXXXXXXXXXXXXXXXXXXXXXXXXXXXXXXXXXXXXXXXXXXXXXXXXXXXX
Sen. sequence21  (333)  XXXXXXXXXXXXXXXXXXXXXXXXXXXXXXXXXXXXXXXXXXXXXXXXXXXXXXXXXXXXXXXXXXXXXX
Sen. sequence22  (351)  XXXXXXXXXXXXXXXXDKCARNPLAIRVVGSLLCGQDKSKWLSFHEXCLANIRKSHNDIMPILNLSYHHLEPPIR
```

FIG 3 G

```
                      421                                                                          490
Res. sequence   (421) RCFSYCAMFPKDFLIGKTLINLWMAQGYIVPLDKDQSIDDASEEYISILIRCFFENGEKDGVIKIH
Sen. sequence1  (421) RCFSYCAMFPKDFLIGKKTLINLWMAQGYIVPLDKDQSIDDASEEYISILLQRCFFENIGTEKDYVIKIH
Sen. sequence2  (421) RCFSYCAMFPKDFLIGKKTLINLWMAQGYIVPLDKDQSIDDASEEYISILLQRCFFENIGTEKDYVIKIH
Sen. sequence3  (421) RCFSYCAMFPKDFLIGKKTLINLWMAQGYIVPLDKDQSIDDASEEYISILLQRCFFENIGTEKDYVIKIH
Sen. sequence4  (421) RCFSYCAMFPKDFLIGKKTLINLWMAQGYIVPLDKDQSIDDASEEYISILLQRCFFENIGTEKDYVIKIH
Sen. sequence5  (421) RCFSYCAMFPKDFLIGKKTLINLWMAQGYIVPLDKDQSIDDASEEYISILLQRCFFENIGTEKDYVIKIH
Sen. sequence6  (421) RCFSYCAMFPKDFLIGKKTLINLWMAQGYIVPLDKDQSIDDASEEYISILLQRCFFENIGTEKDYVIKIH
Sen. sequence8  (421) RCFSYCAMFPKDFLIGKKTLINLWMAQGYIVPLDKDQSIDDASEEYISILLQRCFFENIGTEKDYVIKIH
Sen. sequence9  (421) RCFSYCAMFPKDFLIGKKTLINLWMAQGYIVPLDKDQSIDDASEEYISILLQRCFFENIGTEKDYVIKIH
Sen. sequence10 (421) RCFSYCAMFPKDFLIGKKTLINLWMAQGYIVPLDKDQSIDDASEEYISILLQRCFFENIGTEKDYVIKIH
Sen. sequence11 (421) RCFSYCAMFPKDFLIGKKTLINLWMAQGYIVPLDKDQSIDDASEEYISILLQRCFFENIGTEKDYVIKIH
Sen. sequence12 (421) RCFSYCAMFPKDFLIGKKTLINLWMAQGYIVPLDKDQSIDDASEEYISILLQRCFFENIGTEKDYVIKIH
Sen. sequence14 (421) RCFSYCAMFPKDFLIGKKTLINLWMAQGYIVPLDKDQSIDDASEEYISILLQRCFFENIGTEKDYVIKIH
Sen. sequence15 (421) RCFSYCAMFPKDFLIGKKTLINLWMAQGYIVPLDKDQSIDDASEEYISILLQRCFFENIGTEKDYVIKIH
Sen. sequence16 (421) RCFSYCAMFPKDFLIGKKTLINLWMAQGYIVPLDKDQSIDDASEEYISILLQRCFFENIGTEKDYVIKIH
Sen. sequence17 (421) RCFSYCAMFPKDFLIGKKTLINLWMAQGYIVPLDKDQSIDDASEEYISILLQRCFFENIGTEKDYVIKIH
Sen. sequence18 (420) RCFSYCVVFPKDFLIGKKTLINLWMAQGYIVPLDKDQSIDDASEEYISILLQRCFFENIGTEKDVVIKIH
Sen. sequence19 (421) RCFSYCAMFPKDFLIGKKTLINLWMAQGYIVPLDKDQSIDDASEEYISILLQRCFFENIGTEKDYVIKIH
Sen. sequence20 (421) XXXXXXXXXXXXXXXXXXXXXXXXXXXXXXXXXXXXXXXXXXXXXXXXXXXXXXXXXXXXXXXXXXXXXX
Sen. sequence21 (378) XXXXXXXXXXXXXXXXXXXXXXXXXXXXXXXXXXXXXXXXXXXXXXXXXXXXXXXXXXXXXXXXXXXXXX
Sen. sequence22 (421) RCFSYCAVFPKDFLIGKKTLINLWMAQGYIVPLDKDQSIDDASEEYISILXQRCFFENIGTEKDDVIKIH
```

FIG 3 H

```
                        491                                                                                    560
Res. sequence    (491)  DLMHDIAQNVMGKELCTTKNISGSLDKVRHLSLARTSFARYSFNATHIRSYF░AGYWCQDAEINQFSVE
Sen. sequence1   (491)  DLMHDIAQNVMGKELCTTKNISGSLDKNVRHLSLARTSFARYSFNATHIRSYFYAGYWCQDAEINQFSVE
Sen. sequence2   (491)  DLMHDIAQNVMGKELCTTKNISGSLDKNVRHLSLARTSFARYSFNATHIRSYFYAGYWCQDAEIXQFSVE
Sen. sequence3   (491)  DLMHDIAQNVMGKELCTTKNISGSLDKNVRHLSLARTSFARYSFNATHIRSYFYAGYWCQDAEINQFSVE
Sen. sequence4   (491)  DLMHDIAQNVMGKELCTTKNISGSLDKNVRHLSLARTSFARYSFNATHIRSYFYAGYWCQDAEINQFSVE
Sen. sequence5   (491)  DLMHDIAQNVMGKELCTTKNISGSLDKNVRHLSLARTSFARYSFNATHIRSYFYAGYWCQDAEINQFSVE
Sen. sequence6   (491)  DLMHDIAQNVMGKELCTTKNISGSLDKNVRHLSLARTSFARYSFNATHIRSYFXAGYWCQDAEINQFSVE
Sen. sequence8   (491)  DLMHDIAQNVMGKELCTTKNISGSLDKNVRHLSLARTSFARYSFNATHIRSYFYAGYWCQDAEINQFSVE
Sen. sequence9   (491)  DLMHDIAQNVMGKELCTTKNISGSLDKNVRHLSLARTSFARYSFNATHIRSYFYAGYWCQDAEINQFSVE
Sen. sequence10  (491)  DLMHDIAQNVMGKELCTTKNISGSLDKNVRHLSLARTSFARYSFNATHIRSYFYAGYWCQDAEINQFSVE
Sen. sequence11  (491)  DLMHDIAQNVMGKELCTTKNISGSLDKNVRHLSLARTSFARYSFNATHIRSYFYAGYWCQDAEINQFSVE
Sen. sequence12  (491)  DLMHDIAQNVMGKELCTTKNISGSLDKNVRHLSLARTSFARYSFNATHIRSYFYAGYWCQDAEINQFSVE
Sen. sequence14  (491)  DLMHDIAQNVMGKELCTTKNISGSLDKNVRHLSLARTSFARYSFNATHIRSYFYAGYWCQDAEINQFSVE
Sen. sequence15  (491)  DLMHDIAQNVMGKELCTTKNISGSLDKNVRHLSLARTSFARYSFNATHIRSYFYAGYWCQDAEINQFSVE
Sen. sequence16  (491)  DLMHDIAQNVMGKELCTTKNISGSLDKNVRHLSLARTSFARYSFNATHIRSYFYAGYWCQDAEINQFSVE
Sen. sequence17  (491)  DLMHDIAQNVMGKELCTTKNISGSLDKNVRHLSLARTSFARYSFNATHIRSYFYAGYWCQDAEINQFSVE
Sen. sequence18  (490)  DLMHDIAQNVMGKELCTTKNISGSLDKNVRHLSLARTSFARYSFNATHIRSYFYAGYWCQNAEINQFSVE
Sen. sequence19  (491)  DLMHDIAQNVMGKELCTTKNISGSLDKNVRHLSLARTSFARYSFNATHIRSYFYAGYWCQDAEINQFSVE
Sen. sequence20  (491)  DLMHDIAQNVMGKELCTTKNISGSLDKXXXXXXXXXXXXXXXXXXXXXXXXXXXXXXXXXXXXXXXXXXX
Sen. sequence21  (448)  XXXXXXXXXXXXXXXXXXXXXXXXXXXXXXXXXXXXXXXXXXXXXXXXXAGYWCQESEINQFSVE
Sen. sequence22  (491)  DLMHDIAQNVMGKELCTTKNISGSLDKNVRHLSLXXXXXXXXXXXXXXXXXXXXXXXXXXXXXXXXXXXX
```

FIG 3 I

```
                     561                                                                        630
Res. sequence  (561) ALVPNCLCLRA░DLAWSKIKSLPDSIGGLLHLRYLDLSYNEDLEVLPNSIAKLYNLQTLQLKGCKRLEGL
Sen. sequence1 (561) ALVPNCLCLRALDLAWSKIKSVPDSIGGLLHLRYLDLSYNEDLEVLPNSIAKLYNLQTLQLKGCKRLEGL
Sen. sequence2 (561) ALVPNCLCLRALDLAWSKIKSVPDSIGGLLHLRYLDLSYNEDLEVLPNSIAKLYNLQTLQLKGCKRLEGL
Sen. sequence3 (561) ALVPNCLCLRALDLAWSKIKSVPDSIGGLLHLRYLDLSYNEDLEVLPNSIAKLYNLQTLQLKGCKRLEGL
Sen. sequence4 (561) ALVPNCLCLRALDLAWSKIKSVPDSIGGLLHLRYLDLSYNEDLEVLPNSIAKLYNLQTLQLKGCKRLEGL
Sen. sequence5 (561) ALVPNCLCLRALDLAWSKIKSVPDSIGGLLHLRYLDLSYNEDLEVLPNSIAKLYNLQTLQLKGCKRLEGL
Sen. sequence6 (561) ALVPNCLCLRALDLAWSKIKSVPDSIGGLLHLRYLDLSYNEDLEVLPNSIAKLYNLQTLQLKGCKRLEGL
Sen. sequence8 (561) ALVPNCLCLRALDLAWSKIKSVPDSIGGLLHLRYLDLSYNEDLEVLPNSIAKLYNLQTLQLKGCKRLEGL
Sen. sequence9 (561) ALVPNCLCLRALDLAWSKIKSVPDSIGGLLHLRYLDLSYNEDLEVLPNSIAKLYNLQTLQLKGCKRLEGL
Sen. sequence10(561) ALVPNCLCLRALDLAWSKIKSVPDSIGGLLHLRYLDLSYNEDLEVLPNSIAKLYNLQTLQLKGCKRLEGL
Sen. sequence11(561) ALVPNCLCLRALDLAWSKIKSVPDSIGGLLHLRYLDLSYNEDLEVLPNSIAKLYNLQTLQLKGCKRLEGL
Sen. sequence12(561) ALVPNCLCLRALDLAWSKIKSVPDSIGGLLHLRYLDLSYNEDLEVLPNSIAKLYNLQTLQLKGCKRLEGL
Sen. sequence14(561) ALVPNCLCLRALDLAWSKIKSVPDSIGGLLHLRYLDLSYNEDLEVLPNSIAKLYNLQTLQLKGCKRLEGL
Sen. sequence15(561) ALVPNCLCLRALDLAWSKIKSVPDSIGGLLHLRYLDLSYNEDLEVLPNSIAKLYNLQTLQLKGCKRLEGL
Sen. sequence16(561) ALVPNCLCLRALDLAWSKIKSVPDSIGGLLHLRYLDLSYNEDLEVLPNSIAKLYNLQTLQLKGCKRLEGL
Sen. sequence17(561) ALVPNCLCLRALDLAWSKIKSVPDSIGGLLHLRYLDLSYNEDLEVLPNSIAKLYNLQTLQLKGCKRLEGL
Sen. sequence18(560) ALVPNCLCLRALDLAWSKIKSVPDSIGGLLHLRYLDISYNEDLEVLPNSIAKLYNLQTLQLKGCKRLEGL
Sen. sequence19(561) ALVPNCLCLRALDLAWSKIKSVPDSIGGLLHLRYLDLSYNEDLEVLPNSIAKLYNLQTLQLKGCKRLEGL
Sen. sequence20(561) ALVPNCLCLRALDLAWSKIKSLPDSIGGLLHLRYLDLSYNEDLEVLPNSIAKLYNLQTLQLKGCKRLEGL
Sen. sequence21(504) ALVPNCLCLRALDLAWSKIKSLPDSIGGLLHLRYLDLSYNEDLEVLPNSIAKLYNLQTLQLKGCKRLEGL
Sen. sequence22(533) XXXXNCLCLRALDLAWSKIKSLPDSIGGLLHLRYLDLSYNEDLEVLPNSIAKLYNLQTLQLKGCKRLEGL
```

FIG 3 J

```
                          631                                                                           700
Res. sequence     (631) PKHLSRLVKLQTLDI░GCNNVTYMPKGMGK░TCLHTLSKFIVGGEGSCSSWKQ░FDGLEDLKALNNLKGH
Sen. sequence1    (631) PKHLSRLVKLQTLDIYGCNNVTYMPKGMGRMTCLHTLSKFIVGGEGSCSSWKQWFDGQEDLKALNNLKGH
Sen. sequence2    (631) PKHLSRLVKLQTLDIYGCNNVTYMPKGMGRMTCLHTLSKFIVGGEGSCSSWKQWFDGQEDLKALNNLKGH
Sen. sequence3    (631) PKHLSRLVKLQTLDIYGCNNVTYMPKGMGRMTCLHTLSKFIVGGEGSCSSWKQWFDGQEDLKALNNLKGH
Sen. sequence4    (631) PKHLSRLVKLQTLDIYGCNNVTYMPKGMGRMTCLHTLSKFIVGGEGSCSSWKQWFDGQEDLKALNNLKGH
Sen. sequence5    (631) PKHLSRLVKLQTLDIYGCNNVTYMPKGMGRMTCLHTLSKFIVGGEGSCSSWKQWFDGQEDLKALNNLKGH
Sen. sequence6    (631) PKHLSRLVKLQTLDIYGCNNVTYMPKGMGRMTCLHTLSKFIVGGEGSCSSWKQWFDGQEDLKALNNLKGH
Sen. sequence8    (631) PKHLSRLVKLQTLDIYGCNNVTYMPKGMGRMTCLHTLSKFIVGGEGSCSSWKQWFDGQEDLKALNNLKGH
Sen. sequence9    (631) PKHLSRLVKLQTLDIYGCNNVTYMPKGMGRMTCLHTLSKFIVGGEGSCSSWKQWFDGQEDLKALNNLKGH
Sen. sequence10   (631) PKHLSRLVKLQTLDIYGCNNVTYMPKGMGRMTCLHTLSKFIVGGEGSCSSWKQWFDGQEDLKALNNLKGH
Sen. sequence11   (631) PKHLSRLVKLQTLDIYGCNNVTYMPKGMGKMTCLHTLSKFIVGGEGSCSSWKQWFDGQEDLKALNNLKGH
Sen. sequence12   (631) PKHLSRLVKLQTLDIYGCNNVTYMPKGMGKMTCLHTLSKFIVGGEGSCSSWKQWFDGQEDLKALNNLKGH
Sen. sequence14   (631) PKHLSRLVKLQTLDIYGCNNVTYMPKGMGKMTCLHTLSKFIVGGEGSCSSWKQWFDGQEDLKALNNLKGH
Sen. sequence15   (631) PKHLSRLVKLQTLDIYGCNNVTYMPKGMGKMTCLHTLSKFIVGGEGSCSSWKQWFDGQEDLKALNNLKGH
Sen. sequence16   (631) PKHLSRLVKLQTLDIYGCNNVTYMPKGMGKMTCLHTLSKFIVGGEGSCSSWKQWFDGQEDLKALNNLKGH
Sen. sequence17   (631) PKHLSRLVKLQTLDIYGCNNVTYMPKGMGKMTCLHTLSKFIVGGEGSCSSWKQWFDGQEDLKALNNLKGH
Sen. sequence18   (630) PKHLSRLVKLQTLDIYGCNNVTYMPKGMGKMTCLHTLSKFIVGGEGSCSSWKQWFDGLEDLKALNNLKGH
Sen. sequence19   (631) PKHLSRLVKLQTLDIYGCNNVTYMPKGMGKMTCLHTLSKFIVGGEGSCSSWKQWFDGQEDLKALNNLKGH
Sen. sequence20   (631) PKHLSRLVKLQTLDIYGCNNVTYMPKGMGKMTCLHTLSKFIVGGEGSCSSWKQWFDGQEDLKALNNLKGH
Sen. sequence21   (574) PKHLSRLVKLQTLDIYGCNNVTYMPKGMGKMTCLHTLSKFIVGGEGSCSSWKKRFDGLEDLKALNNLKGH
Sen. sequence22   (599) PKHLSRLVKLQTLDIYGCNNVTYMPKGMGKMTCLHTLSKFIVGGEGSCSSWKKRFDGLEDLKALNNLKGH
```

FIG 3 K

```
                        701                                                                          770
Res. sequence    (701) LEIQIRWP NTTDAVKEDV REGLYLNHKEHLNHIVVDFRCEEGGGRMDDEEARRLMEELRPHPYLENLA
Sen. sequence1   (701) LEIQIRWPENTTDAVKEDVKREGLYLNHKEHLNHIVVDFRCEEGGGRMDDEEARRLMEELRPHPYLENLA
Sen. sequence2   (701) LEIQIRWPENTTDAVKEDVKREGLYLNHKEHLNHIVVD---------------------------------
Sen. sequence3   (701) LEIQIRWPENTTDAVKEDVKREGLYLNHKEHLNHIVVD---------------------------------
Sen. sequence4   (701) LEIQIRWPENTTDAVKEDVKREGLYLNHKEHLNHIVVD---------------------------------
Sen. sequence5   (701) LEIQIRWPENTTDAVKEDVKREGLYLNHKEHLNHIVVD---------------------------------
Sen. sequence6   (701) LEIQIRWPENTTDAVKEDVKREGLYLNHKEHLNHIVVD---------------------------------
Sen. sequence8   (701) LEIQIRWPENTTDAVKEDVKREGLYLN--------------------------------------------
Sen. sequence9   (701) LEIQIRWPENTTDAVKEDVKREGLYLNH-------------------------------------------
Sen. sequence10  (701) LEIQIRWPENTTDAVKEDVKREGLYLNH-------------------------------------------
Sen. sequence11  (701) LEIQIRWPENTTDAVKEDVKREGLYLNHKEHLNHIVVDFRCEEGGGRMDDEEARRLMEELRPHPYLENLA
Sen. sequence12  (701) LEIQIRWPENTTDAVKEDVKREGLYLNHKEHLNHIVVD---------------------------------
Sen. sequence14  (701) LEIQIRWPENTTDAVKEDVKREGLYLNHKEHLNHIVVD---------------------------------
Sen. sequence15  (701) LEIQIRWPENTTDAVKEDVKREGLYLNHKEHLNHIVVD---------------------------------
Sen. sequence16  (701) LEIQIRWPENTTDAVKEDVKREGLYLNHKEHLNHIVVD---------------------------------
Sen. sequence17  (701) LEIQIRWPENTTDAVKEDVKREGLYLNHKEHLNHIVVD---------------------------------
Sen. sequence18  (700) LEIQIRWPENTTDVVKEDVKREGLYLNHKEHLNHIVVD---------------------------------
Sen. sequence19  (701) LEIQIRWPENTTDAVKEDVKREGLYLNHKEHLNHIVVD---------------------------------
Sen. sequence20  (701) LEIQIRWPENTTDAVKEDVKREGLYLNHKEHLNHIVVD---------------------------------
Sen. sequence21  (644) LEIQIRWPENTTDAVKEDVKREGLYLNH-------------------------------------------
Sen. sequence22  (669) LEIQIRWPENTTDAVKEDVKREGLYLNHKEHLNHIVVD---------------------------------
```

FIG 3 L

```
                                771                                                                           840
Res. sequence      (771)  VKAYYGVKMPGWATLLPNLTELFLSDCGELENLPCLGNLDHLKVLRLSHLAKLEYIEEDSSANFRCRPG
Sen. sequence1     (771)  VKAYYGAKMPGWATLLPNLTELYLSDCGESECLPCMGNLDCLKVLRLSHLAKLEYIEEDSTSANFSFRPG
Sen. sequence10    (771)  VKAYYGAKMPGWATLLPNLTELYLSDCGESECLPCMGNLDCLKVLRLSHLAKLEYIEEDSTSANFSFRPG 841                                                                           910
Res. sequence      (841)  PESAGLSLYFPSLERLELKRLCKLKGWRRGEGLGDDHQPFNESSS>Ret.Ins<NTQVQLQLCIPQLKSLRIERCPLLT
Sen. sequence1     (841)  PESAGLSLYFPSLELLELKRLHKLKGWRRREGLGDDHQPFNESSS>Ret.Ins<--------------------------
Sen. sequence10    (841)  PESAGLSLYFPSLELLELKRLHKLKGWRRREGLGDDHQPFNESSS>Ret.Ins<--------------------------

911                                                                           980
Res. sequence      (911)  FMPLCPKTEKLHLVVFNERLRIVHAKRDENFYAPLHSSSSDPENPRNTIPIPMFREVYINNVAWLNSLPM 981                                                                          1050
Res. sequence      (981)  EAFRCLTHMTIKNDEVESLGEVGEVFRSCSSSLRSLNITGCSNLRSVSGGLEHLTALEMLEIYDTHKLSL 1051                                                                          1120
Res. sequence     (1051)  SEDPEGVVPWKSLHHSLSYLQLMNLPQLVNLPDSMQFLAALRTLSIVHCTKLQSVPDWMPRLTSLRKLMV 1121                         1163
Res. sequence     (1121)  SFCSAHLERRCQNPTGVDWPNIQHIPSIDVTSSLPKFLVLPYE
```

FIG 5

| Recombinant Line | Population | Target Region Physical Position (bp) / Marker | | | | | | | | | | | | | | | | Plants | | | | ELISA values | | | | Splicing | | | | Assertion |
|---|---|---|---|---|---|---|---|---|---|---|---|---|---|---|---|---|---|---|---|---|---|---|---|---|---|---|---|---|---|---|
| | | s3e5299xxx / 9354172 | s3e5299s02 / 9354296 | s3m0090s01 / 9404779 | s3mp00gs01 / 9405037 | s3e5800s01 / 9411766 | s3e5829s02 / 9414333 | s3e5875s01 / 9416551 | s3e5875s01 / 9417771 | s3e5856s01 / 9418031 | s3e5830s01 / 9418784 | s3e5853s01 / 9419705 | s3e5833s03 / 9430745 | s3e5873s01 / 9431596 | s3e5874s01 / 9432522 | s3e5834s01 / 9433793 | s3e5835s01 / 9434936 | sxi8090s01 / 9435438 | s3e5332xxx / 9442775 | Number of descendants | Number RR | Number Rs | Number ss | Average all | Average RR | Average Rs | Average ss | Population splices | DIFF_RR-ss | T-Test | Wilcoxon | Position of the gene |
| ZR11007_03075 | 111T_3515 | H | H | H | H | H | B | b | b | b | b | b | b | b | b | b | b | b | B | 152 | 45 | 61 | 36 | 0.161 | 0.282 | 0.107 | 0.117 | no | 0.165 | 0.96 | 0.54 | right of s3e5800s01 |
| ZR08093_02718 | 111PB3553 | H | H | H | H | H | A | A | A | A | A | A | A | A | A | A | A | A | A | 177 | 40 | 94 | 43 | 2.686 | 2.608 | 2.736 | 2.652 | no | -0.04 | 0.39 | 0.43 | right of s3e5800s01 |
| ZR08093_04549 | 111PB3857 | H | H | H | H | H | A | A | A | A | A | A | A | H | H | H | H | H | H | 50 | 14 | 30 | 7 | 2.00 | 1.94 | 2.09 | 1.89 | no | 0.05 | 0.54 | 0.51 | left of s3e5873s01 |
| ZR08093_05621 | 111PB3645 | H | H | A | A | A | A | A | A | A | A | A | A | B | B | B | B | B | B | 73 | 27 | 28 | 17 | 2.334 | 1.777 | 2.397 | 3.091 | yes | -1.313 | 0.00 | 0.00 | left of s3e5874s01 |
| ZR08093_03547 | 111PB3579 | H | H | H | H | H | A | A | A | A | A | A | A | · | A | A | A | A | A | 177 | 41 | 97 | 39 | 1.703 | 1.121 | 1.683 | 2.474 | yes | -1.35 | 0.00 | 0.00 | left of s3e5834s01 |
| ZR08093_02513 | 111PB3546 | H | H | H | H | H | A | A | A | A | A | A | A | A | · | B | B | B | B | 174 | 45 | 87 | 42 | 1.848 | 1.146 | 1.845 | 2.630 | yes | -1.48 | 0.00 | 0.00 | left of s3e5834s01 |
| ZR08093_03702 | 111PB3585 | H | H | H | H | H | A | A | A | A | A | A | A | A | A | A | B | B | B | 79 | 13 | 45 | 20 | 1.776 | 0.699 | 1.455 | 3.183 | yes | -2.484 | 0.00 | 0.00 | left of s3e5834s01 |
| ZR08093_01718 | 111PB3523 | H | H | H | H | H | B | H | H | H | H | H | H | H | H | H | H | B | B | 169 | 50 | 76 | 43 | 1.736 | 1.157 | 1.786 | 2.466 | yes | -1.31 | 0.00 | 0.00 | left of s3e5834s01 |

1051

RHIZOMANIA-RESISTANT GENE

This application is the U.S. National Phase of International Patent Application Ser. No. PCT/DE2014/000310, filed on Jun. 6, 2014, which claims the benefit of German Patent Application Ser. No. 102013010026.7, filed on Jun. 17, 2013. The contents of the foregoing applications are hereby incorporated in their entireties.

SEQUENCE LISTING

The instant application contains a Sequence Listing which has been submitted electronically in ASCII format and is hereby incorporated by reference in its entirety. Said ASCII copy, created on Aug. 12, 2016, is named 245761_000015_SL.txt and is 327,226 bytes in size.

FIELD OF THE INVENTION

The present invention relates to a nucleic acid molecule that encodes a polypeptide that is able to convey a resistance to a pathogen, in particular to "Beet Necrotic Yellow Vein Virus" in a plant, in particular of the *Beta* genus in which the polypeptide is expressed. The invention also relates to a polypeptide that is able to convey a resistance to a pathogen in a plant, in particular a resistance to BNYVV in a plant of the *Beta* genus, in which the polypeptide is expressed and that is encoded by the nucleic acid molecule according to the invention. The invention also relates to a transgenic plant, plant cell, plant organ, plant tissue, plant part or a seed of a plant that comprise the nucleic acid molecule or parts thereof, and also to methods for producing a transgenic plant or plant cell of this type. The invention also includes methods for detecting the resistance-conveying nucleic acid molecule and methods for the selection of plants or plant cells that have the resistance-conveying nucleic acid molecule.

BACKGROUND OF THE INVENTION

Rhizomania is the most serious sugar beet disease worldwide in terms of profitability and may cause earnings losses of 50% and more. The disease, which is also referred to as "root madness", is caused by the "Beet Necrotic Yellow Vein Virus" (BNYVV) and is transmitted by the soil-borne protozoa *Polymyxa betae*. A BNYVV infection manifests itself in an increased proliferation of the thin roots and secondary roots and in the formation of a greatly reduced root body with reduced sugar content. Infected plants demonstrate a reduced water uptake and are thus more sensitive to dry stress. When the infection spreads to the entire plant, this results in a yellowing of the leaf veins, in necrotic lesions, and yellow flecks on the leaves. Since a curative combatting of the disease is not possible, as is the case with other viral diseases, damage can be prevented only via the cultivation of resistant species. Three major genes against rhizomania are currently being examined in essence: RZ-1 (also referred to as "Holly"), RZ-2 and RZ-3. In addition, further rhizomania resistance genes are described in the literature, although these are of lesser significance. Here, the resistance gene RZ-1 is already incorporated into most breeding lines (seed parent and/or pollinator parent components). It has been found, however, that the resistance conveyed by RZ-1 is insufficient in heavily infected regions or in regions having diverse BNYVV pathotypes (for example Sohi & Maleki, 2004). For this reason, it was already proposed some time ago to combine RZ-1 with, for example, RZ-2 or RZ-3. RZ-2 and RZ-3 originate from *Beta vulgaris* subsp. *maritime* sources (WB42, WB41) and genetically map in the same region on chromosome 3 of the sugar beet genome, whereas RZ-1 likewise maps on chromosome 3, but south of RZ-2 and RZ-3. Scholten et al. (1999) determined a distance of 20-25 cM between the RZ major genes RZ-1 and RZ-2. Gidner et al. (2005) found a shorter distance of 5 cM between RZ-1 and RZ-2 and did not conclude that RZ-2 and RZ-3 map on the same locus. Schmidlin et al. (2008) identified differently induced genes by means of expression analysis in infected beets, however these did not correspond to RZ-2 or RZ-3. In the study by Larson et al. (2008), some BNYVV-induced proteins were detected in the sugar beet using the MALDI-TOF-MS method, however the proteins which were encoded by RZ-1, RZ-2 or RZ-3 could not be identified by the scientists. In addition, the sequence region, in particular around this resistance gene, is repetitive, which makes the development of diagnostic markers particularly difficult. Until now, neither high-resolution marker maps nor verified candidate genes were publicly available for the specified rhizomania resistance genes. In addition, the functional background of these resistance genes, i.e. the genetic structure, previously was not fully known. For sustainable cultivation against rhizomania intended to counteract the risk of resistance-breaking BNYVV isolates, it is necessary to constantly identify new resistance genes and to integrate these into the gene pool of the crop plants such as sugar beet.

SUMMARY OF THE INVENTION

The present invention has been developed on the basis of the above-described prior art, wherein one object of the present invention is to provide a nucleic acid molecule and/or a polypeptide that is able to convey resistance against rhizomania in a plant. A further object is to provide a transgenic rhizomania-resistant plant and a method for the production thereof. A further object of the present invention is to provide methods for using and developing molecular markers that enable an efficient cultivation against rhizomania and the development of new resistant plant lines.

Embodiments of the present invention that achieve the objects are based on the genetic fine-mapping, identification, isolation and characterisation of a gene originating from the donor *Beta vulgaris* subsp. *maritima* and encoding for a polypeptide or protein able to convey resistance against a pathogen in a plant in which the polypeptide is expressed.

Some of the terms used in this application will first be explained in greater detail hereinafter:

The term "approximately" in conjunction with the specification of a length of a nucleotide sequence means a deviation by ±200 base pairs, preferably by ±100 base pairs and particularly preferably by ±50 base pairs.

A "plant of the *Beta* genus" belongs to the foxtail family (Amaranthaceae). These plants include plants of the species *Beta macrocarpa*, *Beta vulgaris*, *Beta lomatogona*, *Beta macrorhiza*, *Beta corolliflora*, *Beta trigyna* and *Beta nana*. A plant of the species *Beta vulgaris* is in particular a plant of the sub-species *Beta vulgaris* subsp. *maritima* (Seemangold) or *Beta vulgaris* subsp. *vulgaris*. These include, for example, *Beta vulgaris* subsp. *vulgaris* var. *altissima* (sugar beet in the narrower sense), *Beta vulgaris* ssp. *vulgaris* var. *vulgaris* (Mangold), *Beta vulgaris* ssp. *vulgaris* var. *conditiva* (beetroot), *Beta vulgaris* ssp. *vulgaris* var. *crassa/alba* (fodder beet). The term "hybridise" or "hybridisation" is understood to mean a process in which a single-strand nucleic acid molecule attaches to a nucleic acid strand that is complementary to the greatest possible extent, i.e. forms base pairs.

Standard methods for hybridisation are described for example in Sambrook et al. 2001. This is preferably understood to mean that at least 60%, more preferably at least 65%, 70%, 75%, 80% or 85%, particularly preferably 90%, 91%, 92%, 93%, 94%, 95%, 96%, 97%, 98% or 99% of the bases of the nucleic acid molecule form a base pairing with the nucleic acid strand that is complementary to the greatest possible extent. The possibility of such an annealing is dependent on the stringency of the hybridisation conditions. The term "stringency" relates to the hybridisation conditions. High stringency is then given when a base pairing is hindered, and low stringency is given when a base pairing is facilitated. The stringency of the hybridisation conditions is dependent for example on the salt concentration or ion strength and temperature. Generally, the stringency can be increased by an increase of the temperature and/or a lowering of the salt content. "Stringent hybridisation conditions" are understood to mean conditions under which a hybridisation takes place predominantly only between homologous nucleic acid molecules. The term "hybridisation conditions" here does not relate only to the conditions prevailing during the actual attachment of the nucleic acids, but also to the conditions prevailing during the subsequent washing steps. Stringent hybridisation conditions are, for example, conditions under which predominantly only those nucleic acid molecules hybridise that have at least 70%, preferably at least 75%, at least 80%, at least 85% or at least 90%, particularly preferably at least 95%, at least 96%, at least 97%, at least 98% or at least 99% sequence identity. Stringent hybridisation conditions for example are: hybridisation in 4×SSC at 65° C. and subsequent multiple washing in 0.1×SSC at 65° C. for a total of approximately 1 hour. The term "stringent hybridisation conditions" used here may also mean: hybridisation at 68° C. in 0.25 M sodium phosphate, pH 7.2, 7% SDS, 1 mM EDTA and 1% BSA for 16 hours and subsequent washing twice with 2×SSC and 0.1% SDS at 68° C. Hybridisation preferably takes place under stringent conditions.

An "isolated nucleic acid molecule" is understood to mean a nucleic acid molecule dissolved out from its natural or original environment. The term also includes a synthetically produced nucleic acid molecule. An "isolated polypeptide" is understood to mean a polypeptide dissolved out from its natural or original environment. The term also includes a synthetically produced polypeptide.

A "molecular marker" is a nucleic acid that is polymorphous in a plant population. Such a marker is thus able to detect and differentiate different allelic states (alleles). Known analytical methods used for this purpose are RFLP, AFLP, SNP, SSR or KASP, for example. The term "molecular marker" relates to nucleotide sequences that are complementary or at least complementary to the greatest possible extent or homologous to genomic sequences, for example nucleic acids used as probes or primers. Markers that describe polymorphisms can be detected with use of well-established methods. These include, for example, PCR-based sequence-specific amplification, a detection of 'restriction fragment length polymorphisms' (RFLPs), a detection of polynucleotide polymorphisms by means of 'allele specific hybridisation' (ASH), a detection of amplified variable sequences of the plant genome, a detection of a 'self-sustained sequence replication', a detection of 'simple sequence repeats' (SSRs), or a detection of 'single nucleotide polymorphisms' (SNPs), or a detection of 'amplified fragment length polymorphisms' (AFLPs). Furthermore, the methods for detection of 'expressed sequence tags' (ESTs) and SSR markers derived from EST sequences and 'randomly amplified polymorphic DNA' (RAPD) are also known.

A "promoter" means a non-translated regulatory DNA sequence, typically upstream of an encoding region, which contains the binding point for the RNA polymerase and initiates the transcription of the DNA.

A "pathogen" means an organism that in interaction with a plant leads to disease symptoms at one or more organs of the plant. These pathogens include, for example, animal, fungal, bacterial or viral organisms or oomycetes.

A "pathogen infection" is understood to mean the earliest moment at which a pathogen interacts with a plant host tissue. By way of example in the case of the viral pathogen BNYVV, this is transmitted by the protozoa *Polymyxa betae*. *Polymyxa* forms spores that can survive in the ground for many decades. The virus also lives in these spores. When these dormant spores germinate to form mobile zoospores, the virus can pass via these spores into cells of the plant host tissue and can interact there with the host (Esser 2000).

Plant "organs" for example mean leaves, shoot axis, stem, roots, hypocotyl, vegetative buds, meristems, embryos, anthers, ovules or fruits. Plant "parts" mean a combination of a number of organs, for example a flower or a seed, or part of an organ, for example a cross section through the stem. Plant "tissues" are, for example, callus tissue, storage tissue, meristematic tissue, leaf tissue, stem tissue, root tissue, plant tumour tissue or reproductive tissue. Plant "cells" for example are to be understood to mean isolated cells with a cell wall or aggregates thereof or protoplasts.

The term "resistance" is to be understood broadly and covers the scope of protection from a delay to complete inhibition of the development of the disease. An example of a pathogen of significance is Beet Necrotic Yellow Vein Virus (BNYVV). A resistant plant cell of the invention or resistant plant of the invention preferably achieves a resistance to BNYVV. A resistance to a pathogen is to be equated with a resistance to the disease caused by this pathogen, for example a resistance to BNYVV and a resistance to rhizomania.

"Transgenic plant" relates here to a plant in the genome of which at least one nucleic acid has been integrated. This may be a heterologous nucleic acid here. The nucleic acid is preferably integrated in a stable manner, which means that the integrated nucleic acid is retained in the plant in a stable manner, can be expressed, and also can be passed on in a stable manner to the descendant.

The present invention discloses a nucleic acid molecule which includes a polypeptide that is able to convey a resistance to a pathogen in a plant in which the polypeptide is expressed. The nucleic acid molecule comprises a nucleotide sequence selected from a) a nucleotide sequence that encodes a polypeptide having an amino acid sequence according to SEQ ID NO: 2 or SEQ ID NO: 3, b) a nucleotide sequence comprising the encoding sequence of the DNA sequence according to SEQ ID NO: 1, c) a nucleotide sequence that hybridises with the complementary sequence of nucleotide sequence according to a) or b) under stringent conditions, d) a nucleotide sequence that encodes a polypeptide which is derived by substitution, deletion and/or addition of one or more amino acids of the amino acid sequence encoded by the nucleotide sequence according to a) or b) from a polypeptide encoded by the nucleotide sequence according to a) or b), e) a nucleotide sequence that encodes a polypeptide which has an amino acid sequence at least 60% identical to an amino acid sequence encoded by the nucleotide sequence according to a) or b), or f) a nucleotide sequence that encodes at least one nucleotide-binding domain (NBS or NB-ARC) corresponding to amino acid positions 168-227 of SEQ ID NO: 2 or corresponding to amino acid positions 182-241 of SEQ ID NO: 3, at least one leucine-rich domain (LRR) corresponding to amino acid positions 591-613 of SEQ ID NO: 2 or corresponding to amino acid positions 605-627 of SEQ ID NO: 3 and/or at least one internal repetitive domain (IR) corresponding to amino acid positions 1013-1072 of SEQ ID NO: 2 or corresponding to amino acid positions 1027-1086 of SEQ ID NO: 3.

The nucleic acid molecule may be an isolated nucleic acid molecule. It is preferably DNA, and particularly preferably cDNA (encoding DNA). The polypeptide encoded by the nucleic acid molecule according to the invention preferably conveys a resistance to the viral pathogen "Beet Necrotic Yellow Vein Virus" (BNYVV), which causes the plant disease rhizomania. Furthermore, the polypeptide encoded by the nucleic acid molecule according to the invention, in particular a plant of the *Beta* genus, conveys a resistance to a pathogen. The plant is preferably a plant of the *Beta vulgaris* species, particularly preferably a plant of the subspecies *Beta vulgaris* subsp. *maritime* or *Beta vulgaris* subsp. *vulgaris*; these include, for example, the crop types constituted by sugar beet, beetroot, fodder beet, leaf beet, Swiss chard.

In one embodiment of the nucleic acid molecule according to the invention the nucleic acid molecule comprises the nucleotide sequence according to a). The amino acid sequence according to SEQ ID NO: 2 of the encoded polypeptide and/or according to SEQ ID NO: 3 of the encoded polypeptide constitutes the resistance protein of the RZ-3 gene. Here, this is a resistance gene protein of the NBS-LRR type, which is characterised by a certain structural motif. The general structure of such resistance proteins in plants has already been well examined (Martin et al. 2003). However, the principle of the structural formation in particular of what is known as the LRR domain, which is a potential identification domain for mostly unknown pathogenic effectors, is not foreseeable. Consequently, the identification of a BNYVV-resistance-conveying gene or protein on the basis purely of the known structural motifs is not possible. The identification of the RZ-3 resistance gene took place over the course of a map-based cloning process, which required intensive genetic mapping and fine-mapping of the target region in which the RZ-3 resistance gene was initially suspected. The development work will be described in greater detail further below.

The identified resistance protein belongs to the NBS-LRR type and has a nucleotide-binding domain (NBS, also known as NB-ARC) (nucleotide-binding adaptor shared by APAF-1, R proteins, and CED-4)) corresponding to amino acid positions 168-227 of SEQ ID NO: 2 or corresponding to amino acid positions 182-241 of SEQ ID NO: 3, a leucine-rich domain (LRR) corresponding to amino acid positions 591-613 of SEQ ID NO: 2 or corresponding to amino acid positions 605-627 of SEQ ID NO: 3 and/or at least one internal repetitive domain (IR; internal repeat domain) corresponding to amino acid positions 1013-1072 of SEQ ID NO: 2 or corresponding to amino acid positions 1027-1086 of SEQ ID NO: 3. The NBS domain is encoded by nucleotides 2019-2882 of SEQ ID NO: 1, the LRR domain is encoded by nucleotides 3288-3356 of SEQ ID NO: 1 and the IR domain is encoded by nucleotides 4554-4871 of SEQ ID NO: 1. The NB-ARC domain is a central nucleotide-binding domain. It is likely a functional ATPase domain, which expectedly regulates the activity of a resistance protein. The NB-ARC domain consists of three sub-domains: NB, ARC1 and ARC2. Characteristic motifs of the NB-ARC domains are APAF-1 (apoptotic protease-activating factor-1), which is supposedly responsible for the hypersensitive reaction, hhGRExE, Walker-A- or P-loop, Walker-B, GxP, RNBS-A to D and MHD (Ooijen et al., 2008). Some of the specified motifs can already be identified. In a further embodiment of the nucleic acid molecule according to the invention the nucleic acid molecule comprises the nucleotide sequence according to b). The nucleotide sequence comprises the encoding sequences of the DNA sequence according to SEQ ID NO: 1, which encode for the amino acid sequences according to SEQ ID NO: 2 and 3.

In a further embodiment of the nucleic acid molecule the nucleic acid molecule comprises the nucleotide sequence according to d). This nucleotide sequence encodes a polypeptide constituting a derivative of the polypeptide encoded by the nucleotide sequence according to a) or b). A derivative of the polypeptide constitutes a derived amino acid sequence, which has at least one substitution, deletion or addition of one or more amino acids, wherein the functionality of the encoded polypeptide/protein is maintained. In the case of the substitution of an amino acid by another amino acid having the same or equivalent or similar chemical-physical properties, reference is made to a "conservative exchange" or "semi-conservative exchange". Examples of physical-chemical properties of an amino acid are, for example, the hydrophobicity or the charge. It is known to a person skilled in the art which amino acid substitution constitutes a conservative or semi-conservative exchange. The common general knowledge in the art additionally allows a person skilled in the art to recognise, identify and detect the amino acid deletions and additions harmful to the functionality of the resistance protein RZ-3 and also those positions at which these are possible. It is known to a person skilled in the art that in the case of the present NBS-LRR protein for modifications of the amino acid sequence (substitutions, deletions or additions of one or more amino acids), the functionality of the above-defined preserved domains must be retained in particular and therefore only limited modifications of the above-mentioned type are possible in these domains. The nucleotide sequence of this embodiments then encodes for a derivative or for a derived amino acid sequence when the nucleotide sequence is homologous or identical at least to an extent of 60%, 65%, 70%, 75%, 80%, 85%, 90%, 92%, 94%, 96%, 97%, 98%, 99% to the nucleotide sequence according to a) or b). Such nucleotide sequences, which encode for a derivative or for a derived amino acid sequence, preferably can be produced either directly or indirectly (for example via amplification or replication steps) form a starting nucleotide sequence corresponding over the entire length or at least partially to SEQ ID NO: 1 or another sequence disclosed here.

In a further embodiment of the nucleic acid molecule according to the invention the nucleic acid molecule comprises the nucleotide sequence according to e). This nucleotide sequence codes a polypeptide which has an amino acid sequence identical to an extent of at least 60%, 65%, 70%, 75%, 80%, 85%, 90%, 92%, 94%, 96%, 97%, 98%, 99% to an amino acid sequence encoded by the nucleotide sequence according to a) or b).

In a further embodiment of the nucleic acid molecule according to the invention, the nucleic acid molecule comprises the nucleotide sequence according to f). The nucleotide sequence here encodes at least one nucleotide-binding domain (NBS) corresponding to amino acid positions 168-227 of SEQ ID NO: 2 or corresponding to amino acid positions 182-241 of SEQ ID NO: 3, at least one leucine-rich domain (LRR) corresponding to amino acid positions 591-613 of SEQ ID NO: 2 or corresponding to amino acid positions 605-627 of SEQ ID NO: 3 and/or at least one internal repetitive domain (IR) corresponding to amino acid positions 1013-1072 of SEQ ID NO: 2 or corresponding to amino acid positions 1027-1086 of SEQ ID NO: 3. The nucleotide sequence preferably encodes for a polypeptide comprising at least one nucleotide-binding domain (NBS) corresponding to amino acid positions 168-227 of SEQ ID NO: 2 or corresponding to amino acid positions 182-241 of SEQ ID NO: 3, at least one leucine-rich domain (LRR) corresponding to amino acid positions 591-613 of SEQ ID NO: 2 or corresponding to amino acid positions 605-627 of SEQ ID NO: 3 and at least one internal repetitive domain (IR) corresponding to amino acid positions 1013-1072 of SEQ ID NO: 2 or corresponding to amino acid positions 1027-1086 of SEQ ID NO: 3. These domains are particularly preferably arranged in the polypeptide sequentially from the N- to the C-terminus in the order NBS-LRR-IR, wherein in each case one or more further amino acids may be present between domains.

The present invention also relates to a polypeptide that is able to convey a resistance to a pathogen in a plant in which the polypeptide is expressed and that is encoded by the nucleic acid molecule according to the invention, wherein the pathogen is preferably BNYVV and/or the plant is preferably a plant of the *Beta* genus, in particular a plant of the species *Beta vulgaris*. The polypeptide particularly preferably has an amino acid sequence according to SEQ ID NO: 2 or according to SEQ ID NO: 3. The polypeptide may be an isolated polypeptide.

In a further aspect the present invention relates to a vector comprising the nucleic acid molecule according to the invention. The vector may be a plasmid, a cosmid, a phage or expression vector, a transformation vector, shuttle vector or cloning vector, it may be double-stranded or single-stranded, linear or circular, or may transform a prokaryotic or eukaryotic host either by integration into the genome thereof or extrachromosomally. The nucleic acid molecule according to the invention is preferably operatively linked in an expression vector to one or more regulatory sequences allowing the transcription and optionally the expression in a prokaryotic or eukaryotic host cell. By way of example, the nucleic acid molecule is under the control of a suitable promoter or a terminator. Suitable promoters may be promoters that are constitutively induced (Ex.: 35S promoter from the "Cauliflower mosaic virus" (Odell et al. 1985), and promoters that are pathogen-inducible are particularly suitable (Ex.: PR1 promoter from Petersilie (Rushton et al., 1996). Particularly suitable pathogen-inducible promoters are synthetic or chimeric promoters, which are not present in nature, are formed from a number of elements, and contain a minimal promoter and also have, upstream of the minimal promoter, at least one cis-regulatory element serving as binding point for special transcription factors. Chimeric promoters are designed in accordance with the desired requirements and are induced or repressed by different factors. Examples of such promoters can be found in WO 00/29592, WO 2007/147395 and WO 2013/091612. A suitable terminator is for example the nos terminator (Depicker et al., 1982).

In addition to the above-described vectors, the present invention also provides a method comprising the introduction of a described vector into a host cell. The vector may be introduced for example by conjugation, mobilisation, biolistic transformation, *agrobacterium*-conveyed transformation, transfection, transduction, vacuum infiltration or electroporation. A person skilled in the art is familiar with such methods and also methods for the preparation of described vectors (Sambrook et al. 2001).

In a further aspect the present invention relates to a host cell comprising the nucleic acid molecule according to the invention or the vector of the present invention. A host cell in the sense of the invention may be a prokaryotic (for example bacterial) or eukaryotic cell (for example a plant cell or a yeast cell). The host cell is preferably an *agrobacterium* such as *Agrobacterium tumefaciens* or *Agrobacterium rhizogenes* or a plant cell comprising the nucleic acid molecule according to the invention or the vector of the present invention. Numerous methods such as conjugation or electroporation are known to a person skilled in the art, by means of which said person can introduce the nucleic acid molecule according to the invention or the vector of the present invention into an *agrobacterium*, and methods such as diverse transformation methods (biolistic transformation, *agrobacterium*-mediated transformation) are also known to such a person, by means of which said person can introduce the nucleic acid molecule according to the invention or the vector of the present invention into a plant cell (Sambrook et al. 2001).

In a further aspect the present invention relates to a transgenic plant cell comprising the nucleic acid molecule according to the invention as transgene or comprising the vector of the present invention. A transgenic plant cell of this type by way of example is a plant cell that is transformed, preferably in a stable manner, with the nucleic acid molecule according to the invention or with the vector of the present invention. In a preferred embodiment of the transgenic plant cell, the nucleic acid molecule is operatively linked to one or more regulatory sequences allowing the transcription and optionally the expression in the plant cell. The overall construct from the nucleic acid molecule according to the invention and the regulatory sequence(s) then constitutes the transgene. Such regulatory sequences by way of example are a promoter or a terminator. Numerous functional promoters and terminators applicable in plants are known to a person skilled in the art. A transgenic plant cell of the present invention, in particular a cell of a plant of the *Beta* genus, preferably demonstrates a higher resistance to a pathogen, in particular BNYVV, than a corresponding non-transformed plant cell (the plant cell without the transgene). The level of the resistance by way of example to BNYVV can be defined qualitatively in plants of the *Beta* genus by determination of rating scores (rating score schemes for plants of the *Beta* genus are known from the prior art, for example for sugar beet Mechelke (1997)). A higher resistance presents itself in an improvement of the resistance by at least one rating score, by at least two rating scores, or by at least three or more rating scores. The present invention furthermore also relates to a method for producing a transgenic plant cell of the present invention comprising a step of introducing the nucleic acid molecule according to the invention or the vector of the present invention into a plant cell. By way of example, the introduction may take place by transformation, preferably by stable transformation. These suitable introduction techniques, such as biolistic transformation, *agrobacterium*-mediated transformation or electroporation, are known to a person skilled in the art (Sambrook et al. 2001).

In a further aspect the present invention relates to a transgenic plant or a part thereof, comprising a transgenic plant cell as described above. Here, a part may be a cell, a tissue, an organ or a combination of a number of cells, tissues or organs. A combination of a number of organs is, for example, a flower or a seed. In a particular embodiment the invention relates to a seed from the transgenic plant, wherein the seed comprises the nucleic acid molecule according to the invention as transgene. A transgenic plant of the present invention, in particular a plant of the *Beta* genus, preferably has a higher resistance to a pathogen, in particular BNYVV, than a corresponding non-transformed plant (plant without the transgene). The level of resistance for example to BNVYY may be defined qualitatively in plants of the *Beta* genus by determination of rating scores (rating score schemes for plants of the *Beta* genus are known from the prior art, for example for sugar beet Mechelke (1997)). A higher resistance presents itself in an improvement of the resistance by at least one rating score, by at least two rating scores, or by at least three or more rating scores. The invention also relates to a method for producing a transgenic plant comprising a step of introducing the nucleic acid molecule according to the invention or the vector of the present invention into a plant cell and optionally a step of selecting a transgenic plant cell. Furthermore, such a method for producing a transgenic plant is characterised by a subsequent step that includes regenerating the transgenic plant from the transgenic plant cell produced in the first step. Methods for regeneration are known from the prior art to a person skilled in the art.

In a further aspect the present invention also relates to a method for conveying or increasing a resistance to a pathogen, in particular BNYVV, in a plant, preferably a plant of the *Beta* genus, comprising a step of transforming a plant cell with the nucleic acid molecule according to the invention or the vector of the present invention. This method preferably leads to an improvement of the resistance by at least one rating score, particularly preferably to an improvement of the resistance by at least two, three or more rating scores. Rating score schemes for plants of the *beta* genus are known from the prior art, for example for sugar beet Mechelke (1997).

In a further aspect the present invention relates to a regulatory sequence of a promoter which controls the expression of a gene comprising the nucleic acid molecule according to the invention, characterised in that the regulatory sequence is able to convey or to modulate the expression of a heterologous DNA sequence as a result of a pathogen infection, and the regulatory sequence comprises a nucleic acid molecule having a nucleotide sequence according to SEQ ID NO: 1 of nucleotides 1-1403. The heterologous DNA sequence is preferably a nucleotide sequence which encodes for a component of the plant pathogen defence (Ex.: resistance gene (R-gene) or gene encoding for enzymes involved in the signal transfer, such as kinases or phosphatases and for G-protein) or which encodes for a pathogenic effector (what are known as avirulence genes (avr)). Furthermore, the present invention includes a recombinant DNA molecule which comprises the above-described regulatory sequence. The recombinant DNA molecule is preferably operatively linked to a heterologous DNA sequence.

In a further aspect the present invention relates to a host cell transformed with the above-described regulatory sequence or with the specified recombinant DNA molecule and to a transgenic plant, plant tissue or plant cell comprising the regulatory sequence or the recombinant DNA molecule as transgene. The invention also provides a method for producing a transgenic plant cell comprising a step of introducing the regulatory sequence of the invention or the recombinant DNA molecule and optionally a step of selecting a transgenic plant cell. The invention also provides a method for producing a transgenic plant comprising a step of introducing the regulatory sequence of the invention or the recombinant DNA molecule into a plant cell and optionally a step of selecting a transgenic plant cell. Such a method for producing a transgenic plant is furthermore characterised by a subsequent step that includes regenerating the transgenic plant from the transgenic plant cell produced in the first step.

As already mentioned above, the RZ-3 resistance gene was identified during the course of a map-based cloning process. The process performed for example comprised the following steps: genetic fine-mapping, physical mapping, construction of a very large splicing population of more than 8000 F2 splicing descendants, recombinant screening, marker development in the target region, comparative BAC sequencing in resistant and sensitive genotypes, bioinformatic analyses, protein predictions and comparison of the proteins. Such laborious development work is extremely costly and it is unknown whether it is actually successful in identifying the gene. Following integration of the RZ-3 locus from *Beta vulgaris* subsp. *maritima* in a plant of the *Beta* genus, specifically in sugar beet (*Beta vulgaris* subsp. *vulgaris* var. *altissima*), markers having a good diagnostic value were developed for the tracking of the RZ-3 genome segment in the fine-mapping, which proved to be particularly difficult, since the target region is repetitive over wide areas. Surprisingly, however, it was possible to successfully develop a few diagnostic markers that in part also functioned only with a certain marker technique, such as pyrosequences, i.e. as PSQ markers, or that were zero allelic.

In spite of these technical difficulties, it was possible to delimit the RZ-3 locus to a genomic region of 0.67 cM by comprehensive analysis with use of these markers. This corresponds to a physical length of approximately 340,000 bp. In spite of intensive developments, it was only possible to a limited extent to further reduce the *Beta vulgaris* subsp. *maritima* introgression around the gene in a marker-assisted manner and to identify candidate genes for the RZ-3 gene. A further shortening of the introgression, however, is desirable in any case from a cultivation viewpoint in order to eliminate any potential "linkage drag", closely coupled to the RZ-3 gene. Lastly, a target region could be limited to just approximately 0.07 cM in a number of steps by means of fine-mapping and with incorporation of sequence information from physical maps. This, however, was only possible since a total of 8004 were examined, including informative recombinant BC2S1 or BC2S2 plants, which were analysed intensively with 90-180 descendants in each case. This was necessary since the resistance expression was not always clear for unknown reasons. These descendants were genotyped into individual plants and phenotyped in parallel. By means of statistical methods (t-test, power analysis), the phenotypes of the informative recombinants (homozygote resistant—RR; heterozygote resistant—Rs; homozygote susceptible—ss) were detected and therefore conclusions could be made regarding the genotype of the informative recombinants.

In the relatively small target region of approximately 38,000 bp, ten genes could be annotated in the susceptible genotype. Overlapping clones from a resistant BAC library were identified for this target region with the aid of new markers, which describe specifically the target region, and were then sequenced. Due to the repetitiveness of the target region, the sequence of the susceptible genotype presented numerous small portions with unknown sequence content. For this reason, the assembling of the RR and ss sequences was particularly demanding. However, it was possible to identify a putative resistance gene. This contained, in practically all ss genotypes, a retrotransposon having a length of approximately 8000 bp between the LRR domain and the IR domain, which could not be detected in RR genotypes. An amino acid sequence predicted from the putative resistance gene sequence showed that the gene presumably encodes for an NB-ARC-LRR protein. It can be assumed that this insertion of the retrotransposon destroys the function of the gene in susceptible ss genotypes, since it separates the internal repeat domain (IR) from the two other domains (NB-ARC and LRR). The comparison of the NBS-LRR gene in ss genotypes with that in RR genotypes also showed diagnostic polymorphisms, which can be inferred from FIGS. 1, 2 and 3. Based on these polymorphisms in the NBS-LRR gene, markers were developed and tested in a wide set of approximately 100 ss and RR genotypes. The marker patterns, but also the comparative sequencing in the target gene, confirmed that the insertion is practically always coupled with the sensitivity. However, a few ss genotypes were found that did not have the retrotransposon insertion and were still susceptible. These ss genotypes, however, could be clearly distinguished from the RR genotypes by means of markers that describe the diagnostic polymorphisms according to FIGS. 1, 2 and/or 3.

In the analysed population, recombinants were identified in the target region that show a recombination between the NBS-LRR gene and the downstream, adjacent annotated putative gene, which could code for an ankyrin repeat protein. In the case of two plants, the recombinations can be found between the NBS-LRR gene and the upstream, adjacent annotated putative gene, which could code for a DUF565 protein (protein with unknown function). By means of the resistance analysis of the descendants of all these recombinant plants (single-gene removal upstream and downstream of the NBS-LRR gene), it was possible to demonstrate quite clearly that the gene between the ankyrin repeat gene and the DUF565 gene, specifically the NBS-LLR gene characterised here, is responsible for the resistance in the RR genotype. FIG. 4 shows the physical map of the RZ-3 target region with the developed markers. The genotype data of eight dense recombinant lines, and also the statistical analysis of the descendants thereof are illustrated in FIG. 5.

In a further aspect the present invention relates to a method for identifying a nucleic acid molecule that encodes a protein able to convey a resistance to the pathogen BNYVV in a plant of the *Beta* genus in which the protein is expressed. The method comprises the detection of the absence of an insertion in the encoding nucleotide sequence of the nucleic acid molecule. The method preferably comprises the detection of the absence of an insertion, in particular of a retrotransposon, in the coding nucleotide sequence of the nucleic acid molecule. The retrotransposon may be, for example, approximately 500 bp, approximately 1000 bp, approximately 2000 bp, approximately 4000 bp, approximately 8000 bp, or more than approximately 8000 bp long. In a particular embodiment of the method the nucleic acid molecule is the nucleic acid molecule according to the invention as described above and encodes the resistance-conveying RZ-3 gene or a functional homologue of RZ-3. The plant of the *Beta* genus is preferably *Beta vulgaris* subsp. *maritima* or *Beta vulgaris* subsp. *vulgaris* var. *altissima* (sugar beet). A person skilled in the art knows which methods are suitable for detecting the absence of the insertion. By way of example, a person skilled in the art in the knowledge of the nucleic acid molecule according to the invention disclosed here can develop molecular markers which detect the presence or the absence of an insertion in the above-described region in the NBS-LLR gene (see the examples for an exemplary approach). The present invention includes such markers and use thereof for the detection of the presence or absence of the insertion for the selection of resistant, in particular BNYVV-resistant, plants, in particular *Beta vulgaris* subsp. *maritima* or *Beta vulgaris* subsp. *vulgaris* var. *altissima* (sugar beet). Such markers preferably describe loci at the insertion points of the retrotransposon. Insertion points mean transition points between genomic DNA and retrotransposon on 5' and/or 3' side of the insertion. Transition points are to be defined broadly, and marker loci may be arranged on the DNA at a distance of less than 1000 nucleotides, preferably less than 800 or 600 nucleotides, particularly preferably less than 400, 200, 150, 100, 50, 40, 30, 20 or 10 nucleotides upstream or downstream of an insertion point. Alternatively or in addition to the step of detecting the presence or absence of an insertion in the encoding nucleotide sequence of the nucleic acid molecule, the method may also comprise the detection of at least one polymorphism according to FIGS. 1, 2 and/or 3, preferably of at least 2 or 3 polymorphisms according to FIGS. 1, 2 and/or 3, particularly preferably of at least four, five or more polymorphisms according to FIGS. 1, 2 and/or 3 in the encoding nucleotide sequence of the nucleic acid molecule according to the invention with use of molecular markers which identify the polymorphisms, in particular diagnostic polymorphisms. This detection preferably takes place with use of at least one molecular marker per polymorphism, in particular per diagnostic polymorphism. A person skilled in the art knows which marker techniques are to be applied for the detection of a corresponding polymorphism, and how to construct molecular markers for this (literature). Furthermore, the present invention includes molecular markers which describe or detect a polymorphism according to FIGS. 1, 2 and/or 3, and also the use of a molecular marker for the detection of a polymorphism according to FIGS. 1, 2 and/or 3. Furthermore, the above identification methods also constitute methods for the selection of a plant which has a resistance to BNYVV. The selection method comprises a terminating step of selecting a resistant plant.

Furthermore, it was also possible to demonstrate that in the examined RR genotypes there were a genomic DNA sequence portion according to SEQ ID NO: 4 upstream of and adjacent to RZ-3 (SEQ ID NO: 1) as well as a genomic DNA sequence portion according to SEQ ID NO: 5 downstream of and adjacent to RZ-3 (SEQ ID NO: 1), which are closely coupled to the RZ-3 gene and are therefore extremely suitable as DNA regions for the development of diagnostic markers for RZ-3. The present invention therefore relates to a method for selecting a plant which has a resistance to BNYVV. The selection method comprises the use of a molecular marker on a DNA sequence according to SEQ ID NO: 4 and/or on a DNA sequence according to SEQ ID NO: 5 and a terminating step of selecting a resistant plant. A person skilled in the art knows how to develop and use markers on the basis of the disclosed sequence information. By means of the present invention, the further following advantages can be obtained for the cultivation and development of new resistant plant lines of the *Beta* genus:

Sequence information and also the identified polymorphisms, which allow a distinction between resistant RR and susceptible ss alleles of the disclosed gene, make the marker development possible directly in the gene, which constitutes a significant facilitation for the plant grower in particular in view of the development of optimised elite lines without "linkage drag". In addition, the knowledge of the sequential structure can be used for the identification of further resistance genes, in particular against rhizomania, which for example are partially homologous.

The use disclosed here of the resistant gene allele in cis- or trans-genetic approaches opens up the possibility of developing new resistant species of the *Beta* genus, which on account of the dose effect have a higher resistance or in which, as a result of the stacking of the disclosed gene with other resistance genes, a resistance interruption can be avoided and the resistance expression can be optimised. Modifications of the gene by means of tilling or selective engineering are also conceivable for the development of new resistance alleles.

The present invention also relates to the use of the identified resistant RZ3 gene allele in a genetic or molecular stack with other genetic elements, which can convey agronomically advantageous properties, in a plant. As a result, the economical value of crop plants can be significantly increased, for example by increasing the yield performance or by developing new cultivation areas for a plant that were not accessible previously for the cultivation of these plants, inter alia due to biotic factors such as heavy pathogen pressure or abiotic factors such as dryness. An agronomically advantageous property is, for example, a tolerance to a herbicide, such as glyphosate, glufosinate or ALS inhibitors. Numerous further herbicides and the applicability thereof are known from the prior art to a person skilled in the art. Said person can refer to the prior art in order to gain knowledge as to which genetic elements are to be used and in which way in order to implement a corresponding tolerance in plants. A further example of an agronomically advantageous property is an additional pathogen resistance, wherein pathogens may be, for example, insects, viruses, nematodes, bacteria or fungi. By way of example, by combining different pathogen resistances/tolerances, a broad pathogen defence for a plant can be achieved, since genetic elements may have effects that supplement one another. Numerous resistance genes for example are known for this purpose to a person skilled in the art as genetic elements. A further example of an agronomically advantageous property is a tolerance of cool temperatures or frost. Plants that have this property could be sewn earlier in the year or for example or could remain longer in the field, even during periods of frost, which for example may lead to increased revenue. Here too, a person skilled in the art could refer to the prior art in order to find suitable genetic elements. Further examples for agronomically advantageous properties are water utilisation efficiency, nitrogen utilisation efficiency and harvest. Genetic elements that can be used to convey such properties could be found in the prior art. Numerous modifications for pathogen defence are also known to a person skilled in the art. Besides the frequently described families of the R genes, the Avr/R approach, the Avr gene complementation (WO 2013/127379), the auto-activation of an R-gene (WO 2006/128444), the HIGS (host induced gene silencing) approach (for example WO2013/050024) or the VIGS (virus induced gene silencing) approach could be used advantageously. In particular, the auto-activation of an R gene could be of significance for the present invention. A nucleic acid that encodes for an auto-activated resistance protein for producing a resistance to pathogens in plants is to be created for this purpose. This nucleic acid then has only a limited part of an NBS-LRR resistance gene, such as the RZ3 gene, which extends downstream from the 5'-end of the encoding region of the NBS-LRR resistance gene to the start of the NBS domain of the NBS-LRR resistance gene, wherein the NBS-LRR resistance gene is not a TIR-NBS-LRR resistance gene.

Furthermore, the invention also includes the use of the resistant RZ3 gene allele, identified with an above-described method, for combination with one of the above modifications or with an above-described genetic element which can convey one or more or agronomically advantageous properties in a plant.

Variants and embodiments of the present invention will be described in an exemplary manner with reference to the accompanying figures and sequences:

Sequences:

SEQ ID NO: 1 genomic DNA sequence of the resistance gene RZ-3. The sequence comprises nucleotide 1 to 1403 of the regulatory region of the promoter SEQ ID NO: 2 predicted protein sequence of the resistance protein RZ-3_1

SEQ ID NO: 3 predicted protein sequence of the resistance protein RZ-3_2

SEQ ID NO: 4 adjacent chromosomal region upstream of RZ-3 (SEQ ID NO: 1)

SEQ ID NO: 5 adjacent chromosomal region downstream of RZ-3 (SEQ ID NO: 1)

SEQ ID NO: 6 consensus sequence of the genomic sequence of the RZ-3 gene in ss genotypes SEQ ID NO: 7 target sequence in the RZ3 gene of the RNAi construct in the vector pZFN-C48-RNAi.

FIGURES

Figure 1E:
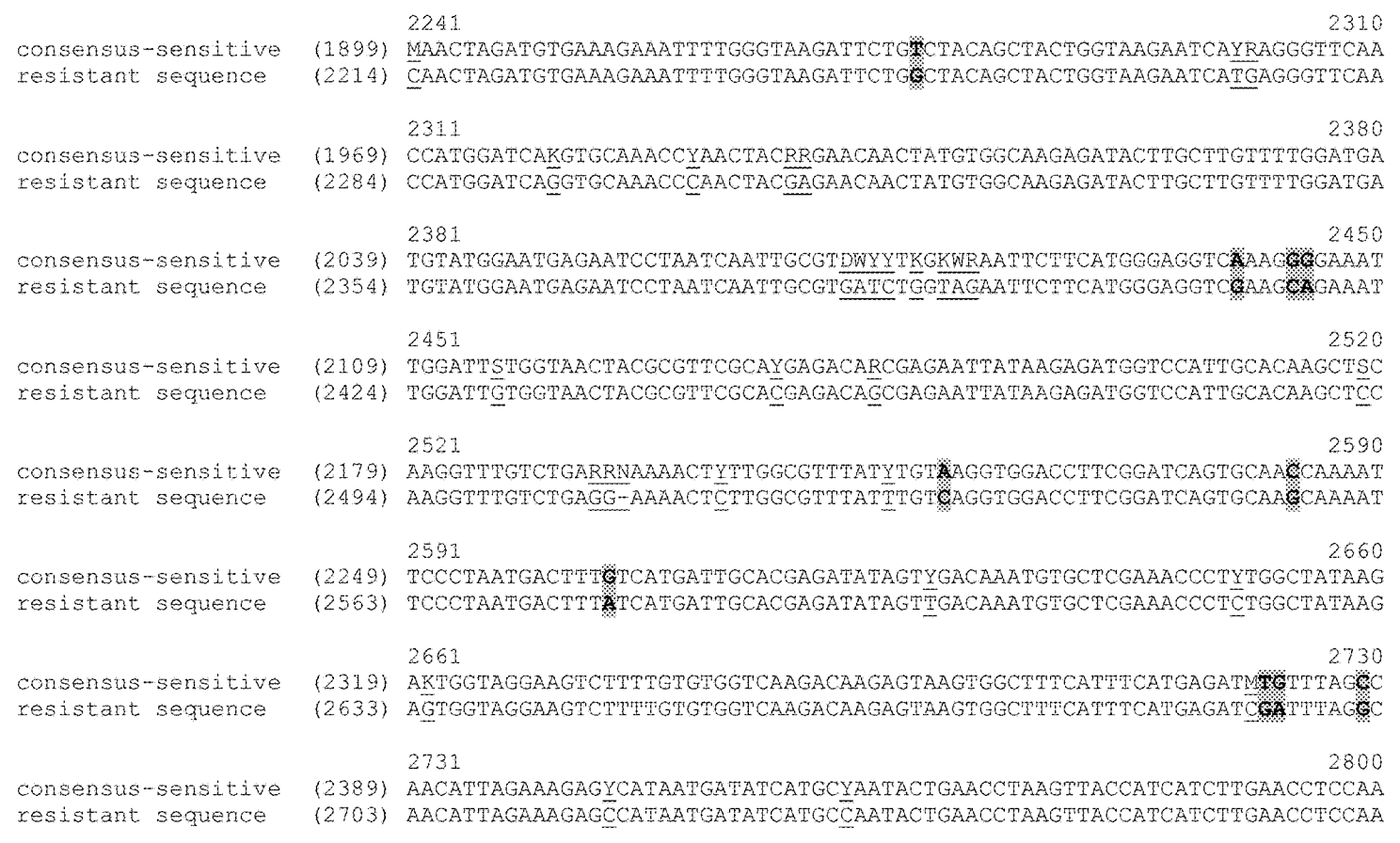
Figure 1G:
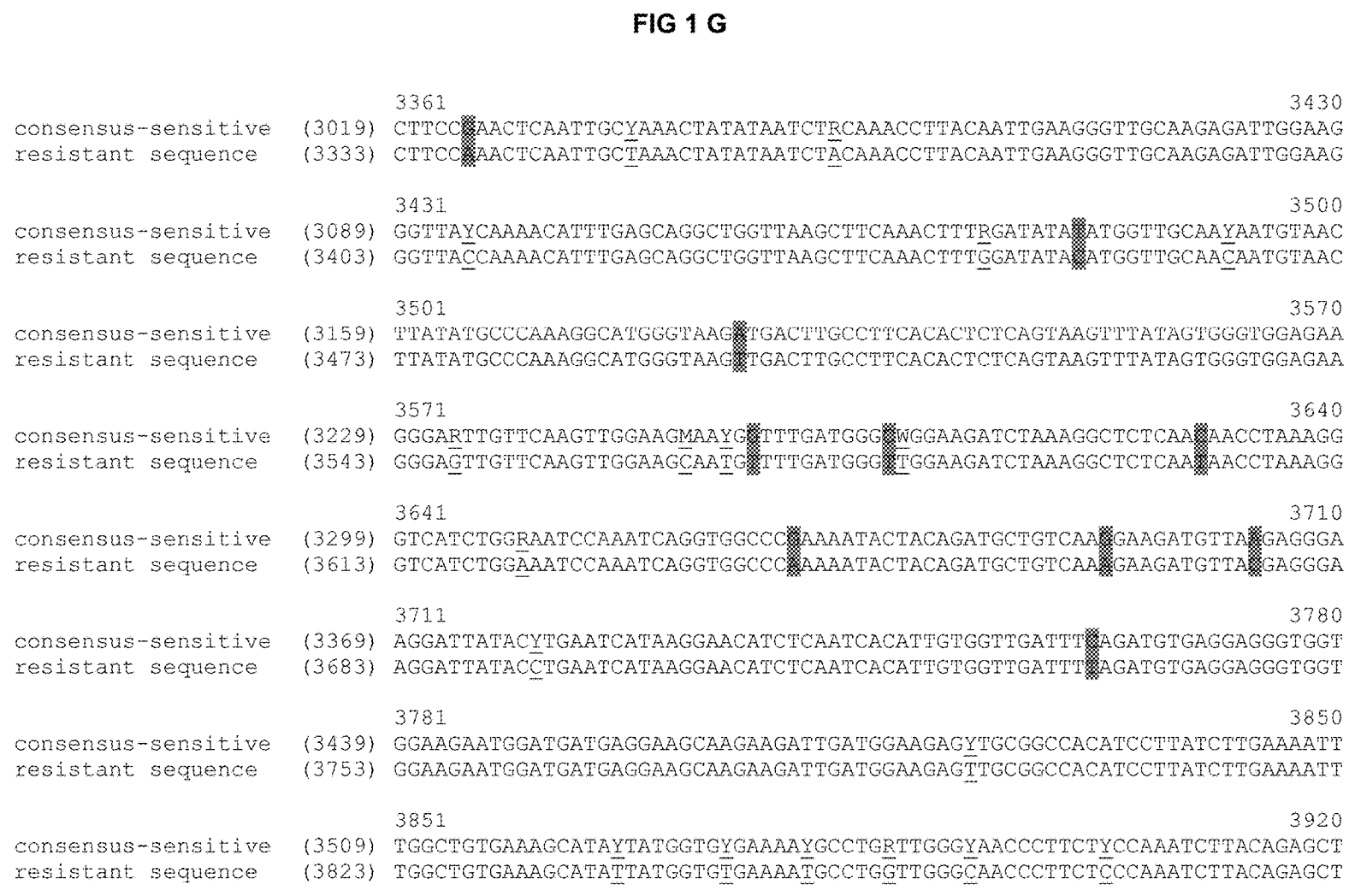

FIG. 1 A-I: nucleotide sequence comparison between consensus sequence of the genomic sequence of the RZ-3 gene in ss genotypes (SEQ ID NO: 52) and the RZ-3 gene of the RR genotypes (SEQ ID NO: 1). Diagnostic polymorphisms are shown in grey and bold. Polymorphisms that are not diagnostic are underlined. The potential transcription start points in the gene are characterized by arrows. They lead to two polypeptide variants RZ-3_1 and RZ-3_2. The position of the retrotransposon is characterized by a black triangle at the top.

FIG. 2 A-L: amino acid sequence comparison of the predicted polypeptide from the RR genotype (RZ-3$_{13}$ 1; SEQ ID NO: 2) and polypeptides from 22 different ss genotypes (SEQ ID NOS 8-29, respectively, in order of appearance). Diagnostic polymorphisms are shown in grey and bold. Polymorphisms that are not diagnostic are underlined.

FIG. 3 A-L: amino acid sequence comparison of the predicted polypeptide from the RR genotypes (RZ-3_2; SEQ ID NO: 3) and polypeptides from 22 different ss genotypes (SEQ ID NOS 30-51, respectively, in order of appearance). Diagnostic polymorphisms are shown in grey and bold. Polymorphisms that are not diagnostic are underlined.

FIG. 4: physical map of the RZ-3 target region. Five genes were annotated in the illustrated target region of the sensitive reference genotype: ("2" (DUF565), "3" (hypothetical protein), "4" (NBS-LRR candidate gene), "5" (retrotransposon) and "6" (ankyrin repeat)). The NBS-LRR candidate gene ("4") contains a retrotransposon ("5") in the sensitive reference sequence. This retrotransposon is missing completely in the resistance sequence, and therefore only four genes can still be annotated in the resistant genotype "2", "3", "4" and "6"). The positions of the densest recombinations (recombinants: 111T_3515/ZR11007_03075 with numeral "7" and 111PB3645/ZR08093_05621 with numeral "8") are illustrated at the top. With the aid thereof, the shorter target region "1" could be limited. The markers developed for this purpose from the recombinant analysis are reproduced as black dashes in the lower part of the figure. A gene segment ("9") selected in part from the domain region "10" as target sequence was used for the validation of the gene in the RNAi approach for the gene splicing of the resistant RZ-3 gene allele.

FIG. 5: marker analysis of the densest recombinants in the RZ-3 target region (small letters in bold-framed region are marker data generated in silico). The eight recombinant lines were phenotyped and genotyped with a total of 1051 descendants. The descendants were divided into 3 groups (RR resistant homozygote, Rs heterozygote, ss sensitive homozygote) on the basis of the marker data in the NBS-LRR candidate gene or the splicing flanking region in the event that the NBS-LRR candidate gene is homozygote RR or ss. In addition, the corresponding ELISA values are reproduced. A splicing or non-splicing of the descendants was examined by t-test and Wilcoxon statistic. The candidate gene could be quite clearly delimited between the markers s3e5800s01 and s3e5873s01 on the basis of the results.

Figure 6:
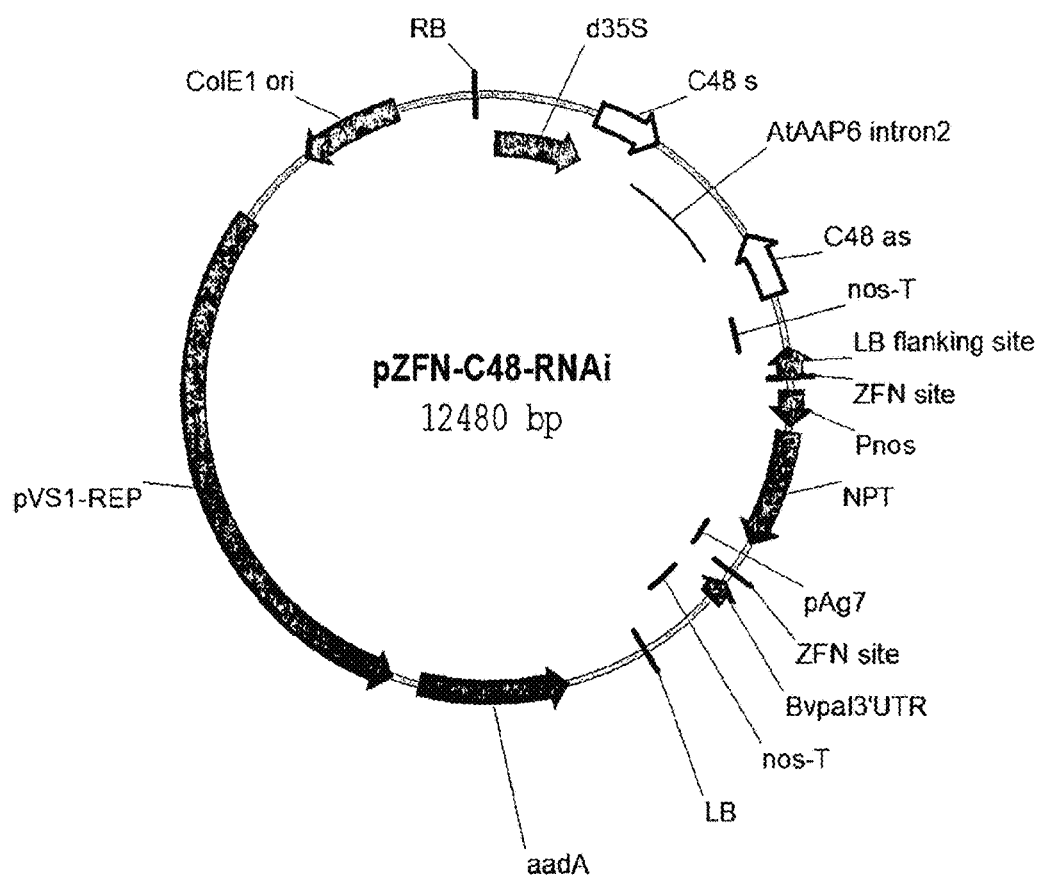

FIG. 6: transformation vector pZFN-C48-RNAi: d35S-promoter; C48 s: C48 sequence sense orientation; AtAAP6 intron2: *Arabidopsis thaliana* amino acid permease 6 intron; C48 as: C48 sequence antisense orientation; Nos-T: nos terminator; LB flanking site: Left border flanking site; ZFN site: Zinc-finger nuclease recognition site (complementary); Pnos: Nos promoter; NPT: coding sequence; neomycin phosphotransferase (npt) gene; pAG7: pAG7 terminator; Bvpal3'UTR: 3' untranslated region of the *Beta vulgaris* Pal gene; LB: Left border; aadA: coding sequence; aminoglycoside-3"-adenylyltransferases (AAD); pVS1-REP: pVS1 replication origin; ColE1 ori: ColE1 replication origin; RB: right border.

EXAMPLES

Mapping and Fine-Mapping of the RZ-3 Gene/Genetic Physical Map

The RZ-3 resistance (also referred to as C48 resistance or C48) was mapped in a number of steps by means of mapping and fine-mapping on chromosome 3 between 57.1 and 57.8 cM (internal reference map), i.e. at a genetic distance between two flanking markers of 0.0714 cM in the genetic map. A total of 8004 plants for the crossing S504 (sensitive genotype)×T74 (resistant genotype) were examined for the mapping. Parallel to the C48 QTL mapping new informative markers were developed in a target-oriented manner following each mapping step and were used for the limitation of the C48 target region.

The fine-mapping coordinates were additionally confirmed with the analysis of the descendants of the informative recombinants. Informative recombinant BC2S1 or BC2S2 plants were analysed intensively for this purpose, in each case with 90-180 descendants. These descendants were genotyped and phenotyped in parallel on an individual plant basis. By means of static methods (t-test, power analysis), the phenotypes of the informative recombinants (homozygote resistant RR/heterozygote Rs/homozygote susceptible ss) were detected and conclusions could therefore be made regarding the genotype of the informative recombinants. Provided the homozygote classes of the descendants (RR versus ss) differed in terms of resistance, the gene was present in the heterozygote region (Rs) of the parent plant; otherwise it was present in the homozygote region (RR or ss) of the parent plant.

A physical map was generated for a rhizomania-sensitive genotype by projecting markers and genetic positions thereof onto the chromosome sequences. With the limitation of the C48 QTL region, new informative markers were developed on the basis of the reference sequence and additional comparative sequencings in resistant genotypes (next generation sequencing and Sanger sequencing).

The region identified by the fine-mapping comprises a sequence length of 37996 base pairs (positions of flanking SNP markers) in the sensitive reference sequence. The collinearity between the genetic and the physical map in the target region is consistent (sequence of 12 markers in the target region).

Identification and Sequencing of Resistant BAC Clones

A BAC library has been developed for a selected RZ-3 (C48) resistant genotype. This BAC bank was sampled with the used markers in the C48 QTL region. A number of BAC clones were found for the above-identified target region. Of these, three BAC clones of different length, which detected the target region completely, were selected for sequencing. The BAC clones were sequenced and a "de novo" assembling was carried out on the basis of the resultant sequence-reads. Among the resultant resistant sequence contigs, the greatest sequence had a length of 110909 bp (34537 reads) and comprised the target region completely.

Comparison of Sensitive and Resistant Sequences—Sequence Evaluation

The collinearity of the two ss and RR sequences was compared with use of different software tools. For both resistant and sensitive sequences, a gene annotation was performed using Maker and Pedant softwares. The gene annotation on both sequences demonstrated the same sequence of putative genes. Surprisingly, however, a significant difference in one of these genes could be determined, specifically in the gene of the present invention (RZ-3). A retrotransposon could be annotated in the sensitive genotype in this identified NBS-LRR gene. The insertion of the retrotransposon passed in the gene between the two domains of the LRR domain and the IR domain. The resistant genotype does not have this insertion and is reproduced in SEQ ID NO: 1. Furthermore, the predicted polypeptide sequences were then compared and evaluated (illustrated partially in FIGS. 2 and 3).

Comparative Sequencing of the NB-ARC-LRR Candidate Gene

The NB-ARC-LRR candidate gene was sequenced comparatively in two steps. The retrotransposon insertion point was verified in a genotype set having a total of 92 resistant and sensitive genotypes. This analysis showed that none of the resistant genotypes had a retrotransposon insertion. Of these sensitive genotypes, the insertion could be detected in more than 90% of cases. The detection of the insertion therefore appears to be coupled with the susceptible genotype. Due to the found inconsistencies (approximately 10% of the remaining susceptible genotypes without insertion) however, the sequencing was extended with promoter region in the second step for the entire gene before the insertion point (SEQ ID NO: 1). On the whole, 31 selected resistant and susceptible genotypes inclusive of the inconsistent genotypes were sequenced and compared. As a result, all resistant genotypes, which are to be attributed to seven different resistance sources, were 100% identical to the compared approximately 4100 base pairs. In addition, completely diagnostic polymorphisms were found in the nucleotide sequence, of which a number lead to amino acid substitutions in the protein sequence (see FIGS. 1, 2 and 3). Some of these substitutions, particularly in the domain regions, could cause the functional loss of the identified resistance protein in the ss genotypes. Furthermore, three INDELs coupled fully with the resistance (Linkage disequilibrium=1) were also found in the promoter region (FIG. 1). These INDELs are also to be considered as potential candidates for the functional loss.

Verification of the Gene by Means of Dense Recombinants

In the analysed population with 8004 plants, 16 recombinants were identified in the target region (fine-mapped region with 37996 base pairs). Of these 16 genotypes, 9 plants contained the recombination between the NB-ARC-LRR protein and the adjacent ankyrin repeat protein on the right-hand side. In the case of two plants the recombinations are between the NB-ARC-LRR protein and the adjacent DUF565 proteins to the left (protein with unknown function). By means of the analysis of the progeny of all of these recombinant plants (a gene distance to the left and right) it was possible to demonstrate quite clearly that the gene lies between DUF565 and the ankyrin repeat protein, specifically that only the NB-ARC protein is responsible for the resistance.

Exemplary Detection of the Absence of the Transposon Insertion

For the detection of the retrotransposon insertion, 3 special dominant primer combinations were developed. The first and the second primer combinations are able to detect the insertion, since in each case one primer of the two primer pairs sits in the retrotransposon (left or right flank of the retrotransposon) and the second primer binds directly before or after the retrotransposon. A third primer pair detects the absence of the retrotransposon in that the primers find a binding point before and after the retrotransposon. A PCR product may then be produced under standard conditions only when the retrotransposon is missing, otherwise, with the retrotransposon, the PCT product would be too large and no amplicon would be created in this case.

Verification of the Gene by Means of RNAi Approach

Besides the above-described verification of the gene by means of dense recombinants, a further detection of the resistance effect of the gene was also performed by means of RNA interference. For this purpose, a resistant standard sugar beet genotype was transformed with a DNA construct, which encodes a double-stranded hairpin RNA. This dsRNA was able to effect a gene silencing post-transcriptionally, which would reduce or switch off the effect of the resistant RZ-3 gene allele, whereby the previously resistant sugar beet genotype should become sensitive to rhizomania.

In order to provide a suitable DNA construct, a defined target sequence region of the resistant RZ3 gene allele of 434 base pair length (SEQ ID NO: 7; FIG. 4) was selected, amplified by PCR and cloned both in sense and antisense direction in the vector pZFN, which is suitable for the synthesis of hairpin structures (FIG. 6). This vector has a doubled CaMV 35S promoter, a multiple cloning point, an intron from the gene AtAAP6, which encodes in *Arabidopsis thaliana* for an amino acid permease, a further multiple cloning point, and a nos terminator. The transformation of the sugar beet with the provided vector was performed in accordance with the protocol of Lindsey & Gallois (1990) with use of the antibiotic kanamycin as selection marker. Following a number of selection steps, successful transformation was examined on transgenic shoots via PCR by means of detection of the presence of the nptII gene, the AAP6 intron and the two t-DNA border sequences (LB/RB) and the absence of vir. Positive shoots were clonally multiplied in vitro to 30 shoots in each case, rooted, and transferred into earth in the greenhouse. Approximately 2 weeks later the transgenic sugar beet plants were planted in earth contaminated by rhizomania, in which they were cultivated for 8 to 10 weeks. As control, non-transformed plants of the same resistant genetic standard transformation background were used under the same conditions. In order to detect the spread of rhizomania, the roots of the sugar beet plants were harvested and quantified by means of ELISA test of the BNYVV attack, wherein a low ELISA value indicated a resistance and a high value indicated a sensitivity (Mechelke 1997, Clark & Adams 1977). The ELISA value of the transformed sugar beet, with a mean value of 3.55, was significantly higher than the ELISA value of the control, which was also resistant, with a mean value of 1.27 and was compatible to the sensitive standard D108_ss (Table 1). The results of the ELISA test accordingly showed that a previously resistant plant was sensitive to BNYVV as a result of the specific gene silencing of the resistant RZ-3 allele in the transformation background. Consequently, the gene of the present invention could be clearly verified as the resistance gene RZ3.

TABLE 1

Results of the ELISA-test following statistical analyses (D108_ss = sensitive standard; 6921_RR = resistant transformation background; 6921_RNAi = resistant transformation background with dsRNA directed against RZ3 gene).

|  | D108_ss | 6921_RR | 6921_RNAi |
| --- | --- | --- | --- |
| n | 6 | 25 | 64 |
| mean value | 3.98 | 1.27 | 3.55 |
| standard error | 0.02 | 0.25 | 0.11 |
| standard deviation | 0.06 | 1.24 | 0.87 |

T-test (significance level): $p < 0.0001$

REFERENCES

Clark, M. F.; Adams, A. N. (1977): Characteristics of the microplate method of enzyme-linked immunosorbent assay for the detection of plant viruses. J. Gen. Virol. 34, 475-483

Depicker A, Stachel S, Dhaese P, Zambryski P, Goodman HM (1982) Nopaline synthase: transcript mapping and DNA sequence. J Mol Appl Genet. 1(6): 561-73.

Esser K (2000) Kryptogamen 1: Cyanobakterien Algen Pilze Flechten Praktikum and Lehrbuch. Springer Publishing House, Berlin, Heidelberg, 3$^{rd}$ edition. 2000.

Gidner S, Lennefors B L, Nilsson N O, Bensefelt J, Johansson E, Gyllenspetz U, Kraft T (2005) QTL mapping of BNYVV resistance from the WB41 source in sugar beet. Genome 48: 279-285.

Larson R L, Wintermantel W M, Hill A, Fortis L, Nunez A (2008) Proteome changes in sugar beet in response to Beet necrotic yellow vein virus. Physiological and Mol. Pl. Pathol. 72: 62-72.

Lindsey, K., and P. Gallois (1990) "Transformation of sugar beet (*Beta vulgaris*) by *Agrobacterium tumefaciens*." Journal of experimental botany 41.5: 529-536.

Martin G B, Bogdanove A J; Sessa G (2003) Understanding the functions of plant disease resistance proteins. Annual Review of Plant Biology 54: 23-61.

Mechelke W (1997) Probleme in der Rizomaniaresistenzzüchtung, Vorträge für Pflanzenzüchtung, Resistenzzüchtung bei Zuckerrüben, Gesellschaft für Pflanzenzüchtung e.V., 113-123.

Odell J T, Nagy F, Chua N-H (1985) Identification of DNA sequences required for activity of the cauliflower mosaic virus 35S promoter. Nature 313, 810-812

Rushton P J, Torres J T, Parniske M, Wernert P, Hahlbrock K, and Somssich I E (1996) Interaction of elicitor-induced DNA-binding proteins with elicitor response elements in the promoters of parsley PR1 genes. EMBO J. 15(20): 5690-5700.

Sambrook J, Russell D W (2001) Molecular Cloning. A laboratory manual, Cold Spring Harbor Laboratory Press, 3. Aufl. 2001.

Schmidlin LEDEB, Weyens G, Lefebvre M, Gilmer D (2008) Identification of differentially expressed root genes upon rhizomania disease. Mol. Plant Pathol. 9(6): 741-51.

Scholten O E, Bock TSMD, Klein-Lankhorst R M, Lange W (1999) Inheritance of resistance to Beet necrotic yellow vein virus in *Beta vulgaris* conferred by a second gene for resistance. Theor. Appl. Genet. 99:740-746.

Sohi H H, Maleki M (2004) Evidence for presence of types A and B of beet necrotic yellow vein virus (BNYVV) in Iran. Virus Genes 29(3): 353-8.

Van Ooijen G, Mayr G, Kasiem M M A, Albrecht M, Cornelissen B J C, Takken F L W (2008) Structure—function analysis of the NB-ARC domain of plant disease resistance proteins. Journal of Experimental Botany, 59(6): 1383-1397

WO/2000/29592 (Max-Planck-Gesellschaft zur Förderung der Wissenschaften e.V.). Chimeric promoters capable of mediating gene expression in plants upon pathogen infection and uses thereof.

WO/2006/128444 (KWS SAAT AG). AUTOACTIVATED RESISTANCE PROTEIN.

WO/2007/147395 (KWS SAAT AG). Pathogen induzierbarer synthetischer Promotor.

WO/2013/127379 (KWS SAAT AG). PATHOGEN-RESISTANT TRANSGENIC PLANT.

WO/2013/050024 (KWS SAAT AG). TRANSGENIC PLANT OF THE SPECIES *BETA VULGARIS* HAVING ENHANCED RESISTANCE TO *CERCOSPORA*.

WO/2013/091612 (KWS SAAT AG). NOVEL PLANT-DERIVED CIS-REGULATORY ELEMENTS FOR THE DEVELOPMENT OF PATHOGEN-RESPONSIVE CHIMERIC PROMOTORS.

The invention claimed is:

1. An isolated nucleic acid molecule comprising a nucleotide sequence selected from the group consisting of:
   a) a nucleotide sequence that encodes a polypeptide comprising the amino acid sequence SEQ ID NO: 2 or SEQ ID NO: 3,
   b) a nucleotide sequence comprising the sequence of SEQ ID NO: 1,
   c) a nucleotide sequence that encodes a polypeptide which comprises an amino acid sequence at least 85% identical to SEQ ID NO: 2 or SEQ ID NO: 3, and
   d) a nucleotide sequence that encodes a polypeptide comprising at least one nucleotide-binding domain (NBS) corresponding to amino acid positions 168-227 of SEQ ID NO: 2 or corresponding to amino acid positions 182-241 of SEQ ID NO: 3, at least one leucine-rich domain (LRR) corresponding to amino acid positions 591-613 of SEQ ID NO: 2 or corresponding to amino acid positions 605-627 of SEQ ID NO: 3, and at least one internal repetitive domain (IR) corresponding to amino acid positions 1013-1072 of SEQ ID NO: 2 or corresponding to amino acid positions 1027-1086 of SEQ ID NO: 3;
   wherein the nucleic acid molecule is operably linked to a heterologous promoter.

2. A vector that comprises the isolated nucleic acid molecule according to claim 1.

3. A plant cell that comprises a nucleotide sequence selected from the group consisting of:
   a) a nucleotide sequence that encodes a polypeptide comprising the amino acid sequence SEQ ID NO: 2 or SEQ ID NO: 3,
   b) a nucleotide sequence comprising the sequence of SEQ ID NO: 1,
   c) a nucleotide sequence that encodes a polypeptide which comprises an amino acid sequence at least 85% identical to SEQ ID NO: 2 or SEQ ID NO: 3 or to a polypeptide encoded by SEQ ID NO: 1, and
   d) a nucleotide sequence that encodes a polypeptide comprising at least one nucleotide-binding domain (NBS) corresponding to amino acid positions 168-227 of SEQ ID NO: 2 or corresponding to amino acid positions 182-241 of SEQ ID NO: 3, at least one leucine-rich domain (LRR) corresponding to amino acid positions 591-613 of SEQ ID NO: 2 or corresponding to amino acid positions 605-627 of SEQ ID NO: 3, and at least one internal repetitive domain (IR) corresponding to amino acid positions 1013-1072 of SEQ ID NO: 2 or corresponding to amino acid positions 1027-1086 of SEQ ID NO: 3,
   wherein said nucleotide sequence is heterologous to said cell.

4. A cell that comprises the vector according to claim 2.

5. The cell according to claim 4, wherein the cell is a plant cell.

6. A plant or a part thereof, comprising the plant cell according to claim 3.

7. A plant or a part thereof, comprising the plant cell according to claim 5.

8. A seed of a plant, wherein the seed comprises the nucleic acid molecule according to claim 1 as a transgene or as a cisgene.

9. The cell according to claim 3, wherein the cell comprises the nucleotide sequence as an introgressed region.

10. A method for producing a transgenic plant cell, wherein the method comprises a step of introducing the nucleic acid molecule according to claim 1 into the plant cell.

11. A method for producing a transgenic plant, wherein the method comprises the following steps
   a) introducing the nucleic acid molecule according to claim 1 into a plant cell, and
   b) regenerating the transgenic plant from the transgenic plant cell from step a).

12. The nucleic acid molecule of claim 1, wherein said nucleic acid molecule does not comprise a regulatory sequence comprising nucleotides 1-1403 of SEQ ID NO: 1.

13. A cell according to claim 4 wherein the cell is a host cell.

14. A seed of a plant, wherein the seed comprises the plant cell according to claim 9.

15. A plant or part thereof, wherein the plant or part thereof comprises the plant cell according to claim 9.

16. A method for identifying and introducing a nucleic acid molecule which encodes a protein that is able to convey a resistance to Beet Necrotic Yellow Vein Virus (BNYVV) into a plant of the *Beta* genus in which the protein is expressed, wherein the method comprises the following steps:
   a) providing genomic DNA of a plant of the *Beta* genus,
   b) detecting in the genomic DNA the absence of an insertion in the nucleotide sequence encoding a polypeptide comprising the amino acid sequence of SEQ ID NO: 2 or 3 by using a molecular marker,
   c) isolating the nucleotide sequence without the insertion, and
   d) introducing the isolated [a]nucleotide sequence without the insertion into a plant or plant part.

17. A method for identifying a nucleic acid molecule which encodes a protein that is able to convey a resistance to Beet Necrotic Yellow Vein Virus (BNYVV) in a plant of the *Beta* genus in which the protein is expressed, wherein the method comprises the following steps:
   a) providing genomic DNA of a plant of the *Beta* genus, and
   b) detecting at least one polymorphism in the nucleotide sequence encoding a polypeptide comprising the amino acid sequence SEQ ID NO: 2 or SEQ ID NO: 3 by detecting the presence or absence of a nucleotide selected from C at position 94 of SEQ ID NO: 1, T at position 95 of SEQ ID NO: 1, T at position 96 of SEQ ID NO: 1, C at position 97 of SEQ ID NO: 1, C at position 98 of SEQ ID NO: 1, T at position 99 of SEQ ID NO: 1, C at position 100 of SEQ ID NO: 1, T at position 101 of SEQ ID NO: 1, G at position 102 of SEQ ID NO: 1, T at position 103 of SEQ ID NO: 1, T at position 104 of SEQ ID NO: 1, C at position 105 of SEQ ID NO: 1, T at position 106 of SEQ ID NO: 1, G at position 107 of SEQ ID NO: 1, T at position 108 of SEQ ID NO: 1, T at position 109 of SEQ ID NO: 1, T at position 110 of SEQ ID NO: 1, T at position 111 of SEQ ID NO: 1, A at position 112 of SEQ ID NO: 1, A at position 113 of SEQ ID NO: 1, A at position 114 of SEQ ID NO: 1, A at position 118 of SEQ ID NO: 1, A at position 119 of SEQ ID NO: 1, C at position 120 of SEQ ID NO: 1, G at position 121 of SEQ ID NO: 1, T at position 123 of SEQ ID NO: 1, C at position 130 of SEQ ID NO: 1, T at position 131 of SEQ ID NO: 1, A at position 133 of SEQ ID NO: 1, G at position 135 of SEQ ID NO: 1, C at position 136 of SEQ ID NO: 1, A at position 137 of SEQ ID NO: 1, A at position 138 of SEQ ID NO: 1, C at position 139 of SEQ ID NO: 1, C at position 140 of SEQ ID NO: 1, C at position 141 of SEQ ID NO: 1, A at position 142 of SEQ ID NO: 1, A at position 143 of SEQ ID NO: 1, C at position 144 of SEQ ID NO: 1, C at position 145 of SEQ ID NO: 1, C at position 146 of SEQ ID NO: 1, A at position 147 of SEQ ID NO: 1, C at position 148 of SEQ ID NO: 1, T at position 149 of SEQ ID NO: 1, T at position 150 of SEQ ID NO: 1, T at position 151 of SEQ ID NO: 1, T at position 152 of SEQ ID NO: 1, T at position 153 of SEQ ID NO: 1, T at position 154 of SEQ ID NO: 1, A at position 155 of SEQ ID NO: 1, A at position 156 of SEQ ID NO: 1, T at position 157 of SEQ ID NO: 1, A at position 158 of SEQ ID NO: 1, A at position 159 of SEQ ID NO: 1, T at position 160 of SEQ ID NO: 1, A at position 161 of SEQ ID NO: 1, A at position 162 of SEQ ID NO: 1, A at position 163 of SEQ ID NO: 1, T at position 164 of SEQ ID NO: 1, A at position 165 of SEQ ID NO: 1, T at position 166 of SEQ ID NO: 1, T at position 167 of SEQ ID NO: 1, T at position 168 of SEQ ID NO: 1, T at position 169 of SEQ ID NO: 1, T at position 170 of SEQ ID NO: 1, A at position 171 of SEQ ID NO: 1, G at position 172 of SEQ ID NO: 1, T at position 173 of SEQ ID NO: 1, T at position 174 of SEQ ID NO: 1, G at position 175 of SEQ ID NO: 1, T at position 176 of SEQ ID NO: 1, G at position 177 of SEQ ID NO: 1, T at position 178 of SEQ ID NO: 1, G at position 179 of SEQ ID NO: 1, C at position 180 of SEQ ID NO: 1, A at position 181 of SEQ ID NO: 1, C at position 182 of SEQ ID NO: 1, G at position 183 of SEQ ID NO: 1, T at position 184 of SEQ ID NO: 1, A at position 185 of SEQ ID NO: 1, A at position 186 of SEQ ID NO: 1, A at position 187 of SEQ ID NO: 1, A at position 188 of SEQ ID NO: 1, A at position 189 of SEQ ID NO: 1, A at position 190 of SEQ ID NO: 1, T at position 191 of SEQ ID NO: 1, A at position 192 of SEQ ID NO: 1, T at position 193 of SEQ ID NO: 1, A at position 194 of SEQ ID NO: 1, A at position 195 of SEQ ID NO: 1, A at position 196 of SEQ ID NO: 1, A at position 197 of SEQ ID NO: 1, A at position 198 of SEQ ID NO: 1, A at position 199 of SEQ ID NO: 1, G at position 200 of SEQ ID NO: 1, T at position 201 of SEQ ID NO: 1, T at position 202 of SEQ ID NO: 1, A at position 203 of SEQ ID NO: 1, T at position 204 of SEQ ID NO: 1, A at position 205 of SEQ ID NO: 1, A at position 206 of SEQ ID NO: 1, T at position 207 of SEQ ID NO: 1, T at position 208 of SEQ ID NO: 1, T at position 209 of SEQ ID NO: 1, G at position 210 of SEQ ID NO: 1, A at position 211 of SEQ ID NO: 1, T at position 212 of SEQ ID NO: 1, A at position 213 of SEQ ID NO: 1, G at position 346 of SEQ ID NO: 1, G at position 400 of SEQ ID NO: 1, T at position 459 of SEQ ID NO: 1, A at position 466 of SEQ ID NO: 1, A at position 468 of SEQ ID NO: 1, T at position 702 of SEQ ID NO: 1, A at position 703 of SEQ ID NO: 1, A at position 704 of SEQ ID NO: 1, G at position 705 of SEQ ID NO: 1, T at position 706 of SEQ ID NO: 1, G at position 707 of SEQ ID NO: 1, C at position 708 of SEQ ID NO: 1, A at position 709 of SEQ ID NO: 1, A at position 710 of SEQ ID NO: 1, C at position 711 of SEQ ID NO: 1, A at position 712 of SEQ ID NO: 1, T at position 713 of SEQ ID NO: 1, T at position 714 of SEQ ID NO: 1, T at position 715 of SEQ ID NO: 1, G at position 716 of SEQ ID NO: 1, C at position 717 of SEQ ID NO: 1, A at position 718 of SEQ ID NO: 1, T at position 719 of SEQ ID NO: 1, A at position 720 of SEQ ID NO: 1, A at position 721 of SEQ ID NO: 1, T at position 722 of SEQ ID NO: 1, G at position 723 of SEQ ID NO: 1, T at position 724 of SEQ ID NO: 1, T at position 725 of SEQ ID NO: 1, T at position 726 of SEQ ID NO: 1, A at position 727 of SEQ ID NO: 1, C at position 728 of SEQ ID NO: 1, T at position 729 of SEQ ID NO: 1, A at position 730 of SEQ ID NO: 1, T at position 731 of SEQ ID NO: 1, T at position 732 of SEQ ID NO: 1, C at position 733 of SEQ ID NO: 1, A at position 734 of SEQ ID NO: 1, C at position 735 of SEQ ID NO: 1, A at position 736 of SEQ ID NO: 1, G at position 737 of SEQ ID NO: 1, T at position 738 of SEQ ID NO: 1, T at position 739 of SEQ ID NO: 1, T at position 740 of SEQ ID NO: 1, A at position 741 of SEQ ID NO: 1, A at position 742 of SEQ ID NO: 1, A at position 743 of SEQ ID NO: 1, C at position 744 of SEQ ID NO: 1, T at position 745 of SEQ ID NO: 1, T at position 746 of SEQ ID NO: 1, T at position 747 of SEQ ID NO: 1, A at position 748 of SEQ ID NO: 1, A at position 749 of SEQ ID NO: 1, T at position 750 of SEQ ID NO: 1, T at position 751 of SEQ ID NO: 1, A at position 752 of SEQ ID NO: 1, G at position 753 of SEQ ID NO: 1, C at position 754 of SEQ ID NO: 1, T at position 755 of SEQ ID NO: 1, T at position 756 of SEQ ID NO: 1, T at position 757 of SEQ ID NO: 1, G at position 758 of SEQ ID NO: 1, G at position 759 of SEQ ID NO: 1, T at position 760 of SEQ ID NO: 1, G at position 761 of SEQ ID NO: 1, A at position 762 of SEQ ID NO: 1, T at position 763 of SEQ ID NO: 1, T at position 764 of SEQ ID NO: 1, T at position 765 of SEQ ID NO: 1, A at position 766 of SEQ ID NO: 1, C at position 767 of SEQ ID NO: 1, A at position 768 of SEQ ID NO: 1, T at position 769 of SEQ ID NO: 1, T at position 770 of SEQ ID NO: 1, T at position 771 of SEQ ID NO: 1, T at position 772 of SEQ ID NO: 1, A at position 773 of SEQ ID NO: 1, G at position 774 of SEQ ID NO: 1, G at position 775 of SEQ ID NO: 1, A at position 776 of SEQ ID NO: 1, A at position 777 of SEQ ID NO: 1, A at position 778 of SEQ ID NO: 1, A at position 779 of SEQ ID NO: 1, A at position 780 of SEQ ID NO: 1, A at position 781 of SEQ ID NO: 1, C at position 782 of SEQ ID NO: 1, A at position 783 of SEQ ID NO: 1, T at position 784 of SEQ ID NO: 1, A at position 785 of SEQ ID NO: 1, G at position 786 of SEQ ID NO: 1, T at position 787 of SEQ ID NO: 1, C at position 788 of SEQ ID NO: 1, A at position 789 of SEQ ID NO: 1, T at position 790 of SEQ ID NO: 1, G at position 791 of SEQ ID NO: 1, T at position 792 of SEQ ID NO: 1, G at position 793 of SEQ ID NO: 1, G at position 794 of SEQ ID NO: 1, G at position 795 of SEQ ID NO: 1, A at position 796 of SEQ ID NO: 1, T at position 797 of SEQ ID NO: 1, C at position 798 of SEQ ID NO: 1, T at position 799 of SEQ ID NO: 1, T at position 800 of SEQ ID NO: 1, G at position 801 of SEQ ID NO: 1, T at position 802 of SEQ ID NO: 1, T at position 803 of SEQ ID NO: 1, A at position 804 of SEQ ID NO: 1, G at position 805 of SEQ ID NO: 1, A at position 806 of SEQ ID NO: 1, T at position 807 of SEQ ID NO: 1, T at position 808 of SEQ ID NO: 1, C at position 809 of SEQ ID NO: 1, G at position 810 of SEQ ID NO: 1, T at position 811 of SEQ ID NO: 1, C at position 812 of SEQ ID NO: 1, T at position 813 of SEQ ID NO: 1, G at position 814 of SEQ ID NO: 1, A at position 815 of SEQ ID NO: 1, A at position 816 of SEQ ID NO: 1, T at position 817 of SEQ ID NO: 1, G at position 818 of SEQ ID NO: 1, T at position 819 of SEQ ID NO: 1, G at position 820 of SEQ ID NO: 1, A at position 821 of SEQ ID NO: 1, A at position 822 of SEQ ID NO: 1, T at position 823 of SEQ ID NO: 1, T at position 824 of SEQ ID NO: 1, T at position 825 of SEQ ID NO: 1, T at position 826 of SEQ ID NO: 1, T at position 827 of SEQ ID NO: 1, T at position 828 of SEQ ID NO: 1, T at position 829 of SEQ ID NO: 1, A at position 830 of SEQ ID NO: 1, A at position 831 of SEQ ID NO: 1, T at position 832 of SEQ ID NO: 1, A at position 833 of SEQ ID NO: 1, T at position 834 of SEQ ID NO: 1, C at position 835 of SEQ ID NO: 1, A at position 836 of SEQ ID NO: 1, A at position 837 of SEQ ID NO: 1, C at position 838 of SEQ ID NO: 1, T at position 839 of SEQ ID NO: 1, T at position 840 of SEQ ID NO: 1, T at position 841 of SEQ ID NO: 1, T at position 842 of SEQ ID NO: 1, T at position 843 of SEQ ID NO: 1, A at position 844 of SEQ ID NO: 1, T at position 845 of SEQ ID NO: 1, A at position 846 of SEQ ID NO: 1, A at position 847 of SEQ ID NO: 1, T at position 848 of SEQ ID NO: 1, T at position 849 of SEQ ID NO: 1, T at position 850 of SEQ ID NO: 1, T at position 851 of SEQ ID NO: 1, T at position 852 of SEQ ID NO: 1, A at position 853 of SEQ ID NO: 1, C at position 854 of SEQ ID NO: 1, T at position 855 of SEQ ID NO: 1, T at position 856 of SEQ ID NO: 1, A at position 857 of SEQ ID NO: 1, T at position 858 of SEQ ID NO: 1, T at position 859 of SEQ ID NO: 1, G at position 860 of SEQ ID NO: 1, A at position 861 of SEQ ID NO: 1, T at position 862 of SEQ ID NO: 1, A at position 863 of SEQ ID NO: 1, A at position 864 of SEQ ID NO: 1, T at position 865 of SEQ ID NO: 1, T at position 866 of SEQ ID NO: 1, G at position 867 of SEQ ID NO: 1, A at position 868 of SEQ ID NO: 1, A at position 869 of SEQ ID NO: 1, G at position 870 of SEQ ID NO: 1, A at position 871 of SEQ ID NO: 1, T at position 872 of SEQ ID NO: 1, A at position 873 of SEQ ID NO: 1, T at position 874 of SEQ ID NO: 1, T at position 875 of SEQ ID NO: 1, A at position 876 of SEQ ID NO: 1, A at position 877 of SEQ ID NO: 1, T at position 878 of SEQ ID NO: 1, G at position 879 of SEQ ID NO: 1, G at position 880 of SEQ ID NO: 1, T at position 881 of SEQ ID NO: 1, T at position 882 of SEQ ID NO: 1, A at position 883 of SEQ ID NO: 1, A at position 884 of SEQ ID NO: 1, A at position 885 of SEQ ID NO: 1, A at position 886 of SEQ ID NO: 1, T at position 887 of SEQ ID NO: 1, A at position 888 of SEQ ID NO: 1, A at position 889 of SEQ ID NO: 1, T at position 890 of SEQ ID NO: 1, G at position 891 of SEQ ID NO: 1, C at position 892 of SEQ ID NO: 1, A at position 893 of SEQ ID NO: 1, T at position 894 of SEQ ID NO: 1, T at position 895 of SEQ ID NO: 1, G at position 896 of SEQ ID NO: 1, G at position 897 of SEQ ID NO: 1, C at position 898 of SEQ ID NO: 1, A at position 899 of SEQ ID NO: 1, A at position 900 of SEQ ID NO: 1, A at position 901 of SEQ ID NO: 1, C at position 902 of SEQ ID NO: 1, G at position 903 of SEQ ID NO: 1, T at position 904 of SEQ ID NO: 1, G at position 905 of SEQ ID NO: 1, A at position 906 of SEQ ID NO: 1, A at position 907 of SEQ ID NO: 1, A at position 908 of SEQ ID NO: 1, A at position 909 of SEQ ID NO: 1, C at position 910 of SEQ ID NO: 1, A at position 911 of SEQ ID NO: 1, A at position 912 of SEQ ID NO: 1, G at position 913 of SEQ ID NO: 1, A at position 914 of SEQ ID NO: 1, A at position 915 of SEQ ID NO: 1, G at position 916 of SEQ ID NO: 1, T at position 917 of SEQ ID NO: 1, G at position 918 of SEQ ID NO: 1, T at position 919 of SEQ ID NO: 1, T at position 920 of SEQ ID NO: 1, G at position 921 of SEQ ID NO: 1, C at position 922 of SEQ ID NO: 1, A at position 923 of SEQ ID NO: 1, C at position 924 of SEQ ID NO: 1, T at position 925 of SEQ ID NO: 1, T at position 926 of SEQ ID NO: 1, A at position 927 of SEQ ID NO: 1, T at position 928 of SEQ ID NO: 1, T at position 929 of SEQ ID NO: 1, T at position 930 of SEQ ID NO: 1, A at position 931 of SEQ ID NO: 1, G at position 932 of SEQ ID NO: 1, A at position 933 of SEQ ID NO: 1, A at position 934 of SEQ ID NO: 1, A at position 935 of SEQ ID NO: 1, C at position 936 of SEQ ID NO: 1, G at position 937 of SEQ ID NO: 1, G at position 938 of SEQ ID NO: 1, A at position 939 of SEQ ID NO: 1, G at position 940 of SEQ ID NO: 1, G at position 941 of SEQ ID NO: 1, A at position 942 of SEQ ID NO: 1, A at position 943 of SEQ ID NO: 1, G at position 944 of SEQ ID NO: 1, T at position 945 of SEQ ID NO: 1, A at position 946 of SEQ ID NO: 1, T at position 947 of SEQ ID NO: 1, A at position 1063 of SEQ ID NO: 1, A at position 1236 of SEQ ID NO: 1, A at position 1303 of SEQ ID NO: 1, G at position 1621 of SEQ ID NO: 1, G at position 1964 of SEQ ID NO: 1, A at position 1979 of SEQ ID NO: 1, C at position 2027 of SEQ ID NO: 1, T at position 2042 of SEQ ID NO: 1, A at position 2072 of SEQ ID NO: 1, G at position 2195 of SEQ ID NO: 1, G at position 2250 of SEQ ID NO: 1, G at position 2413 of SEQ ID NO: 1, C at position 2417 of SEQ ID NO: 1, A at position 2418 SEQ ID NO: 1, C at position 2531 of SEQ ID NO: 1, G at position 2556 of SEQ ID NO: 1, A at position 2577 of SEQ ID NO: 1, G at position 2694 of SEQ ID NO: 1, A at position 2695 of SEQ ID NO: 1, G at position 2701 of SEQ ID NO: 1, T at position 2774 of SEQ ID NO: 1, C at position 2829 of SEQ ID NO: 1, C at position 2835 of SEQ ID NO: 1, C at position 2846 of SEQ ID NO: 1, G at position 2873 of SEQ ID NO: 1, G at position 2932 of SEQ ID NO: 1, T at position 2951 of SEQ ID NO: 1, G at position 2952 of SEQ ID NO: 1, G at position 2958 of SEQ ID NO: 1, G at position 2971 of SEQ ID NO: 1, C at position 2984 of SEQ ID NO: 1, T at position 3041 of SEQ ID NO: 1, G at position 3070 of SEQ ID NO: 1, A at position 3220 of SEQ ID NO: 1, A at position 3231 of SEQ ID NO: 1, A at position 3338 of SEQ ID NO: 1, C at position 3453 of SEQ ID NO: 1, T at position 3498 of SEQ ID NO: 1, T at position 3569 of SEQ ID NO: 1, T at position 3579 of SEQ ID NO: 1, T at position 3602 of SEQ ID NO: 1, A at position 3642 of SEQ ID NO: 1, A at position 3665 of SEQ ID NO: 1, C at position 3676 of SEQ ID NO: 1, T at position 3734 of SEQ ID NO: 1, G at position 4320 of SEQ ID NO: 1, G at position 4325 of SEQ ID NO: 1, A at position 4326 of SEQ ID NO: 1, A at position 4387 of SEQ ID NO: 1, T at position 4409 of SEQ ID NO: 1, G at position 4436 of SEQ ID NO: 1, G at position 4500 of SEQ ID NO: 1, A at position 4526 of SEQ ID NO: 1, C at position 4731 of SEQ ID NO: 1, T at position 4784 of SEQ ID NO: 1, G at position 4785 of SEQ ID NO: 1, G at position 4792 of SEQ ID NO: 1, T at position 4796 of SEQ ID NO: 1, A at position 4805 of SEQ ID NO: 1, C at position 4816 of SEQ ID NO: 1, C at position 4824 of SEQ ID NO: 1, and T at position 4978 of SEQ ID NO: 1; and c) crossing a plant of the *Beta* genus not resistant to BNYVV with the plant of the *Beta* genus in which the at least one polymorphism is detected in part (b).

18. A plant or a part thereof, comprising the nucleic acid molecule according to claim 1 as a transgene or as a cisgene.

19. A seed of a plant, wherein the seed comprises the plant cell according to claim 3.

20. A method for selecting a plant of the *Beta* genus which has a resistance to Beet Necrotic Yellow Vein Virus (BNYVV), wherein the method comprises the following steps:
    a) providing genomic DNA of plants of the *Beta* genus;
    b) detecting the absence of an insertion in the nucleotide sequence encoding a polypeptide comprising the amino acid sequence SEQ ID NO: 2 or SEQ ID NO: 3 by using molecular marker;
    c) selecting a plant of the *Beta* genus in which the insertion is absent and which is BNYVV-resistant; and
    d) breeding the plant of c) with a plant of the *Beta* genus that is not resistant to BNYVV.

21. A method for identifying a nucleic acid molecule which encodes a protein that is able to convey a resistance to Beet Necrotic Yellow Vein Virus (BNYVV) in a plant of the *Beta* genus in which the protein is expressed, wherein the method comprises the following step:
    a) providing genomic DNA of a plant of the *Beta* genus;
    b) detecting at least one polymorphism in the nucleotide sequence encoding a polypeptide comprising the amino acid sequence SEQ ID NO: 2 or SEQ ID NO: 3 by detecting the presence or absence of a nucleotide selected from C at position 94 of SEQ ID NO: 1, T at position 95 of SEQ ID NO: 1, T at position 96 of SEQ ID NO: 1, C at position 97 of SEQ ID NO: 1, C at position 98 of SEQ ID NO: 1, T at position 99 of SEQ ID NO: 1, C at position 100 of SEQ ID NO: 1, T at position 101 of SEQ ID NO: 1, G at position 102 of SEQ ID NO: 1, T at position 103 of SEQ ID NO: 1, T at position 104 of SEQ ID NO: 1, C at position 105 of SEQ ID NO: 1, T at position 106 of SEQ ID NO: 1, G at position 107 of SEQ ID NO: 1, T at position 108 of SEQ ID NO: 1, T at position 109 of SEQ ID NO: 1, T at position 110 of SEQ ID NO: 1, T at position 111 of SEQ ID NO: 1, A at position 112 of SEQ ID NO: 1, A at position 113 of SEQ ID NO: 1, A at position 114 of SEQ ID NO: 1, A at position 118 of SEQ ID NO: 1, A at position 119 of SEQ ID NO: 1, C at position 120 of SEQ ID NO: 1, G at position 121 of SEQ ID NO: 1, T at position 123 of SEQ ID NO: 1, C at position 130 of SEQ ID NO: 1, T at position 131 of SEQ ID NO: 1, A at position 133 of SEQ ID NO: 1, G at position 135 of SEQ ID NO: 1, C at position 136 of SEQ ID NO: 1, A at position 137 of SEQ ID NO: 1, A at position 138 of SEQ ID NO: 1, C at position 139 of SEQ ID NO: 1, C at position 140 of SEQ ID NO: 1, C at position 141 of SEQ ID NO: 1, A at position 142 of SEQ ID NO: 1, A at position 143 of SEQ ID NO: 1, C at position 144 of SEQ ID NO: 1, C at position 145 of SEQ ID NO: 1, C at position 146 of SEQ ID NO: 1, A at position 147 of SEQ ID NO: 1, C at position 148 of SEQ ID NO: 1, T at position 149 of SEQ ID NO: 1, T at position 150 of SEQ ID NO: 1, T at position 151 of SEQ ID NO: 1, T at position 152 of SEQ ID NO: 1, T at position 153 of SEQ ID NO: 1, T at position 154 of SEQ ID NO: 1, A at position 155 of SEQ ID NO: 1, A at position 156 of SEQ ID NO: 1, T at position 157 of SEQ ID NO: 1, A at position 158 of SEQ ID NO: 1, A at position 159 of SEQ ID NO: 1, T at position 160 of SEQ ID NO: 1, A at position 161 of SEQ ID NO: 1, A at position 162 of SEQ ID NO: 1, A at position 163 of SEQ ID NO: 1, T at position 164 of SEQ ID NO: 1, A at position 165 of SEQ ID NO: 1, T at position 166 of SEQ ID NO: 1, T at position 167 of SEQ ID NO: 1, T at position 168 of SEQ ID NO: 1, T at position 169 of SEQ ID NO: 1, T at position 170 of SEQ ID NO: 1, A at position 171 of SEQ ID NO: 1, G at position 172 of SEQ ID NO: 1, T at position 173 of SEQ ID NO: 1, T at position 174 of SEQ ID NO: 1, G at position 175 of SEQ ID NO: 1, T at position 176 of SEQ ID NO: 1, G at position 177 of SEQ ID NO: 1, T at position 178 of SEQ ID NO: 1, G at position 179 of SEQ ID NO: 1, C at position 180 of SEQ ID NO: 1, A at position 181 of SEQ ID NO: 1, C at position 182 of SEQ ID NO: 1, G at position 183 of SEQ ID NO: 1, T at position 184 of SEQ ID NO: 1, A at position 185 of SEQ ID NO: 1, A at position 186 of SEQ ID NO: 1, A at position 187 of SEQ ID NO: 1, A at position 188 of SEQ ID NO: 1, A at position 189 of SEQ ID NO: 1, A at position 190 of SEQ ID NO: 1, T at position 191 of SEQ ID NO: 1, A at position 192 of SEQ ID NO: 1, T at position 193 of SEQ ID NO: 1, A at position 194 of SEQ ID NO: 1, A at position 195 of SEQ ID NO: 1, A at position 196 of SEQ ID NO: 1, A at position 197 of SEQ ID NO: 1, A at position 198 of SEQ ID NO: 1, A at position 199 of SEQ ID NO: 1, G at position 200 of SEQ ID NO: 1, T at position 201 of SEQ ID NO: 1, T at position 202 of SEQ ID NO: 1, A at position 203 of SEQ ID NO: 1, T at position 204 of SEQ ID NO: 1, A at position 205 of SEQ ID NO: 1, A at position 206 of SEQ ID NO: 1, T at position 207 of SEQ ID NO: 1, T at position 208 of SEQ ID NO: 1, T at position 209 of SEQ ID NO: 1, G at position 210 of SEQ ID NO: 1, A at position 211 of SEQ ID NO: 1, T at position 212 of SEQ ID NO: 1, A at position 213 of SEQ ID NO: 1, G at position 346 of SEQ ID NO: 1, G at position 400 of SEQ ID NO: 1, T at position 459 of SEQ ID NO: 1, A at position 466 of SEQ ID NO: 1, A at position 468 of SEQ ID NO: 1, T at position 702 of SEQ ID NO: 1, A at position 703 of SEQ ID NO: 1, A at position 704 of SEQ ID NO: 1, G at position 705 of SEQ ID NO: 1, T at position 706 of SEQ ID NO: 1, G at position 707 of SEQ ID NO: 1, C at position 708 of SEQ ID NO: 1, A at position 709 of SEQ ID NO: 1, A at position 710 of SEQ ID NO: 1, C at position 711 of SEQ ID NO: 1, A at position 712 of SEQ ID NO: 1, T at position 713 of SEQ ID NO: 1, T at position 714 of SEQ ID NO: 1, T at position 715 of SEQ ID NO: 1, G at position 716 of SEQ ID NO: 1, C at position 717 of SEQ ID NO: 1, A at position 718 of SEQ ID NO: 1, T at position 719 of SEQ ID NO: 1, A at position 720 of SEQ ID NO: 1, A at position 721 of SEQ ID NO: 1, T at position 722 of SEQ ID NO: 1, G at position 723 of SEQ ID NO: 1, T at position 724 of SEQ ID NO: 1, T at position 725 of SEQ ID NO: 1, T at position 726 of SEQ ID NO: 1, A at position 727 of SEQ ID NO: 1, C at position 728 of SEQ ID NO: 1, T at position 729 of SEQ ID NO: 1, A at position 730 of SEQ ID NO: 1, T at position 731 of SEQ ID NO: 1, T at position 732 of SEQ ID NO: 1, C at position 733 of SEQ ID NO: 1, A at position 734 of SEQ ID NO: 1, C at position 735 of SEQ ID NO: 1, A at position 736 of SEQ ID NO: 1, G at position 737 of SEQ ID NO: 1, T at position 738 of SEQ ID NO: 1, T at position 739 of SEQ ID NO: 1, T at position 740 of SEQ ID NO: 1, A at position 741 of SEQ ID NO: 1, A at position 742 of SEQ ID NO: 1, A at position 743 of SEQ ID NO: 1, C at position 744 of SEQ ID NO: 1, T at position 745 of SEQ ID NO: 1, T at position 746 of SEQ ID NO: 1, T at position 747 of SEQ ID NO: 1, A at position 748 of SEQ ID NO: 1, A at position 749 of SEQ ID NO: 1, T at position 750 of SEQ ID NO: 1, T at position 751 of SEQ ID NO: 1, A at position 752 of SEQ ID NO: 1, G at position 753 of SEQ ID NO: 1, C at position 754 of SEQ ID NO: 1, T at position 755 of SEQ ID NO: 1, T at position 756 of SEQ ID NO: 1, T at position 757 of SEQ ID NO: 1, G at position 758 of SEQ ID NO: 1, G at position 759 of SEQ ID NO: 1, T at position 760 of SEQ ID NO: 1, G at position 761 of SEQ ID NO: 1, A at position 762 of SEQ ID NO: 1, T at position 763 of SEQ ID NO: 1, T at position 764 of SEQ ID NO: 1, T at position 765 of SEQ ID NO: 1, A at position 766 of SEQ ID NO: 1, C at position 767 of SEQ ID NO: 1, A at position 768 of SEQ ID NO: 1, T at position 769 of SEQ ID NO: 1, T at position 770 of SEQ ID NO: 1, T at position 771 of SEQ ID NO: 1, T at position 772 of SEQ ID NO: 1, A at position 773 of SEQ ID NO: 1, G at position 774 of SEQ ID NO: 1, G at position 775 of SEQ ID NO: 1, A at position 776 of SEQ ID NO: 1, A at position 777 of SEQ ID NO: 1, A at position 778 of SEQ ID NO: 1, A at position 779 of SEQ ID NO: 1, A at position 780 of SEQ ID NO: 1, A at position 781 of SEQ ID NO: 1, C at position 782 of SEQ ID NO: 1, A at position 783 of SEQ ID NO: 1, T at position 784 of SEQ ID NO: 1, A at position 785 of SEQ ID NO: 1, G at position 786 of SEQ ID NO: 1, T at position 787 of SEQ ID NO: 1, C at position 788 of SEQ ID NO: 1, A at position 789 of SEQ ID NO: 1, T at position 790 of SEQ ID NO: 1, G at position 791 of SEQ ID NO: 1, T at position 792 of SEQ ID NO: 1, G at position 793 of SEQ ID NO: 1, G at position 794 of SEQ ID NO: 1, G at position 795 of SEQ ID NO: 1, A at position 796 of SEQ ID NO: 1, T at position 797 of SEQ ID NO: 1, C at position 798 of SEQ ID NO: 1, T at position 799 of SEQ ID NO: 1, T at position 800 of SEQ ID NO: 1, G at position 801 of SEQ ID NO: 1, T at position 802 of SEQ ID NO: 1, T at position 803 of SEQ ID NO: 1, A at position 804 of SEQ ID NO: 1, G at position 805 of SEQ ID NO: 1, A at position 806 of SEQ ID NO: 1, T at position 807 of SEQ ID NO: 1, T at position 808 of SEQ ID NO: 1, C at position 809 of SEQ ID NO: 1, G at position 810 of SEQ ID NO: 1, T at position 811 of SEQ ID NO: 1, C at position 812 of SEQ ID NO: 1, T at position 813 of SEQ ID NO: 1, G at position 814 of SEQ ID NO: 1, A at position 815 of SEQ ID NO: 1, A at position 816 of SEQ ID NO: 1, T at position 817 of SEQ ID NO: 1, G at position 818 of SEQ ID NO: 1, T at position 819 of SEQ ID NO: 1, G at position 820 of SEQ ID NO: 1, A at position 821 of SEQ ID NO: 1, A at position 822 of SEQ ID NO: 1, T at position 823 of SEQ ID NO: 1, T at position 824 of SEQ ID NO: 1, T at position 825 of SEQ ID NO: 1, T at position 826 of SEQ ID NO: 1, T at position 827 of SEQ ID NO: 1, T at position 828 of SEQ ID NO: 1, T at position 829 of SEQ ID NO: 1, A at position 830 of SEQ ID NO: 1, A at position 831 of SEQ ID NO: 1, T at position 832 of SEQ ID NO: 1, A at position 833 of SEQ ID NO: 1, T at position 834 of SEQ ID NO: 1, C at position 835 of SEQ ID NO: 1, A at position 836 of SEQ ID NO: 1, A at position 837 of SEQ ID NO: 1, C at position 838 of SEQ ID NO: 1, T at position 839 of SEQ ID NO: 1, T at position 840 of SEQ ID NO: 1, T at position 841 of SEQ ID NO: 1, T at position 842 of SEQ ID NO: 1, T at position 843 of SEQ ID NO: 1, A at position 844 of SEQ ID NO: 1, T at position 845 of SEQ ID NO: 1, A at position 846 of SEQ ID NO: 1, A at position 847 of SEQ ID NO: 1, T at position 848 of SEQ ID NO: 1, T at position 849 of SEQ ID NO: 1, T at position 850 of SEQ ID NO: 1, T at position 851 of SEQ ID NO: 1, T at position 852 of SEQ ID NO: 1, A at position 853 of SEQ ID NO: 1, C at position 854 of SEQ ID NO: 1, T at position 855 of SEQ ID NO: 1, T at position 856 of SEQ ID NO: 1, A at position 857 of SEQ ID NO: 1, T at position 858 of SEQ ID NO: 1, T at position 859 of SEQ ID NO: 1, G at position 860 of SEQ ID NO: 1, A at position 861 of SEQ ID NO: 1, T at position 862 of SEQ ID NO: 1, A at position 863 of SEQ ID NO: 1, A at position 864 of SEQ ID NO: 1, T at position 865 of SEQ ID NO: 1, T at position 866 of SEQ ID NO: 1, G at position 867 of SEQ ID NO: 1, A at position 868 of SEQ ID NO: 1, A at position 869 of SEQ ID NO: 1, G at position 870 of SEQ ID NO: 1, A at position 871 of SEQ ID NO: 1, T at position 872 of SEQ ID NO: 1, A at position 873 of SEQ ID NO: 1, T at position 874 of SEQ ID NO: 1, T at position 875 of SEQ ID NO: 1, A at position 876 of SEQ ID NO: 1, A at position 877 of SEQ ID NO: 1, T at position 878 of SEQ ID NO: 1, G at position 879 of SEQ ID NO: 1, G at position 880 of SEQ ID NO: 1, T at position 881 of SEQ ID NO: 1, T at position 882 of SEQ ID NO: 1, A at position 883 of SEQ ID NO: 1, A at position 884 of SEQ ID NO: 1, A at position 885 of SEQ ID NO: 1, A at position 886 of SEQ ID NO: 1, T at position 887 of SEQ ID NO: 1, A at position 888 of SEQ ID NO: 1, A at position 889 of SEQ ID NO: 1, T at position 890 of SEQ ID NO: 1, G at position 891 of SEQ ID NO: 1, C at position 892 of SEQ ID NO: 1, A at position 893 of SEQ ID NO: 1, T at position 894 of SEQ ID NO: 1, T at position 895 of SEQ ID NO: 1, G at position 896 of SEQ ID NO: 1, G at position 897 of SEQ ID NO: 1, C at position 898 of SEQ ID NO: 1, A at position 899 of SEQ ID NO: 1, A at position 900 of SEQ ID NO: 1, A at position 901 of SEQ ID NO: 1, C at position 902 of SEQ ID NO: 1, G at position 903 of SEQ ID NO: 1, T at position 904 of SEQ ID NO: 1, G at position 905 of SEQ ID NO: 1, A at position 906 of SEQ ID NO: 1, A at position 907 of SEQ ID NO: 1, A at position 908 of SEQ ID NO: 1, A at position 909 of SEQ ID NO: 1, C at position 910 of SEQ ID NO: 1, A at position 911 of SEQ ID NO: 1, A at position 912 of SEQ ID NO: 1, G at position 913 of SEQ ID NO: 1, A at position 914 of SEQ ID NO: 1, A at position 915 of SEQ ID NO: 1, G at position 916 of SEQ ID NO: 1, T at position 917 of SEQ ID NO: 1, G at position 918 of SEQ ID NO: 1, T at position 919 of SEQ ID NO: 1, T at position 920 of SEQ ID NO: 1, G at position 921 of SEQ ID NO: 1, C at position 922 of SEQ ID NO: 1, A at position 923 of SEQ ID NO: 1, C at position 924 of SEQ ID NO: 1, T at position 925 of SEQ ID NO: 1, T at position 926 of SEQ ID NO: 1, A at position 927 of SEQ ID NO: 1, T at position 928 of SEQ ID NO: 1, T at position 929 of SEQ ID NO: 1, T at position 930 of SEQ ID NO: 1, A at position 931 of SEQ ID NO: 1, G at position 932 of SEQ ID NO: 1, A at position 933 of SEQ ID NO: 1, A at position 934 of SEQ ID NO: 1, A at position 935 of SEQ ID NO: 1, C at position 936 of SEQ ID NO: 1, G at position 937 of SEQ ID NO: 1, G at position 938 of SEQ ID NO: 1, A at position 939 of SEQ ID NO: 1, G at position 940 of SEQ ID NO: 1, G at position 941 of SEQ ID NO: 1, A at position 942 of SEQ ID NO: 1, A at position 943 of SEQ ID NO: 1, G at position 944 of SEQ ID NO: 1, T at position 945 of SEQ ID NO: 1, A at position 946 of SEQ ID NO: 1, T at position 947 of SEQ ID NO: 1, A at position 1063 of SEQ ID NO: 1, A at position 1236 of SEQ ID NO: 1, A at position 1303 of SEQ ID NO: 1, G at position 1621 of SEQ ID NO: 1, G at position 1964 of SEQ ID NO: 1, A at position 1979 of SEQ ID NO: 1, C at position 2027 of SEQ ID NO: 1, T at position 2042 of SEQ ID NO: 1, A at position 2072 of SEQ ID NO: 1, G at position 2195 of SEQ ID NO: 1, G at position 2250 of SEQ ID NO: 1, G at position 2413 of SEQ ID NO: 1, C at position 2417 of SEQ ID NO: 1, A at position 2418 of SEQ ID NO: 1, C at position 2531 of SEQ ID NO: 1, G at position 2556 of SEQ ID NO: 1, A at position 2577 of SEQ ID NO: 1, G at position 2694 of SEQ ID NO: 1, A at position 2695 of SEQ ID NO: 1, G at position 2701 of SEQ ID NO: 1, T at position 2774 of SEQ ID NO: 1, C at position 2829 of SEQ ID NO: 1, C at position 2835 of SEQ ID NO: 1, C at position 2846 of SEQ ID NO: 1, G at position 2873 of SEQ ID NO: 1, G at position 2932 of SEQ ID NO: 1, T at position 2951 of SEQ ID NO: 1, G at position 2952 of SEQ ID NO: 1, G at position 2958 of SEQ ID NO: 1, G at position 2971 of SEQ ID NO: 1, C at position 2984 of SEQ ID NO: 1, T at position 3041 of SEQ ID NO: 1, G at position 3070 of SEQ ID NO: 1, A at position 3220 of SEQ ID NO: 1, A at position 3231 of SEQ ID NO: 1, A at position 3338 of SEQ ID NO: 1, C at position 3453 of SEQ ID NO: 1, T at position 3498 of SEQ ID NO: 1, T at position 3569 of SEQ ID NO: 1, T at position 3579 of SEQ ID NO: 1, T at position 3602 of SEQ ID NO: 1, A at position 3642 of SEQ ID NO: 1, A at position 3665 of SEQ ID NO: 1, C at position 3676 of SEQ ID NO: 1, T at position 3734 of SEQ ID NO: 1, G at position 4320 of SEQ ID NO: 1, G at position 4325 of SEQ ID NO: 1, A at position 4326 of SEQ ID NO: 1, A at position 4387 of SEQ ID NO: 1, T at position 4409 of SEQ ID NO: 1, G at position 4436 of SEQ ID NO: 1, G at position 4500 of SEQ ID NO: 1, A at position 4526 of SEQ ID NO: 1, C at position 4731 of SEQ ID NO: 1, T at position 4784 of SEQ ID NO: 1, G at position 4785 of SEQ ID NO: 1, G at position 4792 of SEQ ID NO: 1, T at position 4796 of SEQ ID NO: 1, A at position 4805 of SEQ ID NO: 1, C at position 4816 of SEQ ID NO: 1, C at position 4824 of SEQ ID NO: 1, and T at position 4978 of SEQ ID NO: 1;

c) selecting a plant of the *Beta* genus in which the at least one polymorphism has been detected; and d) breeding the plant of c), with a plant of the *Beta* genus that is not resistant to BNYVV.

22. The cell according to claim 3, wherein the nucleotide sequence of part c) encodes a polypeptide which comprises an amino acid sequence at least 85% identical to SEQ ID NO: 2 or SEQ ID NO: 3.

23. The cell according to claim 3, wherein the nucleotide sequence confers resistance to Rhizomania.

24. The cell according to claim 3, wherein the cell comprises the nucleotide sequence as an introgressed region, and wherein the cell comprises the nucleotide sequence of part c) that encodes a polypeptide which comprises an amino acid sequence at least 98% identical to SEQ ID NO: 2 or SEQ ID NO: 3.

* * * * *

SEQUENCE LISTING

```
<160> NUMBER OF SEQ ID NOS: 52

<210> SEQ ID NO 1
<211> LENGTH: 5009
<212> TYPE: DNA
<213> ORGANISM: Beta vulgaris

<400> SEQUENCE: 1
caaatcttct ggcatcaatg gcggtgttgc cgttcatcaa tttaacatca atggaggtaa      60
gagtcatgtt ttttcaacaa tataaaactt atacttcctc tgttctgttt taaatgaaac     120
gtttgttttc tcacgcaacc caacccactt ttttaataat aaatatttt agttgtgtgc      180 acgtaaaaaa tataaaaaag ttataatttg atagtatctt gtttgagatt gtgattatta     240
agagagtcaa gtctcacaat attcgaaagt ctacgtaatc cacctcaaat tgacgaagaa     300
aacaagcagg aaaggattaa gtaagttcgt ggaaccacta gaattgattt tcaaatatag     360
ctctacctaa tatatggcct acttttaatt ttaaataagg agaaggtaat gtgattagaa     420
acaaattggt cttaaattat tcattaagct taataatgta taaacataat caagtgctat     480
cttcttttca gggccgtctt gaagattttg gggcccggtt ctattatgaa aattgggccc     540
ctaaatttat agaaaataaa gatggaaggt tagagttcta aagatagaaa gttgaaaatc     600
taaatataaa tcattgacaa atttattaag ggtgagaaac aagggtgttt tcttcaaata     660
tgaagcaaaa ttttcaaaat aatacttcct ccgtttctaa ataagtgcaa catttgcata     720
atgtttacta ttcacagttt aaactttaat tagctttggt gatttacatt ttaggaaaaa     780
acatagtcat gtgggatctt gttagattcg tctgaatgtg aatttttta atatcaactt     840 tttataattt ttacttattg ataattgaag atattaatgg ttaaaataat gcattggcaa     900
acgtgaaaac aagaagtgtt gcacttattt agaaacggag gaagtatatt ttgggccttt     960 ataatttttgg agaccctgcg ctgttgggct ccttgcacac cttcatctac ccctctgctt    1020
cttttgatac aattttttcag cgacatgatt gtcgattgat gcatatatta ttgtatactc    1080
gatccatatt gtttaagatg aattgtttgt ctttgatggt ctccaatgca tattttgtat    1140
```

```
acttaggaat tctaattatg tactattagt agacattgag atgaatacat aattgccata    1200
atgaagtatg attattttag ttatatactt tctccattcc aaatatataa atgtaacact    1260
tgtgtacttt atgcgtacta atgcataaca acgtgcactc tcatgtgttt aattatatac    1320
tttttgagag aagtgttaca ttggggacca tgggactgtg tataatttga ccgcaaaatc    1380
gaagtgtcgc atttgattga aaatggagag agtagtatat agatggaaca cagcagagac    1440
tgctggtcat ctttggccaa caaacccaaa attgatatta atcccttatt caggtcattt    1500 catcttttg acacaaaatg atgttgtag gcactgcgct atctgctgcc caatctctgt     1560
ttgcagccct gcaaagttct gagctcaaag agatcctctc gatctttggc tacaaatccc    1620
gacttgatga cctccaacgc actgtctcta ccatcaacgc tgtattccgt gatgctgaga    1680
ccaaacagga gctcactcat gaagcacagc attggctcga ggaactcaag gatgctgtct    1740 tgaagcaga tgatctgttc gacgagtttg tcactcttgc cgagcagaag caacttgtag    1800
aggctggtgg cagtctttcc aaaaagatgc gccaattctt ttctgattcc aaccccttg    1860 gcattgctta taggatgtca cgaggggtta agaagatcaa gaagaagttg gatgctatcg    1920
cttacaatca tcaatttagc tttaagatt atcttgagcc tatgaaagag agaaggctag     1980
agactggttc tgtcgtgaac gcaggtgata tcattggaag agaggacgac ttggagaaga    2040
ttgtaggttt gttgcttgat tctaacatcc aacgtgatgt gtctttcctt actattgtgg    2100
gaatgggagg gttgggtaaa actgctcttg cccaactcgt gtacaatgat ccaagggtca    2160
gaactgcttt tccattgaga tgttggaatt gtgtgtctga tcaagatcaa aagcaactag    2220
atgtgaaaga aatttttggt aagattctgg ctacagctac tggtaagaat catgagggtt    2280
caaccatgga tcaggtgcaa acccaactac gagaacaact atgtggcaag agatacttgc    2340
ttgttttgga tgatgtatgg aatgagaatc ctaatcaatt gcgtgatctg gtagaattct    2400
tcatgggagg tcgaagcaga aattggattg tggtaactac gcgttcgcac gagacagcga    2460
gaattataag agatggtcca ttgcacaagc tccaaggttt gtctgaggaa aactcttggc    2520
gtttatttgt caggtggacc ttcggatcag tgcaagcaaa attccctaat gactttatca    2580
tgattgcacg agatatagtt gacaaatgtg ctcgaaaccc tctggctata agagtggtag    2640
gaagtctttt gtgtggtcaa gacaagagta agtggctttc atttcatgag atcgatttag    2700
gcaacattag aaagagccat aatgatatca tgccaatact gaacctaagt taccatcatc    2760
ttgaacctcc aattaagaga tgctttagtt attgtgcagt gtttccaaag gatttcctta    2820
tagggaagca gacgctgata aacctctgga tggcacaagg ttatattgtt ccgttagaca    2880
aagatcaaag catagatgat gctagtgagg aatacatatc aattttgttg cggagatgtt    2940
ttttcgaaaa tgtcggagca gaaaagatg gtgttattaa gatccatgat ctcatgcatg     3000
atattgctca aaatgtcatg gggaaggagc tttgtacgac taaaaacatt agtggcagct    3060
tggataaaag tgttcgccat ctatctcttg ccagaactag ttttgcaaga tactctttca    3120
atgcaactca tattcgctcc tatttctgtg ctggctactg gtgtcaggat gctgagataa    3180
accagttttc agttgaggca ttagtaccaa actgtttgta cctaagggca atggacctcg    3240
cttggtcgaa gataaaaagt ttaccagact cgattggtgg attgttgcat tgaggtact     3300 tagatctttc gtataacgaa gatctggaag tacttccaaa ctcaattgct aaactatata    3360
atctacaaac cttacaattg aagggttgca agagattgga agggttacca aaacatttga    3420
gcaggctggt taagcttcaa actttggata tacatggttg caacaatgta acttatatgc    3480
ccaaaggcat gggtaagttg acttgccttc acactctcag taagtttata gtgggtggag    3540
```

```
aagggagttg ttcaagttgg aagcaatgtt ttgatgggtt ggaagatcta aaggctctca    3600
ataacctaaa gggtcatctg gaaatccaaa tcaggtggcc caaaaatact acagatgctg    3660
tcaaagaaga tgttacgagg gaaggattat acctgaatca taaggaacat ctcaatcaca    3720
ttgtggttga ttttagatgt gaggagggtg gtggaagaat ggatgatgag gaagcaagaa    3780
gattgatgga agagttgcgg ccacatcctt atcttgaaaa tttggctgtg aaagcatatt    3840
atggtgtgaa aatgcctggt tgggcaaccc ttctcccaaa tcttacagag ctttttcttt    3900
ctgattgtgg ggaactggag aaccttccat gcctgggaaa cttggatcat ctaaaagtcc    3960
tccgactttc gcatttggca aaattggagt acattgaaga agatagctca tcagctaatt    4020
tcaggtgtag gcctggacca gaaagtgcag gactatcatt atacttcccc tcccttgaac    4080
gccttgagtt gaagcgtttg tgtaagttaa aaggatggag gagaggggaa gggttaggag    4140
atgatcacca gccttttaat gaaagcagca gcaatacaca agtccaatta caattatgtc    4200
ttcctcaatt gaagtcattg agaatagaaa gatgcccatt gctgacattt atgccgctgt    4260
gtcccaagac agaaaaactg catttagttg tatttaatga acgactccgg atagtgcatg    4320
ctaagagaga tgagaatttc tatgctccat tacattcatc atcatctgat cctgaaaacc    4380
cgaggaacac tattcccatt cccatgttta gagaggtata cataaacaat gtggcgtggc    4440
taaattcgct gcctatggag gcttttaggt gtctcactca tatgacaata aaaaacgacg    4500
aggtagagag tttgggagaa gttggagagg tgtttcggag ctgctcatct tctttgcgat    4560
ccttgaatat cacaggttgc tccaacttaa gaagtgtttc tggagggctg agcatctca    4620 ctgctttgga gatgttagaa atatacgaca cccataagct gagtctatca gaagacccag    4680
aaggtgttgt gccatggaaa tcccttcatc actccctcag ctacttgcaa ctgatgaatc    4740
tcccacagct ggtcaacctg cctgattcga tgcagttctt ggctgccctc cgaactcttt    4800
caatagtgca ttgcactaaa ctgcaatcag tgccagattg gatgcccaga ctcacttctc    4860
tcaggaagct tatggtttca ttctgttccg cacatctgga gagaagatgc caaaatccaa    4920
ctggggtgga ctggcctaac attcaacaca tcccctccat tgatgtcacc tctagccttc    4980
ctaagttttt agtgttgccg tatgaatag                                      5009
```

<210> SEQ ID NO 2
<211> LENGTH: 1163
<212> TYPE: PRT
<213> ORGANISM: Beta vulgaris

<400> SEQUENCE: 2

```
Met Asp Val Val Gly Thr Ala Leu Ser Ala Ala Gln Ser Leu Phe Ala
1               5                   10                  15

Ala Leu Gln Ser Ser Glu Leu Lys Glu Ile Leu Ser Ile Phe Gly Tyr
            20                  25                  30

Lys Ser Arg Leu Asp Asp Leu Gln Arg Thr Val Ser Thr Ile Asn Ala
        35                  40                  45

Val Phe Arg Asp Ala Glu Thr Lys Gln Glu Leu Thr His Glu Ala Gln
    50                  55                  60

His Trp Leu Glu Glu Leu Lys Asp Ala Val Phe Glu Ala Asp Asp Leu
65                  70                  75                  80

Phe Asp Glu Phe Val Thr Leu Ala Glu Gln Lys Gln Leu Val Glu Ala
                85                  90                  95

Gly Gly Ser Leu Ser Lys Lys Met Arg Gln Phe Phe Ser Asp Ser Asn
            100                 105                 110
```

```
Pro Leu Gly Ile Ala Tyr Arg Met Ser Arg Gly Val Lys Lys Ile Lys
    115                 120                 125

Lys Lys Leu Asp Ala Ile Ala Tyr Asn His Gln Phe Ser Phe Lys Ile
    130                 135                 140

Asp Leu Glu Pro Met Lys Glu Arg Arg Leu Glu Thr Gly Ser Val Val
145                 150                 155                 160

Asn Ala Gly Asp Ile Ile Gly Arg Glu Asp Leu Glu Lys Ile Val
                165                 170                 175

Gly Leu Leu Leu Asp Ser Asn Ile Gln Arg Asp Val Ser Phe Leu Thr
            180                 185                 190

Ile Val Gly Met Gly Gly Leu Gly Lys Thr Ala Leu Ala Gln Leu Val
            195                 200                 205

Tyr Asn Asp Pro Arg Val Arg Thr Ala Phe Pro Leu Arg Cys Trp Asn
    210                 215                 220

Cys Val Ser Asp Gln Asp Gln Lys Gln Leu Asp Val Lys Glu Ile Leu
225                 230                 235                 240

Gly Lys Ile Leu Ala Thr Ala Thr Gly Lys Asn His Glu Gly Ser Thr
                245                 250                 255

Met Asp Gln Val Gln Thr Gln Leu Arg Glu Gln Leu Cys Gly Lys Arg
            260                 265                 270

Tyr Leu Leu Val Leu Asp Asp Val Trp Asn Glu Asn Pro Asn Gln Leu
    275                 280                 285

Arg Asp Leu Val Glu Phe Phe Met Gly Gly Arg Ser Arg Asn Trp Ile
    290                 295                 300

Val Val Thr Thr Arg Ser His Glu Thr Ala Arg Ile Ile Arg Asp Gly
305                 310                 315                 320

Pro Leu His Lys Leu Gln Gly Leu Ser Glu Glu Asn Ser Trp Arg Leu
                325                 330                 335

Phe Val Arg Trp Thr Phe Gly Ser Val Gln Ala Lys Phe Pro Asn Asp
            340                 345                 350

Phe Ile Met Ile Ala Arg Asp Ile Val Asp Lys Cys Ala Arg Asn Pro
    355                 360                 365

Leu Ala Ile Arg Val Val Gly Ser Leu Leu Cys Gly Gln Asp Lys Ser
    370                 375                 380

Lys Trp Leu Ser Phe His Glu Ile Asp Leu Gly Asn Ile Arg Lys Ser
385                 390                 395                 400

His Asn Asp Ile Met Pro Ile Leu Asn Leu Ser Tyr His His Leu Glu
                405                 410                 415

Pro Pro Ile Lys Arg Cys Phe Ser Tyr Cys Ala Val Phe Pro Lys Asp
            420                 425                 430

Phe Leu Ile Gly Lys Gln Thr Leu Ile Asn Leu Trp Met Ala Gln Gly
    435                 440                 445

Tyr Ile Val Pro Leu Asp Lys Asp Gln Ser Ile Asp Asp Ala Ser Glu
    450                 455                 460

Glu Tyr Ile Ser Ile Leu Leu Arg Arg Cys Phe Phe Glu Asn Val Gly
465                 470                 475                 480

Ala Glu Lys Asp Gly Val Ile Lys Ile His Asp Leu Met His Asp Ile
                485                 490                 495

Ala Gln Asn Val Met Gly Lys Glu Leu Cys Thr Thr Lys Asn Ile Ser
            500                 505                 510

Gly Ser Leu Asp Lys Ser Val Arg His Leu Ser Leu Ala Arg Thr Ser
        515                 520                 525
```

```
Phe Ala Arg Tyr Ser Phe Asn Ala Thr His Ile Arg Ser Tyr Phe Cys
        530                 535                 540
Ala Gly Tyr Trp Cys Gln Asp Ala Glu Ile Asn Gln Phe Ser Val Glu
545                 550                 555                 560
Ala Leu Val Pro Asn Cys Leu Tyr Leu Arg Ala Met Asp Leu Ala Trp
                565                 570                 575
Ser Lys Ile Lys Ser Leu Pro Asp Ser Ile Gly Gly Leu Leu His Leu
        580                 585                 590
Arg Tyr Leu Asp Leu Ser Tyr Asn Glu Asp Leu Glu Val Leu Pro Asn
        595                 600                 605
Ser Ile Ala Lys Leu Tyr Asn Leu Gln Thr Leu Gln Leu Lys Gly Cys
610                 615                 620
Lys Arg Leu Glu Gly Leu Pro Lys His Leu Ser Arg Leu Val Lys Leu
625                 630                 635                 640
Gln Thr Leu Asp Ile His Gly Cys Asn Asn Val Thr Tyr Met Pro Lys
                645                 650                 655
Gly Met Gly Lys Leu Thr Cys Leu His Thr Leu Ser Lys Phe Ile Val
                660                 665                 670
Gly Gly Glu Gly Ser Cys Ser Ser Trp Lys Gln Cys Phe Asp Gly Leu
                675                 680                 685
Glu Asp Leu Lys Ala Leu Asn Asn Leu Lys Gly His Leu Glu Ile Gln
        690                 695                 700
Ile Arg Trp Pro Lys Asn Thr Thr Asp Ala Val Lys Glu Asp Val Thr
705                 710                 715                 720
Arg Glu Gly Leu Tyr Leu Asn His Lys Glu His Leu Asn His Ile Val
                725                 730                 735
Val Asp Phe Arg Cys Glu Glu Gly Gly Arg Met Asp Asp Glu Glu
                740                 745                 750
Ala Arg Arg Leu Met Glu Glu Leu Arg Pro His Pro Tyr Leu Glu Asn
        755                 760                 765
Leu Ala Val Lys Ala Tyr Tyr Gly Val Lys Met Pro Gly Trp Ala Thr
770                 775                 780
Leu Leu Pro Asn Leu Thr Glu Leu Phe Leu Ser Asp Cys Gly Glu Leu
785                 790                 795                 800
Glu Asn Leu Pro Cys Leu Gly Asn Leu Asp His Leu Lys Val Leu Arg
                805                 810                 815
Leu Ser His Leu Ala Lys Leu Glu Tyr Ile Glu Glu Asp Ser Ser Ser
                820                 825                 830
Ala Asn Phe Arg Cys Arg Pro Gly Pro Glu Ser Ala Gly Leu Ser Leu
                835                 840                 845
Tyr Phe Pro Ser Leu Glu Arg Leu Glu Leu Lys Arg Leu Cys Lys Leu
850                 855                 860
Lys Gly Trp Arg Arg Gly Glu Gly Leu Gly Asp Asp His Gln Pro Phe
865                 870                 875                 880
Asn Glu Ser Ser Ser Asn Thr Gln Val Gln Leu Gln Leu Cys Leu Pro
                885                 890                 895
Gln Leu Lys Ser Leu Arg Ile Glu Arg Cys Pro Leu Leu Thr Phe Met
                900                 905                 910
Pro Leu Cys Pro Lys Thr Glu Lys Leu His Leu Val Val Phe Asn Glu
                915                 920                 925
Arg Leu Arg Ile Val His Ala Lys Arg Asp Glu Asn Phe Tyr Ala Pro
        930                 935                 940
Leu His Ser Ser Ser Ser Asp Pro Glu Asn Pro Arg Asn Thr Ile Pro
```

```
                      945                 950                 955                 960
        Ile Pro Met Phe Arg Glu Val Tyr Ile Asn Asn Val Ala Trp Leu Asn
                            965                 970                 975
        Ser Leu Pro Met Glu Ala Phe Arg Cys Leu Thr His Met Thr Ile Lys
                            980                 985                 990
        Asn Asp Glu Val Glu Ser Leu Gly Glu Val Gly Glu Val Phe Arg Ser
                            995                1000                1005
        Cys Ser Ser Ser Leu Arg Ser Leu Asn Ile Thr Gly Cys Ser Asn
           1010                1015                1020
        Leu Arg Ser Val Ser Gly Gly Leu Glu His Leu Thr Ala Leu Glu
           1025                1030                1035
        Met Leu Glu Ile Tyr Asp Thr His Lys Leu Ser Leu Ser Glu Asp
           1040                1045                1050
        Pro Glu Gly Val Val Pro Trp Lys Ser Leu His His Ser Leu Ser
           1055                1060                1065
        Tyr Leu Gln Leu Met Asn Leu Pro Gln Leu Val Asn Leu Pro Asp
           1070                1075                1080
        Ser Met Gln Phe Leu Ala Ala Leu Arg Thr Leu Ser Ile Val His
           1085                1090                1095
        Cys Thr Lys Leu Gln Ser Val Pro Asp Trp Met Pro Arg Leu Thr
           1100                1105                1110
        Ser Leu Arg Lys Leu Met Val Ser Phe Cys Ser Ala His Leu Glu
           1115                1120                1125
        Arg Arg Cys Gln Asn Pro Thr Gly Val Asp Trp Pro Asn Ile Gln
           1130                1135                1140
        His Ile Pro Ser Ile Asp Val Thr Ser Ser Leu Pro Lys Phe Leu
           1145                1150                1155
        Val Leu Pro Tyr Glu
           1160

<210> SEQ ID NO 3
<211> LENGTH: 1177
<212> TYPE: PRT
<213> ORGANISM: Beta vulgaris

<400> SEQUENCE: 3

Met Glu Arg Val Val Tyr Arg Trp Asn Thr Ala Glu Thr Ala Gly His
        1               5                  10                  15
        Leu Trp Pro Thr Asn Pro Lys Leu Ile Leu Pro Tyr Ser Ala Leu
                        20                  25                  30
        Gln Ser Ser Glu Leu Lys Glu Ile Leu Ser Ile Phe Gly Tyr Lys Ser
                        35                  40                  45
        Arg Leu Asp Asp Leu Gln Arg Thr Val Ser Thr Ile Asn Ala Val Phe
        50                  55                  60
        Arg Asp Ala Glu Thr Lys Gln Glu Leu Thr His Glu Ala Gln His Trp
        65                  70                  75                  80
        Leu Glu Glu Leu Lys Asp Ala Val Phe Glu Ala Asp Leu Phe Asp
                        85                  90                  95
        Glu Phe Val Thr Leu Ala Glu Gln Lys Gln Leu Val Glu Ala Gly Gly
                        100                 105                 110
        Ser Leu Ser Lys Lys Met Arg Gln Phe Phe Ser Asp Ser Asn Pro Leu
                        115                 120                 125
        Gly Ile Ala Tyr Arg Met Ser Arg Gly Val Lys Lys Ile Lys Lys Lys
                        130                 135                 140
```

-continued

Leu Asp Ala Ile Ala Tyr Asn His Gln Phe Ser Phe Lys Ile Asp Leu
145                 150                 155                 160

Glu Pro Met Lys Glu Arg Arg Leu Glu Thr Gly Ser Val Val Asn Ala
                165                 170                 175

Gly Asp Ile Ile Gly Arg Glu Asp Leu Glu Lys Ile Val Gly Leu
            180                 185                 190

Leu Leu Asp Ser Asn Ile Gln Arg Asp Val Ser Phe Leu Thr Ile Val
        195                 200                 205

Gly Met Gly Gly Leu Gly Lys Thr Ala Leu Ala Gln Leu Val Tyr Asn
    210                 215                 220

Asp Pro Arg Val Arg Thr Ala Phe Pro Leu Arg Cys Trp Asn Cys Val
225                 230                 235                 240

Ser Asp Gln Asp Gln Lys Gln Leu Asp Val Lys Glu Ile Leu Gly Lys
                245                 250                 255

Ile Leu Ala Thr Ala Thr Gly Lys Asn His Glu Gly Ser Thr Met Asp
            260                 265                 270

Gln Val Gln Thr Gln Leu Arg Glu Gln Leu Cys Gly Lys Arg Tyr Leu
        275                 280                 285

Leu Val Leu Asp Asp Val Trp Asn Glu Asn Pro Asn Gln Leu Arg Asp
    290                 295                 300

Leu Val Glu Phe Phe Met Gly Arg Ser Arg Asn Trp Ile Val Val
305                 310                 315                 320

Thr Thr Arg Ser His Glu Thr Ala Arg Ile Ile Arg Asp Gly Pro Leu
                325                 330                 335

His Lys Leu Gln Gly Leu Ser Glu Glu Asn Ser Trp Arg Leu Phe Val
            340                 345                 350

Arg Trp Thr Phe Gly Ser Val Gln Ala Lys Phe Pro Asn Asp Phe Ile
        355                 360                 365

Met Ile Ala Arg Asp Ile Val Asp Lys Cys Ala Arg Asn Pro Leu Ala
    370                 375                 380

Ile Arg Val Val Gly Ser Leu Cys Gly Gln Asp Lys Ser Lys Trp
385                 390                 395                 400

Leu Ser Phe His Glu Ile Asp Leu Gly Asn Ile Arg Lys Ser His Asn
                405                 410                 415

Asp Ile Met Pro Ile Leu Asn Leu Ser Tyr His His Leu Glu Pro Pro
            420                 425                 430

Ile Lys Arg Cys Phe Ser Tyr Cys Ala Val Phe Pro Lys Asp Phe Leu
        435                 440                 445

Ile Gly Lys Gln Thr Leu Ile Asn Leu Trp Met Ala Gln Gly Tyr Ile
    450                 455                 460

Val Pro Leu Asp Lys Asp Gln Ser Ile Asp Asp Ala Ser Glu Tyr
465                 470                 475                 480

Ile Ser Ile Leu Leu Arg Arg Cys Phe Phe Glu Asn Val Gly Ala Glu
                485                 490                 495

Lys Asp Gly Val Ile Lys Ile His Asp Leu Met His Asp Ile Ala Gln
            500                 505                 510

Asn Val Met Gly Lys Glu Leu Cys Thr Thr Lys Asn Ile Ser Gly Ser
        515                 520                 525

Leu Asp Lys Ser Val Arg His Leu Ser Leu Ala Arg Thr Ser Phe Ala
    530                 535                 540

Arg Tyr Ser Phe Asn Ala Thr His Ile Arg Ser Tyr Phe Cys Ala Gly
545                 550                 555                 560

Tyr Trp Cys Gln Asp Ala Glu Ile Asn Gln Phe Ser Val Glu Ala Leu

-continued

```
                565                 570                 575
Val Pro Asn Cys Leu Tyr Leu Arg Ala Met Asp Leu Ala Trp Ser Lys
            580                 585                 590

Ile Lys Ser Leu Pro Asp Ser Ile Gly Gly Leu Leu His Leu Arg Tyr
            595                 600                 605

Leu Asp Leu Ser Tyr Asn Glu Asp Leu Glu Val Leu Pro Asn Ser Ile
            610                 615                 620

Ala Lys Leu Tyr Asn Leu Gln Thr Leu Gln Leu Lys Gly Cys Lys Arg
625                 630                 635                 640

Leu Glu Gly Leu Pro Lys His Leu Ser Arg Leu Val Lys Leu Gln Thr
                645                 650                 655

Leu Asp Ile His Gly Cys Asn Asn Val Thr Tyr Met Pro Lys Gly Met
            660                 665                 670

Gly Lys Leu Thr Cys Leu His Thr Leu Ser Lys Phe Ile Val Gly Gly
            675                 680                 685

Glu Gly Ser Cys Ser Ser Trp Lys Gln Cys Phe Asp Gly Leu Glu Asp
            690                 695                 700

Leu Lys Ala Leu Asn Asn Leu Lys Gly His Leu Glu Ile Gln Ile Arg
705                 710                 715                 720

Trp Pro Lys Asn Thr Thr Asp Ala Val Lys Glu Asp Val Thr Arg Glu
                725                 730                 735

Gly Leu Tyr Leu Asn His Lys Glu His Leu Asn His Ile Val Val Asp
            740                 745                 750

Phe Arg Cys Glu Glu Gly Gly Arg Met Asp Asp Glu Ala Arg
            755                 760                 765

Arg Leu Met Glu Glu Leu Arg Pro His Pro Tyr Leu Glu Asn Leu Ala
            770                 775                 780

Val Lys Ala Tyr Tyr Gly Val Lys Met Pro Gly Trp Ala Thr Leu Leu
785                 790                 795                 800

Pro Asn Leu Thr Glu Leu Phe Leu Ser Asp Cys Gly Glu Leu Glu Asn
                805                 810                 815

Leu Pro Cys Leu Gly Asn Leu Asp His Leu Lys Val Leu Arg Leu Ser
            820                 825                 830

His Leu Ala Lys Leu Glu Tyr Ile Glu Glu Asp Ser Ser Ser Ala Asn
            835                 840                 845

Phe Arg Cys Arg Pro Gly Pro Glu Ser Ala Gly Leu Ser Leu Tyr Phe
            850                 855                 860

Pro Ser Leu Glu Arg Leu Glu Leu Lys Arg Leu Cys Lys Leu Lys Gly
865                 870                 875                 880

Trp Arg Arg Gly Glu Gly Leu Gly Asp Asp His Gln Pro Phe Asn Glu
                885                 890                 895

Ser Ser Ser Asn Thr Gln Val Gln Gln Leu Cys Leu Pro Gln Leu
            900                 905                 910

Lys Ser Leu Arg Ile Glu Arg Cys Pro Leu Leu Thr Phe Met Pro Leu
            915                 920                 925

Cys Pro Lys Thr Glu Lys Leu His Leu Val Val Phe Asn Glu Arg Leu
930                 935                 940

Arg Ile Val His Ala Lys Arg Asp Glu Asn Phe Tyr Ala Pro Leu His
945                 950                 955                 960

Ser Ser Ser Ser Asp Pro Glu Asn Pro Arg Asn Thr Ile Pro Ile Pro
                965                 970                 975

Met Phe Arg Glu Val Tyr Ile Asn Asn Val Ala Trp Leu Asn Ser Leu
            980                 985                 990
```

```
Pro Met Glu Ala Phe Arg Cys Leu Thr His Met Thr Ile Lys Asn Asp
    995                 1000                1005

Glu Val Glu Ser Leu Gly Glu Val Gly Glu Val Phe Arg Ser Cys
    1010                1015                1020

Ser Ser Ser Leu Arg Ser Leu Asn Ile Thr Gly Cys Ser Asn Leu
    1025                1030                1035

Arg Ser Val Ser Gly Gly Leu Glu His Leu Thr Ala Leu Glu Met
    1040                1045                1050

Leu Glu Ile Tyr Asp Thr His Lys Leu Ser Leu Ser Glu Asp Pro
    1055                1060                1065

Glu Gly Val Val Pro Trp Lys Ser Leu His His Ser Leu Ser Tyr
    1070                1075                1080

Leu Gln Leu Met Asn Leu Pro Gln Leu Val Asn Leu Pro Asp Ser
    1085                1090                1095

Met Gln Phe Leu Ala Ala Leu Arg Thr Leu Ser Ile Val His Cys
    1100                1105                1110

Thr Lys Leu Gln Ser Val Pro Asp Trp Met Pro Arg Leu Thr Ser
    1115                1120                1125

Leu Arg Lys Leu Met Val Ser Phe Cys Ser Ala His Leu Glu Arg
    1130                1135                1140

Arg Cys Gln Asn Pro Thr Gly Val Asp Trp Pro Asn Ile Gln His
    1145                1150                1155

Ile Pro Ser Ile Asp Val Thr Ser Ser Leu Pro Lys Phe Leu Val
    1160                1165                1170

Leu Pro Tyr Glu
    1175

<210> SEQ ID NO 4
<211> LENGTH: 987
<212> TYPE: DNA
<213> ORGANISM: Beta vulgaris

<400> SEQUENCE: 4 ttcctctttta gatttccata gatttgaaca aattggggtg attttcatag attattcata      60
attctctctc cataattctt ctctctcttt ctccatacat ttttcattcg caatactcag     120
gaactgagta ttgggaattg tccccagttg tcaggttgat gtgcagtaac tttaagagaa     180
gactttcctc tcatgcaaca tgtccctgat ctgttgcttg atggtcgtca tctcactatt     240
ctctaataag ctcgatttgt atgaaacaga tgatactata ttccgtttcg tgcaatgtgc     300
acgaaacgga atatagtatt tgtgcaagg tgcacgaaac ggattcgatt gtttcgtgca      360
cattgcacga aacggaatca actgtttcat gtagtctaca cgaaacgaa tcaattgttt      420 cgtgtagtct acacgaaaca gactaatcat gcattacgaa tcataattac gaaaaaaaat     480
taacaacttg aatcacaatg acgaaaaaaa attcagaaat tatatcagat tgaaattcga     540
ttgggtcaaa attatggtcc attaaatatc aaattaaaat ttgtagatct tcaatgaagt     600
tttttatatc taaccgttag agaggaggag agaatatttt tagagagaga aagggttttt     660
tagaaagaat gtgataataa gggtttttg ggttttttt aggctgcgtt agtaaagtga      720
ggctgcattt agcaaccttt ttttttggt aaatttcatt tcctcgatga acaaggaaac      780
gaaacggcga gatggcggcg ttggtggaat ttcccggcga aacgcagctt cctttcgatt     840
catagttgcc ataaatttgc attttaccca gatttcaaat aattttttact aattcgctca     900 aattgctcat gaaattgttt atttccgcaa atttttttgat taacccctcc agaatttgat     960
```
tcgcaaatat ggcgaagcta ttgagta                                          987

<210> SEQ ID NO 5
<211> LENGTH: 12364
<212> TYPE: DNA
<213> ORGANISM: Beta vulgaris

<400> SEQUENCE: 5

| | | | | | |
|---|---|---|---|---|---|
| ttctgttccg | cacatctgga | gagaagatgc | caaaatccaa | ctggggtgga | ctggcctaac | 60 |
| attcaacaca | tcccctccat | tgatgtcacc | tctagccttc | ctaagttttt | agtgttgccg | 120 |
| tatgaatagg | tatatacttc | tttggttttg | gttcgtgctt | ccatttagct | caaattggaa | 180 |
| atgagcgtat | ggcgtcagat | ggtgaccaat | ctgcagttat | tgcgctacgt | gtatgttctg | 240 |
| gtttatattg | atggcaatgt | tcaatagttc | attataatcc | caatcaaatt | tctttgtcca | 300 |
| tgtttataa | tcccaaatcc | aatttctttg | gaagattgtg | ctgaggagag | cttgatgaag | 360 |
| gaacttgttt | aaggtttttt | ctcttataga | ttatctttct | accattgttt | ataatcccaa | 420 |
| ctgcatcttg | gtctgagaag | gaattcaata | ttttttctag | ttttacttga | ggttaaggct | 480 |
| gtttataatc | acaggctttg | ccaatagtat | aattttata | aagtactact | gtacagatta | 540 |
| tgtgaatctt | caaaggtttg | agagaatcgt | cctaaattca | tgtaaacttg | gagttaagga | 600 |
| gcaggaaatg | gagttacttc | aagtgttaat | gcaatcagct | caaaaaatta | ctaatacaga | 660 |
| acttattcgt | gtcacaactc | agaagccttt | ataaattata | aaagtagtaa | agatttcgtt | 720 |
| tcgaaagtat | tattcatatt | agagtacaat | gaataaattg | ctttggcaaa | gccatctgaa | 780 |
| ggtccttaag | aaatgtttag | tgcaggtgat | ttaacttgct | gtgattatgt | caccaggaga | 840 |
| acttgcttat | caaagaattc | agtagcaagt | tggtcgatac | tcgacagaac | atccttatca | 900 |
| aacatgttag | tgcagaggtc | agagcatgat | accctttcat | tagtattata | ttttacatta | 960 |
| ttaagaaata | tatttacatc | tgaaattata | tatgctgata | caataatctt | atgcattttg | 1020 |
| agttatacat | taaacacggt | gaaaaacatt | atttcgagca | tctgcatttg | tgcttgtggt | 1080 |
| tgtgtaatgg | taaattggca | attgcttgac | ctttgtttaa | ggctgggtaa | gctttcaaaa | 1140 |
| agttgaattg | tttagcagta | gatcagtaac | tatccaaaca | aagaccaagc | tatacgccaa | 1200 |
| ctgtttcttc | acgttcactg | tacaagtgtt | aaagtatctt | caatgggaat | accgaaatct | 1260 |
| aaagtcaatt | atccaattaa | tagtagtcaa | aagtcaaaca | tctctgtatg | aatatgtaga | 1320 |
| ttgaagagtt | tctgtatgca | ttcaattcaa | tgcaacaagt | tgtattcgtt | cacaccttat | 1380 |
| tacttggtca | aaagttgact | aattttacac | aaggaacttt | agcatcaatc | atcatcctac | 1440 |
| tatctacgag | ttgaaagaaa | cttgtacaaa | aacttgtttt | aaccctgata | cagttcagtt | 1500 |
| aagcctgttt | gttgatcagt | ctgcaatttg | aatcactcgt | ccactcgcat | gacttagtgt | 1560 |
| gcgatcttgt | gtctagtttt | ctcgagaccc | cgcctcctga | ccgtgcccag | cccacccaa | 1620 |
| ccattcccag | ctctactagc | tagtatcagc | atacatggga | agagccagga | ctgtaagcat | 1680 |
| gtcgtttacc | gagtcacagc | tgctgtcagc | agcaggagat | ggagatgagg | aattcctaat | 1740 |
| acaagctctt | gctactcaac | ctattgatta | cttcctaacg | cggagcaaaa | acaaaaatgg | 1800 |
| tgaagaacat | tgcaatatta | tccacattgc | agtgttaaat | gaacaagcaa | agttcctcaa | 1860 |
| tcgagcattg | agtatattac | ccatctcaac | tctgcatctc | cttctctgtc | agcaagattt | 1920 |
| ttcctacttt | agctacaacc | ctcttcactg | tgcatcttta | cgaggtaact | ttgctattgt | 1980 |
| caagctcctc | gtcgagtttt | acgaatcatc | atcatcttct | tcttcgtcat | tggttgatcc | 2040 |

```
aagctgtaag ccatggttag ccaaggatgt gaacgggaag acgcctttac aggtggcttt      2100 ggatagggggt agaggtgaat gtgcattaaa aataatggga ttagatgaag aattgctttg     2160
taatatggtt gataataaag gtaacagccc gctatttcaa gctgtacaaa gaggtagtga     2220
acaaattgct atgaagatct tggcatcagg gcattcttat agtactggtg gcgagtatga     2280
gttgactccc cttcatgttc taccaaattg ctcaggtgtg tagtattgat ttgttttca     2340 atttgttaaa atttcttacg ctttctgtcc cttaattttt ctcacatgtg ggtttgacac     2400
agacatttag tgttaagagc aacttcaatg gtcagctatg cactcttcta acttagcttt     2460
ccacctcaac tacattcaag taacattagt ttcaggctac aacgtccttt tgggtgcatt     2520
tcttcacttg aacttatatc aaaaccgagc ttattactct tgattggacc taatcaacca     2580
tgatacgtgt tttcgggaag ttaacagttt cctaatttag ttttcttctg tacaatttca     2640
agataactaa taaagtatta gcaatcttaa ctataaaaaa agaagaaaac actagcctaa     2700
tatcatctga tctgcagagg aagtttgcga acttctactt gacaagcatc cagaaatgat     2760
aaaagcagtc gacaaaaatg gacttacaat cctcacaaaa tgggcaatga tgggtaaact     2820
atggccattt caatttcttt taaagcaaga aaaagttct aggttgagga aggacttcat      2880 caaccttta tgtgcaactg agaagtcgac aggcaacaat cctttacaca cagcagctta     2940
ttaccacaat gaagaaactg cgcaggttgt gcagcttctt gtagaagctt atatagatgc     3000
taaggaacaa ggagtggagc ttcagccgag ccccttggaca tgtgagaata tagaaggaga     3060
tacacctttg atggtatcct taatcaacaa acatgaaaaa ttggcactgt atttcatgtc     3120
tgtggatatg gagaattcag ttgtatatgc aaccaagagt gtactatatt gtgctgtact     3180
gcgtggatgt gatgaagttg cagaagaaac agtggcttca gttgatcctg cctgcttcag     3240
cttcatgcag cttaaagacg atggtgggcg aaatgtcttg catgttgcat caaattgcac     3300
aggtgaggtg agagtaccct attgcttgta tatctttctt cttatttgaa aaatcttgga     3360
ggaactaagc acaagcaagg ccaaggcttc gtcgtgctgt ggtgggctca agaaggcct      3420 atgcacagcc tggcccacat gggtgcaggc ggcctcttta agaaattgag gaggccgaaa     3480
cacggctggc ttttgggct tgtgctcatt ttcaaaattg atgcccatta cagcccacgg      3540
agcactgctg tgatcttgtg tcgtgagtca tgacaggcca gtaacgggct tgtgctgggc     3600
aagtaatatg gcataactat ccttatcatt atttataacc ggaacatctc atatatgcaa     3660
acctttaatt ctgactttga tcagtttatt atagaacatg gaaatcgaac atatctcagc     3720
agcatattca agctattgta aacttctttta aataattaag gtggtagacg tatatgcctt     3780
gtattatttc tggtcaaaat gagtatcagg gaaatctaat aaaacaattt aatctttacc     3840
tatatagcaa gaaaacagtt gggattttga aaacgggaaa atcttgagtc ccatccattt     3900
atttgcttca ttaccacgga actggggaaa tttcacatac ttgaagtttc ggtgcttcat     3960
agattctaac attgaagtgt ttatacagag agaacaggca ccttgttggt ggaaaagcta     4020
gcttggttga tcaacgagcc agatgatgat ggaaagagac ccttgatat agcttcgaaa      4080 gttggtaacg catggcttat aaaattactg ctgacaaaag acccttcctc aaacacaagt     4140
gcgccatttg cttggattga agcatgtaaa aaaggctact tatcagcaat acatgctttc     4200
atagaccatt cccctgattt tagaacattt tgtctccaaa gaaaagactc tcctttacat     4260
cacatacaac tgagaagtta caaagaatac caagaatttc ttgctattcc gttgattcaa     4320
gagatgaaaa atatgctcga tttcagtggt tcaacgccct tgcatcgagc attagaacgt     4380
aaggatatcc tccttgctga agcactgctc tctggcgatg gggttcatag aagcatcaaa     4440
```
gataaaaatg gtaaaactgc taccgacctg ctagtaaagc tgtgcgacca agagtatgaa 4500
tgggtatgtg tctccagtct ccacctaatt cttccaatct agaaaactat gattgcatta 4560
ggaaatactt ctatgtcagt tgtcactatc atcccttgct tgctataagt ctacattgtc 4620
ttggcaaaaa cataaaatga gcataaatat aaaggttaat tttttctagg gaaattgtac 4680
tgcgtatacc ctaaactaga atttgccaaa taaccttaga gattcaaaat atatccataa 4740
ctattaactt tggctaattt gtaatggttc tctcttatac aatttattga ttcaaaccta 4800
tttctgctga ttaaacttga tcattggtaa tattgaagaa aaattctcat ggccttgcaa 4860
gacagtgaag tttccatgaa tctcggaaaa atgacagcca caggataaaa taagactgct 4920
ttagacagca tagtagctct tatgttttac tatatacaag aatatgtaaa agccttgatc 4980
tatgaaatga attgttctat atatattatt atggtgatat gcaagctcct tctttgaatt 5040
caatttcaaa caaaatgcag gatactatgt gcaaacgtac acaaattagt ccgtggctaa 5100
cgacaaacta tatcggaact tcccttgcta ataaggcctt tagatacaca ggcagtacaa 5160
gacttggtac aacaccatca gcaggagaaa tgcgtagcac actttcagtc gtagcagccc 5220
ttctagcaac ccttacattt gcagctgggt ttacacttcc tggaggcctt aacgaagata 5280
ctggcgaagc catcttagca aagaaggttt catttctagt gtttatacta gcagacacat 5340
acgcgatgtg ttgctccatg ttggtgctgt tctgcctcat atggtctatg gttagcgaca 5400
gagataagtc acttctactg attgatcgaa gtgttgtgat actcgtccaa tcactttatg 5460
gaacgttaat agcatttatg gctggagttt acactgctat atcacacaag tctttgtggg 5520
cagctattat agtcattgtt atgtgctctt tcgttgcgat ttcagctaac agagctattc 5580
tggataaagt gcttgataag ttgatccctt cggctgatag taagagaaga aattaaaccc 5640
agacactgga tggatgtctg gatgatgtag gctctcctat aatctttcac tatcttatga 5700
ttttggatat tactgtctgc aaatgttaaa ctcacacatt gctattatag ttctttgtta 5760
tgcaagtatg gattcaactc tggactttgg tcagtctggt aactagttgc agcccatgac 5820
cccaactttt agttattctt atactacctc tgttttgttt ataatacatt ggtacaaatc 5880
ttattcatgt tactagatga acatgctaat gactagtttt ataatcggct tgttagatgg 5940
agctctgagt acacatttga aaaatatatc taattaaaaa tattaaaccg actttaaact 6000
tgtacgatac atgagattat aggaaataaa gaatataagt tttctaatta ttatacggtt 6060
ttaggaaaat ttagcaatta gtttagttat tatattaatt tgatacttag attttcaatt 6120
agattatact agagtatata aaatttccta attatatgta ttcggttttc aatcagaaaa 6180
taatgattta gttttattat aaaattaaat tacttttttt agacggtgct tttctctcca 6240
aagtttcctc ctttattcac acatgctaaa catggaagaa tatatgtagc attattgttt 6300
tcacacatca ttttctaaag gttgtatgat tcttattcca aagcaaatta ccttcgataa 6360
tgttgttact cgatatctaa taaaaaactt ttccatagat gatatcaaga ccttaatgat 6420
tttaataatt atccaaataa tcgccagagc aactagtact ttttaaacaa taatatattt 6480
tttttgacaa tggggtaaac aataatattt cttacataaa cattttcata ttcttagggg 6540
gaaaaaccat taagaaaaat gcatgtatct attggatctc tatacaagtt tattttgata 6600
gttcgagccc taaattttgt cagcaagtca tatgtaagat ttgtgtataa actataaagt 6660
gaactattgt ttatttatta gctatgaatt aggtttcaca aaatattata taaagttgaa 6720
tgatgattaa cggaaactat actgatatta tcatttgaga ttttctcttc atgtaaaaga 6780

-continued

```
ccatttatct tatcccttat ctctactagt ctactttaag ttcttgtgtt atgtttaatt   6840
tttgtcatgt atttacctaa atgctagttt tacattcaca actccttttc ttcactagag   6900
ctatttaaca tttcaaaata cgctataatt ttatattagc aaatataaac gtaatgatcg   6960
ggattcctta tattttttca caaattatta gaataggcgg tctaattttt acataaatta   7020
gatgaactta gaagtgaatt tttcaaacaa acccattcca tttcactcta acccaacact   7080
atcttagtca tcccttatct tttgcttcct ttgttttctt gattctcgaa ctacaacaga   7140
caattttaag aaataactcg gtattttat cgaacggatt aaactagtca ctaaatggat   7200
aaacaagtca ctgaatgggt tagtgaatgt cattcacgaa atagattaaa ttggtcacga   7260
aatagagtca ctatatttaa aaaggtggca tgttctctgc tgaatattag acttgcaccg   7320
tgcctaattt taaagtagg cgatatctta caagacaact gtcattttc cacttccta    7380
ataatgagta atcatgttca tgtatcatac tccttgaaca tgacatatat attttttctag  7440
aatgaaaaat cacctaacac aaaaagggga accaattaga aagagagaaa gaaaagtaac   7500
acaaacaaca atcaaaacat gaaaacaact agcaaaattt attaagtact aattaataca   7560
tctagttacc taaaatgcac tctaattact ttaaaaagtt caaactccaa caatagtgca   7620
aattagcata aacacttgtt acagcaagtt gtgcaaactc agacacacag accacagaag   7680
gcggagtccc cacaccagag gggcaactct aatttctcca acgtctcctt tttctttctc   7740
ttcttctcct ttcatcttct ttgctttctc cctccagaat cttttctctct cttccatttc   7800
caggtttctc tctcctcttc tctgcttctt attttttgaa agatgcaaac ttttactgaa   7860
atttatgttt tgaatagtgt tacttattgt tatgctttaa attctgagtt gggtcacttt   7920
cattttgtt tgaatttaat gggtttttgc tgaattatgc tcttttact ccagtgaacg    7980
gttttcagt ttctgggtgt taactgtatt tagttaatta agattggttt gaattcaaaa    8040
aaaacttagg gtttactatt ttccatgctt aatctttatt ttttaatgtc tgaatatgta   8100
aaaatgtaaa aattctatgt tgaaaaactg agtaaaatag tatcaaatca agttttgaa    8160
gctttgaatt actgatatgt tgtagtttgg tacttggttt gatctgtgag attattcata   8220
agatgctatc tttatttcct gttttctttt tagtgcaaat attctgaata aaatatgcat   8280
tagtttactt ttatatagaa tataagtatt tgggattcta agttatggga cactcaattt   8340
tatatgcaga tccagctgtt ccagactaga ctaacttggt agcttgagct tcacttgttg   8400
tgcttggatc tgttaagctt ggaagttttg ctgatttagc gccatatgtt ctagatgtat   8460
tgtattagtc aagtaaagtt ttgatatcga aatttggacc tttagtggca taagagtggt   8520
ttattcttca tttagaattt tgaccttgag cttagttttg gaattgagtg gttgagaaac   8580
ttcaaacact ttggcttttc agtttattat acccgggttt ttattgagga aggtagtgag   8640
aaagctccag gaaaatttga ctcttgtgtc tacagaaaag tcacttagtc ttctcctata   8700
attttgctgt aatcctggtt ctggacctct aggctctgga atggcagttg gcaaaaacag   8760
cagtaacgct ggatcattaa ctcggccatg tcattgtttc aaggtggcaa acttgaagga   8820
aactattttg gatgctagcg agacatccga gttaaaagat cgttatgttt gggagatca    8880
actaggttgg gggcagtttg gtgtgatccg ggcatgtgct gataagttta ctggagaact   8940
actggcgtgc aagtccattg ccaaagatag acttgtaaca caagatgatg ttcgaagtgt   9000
gaagctcgaa atcgagatta tgagcaagtt gtccggtcat cctcatgttg tcgatctcaa   9060
agctgtttat gaggaagaag attatgtcca cttggtgatg gagctttgtg ccggtgggga   9120
gttgttccac cgattagaga aacaaggaag gtattgcgag tctcaagcca agtcatctt    9180
```

```
caggcatcta atgcaagtag tcttgtattg tcatgataat ggtgttgttc atagagattt      9240
gaagcctgaa aatgttcttt tggcaaccaa gtcttcttct tcgccaatta aattagccga      9300
ttttggtctt gctacatata tcaaaccagg tagaacactc ttcttcatct agtttgtgat      9360
tttagctgtg ttactcggtc tctttcaatt cacctcaata gctgtccatg ttgaattttg      9420
gataatttga tcaagtcagt ctggcccta aacatgttcc tgcgcccaac actaacagtg       9480
tcttaagcct ttggttactg gtcaagcagg ggagagtttg catgggacag tggggagtcc      9540
tttctatata gctcctgaag ttctgtcagg aggttacacc caggctgctg atgtatggag      9600
tgctggcgta attctctaca ttctcttgag ttctatgcca ccattttggg ggaagacaaa      9660
gtcaaggata tttgatgcag ttcgagcagc tgatctgcgc ttcccttctg aactttggga      9720
tcggatatca gaacctgcca aggagctgat caggaaaatg ctttgtgtag atcctttgaa      9780
gcgcttgaca gctgagcaag ttttaggtat atttttaatt tttgcctcct tgctgaatt       9840 cagatgacag ttatatgaca cagtatacat ttgtagaacc caagtgtctg aatagccaat      9900
caccaatgtc tgacaagttt ttttttggctt tcgattacaa aatcatttat tacatatttg     9960
cattaactgt gttattttg acacattaca tgaaatcttc attgcttatt tgtgattctt      10020
tgtgaattgc tgtacattgg aagctgctcc cttttaacat ttgagatgtc cgtaagtggt     10080
gagtgtaact catctgtccc cacggagaca aagcttttgg atgattttag acaaatgca      10140 tttaacgttc tcagcttatc tgacaatgtt atccatggtg tccgtggaca catgtaccaa     10200
cactaaacat ctagtatttc ttgttggttc tttagttttg ctggatatac ttaagggcta    10260
aggctttatt tttgttcctg cagctcactc atggatggaa gaggttactg tagctacgga    10320
agaatcacat gaacatgatt tggcctgctc tgaacattta aaaacccgag atagctcatt    10380
ttcagcgtca tgtatatcca gggatcacga tataagcttt ggcactggat ctgcggtaaa    10440
ttgtgaacct caatctccaa catttacgtg cagatcttca ttctcggcat ttatggcgga    10500
accatccacc cctaccctta tatctgctgg atttttcttc cgtagcagcg gtgatttcac    10560
tgctcttgag tttgtttctc caattccttc cttgcctagc ttcacatttt tcagccctag    10620
gtcagtagat gagcatggaa accaaaataa ggttttttca agcaacaggg agaacactga    10680
cgaaattcat acaggtaact cacttttcta tttgtaataa tttgttattg tcactgattc    10740
tctaatgtca tttttgcatc tctaggtctt gtaacatttt aaacgtcata taaacatcca    10800 tgacattta tgtattttgc tcaactttca agtattttg tatgactttt aaactttcaa      10860
gttttatctg cgtataactt ttcatagcct aaccgtttct ctgttgtata agtatatgcg    10920
aaaaatcatt catcacatga attgtttgaa tctaatgttg gattgtgcag cctaaccaac    10980
tcgagtttct taaaaaaaat tgttctgtaa ttcaattatg tcctccatat cttatctttc    11040
tttactttta aagcactatt gagaaacaga agaaaacccc agtgtgacga ctgtcagatg    11100
tggtttgatt gagattagac tattttatca gtgttgtgtt attgagattc cagtgctgtt    11160
aatatcatta gttccatcgt aagctttaa agttatcaat tcataaaact agatctaatg    11220
cccatcgtat ttttagaagg ggccgacttg gagaagcgat ttgaatcacc tcattcatcg    11280
ctgtgctcag gaattgatgc tagggacctg aaagagaagt cagcagactc taagaggagt    11340
ggaggaacag gggtgaggat ttttgggatc cataacaaga gaaataggac gattgggctt    11400
ggcgaattca accagcttga tattgtggtc actgaatctg tcatccgatg ggcgtcatgc    11460
acccacttac ctaccgcctc atcactcagg tcttctcttg tatgctgata atcatgggcc    11520
```

```
gaccacaatg tatcaaatta acatcataaa tcatgatata aagttgggca acacgcaaac   11580
gtgtgaattc tactgctctg ctacaagatt gaagatataa tgggtttgag tcgcgtgtac   11640
tgttggtgat gatcatccca tattagagag ctaaatgtta gtaactacat tgtaatggat   11700
ctgcagaata agcagattct tcttcaaaag gtgtaaagca tggattttga aagcaatggt   11760
tttctcaacc ttttttgatca tgatttagta gatatatata gggggctttt tgttcttatt   11820
agatgtgatt gttaagcctt cttcatgaac aaacataagc actggtgact tgtgggatgg   11880
tacatagaaa gagttccgtt tcatcgattt tgattttgtc cagatcctcc ttttctttcg   11940
aaaaaaggga aggagagtat ccgaaagatt acccattttg tattttcggt tgtctttaaa   12000
agattgatcc attacctttc ggacaatttg attcctataa tactcctatt tctctacttc   12060
atttcctgcc atatactact atactaaaga caaaattact taatacgaac ttaaaattaa   12120
gaggagaaac aaggtaaaat tggtgagga tgatggagga atcatatgaa agcttacgca   12180
cattatatat ttgggagtat gatgtacact agttaatgaa gatcagacac ttttctatat   12240
cttttgattc gtatgttctt taataaatga agatggtata tttaaaattt cgtgtgtatt   12300
tgaaaatatc atgcacatta gacatccaag tctaagatta attcacaact atctattttt   12360
tttt                                                                12364

<210> SEQ ID NO 6
<211> LENGTH: 4659
<212> TYPE: DNA
<213> ORGANISM: Beta vulgaris
<220> FEATURE:
<221> NAME/KEY: modified_base
<222> LOCATION: (461)..(485)
<223> OTHER INFORMATION: a, c, g, or t
<220> FEATURE:
<221> NAME/KEY: modified_base
<222> LOCATION: (621)..(696)
<223> OTHER INFORMATION: a, c, g, or t
<220> FEATURE:
<221> NAME/KEY: modified_base
<222> LOCATION: (704)..(707)
<223> OTHER INFORMATION: a, c, g, or t
<220> FEATURE:
<221> NAME/KEY: modified_base
<222> LOCATION: (1115)..(1123)
<223> OTHER INFORMATION: a, c, g, or t
<220> FEATURE:
<221> NAME/KEY: modified_base
<222> LOCATION: (1169)..(1170)
<223> OTHER INFORMATION: a, c, g, or t
<220> FEATURE:
<221> NAME/KEY: modified_base
<222> LOCATION: (1879)..(1880)
<223> OTHER INFORMATION: a, c, g, or t
<220> FEATURE:
<221> NAME/KEY: modified_base
<222> LOCATION: (2194)..(2194)
<223> OTHER INFORMATION: a, c, g, or t

<400> SEQUENCE: 6
caaatcttct ggcatcaatg gcggtgttgc cgttcatcaw tttaacatca atggaggtaa     60
gagtcatgtt ttttcaacaa tataaaactt atatgatttt tctgtttttc cccgtatctt    120
gtttgagatt gtgattatta agagagtcaa gtctcacaat attcgaaagt ctacgtaatc    180 caccteaaat tgacgaagaa aacaagcagg aaaggattaa gtaagttcgt ggaaccayta    240
gaattaattt tcaaatatag ctctacctaa tatatggcct acttttaatt ttaaataaga    300
agaaggtaat gtgattagaa acaaattggt cttaaattat tcattaagct taataatgca    360
taaactttat caagtgctat cttctttttca gggccgtctt gaagattttk ggkcccrgtt    420
```

```
ctattatgaa aattgrgccc ctaaatttat asaaaataaa nnnnnnnnnn nnnnnnnnnn        480
nnnnngatgg aaggttagag yyctaaagat agaaagttga aaatctaaat ataaatcatt        540
gacaaattta ttaagggtga gaaacaaggg tgttttcttc aaatatgaag caaaattttc        600
aaaataatat awtttkggsc nnnnnnnnnn nnnnnnnnnn nnnnnnnnnn nnnnnnnnnn        660
nnnnnnnnnn nnnnnnnnnn nnnnnnnnnn nnnnnncttc tttnnnntga tacaattttt        720
sagcgacatg attgtcgatt gatgcttata ttattgtata ctcgatccat attgtttaag        780
atgaattgtt tgtctttgat ggtctccaat gcatattttg tatwmttagg aattytaatt        840
atgtactatt agtasayaty gagaygaata caraatygcc ataatgaagt atgattattt        900
tarttatata ctttctccgt tccaaatata taartgtaac acttgtgtac tttatgcgta        960
ctaatgcata ayaacgtgca ctctccygtg tttaattata tacttttttga gagaagtgwt       1020 acattgggga ccatgggact gtgtataatt tgaccgcaaa atygaagtgt ygcatttgat       1080
tgaaaaygga garrgtagta tatagrtgga acacnnnnnn nnntgctgrt catctttggc       1140
caacaaaccm aaaattgata ttaatccynn twwtymrgkw yttttcatct ttttgacaca       1200
aaatggatgt tgtaggcwct gcgctatctg ctgcccaatc tctgtttgca gccctgcaaa       1260
gttctgagct caaagagatc ctctcgatct ttggctacaa atcccaactt gatgacctcc       1320
aacgcaytgt mtctaccatc aaygctgtat tccgtgatgc tgagaccaaa caggagctca       1380
ctcatgaagc acarcattgg ctcgaggaac tcaaggatgc tgtctttgaa gcagatgatc       1440
tgttcgacga gtttgtcact cttgccgagc agaagcaact tgtagaggct ggtggcagtc       1500
tttccaaaaa gatgcgccaa ttcttttctg attccaaccc ccttggcaty gcttatarga       1560
tgtcacragg ggttaagaag atcaagaaga agttggatgy tatygcttac aatcatcaat       1620 ttagcttttaa gattgatctt gagcctataa aagagagaag gctcgagact ggttctgtcg       1680
tgaacgcagg tgatatcatt ggaagagagg atgacttgga gaagatcgta ggtttgttkc       1740
ttgattctaa catccagcgt gatgtgtctt tccttackat wgtgggaatg ggagggttgg       1800
gtaaaactgc tcttgcccaa ctcgtgtaca atgatccaag ggtcagaact gcttttccat       1860
tgagatgttg gaattgtsnn tctgatcaag atcaaaakma actagatgtg aaagaaattt       1920
tgggtaagat tctgtctaca gctactggta agaatcayra gggttcaacc atggatcakg       1980
tgcaaaccya actacrrgaa caactatgtg gcaagagata cttgcttgtt ttggatgatg       2040
tatggaatga gaatcctaat caattgcgtr wyytkgkwra attcttcatg ggaggtcaaa       2100
ggggaaattg gattstggta actacgcgtt cgcaygagac arcgagaatt ataagagatg       2160
gtccattgca caagctscaa ggtttgtctg arrnaaaact yttggcgttt atytgtaagg       2220
tggaccttcg gatcagtgca accaaaattc cctaatgact ttgtcatgat tgcacgagat       2280
atagtygaca aatgtgctcg aaaccctytg gctataagag tggtaggaag tcttttgtgt       2340
ggtcaagaca agagtaagtg ctttcatttt catgagatmt gtttagccaa cattagaaag       2400
agycataatg atatcatgcy aatactgaac ctaagttacc atcatcttga acctccaatc       2460
akgagatgct ttagttattg tgcartgttt ccaaaggatt tccttatagg aagaagacg        2520 ttgataaacc tttggatggc acaaggttat attgttccat tagacaaaga tcaaagcata       2580
gatgaygcta gtgaggaata catatcaatt ttgytgcaga gatgtttttt cgaaaacatc       2640
ggaacagaaa aagatkatgt tattaagata catgatctca tgcatgatat tgctcaaaat       2700
gtcatgggga aggagctttg tacgacaaaa aacattagtg gcagcttgga taaaaatgtt       2760
```

```
cgccatctat ctcttgccag aactagtttt gcaagatact ctttyaatgc aactcatatt    2820
cgctccyatt tctrtgctgg ctactggtgt caggawkctg agataamcca gttytcagtt    2880
gaggcattag taccaaaytg tttgtgccta agggcattgk acctsgcttg gtcgaagata    2940
aaaagtktac cagactcrat tggtggattg ttgcatttga ggtacttaga tctttcrtat    3000
aasgaagaty tggaagtact tccgaactca attgcyaaac tatataatct rcaaacctta   3060
caattgaagg gttgcaagag attggaaggg ttaycaaaac atttgagcag gctggttaag   3120
cttcaaactt trgatatata tggttgcaay aatgtaactt atatgcccaa aggcatgggt   3180
aagatgactt gccttcacac tctcagtaag tttatagtgg gtggagaagg garttgttca   3240
agttggaagm aayggtttga tgggcwggaa gatctaaagg ctctcaacaa cctaaagggt   3300
catctggraa tccaaatcag gtggcccgaa aatactacag atgctgtcaa ggaagatgtt   3360
aagagggaag gattatacyt gaatcataag gaacatctca atcacattgt ggttgatttc   3420
agatgtgagg agggtggtgg aagaatggat gatgaggaag caagaagatt gatggaagag   3480
ytgcggccac atccttatct tgaaaatttg gctgtgaaag cataytatgg tgygaaaayg   3540
cctgrttggg yaacccttct yccaaatctt acagagcttt wtctttytga ttgtggggaa   3600
yyggagwrcc ttccatgcmt gggaaacttg gwtydtctra amgtyctccg rctttcgcat   3660
ttggcraaat tggagtayat tgragaagat agcwcatcag ctmwtttcag ktktaggcct   3720
ggaccrgaaa gtgcaggact atcattatac ttcccctccc ttgaackcct tgagttgaag   3780
crtttgyrya agttaaaagg atggaggaga rgggaagggt taggagatga tcaccagcct   3840
tttaatgaaa gcagcagcaa taagtcattg agaatagaaa gatgcccatt gctgacatttt  3900 atgccgctgt gtcccaagac agaaaaacdg catttagttg tatttaatga aygactccgg   3960
atagtgcata ctaaaggaga tgagaatttc tatgctccat acattcatc atcatctgat    4020 cctgaaaacc cgaggagcac tattcccatt cccatgttaa gagaggtata cataaacaat   4080
gtggcatggc taaattcgct gcctatggag gcttttaggt gtctcactca tatgacaata   4140
aaaaacgaca aggtagagag tttgggagaa gttggggagg tgtttcggag ctrctcatct   4200
tctttgcgat ccttgaatat cacaggttgc tccaacttaa gaagtgtttc tggagggctg   4260
gagcatctca ctrctttgga gatkttagaa atatacgaca cccataagct gagtctwtca   4320
gaagacccag aaggtgttgt gccatggaaa tcccttcatc actccctcag ctacttgmaa   4380
ttgatgaatc tcccwcagct ggtcaacctg cctgattcga tgcagttctt ggyctccctc   4440
caaacccttt caatggtgca ttgcagtaaa ctggaatcag tgccagattg gatgcccmga   4500
ctcacttcyc tcaggaagct tatggtttca ttctgttccg cacatctgga gagaagatgy   4560
caaaatccaa ctgggtgga ctggcctaac attcaacaca tcccctscat tgatgtcacc    4620
tctagccgtc ctaagttttt agtgttgccg tatgaatag                          4659
```

<210> SEQ ID NO 7
<211> LENGTH: 434
<212> TYPE: DNA
<213> ORGANISM: Beta vulgaris

<400> SEQUENCE: 7

```
gaactcaagg atgctgtctt tgaagcagat gatctgttcg acgagtttgt cactcttgcc      60
gagcagaagc aacttgtaga ggctggtggc agtctttcca aaaagatgcg ccaattcttt     120
tctgattcca accccttgg cattgctat aggatgtcac gaggggttaa gaagatcaag       180
aagaagttgg atgctatcgc ttacaatcat caatttagct ttaagattga tcttgagcct    240
```

```
atgaaagaga gaaggctaga gactggttct gtcgtgaacg caggtgatat cattggaaga    300
gaggacgact tggagaagat tgtaggtttg ttgcttgatt ctaacatcca acgtgatgtg    360
tctttcctta ctattgtggg aatgggaggg ttgggtaaaa ctgctcttgc ccaactcgtg    420
tacaatgatc caag                                                      434
```

<210> SEQ ID NO 8
<211> LENGTH: 885
<212> TYPE: PRT
<213> ORGANISM: Beta vulgaris
<400> SEQUENCE: 8

```
Met Asp Val Val Gly Thr Ala Leu Ser Ala Ala Gln Ser Leu Phe Ala
1               5                   10                  15

Ala Leu Gln Ser Ser Glu Leu Lys Glu Ile Leu Ser Ile Phe Gly Tyr
            20                  25                  30

Lys Ser Gln Leu Asp Asp Leu Gln Arg Thr Val Ser Thr Ile Asn Ala
        35                  40                  45

Val Phe Arg Asp Ala Glu Thr Lys Gln Glu Leu Thr His Glu Ala Gln
    50                  55                  60

His Trp Leu Glu Glu Leu Lys Asp Ala Val Phe Glu Ala Asp Asp Leu
65                  70                  75                  80

Phe Asp Glu Phe Val Thr Leu Ala Glu Gln Lys Gln Leu Val Glu Ala
                85                  90                  95

Gly Gly Ser Leu Ser Lys Lys Met Arg Gln Phe Phe Ser Asp Ser Asn
            100                 105                 110

Pro Leu Gly Ile Ala Tyr Arg Met Ser Arg Gly Val Lys Lys Ile Lys
        115                 120                 125

Lys Lys Leu Asp Ala Ile Ala Tyr Asn His Gln Phe Ser Phe Lys Ile
    130                 135                 140

Asp Leu Glu Pro Ile Lys Glu Arg Arg Leu Glu Thr Gly Ser Val Val
145                 150                 155                 160

Asn Ala Gly Asp Ile Ile Gly Arg Glu Asp Asp Leu Glu Lys Ile Val
                165                 170                 175

Gly Leu Leu Leu Asp Ser Asn Ile Gln Arg Asp Val Ser Phe Leu Thr
            180                 185                 190

Ile Val Gly Met Gly Gly Leu Gly Lys Thr Ala Leu Ala Gln Leu Val
        195                 200                 205

Tyr Asn Asp Pro Arg Val Arg Thr Ala Phe Pro Leu Arg Cys Trp Asn
    210                 215                 220

Cys Val Ser Asp Gln Asp Gln Lys Lys Leu Asp Val Lys Glu Ile Leu
225                 230                 235                 240

Gly Lys Ile Leu Ser Thr Ala Thr Gly Lys Asn His Glu Gly Ser Thr
                245                 250                 255

Met Asp His Val Gln Thr Gln Leu Arg Glu Gln Leu Cys Gly Lys Arg
            260                 265                 270

Tyr Leu Leu Val Leu Asp Asp Val Trp Asn Glu Asn Pro Asn Gln Leu
        275                 280                 285

Arg Tyr Leu Val Glu Phe Phe Met Gly Gly Gln Arg Gly Asn Trp Ile
    290                 295                 300

Val Val Thr Thr Arg Ser His Glu Thr Ala Arg Ile Ile Arg Asp Gly
305                 310                 315                 320

Pro Leu His Lys Leu Gln Gly Leu Ser Glu Glu Asn Ser Trp Arg Leu
                325                 330                 335
```

```
Phe Val Arg Trp Thr Phe Gly Ser Val Gln Pro Lys Phe Pro Asn Asp
                340                 345                 350

Phe Val Met Ile Ala Arg Asp Ile Val Asp Lys Cys Ala Arg Asn Pro
                355                 360                 365

Leu Ala Ile Arg Val Val Gly Ser Leu Leu Cys Gly Gln Asp Lys Ser
                370                 375                 380

Lys Trp Leu Ser Phe His Glu Ile Cys Leu Ala Asn Ile Arg Lys Ser
385                 390                 395                 400

His Asn Asp Ile Met Pro Ile Leu Asn Leu Ser Tyr His His Leu Glu
                    405                 410                 415

Pro Pro Ile Arg Arg Cys Phe Ser Tyr Cys Ala Met Phe Pro Lys Asp
                420                 425                 430

Phe Leu Ile Gly Lys Lys Thr Leu Ile Asn Leu Trp Met Ala Gln Gly
                435                 440                 445

Tyr Ile Val Pro Leu Asp Lys Asp Gln Ser Ile Asp Asp Ala Ser Glu
            450                 455                 460

Glu Tyr Ile Ser Ile Leu Leu Gln Arg Cys Phe Phe Glu Asn Ile Gly
465                 470                 475                 480

Thr Glu Lys Asp Tyr Val Ile Lys Ile His Asp Leu Met His Asp Ile
                    485                 490                 495

Ala Gln Asn Val Met Gly Lys Glu Leu Cys Thr Thr Lys Asn Ile Ser
                500                 505                 510

Gly Ser Leu Asp Lys Asn Val Arg His Leu Ser Leu Ala Arg Thr Ser
            515                 520                 525

Phe Ala Arg Tyr Ser Phe Asn Ala Thr His Ile Arg Ser Tyr Phe Tyr
                530                 535                 540

Ala Gly Tyr Trp Cys Gln Asp Ala Glu Ile Asn Gln Phe Ser Val Glu
545                 550                 555                 560

Ala Leu Val Pro Asn Cys Leu Cys Leu Arg Ala Leu Asp Leu Ala Trp
                    565                 570                 575

Ser Lys Ile Lys Ser Val Pro Asp Ser Ile Gly Gly Leu Leu His Leu
                580                 585                 590

Arg Tyr Leu Asp Leu Ser Tyr Asn Glu Asp Leu Glu Val Leu Pro Asn
            595                 600                 605

Ser Ile Ala Lys Leu Tyr Asn Leu Gln Thr Leu Gln Leu Lys Gly Cys
610                 615                 620

Lys Arg Leu Glu Gly Leu Pro Lys His Leu Ser Arg Leu Val Lys Leu
625                 630                 635                 640

Gln Thr Leu Asp Ile Tyr Gly Cys Asn Asn Val Thr Tyr Met Pro Lys
                    645                 650                 655

Gly Met Gly Lys Met Thr Cys Leu His Thr Leu Ser Lys Phe Ile Val
                660                 665                 670

Gly Gly Glu Gly Ser Cys Ser Ser Trp Lys Gln Trp Phe Asp Gly Gln
            675                 680                 685

Glu Asp Leu Lys Ala Leu Asn Asn Leu Lys Gly His Leu Glu Ile Gln
            690                 695                 700

Ile Arg Trp Pro Glu Asn Thr Thr Asp Ala Val Lys Glu Asp Val Lys
705                 710                 715                 720

Arg Glu Gly Leu Tyr Leu Asn His Lys Glu His Leu Asn His Ile Val
                    725                 730                 735

Val Asp Phe Arg Cys Glu Glu Gly Gly Arg Met Asp Asp Glu Glu
                740                 745                 750
```

Ala Arg Arg Leu Met Glu Glu Leu Arg Pro His Pro Tyr Leu Glu Asn
755                 760                 765

Leu Ala Val Lys Ala Tyr Tyr Gly Ala Lys Met Pro Gly Trp Ala Thr
770                 775                 780

Leu Leu Pro Asn Leu Thr Glu Leu Tyr Leu Ser Asp Cys Gly Glu Ser
785                 790                 795                 800

Glu Cys Leu Pro Cys Met Gly Asn Leu Asp Cys Leu Lys Val Leu Arg
            805                 810                 815

Leu Ser His Leu Ala Lys Leu Glu Tyr Ile Glu Glu Asp Ser Thr Ser
        820                 825                 830

Ala Asn Phe Ser Phe Arg Pro Gly Pro Glu Ser Ala Gly Leu Ser Leu
    835                 840                 845

Tyr Phe Pro Ser Leu Glu Leu Leu Glu Leu Lys Arg Leu His Lys Leu
850                 855                 860

Lys Gly Trp Arg Arg Arg Glu Gly Leu Gly Asp Asp His Gln Pro Phe
865                 870                 875                 880

Asn Glu Ser Ser Ser
                885

<210> SEQ ID NO 9
<211> LENGTH: 738
<212> TYPE: PRT
<213> ORGANISM: Beta vulgaris
<220> FEATURE:
<221> NAME/KEY: MOD_RES
<222> LOCATION: (290)..(293)
<223> OTHER INFORMATION: Any amino acid
<220> FEATURE:
<221> NAME/KEY: MOD_RES
<222> LOCATION: (555)..(555)
<223> OTHER INFORMATION: Any amino acid

<400> SEQUENCE: 9

Met Asp Val Val Gly Thr Ala Leu Ser Ala Ala Gln Ser Leu Phe Ala
1               5                   10                  15

Ala Leu Gln Ser Ser Glu Leu Lys Glu Ile Leu Ser Ile Phe Gly Tyr
                20                  25                  30

Lys Ser Gln Leu Asp Asp Leu Gln Arg Thr Val Ser Thr Ile Asn Ala
            35                  40                  45

Val Phe Arg Asp Ala Glu Thr Lys Gln Glu Leu Thr His Glu Ala Gln
50                  55                  60

His Trp Leu Glu Glu Leu Lys Asp Ala Val Phe Glu Ala Asp Asp Leu
65                  70                  75                  80

Phe Asp Glu Phe Val Thr Leu Ala Glu Gln Lys Gln Leu Val Glu Ala
                85                  90                  95

Gly Gly Ser Leu Ser Lys Lys Met Arg Gln Phe Phe Ser Asp Ser Asn
            100                 105                 110

Pro Leu Gly Ile Ala Tyr Arg Met Ser Arg Gly Val Lys Lys Ile Lys
        115                 120                 125

Lys Lys Leu Asp Ala Ile Ala Tyr Asn His Gln Phe Ser Phe Lys Ile
130                 135                 140

Asp Leu Glu Pro Ile Lys Glu Arg Arg Leu Glu Thr Gly Ser Val Val
145                 150                 155                 160

Asn Ala Gly Asp Ile Ile Gly Arg Glu Asp Asp Leu Glu Lys Ile Val
                165                 170                 175

Gly Leu Leu Leu Asp Ser Asn Ile Gln Arg Asp Val Ser Phe Leu Thr
            180                 185                 190

```
Ile Val Gly Met Gly Gly Leu Gly Lys Thr Ala Leu Ala Gln Leu Val
            195                 200                 205

Tyr Asn Asp Pro Arg Val Arg Thr Ala Phe Pro Leu Arg Cys Trp Asn
210                 215                 220

Cys Val Ser Asp Gln Asp Gln Lys Lys Leu Asp Val Lys Glu Ile Leu
225                 230                 235                 240

Gly Lys Ile Leu Ser Thr Ala Thr Gly Lys Asn His Glu Gly Ser Thr
                245                 250                 255

Met Asp His Val Gln Thr Gln Leu Gln Glu Gln Leu Cys Gly Lys Arg
                260                 265                 270

Tyr Leu Leu Val Leu Asp Asp Val Trp Asn Glu Asn Pro Asn Gln Leu
            275                 280                 285

Arg Xaa Xaa Xaa Xaa Phe Phe Met Gly Gly Gln Arg Gly Asn Trp Ile
        290                 295                 300

Val Val Thr Thr Arg Ser His Glu Thr Thr Arg Ile Ile Arg Asp Gly
305                 310                 315                 320

Pro Leu His Lys Leu Gln Gly Leu Ser Glu Glu Asn Ser Trp Arg Leu
                325                 330                 335

Phe Val Arg Trp Thr Phe Gly Ser Val Gln Pro Lys Phe Pro Asn Asp
            340                 345                 350

Phe Val Met Ile Ala Arg Asp Ile Val Asp Lys Cys Ala Arg Asn Pro
        355                 360                 365

Leu Ala Ile Arg Val Val Gly Ser Leu Leu Cys Gly Gln Asp Lys Ser
    370                 375                 380

Lys Trp Leu Ser Phe His Glu Ile Cys Leu Ala Asn Ile Arg Lys Ser
385                 390                 395                 400

His Asn Asp Ile Met Leu Ile Leu Asn Leu Ser Tyr His His Leu Glu
                405                 410                 415

Pro Pro Ile Arg Arg Cys Phe Ser Tyr Cys Ala Met Phe Pro Lys Asp
            420                 425                 430

Phe Leu Ile Gly Lys Lys Thr Leu Ile Asn Leu Trp Met Ala Gln Gly
        435                 440                 445

Tyr Ile Val Pro Leu Asp Lys Asp Gln Ser Ile Asp Asp Ala Ser Glu
450                 455                 460

Glu Tyr Ile Ser Ile Leu Leu Gln Arg Cys Phe Phe Glu Asn Ile Gly
465                 470                 475                 480

Thr Glu Lys Asp Tyr Val Ile Lys Ile His Asp Leu Met His Asp Ile
                485                 490                 495

Ala Gln Asn Val Met Gly Lys Glu Leu Cys Thr Thr Lys Asn Ile Ser
            500                 505                 510

Gly Ser Leu Asp Lys Asn Val Arg His Leu Ser Leu Ala Arg Thr Ser
        515                 520                 525

Phe Ala Arg Tyr Ser Phe Asn Ala Thr His Ile Arg Ser Tyr Phe Tyr
    530                 535                 540

Ala Gly Tyr Trp Cys Gln Asp Ala Glu Ile Xaa Gln Phe Ser Val Glu
545                 550                 555                 560

Ala Leu Val Pro Asn Cys Leu Cys Leu Arg Ala Leu Asp Leu Ala Trp
                565                 570                 575

Ser Lys Ile Lys Ser Val Pro Asp Ser Ile Gly Leu Leu His Leu
            580                 585                 590

Arg Tyr Leu Asp Leu Ser Tyr Asn Glu Asp Leu Glu Val Leu Pro Asn
        595                 600                 605

Ser Ile Ala Lys Leu Tyr Asn Leu Gln Thr Leu Gln Leu Lys Gly Cys
```

```
            610                 615                 620
Lys Arg Leu Glu Gly Leu Pro Lys His Leu Ser Arg Leu Val Lys Leu
625                 630                 635                 640

Gln Thr Leu Asp Ile Tyr Gly Cys Asn Asn Val Thr Tyr Met Pro Lys
                645                 650                 655

Gly Met Gly Lys Met Thr Cys Leu His Thr Leu Ser Lys Phe Ile Val
                660                 665                 670

Gly Gly Glu Gly Ser Cys Ser Ser Trp Lys Gln Trp Phe Asp Gly Gln
                675                 680                 685

Glu Asp Leu Lys Ala Leu Asn Asn Leu Lys Gly His Leu Glu Ile Gln
                690                 695                 700

Ile Arg Trp Pro Glu Asn Thr Thr Asp Ala Val Lys Glu Asp Val Lys
705                 710                 715                 720

Arg Glu Gly Leu Tyr Leu Asn His Lys Glu His Leu Asn His Ile Val
                725                 730                 735

Val Asp

<210> SEQ ID NO 10
<211> LENGTH: 738
<212> TYPE: PRT
<213> ORGANISM: Beta vulgaris

<400> SEQUENCE: 10

Met Asp Val Val Gly Thr Ala Leu Ser Ala Ala Gln Ser Leu Phe Ala
1               5                   10                  15

Ala Leu Gln Ser Ser Glu Leu Lys Glu Ile Leu Ser Ile Phe Gly Tyr
                20                  25                  30

Lys Ser Gln Leu Asp Asp Leu Gln Arg Thr Val Ser Thr Ile Asn Ala
            35                  40                  45

Val Phe Arg Asp Ala Glu Thr Lys Gln Glu Leu Thr His Glu Ala Gln
        50                  55                  60

His Trp Leu Glu Glu Leu Lys Asp Ala Val Phe Glu Ala Asp Asp Leu
65                  70                  75                  80

Phe Asp Glu Phe Val Thr Leu Ala Glu Gln Lys Gln Leu Val Glu Ala
                85                  90                  95

Gly Gly Ser Leu Ser Lys Lys Met Arg Gln Phe Phe Ser Asp Ser Asn
                100                 105                 110

Pro Leu Gly Ile Ala Tyr Arg Met Ser Arg Gly Val Lys Lys Ile Lys
            115                 120                 125

Lys Lys Leu Asp Ala Ile Ala Tyr Asn His Gln Phe Ser Phe Lys Ile
130                 135                 140

Asp Leu Glu Pro Ile Lys Glu Arg Arg Leu Glu Thr Gly Ser Val Val
145                 150                 155                 160

Asn Ala Gly Asp Ile Ile Gly Arg Glu Asp Asp Leu Glu Lys Ile Val
                165                 170                 175

Gly Leu Leu Leu Asp Ser Asn Ile Gln Arg Asp Val Ser Phe Leu Thr
            180                 185                 190

Ile Val Gly Met Gly Gly Leu Gly Lys Thr Ala Leu Ala Gln Leu Val
        195                 200                 205

Tyr Asn Asp Pro Arg Val Arg Thr Ala Phe Pro Leu Arg Cys Trp Asn
        210                 215                 220

Cys Val Ser Asp Gln Asp Gln Lys Lys Leu Asp Val Lys Glu Ile Leu
225                 230                 235                 240

Gly Lys Ile Leu Ser Thr Ala Thr Gly Lys Asn His Glu Gly Ser Thr
```

```
                    245                 250                 255
Met Asp His Val Gln Thr Gln Leu Gln Glu Gln Leu Cys Gly Lys Arg
                260                 265                 270
Tyr Leu Leu Val Leu Asp Asp Val Trp Asn Glu Asn Pro Asn Gln Leu
                275                 280                 285
Arg Asp Leu Gly Lys Phe Phe Met Gly Gly Gln Arg Gly Asn Trp Ile
            290                 295                 300
Val Val Thr Thr Arg Ser His Glu Thr Thr Arg Ile Ile Arg Asp Gly
305                 310                 315                 320
Pro Leu His Lys Leu Gln Gly Leu Ser Glu Glu Asn Ser Trp Arg Leu
                325                 330                 335
Phe Val Arg Trp Thr Phe Gly Ser Val Gln Pro Lys Phe Pro Asn Asp
            340                 345                 350
Phe Val Met Ile Ala Arg Asp Ile Val Asp Lys Cys Ala Arg Asn Pro
            355                 360                 365
Leu Ala Ile Arg Val Val Gly Ser Leu Leu Cys Gly Gln Asp Lys Ser
        370                 375                 380
Lys Trp Leu Ser Phe His Glu Ile Cys Leu Ala Asn Ile Arg Lys Ser
385                 390                 395                 400
His Asn Asp Ile Met Leu Ile Leu Asn Leu Ser Tyr His His Leu Glu
                405                 410                 415
Pro Pro Ile Arg Arg Cys Phe Ser Tyr Cys Ala Met Phe Pro Lys Asp
            420                 425                 430
Phe Leu Ile Gly Lys Lys Thr Leu Ile Asn Leu Trp Met Ala Gln Gly
        435                 440                 445
Tyr Ile Val Pro Leu Asp Lys Asp Gln Ser Ile Asp Asp Ala Ser Glu
    450                 455                 460
Glu Tyr Ile Ser Ile Leu Leu Gln Arg Cys Phe Phe Glu Asn Ile Gly
465                 470                 475                 480
Thr Glu Lys Asp Tyr Val Ile Lys Ile His Asp Leu Met His Asp Ile
                485                 490                 495
Ala Gln Asn Val Met Gly Lys Glu Leu Cys Thr Thr Lys Asn Ile Ser
            500                 505                 510
Gly Ser Leu Asp Lys Asn Val Arg His Leu Ser Leu Ala Arg Thr Ser
        515                 520                 525
Phe Ala Arg Tyr Ser Phe Asn Ala Thr His Ile Arg Ser Tyr Phe Tyr
    530                 535                 540
Ala Gly Tyr Trp Cys Gln Asp Ala Glu Ile Asn Gln Phe Ser Val Glu
545                 550                 555                 560
Ala Leu Val Pro Asn Cys Leu Cys Leu Arg Ala Leu Asp Leu Ala Trp
                565                 570                 575
Ser Lys Ile Lys Ser Val Pro Asp Ser Ile Gly Gly Leu Leu His Leu
            580                 585                 590
Arg Tyr Leu Asp Leu Ser Tyr Asn Glu Asp Leu Glu Val Leu Pro Asn
        595                 600                 605
Ser Ile Ala Lys Leu Tyr Asn Leu Gln Thr Leu Gln Leu Lys Gly Cys
    610                 615                 620
Lys Arg Leu Glu Gly Leu Pro Lys His Leu Ser Arg Leu Val Lys Leu
625                 630                 635                 640
Gln Thr Leu Asp Ile Tyr Gly Cys Asn Asn Val Thr Tyr Met Pro Lys
                645                 650                 655
Gly Met Gly Lys Met Thr Cys Leu His Thr Leu Ser Lys Phe Ile Val
            660                 665                 670
```

```
Gly Gly Glu Gly Ser Cys Ser Ser Trp Lys Gln Trp Phe Asp Gly Gln
            675                 680                 685

Glu Asp Leu Lys Ala Leu Asn Asn Leu Lys Gly His Leu Glu Ile Gln
        690                 695                 700

Ile Arg Trp Pro Glu Asn Thr Thr Asp Ala Val Lys Glu Asp Val Lys
705                 710                 715                 720

Arg Glu Gly Leu Tyr Leu Asn His Lys Glu His Leu Asn His Ile Val
                725                 730                 735

Val Asp

<210> SEQ ID NO 11
<211> LENGTH: 738
<212> TYPE: PRT
<213> ORGANISM: Beta vulgaris
<220> FEATURE:
<221> NAME/KEY: MOD_RES
<222> LOCATION: (291)..(291)
<223> OTHER INFORMATION: Any amino acid

<400> SEQUENCE: 11

Met Asp Val Val Gly Thr Ala Leu Ser Ala Ala Gln Ser Leu Phe Ala
1               5                   10                  15

Ala Leu Gln Ser Ser Glu Leu Lys Glu Ile Leu Ser Ile Phe Gly Tyr
            20                  25                  30

Lys Ser Gln Leu Asp Asp Leu Gln Arg Thr Val Ser Thr Ile Asn Ala
        35                  40                  45

Val Phe Arg Asp Ala Glu Thr Lys Gln Glu Leu Thr His Glu Ala Gln
50                  55                  60

His Trp Leu Glu Glu Leu Lys Asp Ala Val Phe Glu Ala Asp Asp Leu
65                  70                  75                  80

Phe Asp Glu Phe Val Thr Leu Ala Glu Gln Lys Gln Leu Val Glu Ala
                85                  90                  95

Gly Gly Ser Leu Ser Lys Lys Met Arg Gln Phe Ser Asp Ser Asn
            100                 105                 110

Pro Leu Gly Ile Ala Tyr Arg Met Ser Arg Gly Val Lys Lys Ile Lys
        115                 120                 125

Lys Lys Leu Asp Ala Ile Ala Tyr Asn His Gln Phe Ser Phe Lys Ile
130                 135                 140

Asp Leu Glu Pro Ile Lys Glu Arg Arg Leu Glu Thr Gly Ser Val Val
145                 150                 155                 160

Asn Ala Gly Asp Ile Ile Gly Arg Glu Asp Asp Leu Glu Lys Ile Val
                165                 170                 175

Gly Leu Leu Leu Asp Ser Asn Ile Gln Arg Asp Val Ser Phe Leu Thr
            180                 185                 190

Ile Val Gly Met Gly Gly Leu Gly Lys Thr Ala Leu Ala Gln Leu Val
        195                 200                 205

Tyr Asn Asp Pro Arg Val Arg Thr Ala Phe Pro Leu Arg Cys Trp Asn
    210                 215                 220

Cys Val Ser Asp Gln Asp Gln Lys Leu Asp Val Lys Glu Ile Leu
225                 230                 235                 240

Gly Lys Ile Leu Ser Thr Ala Thr Gly Lys Asn His Glu Gly Ser Thr
                245                 250                 255

Met Asp His Val Gln Thr Gln Leu Gln Glu Gln Leu Cys Gly Lys Arg
            260                 265                 270

Tyr Leu Leu Val Leu Asp Asp Val Trp Asn Glu Asn Pro Asn Gln Leu
```

```
                275                 280                 285
Arg Asp Xaa Val Glu Phe Phe Met Gly Gly Gln Arg Gly Asn Trp Ile
        290                 295                 300
Val Val Thr Thr Arg Ser His Glu Thr Thr Arg Ile Ile Arg Asp Gly
305                 310                 315                 320
Pro Leu His Lys Leu Gln Gly Leu Ser Glu Asn Ser Trp Arg Leu
            325                 330                 335
Phe Val Arg Trp Thr Phe Gly Ser Val Gln Pro Lys Phe Pro Asn Asp
                340                 345                 350
Phe Val Met Ile Ala Arg Asp Ile Val Asp Lys Cys Ala Arg Asn Pro
            355                 360                 365
Leu Ala Ile Arg Val Val Gly Ser Leu Leu Cys Gly Gln Asp Lys Ser
        370                 375                 380
Lys Trp Leu Ser Phe His Glu Ile Cys Leu Ala Asn Ile Arg Lys Ser
385                 390                 395                 400
His Asn Asp Ile Met Leu Ile Leu Asn Leu Ser Tyr His His Leu Glu
                405                 410                 415
Pro Pro Ile Arg Arg Cys Phe Ser Tyr Cys Ala Met Phe Pro Lys Asp
            420                 425                 430
Phe Leu Ile Gly Lys Lys Thr Leu Ile Asn Leu Trp Met Ala Gln Gly
        435                 440                 445
Tyr Ile Val Pro Leu Asp Lys Asp Gln Ser Ile Asp Asp Ala Ser Glu
450                 455                 460
Glu Tyr Ile Ser Ile Leu Leu Gln Arg Cys Phe Phe Glu Asn Ile Gly
465                 470                 475                 480
Thr Glu Lys Asp Tyr Val Ile Lys Ile His Asp Leu Met His Asp Ile
                485                 490                 495
Ala Gln Asn Val Met Gly Lys Glu Leu Cys Thr Thr Lys Asn Ile Ser
            500                 505                 510
Gly Ser Leu Asp Lys Asn Val Arg His Leu Ser Leu Ala Arg Thr Ser
        515                 520                 525
Phe Ala Arg Tyr Ser Phe Asn Ala Thr His Ile Arg Ser Tyr Phe Tyr
        530                 535                 540
Ala Gly Tyr Trp Cys Gln Asp Ala Glu Ile Asn Gln Phe Ser Val Glu
545                 550                 555                 560
Ala Leu Val Pro Asn Cys Leu Cys Leu Arg Ala Leu Asp Leu Ala Trp
                565                 570                 575
Ser Lys Ile Lys Ser Val Pro Asp Ser Ile Gly Gly Leu Leu His Leu
            580                 585                 590
Arg Tyr Leu Asp Leu Ser Tyr Asn Glu Asp Leu Glu Val Leu Pro Asn
        595                 600                 605
Ser Ile Ala Lys Leu Tyr Asn Leu Gln Thr Leu Gln Leu Lys Gly Cys
        610                 615                 620
Lys Arg Leu Glu Gly Leu Pro Lys His Leu Ser Arg Leu Val Lys Leu
625                 630                 635                 640
Gln Thr Leu Asp Ile Tyr Gly Cys Asn Asn Val Thr Tyr Met Pro Lys
                645                 650                 655
Gly Met Gly Lys Met Thr Cys Leu His Thr Leu Ser Lys Phe Ile Val
            660                 665                 670
Gly Gly Glu Gly Ser Cys Ser Ser Trp Lys Gln Trp Phe Asp Gly Gln
        675                 680                 685
Glu Asp Leu Lys Ala Leu Asn Asn Leu Lys Gly His Leu Glu Ile Gln
        690                 695                 700
```

```
Ile Arg Trp Pro Glu Asn Thr Thr Asp Ala Val Lys Glu Asp Val Lys
705                 710                 715                 720

Arg Glu Gly Leu Tyr Leu Asn His Lys Glu His Leu Asn His Ile Val
            725                 730                 735

Val Asp

<210> SEQ ID NO 12
<211> LENGTH: 728
<212> TYPE: PRT
<213> ORGANISM: Beta vulgaris
<220> FEATURE:
<221> NAME/KEY: MOD_RES
<222> LOCATION: (289)..(293)
<223> OTHER INFORMATION: Any amino acid
<220> FEATURE:
<221> NAME/KEY: MOD_RES
<222> LOCATION: (544)..(544)
<223> OTHER INFORMATION: Any amino acid

<400> SEQUENCE: 12

Met Asp Val Val Gly Thr Ala Leu Ser Ala Ala Gln Ser Leu Phe Ala
1               5                   10                  15

Ala Leu Gln Ser Ser Glu Leu Lys Glu Ile Leu Ser Ile Phe Gly Tyr
            20                  25                  30

Lys Ser Gln Leu Asp Asp Leu Gln Arg Thr Val Ser Thr Ile Asn Ala
        35                  40                  45

Val Phe Arg Asp Ala Glu Thr Lys Gln Glu Leu Thr His Glu Ala Gln
    50                  55                  60

His Trp Leu Glu Glu Leu Lys Asp Ala Val Phe Glu Ala Asp Asp Leu
65                  70                  75                  80

Phe Asp Glu Phe Val Thr Leu Ala Glu Gln Lys Gln Leu Val Glu Ala
                85                  90                  95

Gly Gly Ser Leu Ser Lys Lys Met Arg Gln Phe Phe Ser Asp Ser Asn
            100                 105                 110

Pro Leu Gly Ile Ala Tyr Arg Met Ser Arg Gly Val Lys Lys Ile Lys
        115                 120                 125

Lys Lys Leu Asp Ala Ile Ala Tyr Asn His Gln Phe Ser Phe Lys Ile
130                 135                 140

Asp Leu Glu Pro Ile Lys Glu Arg Arg Leu Glu Thr Gly Ser Val Val
145                 150                 155                 160

Asn Ala Gly Asp Ile Ile Gly Arg Glu Asp Asp Leu Glu Lys Ile Val
                165                 170                 175

Gly Leu Leu Leu Asp Ser Asn Ile Gln Arg Asp Val Ser Phe Leu Thr
            180                 185                 190

Ile Val Gly Met Gly Gly Leu Gly Lys Thr Ala Leu Ala Gln Leu Val
        195                 200                 205

Tyr Asn Asp Pro Arg Val Arg Thr Ala Phe Pro Leu Arg Cys Trp Asn
    210                 215                 220

Cys Val Ser Asp Gln Asp Gln Lys Lys Leu Asp Val Lys Glu Ile Leu
225                 230                 235                 240

Gly Lys Ile Leu Ser Thr Ala Thr Gly Lys Asn His Glu Gly Ser Thr
                245                 250                 255

Met Asp His Val Gln Thr Gln Leu Gln Glu Gln Leu Cys Gly Lys Arg
            260                 265                 270

Tyr Leu Leu Val Leu Asp Asp Val Trp Asn Glu Asn Pro Asn Gln Leu
        275                 280                 285
```

-continued

```
Xaa Xaa Xaa Xaa Phe Phe Met Gly Gly Gln Arg Gly Asn Trp Ile
    290             295             300
Val Val Thr Thr Arg Ser His Glu Thr Thr Arg Ile Ile Arg Asp Gly
305             310             315                 320
Pro Leu His Lys Leu Gln Gly Leu Ser Glu Glu Asn Ser Trp Arg Leu
                325             330             335
Phe Val Arg Trp Thr Phe Gly Ser Val Gln Pro Lys Phe Pro Asn Asp
            340             345             350
Phe Val Met Ile Ala Arg Asp Ile Val Asp Lys Cys Ala Arg Asn Pro
        355             360             365
Leu Ala Ile Arg Val Val Gly Ser Leu Leu Cys Gly Gln Asp Lys Ser
370             375             380
Lys Trp Leu Ser Phe His Glu Ile Cys Leu Ala Asn Ile Arg Lys Ser
385             390             395             400
His Asn Asp Ile Met Leu Ile Leu Asn Leu Ser Tyr His His Leu Glu
                405             410             415
Pro Pro Ile Arg Arg Cys Phe Ser Tyr Cys Ala Met Phe Pro Lys Asp
            420             425             430
Phe Leu Ile Gly Lys Lys Thr Leu Ile Asn Leu Trp Met Ala Gln Gly
        435             440             445
Tyr Ile Val Pro Leu Asp Lys Asp Gln Ser Ile Asp Asp Ala Ser Glu
    450             455             460
Glu Tyr Ile Ser Ile Leu Leu Gln Arg Cys Phe Glu Asn Ile Gly
465             470             475             480
Thr Glu Lys Asp Tyr Val Ile Lys Ile His Asp Leu Met His Asp Ile
                485             490             495
Ala Gln Asn Val Met Gly Lys Glu Leu Cys Thr Thr Lys Asn Ile Ser
            500             505             510
Gly Ser Leu Asp Lys Asn Val Arg His Leu Ser Leu Ala Arg Thr Ser
        515             520             525
Phe Ala Arg Tyr Ser Phe Asn Ala Thr His Ile Arg Ser Tyr Phe Xaa
    530             535             540
Ala Gly Tyr Trp Cys Gln Asp Ala Glu Ile Asn Gln Phe Ser Val Glu
545             550             555             560
Ala Leu Val Pro Asn Cys Leu Cys Leu Arg Ala Leu Asp Leu Ala Trp
                565             570             575
Ser Lys Ile Lys Ser Val Pro Asp Ser Ile Gly Gly Leu Leu His Leu
            580             585             590
Arg Tyr Leu Asp Leu Ser Tyr Asn Glu Asp Leu Glu Val Leu Pro Asn
        595             600             605
Ser Ile Ala Lys Leu Tyr Asn Leu Gln Thr Leu Gln Leu Lys Gly Cys
    610             615             620
Lys Arg Leu Glu Gly Leu Pro Lys His Leu Ser Arg Leu Val Lys Leu
625             630             635             640
Gln Thr Leu Asp Ile Tyr Gly Cys Asn Asn Val Thr Tyr Met Pro Lys
                645             650             655
Gly Met Gly Lys Met Thr Cys Leu His Thr Leu Ser Lys Phe Ile Val
            660             665             670
Gly Gly Glu Gly Ser Cys Ser Ser Trp Lys Gln Trp Phe Asp Gly Gln
        675             680             685
Glu Asp Leu Lys Ala Leu Asn Asn Leu Lys Gly His Leu Glu Ile Gln
    690             695             700
Ile Arg Trp Pro Glu Asn Thr Thr Asp Ala Val Lys Glu Asp Val Lys
```

<210> SEQ ID NO 13
<211> LENGTH: 727
<212> TYPE: PRT
<213> ORGANISM: Beta vulgaris
<220> FEATURE:
<221> NAME/KEY: MOD_RES
<222> LOCATION: (291)..(291)
<223> OTHER INFORMATION: Any amino acid

<400> SEQUENCE: 13

```
Met Asp Val Val Gly Thr Ala Leu Ser Ala Ala Gln Ser Leu Phe Ala
1               5                  10                  15

Ala Leu Gln Ser Ser Glu Leu Lys Glu Ile Leu Ser Ile Phe Gly Tyr
            20                  25                  30

Lys Ser Gln Leu Asp Asp Leu Gln Arg Thr Val Ser Thr Ile Asn Ala
        35                  40                  45

Val Phe Arg Asp Ala Glu Thr Lys Gln Glu Leu Thr His Glu Ala Gln
    50                  55                  60

His Trp Leu Glu Glu Leu Lys Asp Ala Val Phe Glu Ala Asp Asp Leu
65                  70                  75                  80

Phe Asp Glu Phe Val Thr Leu Ala Glu Gln Lys Gln Leu Val Glu Ala
                85                  90                  95

Gly Gly Ser Leu Ser Lys Lys Met Arg Gln Phe Phe Ser Asp Ser Asn
            100                 105                 110

Pro Leu Gly Ile Ala Tyr Arg Met Ser Arg Gly Val Lys Lys Ile Lys
        115                 120                 125

Lys Lys Leu Asp Ala Ile Ala Tyr Asn His Gln Phe Ser Phe Lys Ile
    130                 135                 140

Asp Leu Glu Pro Ile Lys Glu Arg Arg Leu Glu Thr Gly Ser Val Val
145                 150                 155                 160

Asn Ala Gly Asp Ile Ile Gly Arg Glu Asp Asp Leu Glu Lys Ile Val
                165                 170                 175

Gly Leu Leu Leu Asp Ser Asn Ile Gln Arg Asp Val Ser Phe Leu Thr
            180                 185                 190

Ile Val Gly Met Gly Gly Leu Gly Lys Thr Ala Leu Ala Gln Leu Val
        195                 200                 205

Tyr Asn Asp Pro Arg Val Arg Thr Ala Phe Pro Leu Arg Cys Trp Asn
    210                 215                 220

Cys Val Ser Asp Gln Asp Gln Lys Lys Leu Asp Val Lys Glu Ile Leu
225                 230                 235                 240

Gly Lys Ile Leu Ser Thr Ala Thr Gly Lys Asn His Glu Gly Ser Thr
                245                 250                 255

Met Asp His Val Gln Thr Gln Leu Arg Glu Gln Leu Cys Gly Lys Arg
            260                 265                 270

Tyr Leu Leu Val Leu Asp Asp Val Trp Asn Glu Asn Pro Asn Gln Leu
        275                 280                 285

Arg Ile Xaa Val Glu Phe Phe Met Gly Gly Gln Arg Gly Asn Trp Ile
    290                 295                 300

Val Val Thr Thr Arg Ser His Glu Thr Ala Arg Ile Ile Arg Asp Gly
305                 310                 315                 320

Pro Leu His Lys Leu Gln Gly Leu Ser Glu Glu Asn Ser Trp Arg Leu
                325                 330                 335
```

-continued

```
Phe Val Arg Trp Thr Phe Gly Ser Val Gln Pro Lys Phe Pro Asn Asp
            340                 345                 350

Phe Val Met Ile Ala Arg Asp Ile Val Asp Lys Cys Ala Arg Asn Pro
            355                 360                 365

Leu Ala Ile Arg Val Val Gly Ser Leu Leu Cys Gly Gln Asp Lys Ser
            370                 375                 380

Lys Trp Leu Ser Phe His Glu Ile Cys Leu Ala Asn Ile Arg Lys Ser
385                 390                 395                 400

His Asn Asp Ile Met Pro Ile Leu Asn Leu Ser Tyr His His Leu Glu
                405                 410                 415

Pro Pro Ile Arg Arg Cys Phe Ser Tyr Cys Ala Met Phe Pro Lys Asp
                420                 425                 430

Phe Leu Ile Gly Lys Lys Thr Leu Ile Asn Leu Trp Met Ala Gln Gly
                435                 440                 445

Tyr Ile Val Pro Leu Asp Lys Asp Gln Ser Ile Asp Asp Ala Ser Glu
            450                 455                 460

Glu Tyr Ile Ser Ile Leu Leu Gln Arg Cys Phe Phe Glu Asn Ile Gly
465                 470                 475                 480

Thr Glu Lys Asp Tyr Val Ile Lys Ile His Asp Leu Met His Asp Ile
                485                 490                 495

Ala Gln Asn Val Met Gly Lys Glu Leu Cys Thr Thr Lys Asn Ile Ser
                500                 505                 510

Gly Ser Leu Asp Lys Asn Val Arg His Leu Ser Leu Ala Arg Thr Ser
            515                 520                 525

Phe Ala Arg Tyr Ser Phe Asn Ala Thr His Ile Arg Ser Tyr Phe Tyr
            530                 535                 540

Ala Gly Tyr Trp Cys Gln Asp Ala Glu Ile Asn Gln Phe Ser Val Glu
545                 550                 555                 560

Ala Leu Val Pro Asn Cys Leu Cys Leu Arg Ala Leu Asp Leu Ala Trp
                565                 570                 575

Ser Lys Ile Lys Ser Val Pro Asp Ser Ile Gly Gly Leu Leu His Leu
            580                 585                 590

Arg Tyr Leu Asp Leu Ser Tyr Asn Glu Asp Leu Glu Val Leu Pro Asn
            595                 600                 605

Ser Ile Ala Lys Leu Tyr Asn Leu Gln Thr Leu Gln Leu Lys Gly Cys
            610                 615                 620

Lys Arg Leu Glu Gly Leu Pro Lys His Leu Ser Arg Leu Val Lys Leu
625                 630                 635                 640

Gln Thr Leu Asp Ile Tyr Gly Cys Asn Asn Val Thr Tyr Met Pro Lys
                645                 650                 655

Gly Met Gly Lys Met Thr Cys Leu His Thr Leu Ser Lys Phe Ile Val
                660                 665                 670

Gly Gly Glu Gly Ser Cys Ser Ser Trp Lys Gln Trp Phe Asp Gly Gln
            675                 680                 685

Glu Asp Leu Lys Ala Leu Asn Asn Leu Lys Gly His Leu Glu Ile Gln
            690                 695                 700

Ile Arg Trp Pro Glu Asn Thr Thr Asp Ala Val Lys Glu Asp Val Lys
705                 710                 715                 720

Arg Glu Gly Leu Tyr Leu Asn
                725

<210> SEQ ID NO 14
<211> LENGTH: 183
```

```
<212> TYPE: PRT
<213> ORGANISM: Beta vulgaris

<400> SEQUENCE: 14

Ser Thr Ile Asn Ala Val Phe Arg Asp Ala Glu Thr Lys Gln Glu Leu
1               5                   10                  15

Thr His Glu Ala Gln His Trp Leu Glu Leu Lys Asp Ala Val Phe
            20                  25                  30

Glu Ala Asp Asp Leu Phe Asp Glu Phe Val Thr Leu Ala Glu Gln Lys
                35                  40                  45

Gln Leu Val Glu Ala Gly Gly Ser Leu Ser Lys Lys Met Arg Gln Phe
    50                  55                  60

Phe Ser Asp Ser Asn Pro Leu Gly Ile Ala Tyr Arg Met Ser Arg Gly
65                  70                  75                  80

Val Lys Lys Ile Lys Lys Leu Asp Ala Ile Ala Tyr Asn His Gln
                85                  90                  95

Phe Ser Phe Lys Ile Asp Leu Glu Pro Ile Lys Glu Arg Arg Leu Glu
                100                 105                 110

Thr Gly Ser Val Val Asn Ala Gly Asp Ile Ile Gly Arg Glu Asp Asp
            115                 120                 125

Leu Glu Lys Ile Val Gly Leu Leu Leu Asp Ser Asn Ile Gln Arg Asp
    130                 135                 140

Val Ser Phe Leu Thr Ile Val Gly Met Gly Gly Leu Gly Lys Thr Ala
145                 150                 155                 160

Leu Ala Gln Leu Val Tyr Asn Asp Pro Arg Val Arg Thr Ala Phe Pro
                165                 170                 175

Leu Arg Cys Trp Asn Cys Leu
            180

<210> SEQ ID NO 15
<211> LENGTH: 728
<212> TYPE: PRT
<213> ORGANISM: Beta vulgaris
<220> FEATURE:
<221> NAME/KEY: MOD_RES
<222> LOCATION: (290)..(293)
<223> OTHER INFORMATION: Any amino acid

<400> SEQUENCE: 15

Met Asp Val Val Gly Thr Ala Leu Ser Ala Ala Gln Ser Leu Phe Ala
1               5                   10                  15

Ala Leu Gln Ser Ser Glu Leu Lys Glu Ile Leu Ser Ile Phe Gly Tyr
            20                  25                  30

Lys Ser Gln Leu Asp Asp Leu Gln Arg Thr Val Ser Thr Ile Asn Ala
        35                  40                  45

Val Phe Arg Asp Ala Glu Thr Lys Gln Glu Leu Thr His Glu Ala Gln
    50                  55                  60

His Trp Leu Glu Glu Leu Lys Asp Ala Val Phe Glu Ala Asp Leu
65                  70                  75                  80

Phe Asp Glu Phe Val Thr Leu Ala Glu Gln Lys Gln Leu Val Glu Ala
                85                  90                  95

Gly Gly Ser Leu Ser Lys Lys Met Arg Gln Phe Phe Ser Asp Ser Asn
            100                 105                 110

Pro Leu Gly Ile Ala Tyr Arg Met Ser Arg Gly Val Lys Lys Ile Lys
        115                 120                 125

Lys Lys Leu Asp Ala Ile Ala Tyr Asn His Gln Phe Ser Phe Lys Ile
    130                 135                 140
```

```
Asp Leu Glu Pro Ile Lys Glu Arg Arg Leu Glu Thr Gly Ser Val Val
145                 150                 155                 160

Asn Ala Gly Asp Ile Ile Gly Arg Glu Asp Leu Glu Lys Ile Val
            165                 170                 175

Gly Leu Leu Leu Asp Ser Asn Ile Gln Arg Asp Val Ser Phe Leu Thr
                180                 185                 190

Ile Val Gly Met Gly Gly Leu Gly Lys Thr Ala Leu Ala Gln Leu Val
            195                 200                 205

Tyr Asn Asp Pro Arg Val Arg Thr Ala Phe Pro Leu Arg Cys Trp Asn
210                 215                 220

Cys Val Ser Asp Gln Asp Gln Lys Lys Leu Asp Val Lys Glu Ile Leu
225                 230                 235                 240

Gly Lys Ile Leu Ser Thr Ala Thr Gly Lys Asn His Glu Gly Ser Thr
                245                 250                 255

Met Asp His Val Gln Thr Gln Leu Gln Glu Gln Leu Cys Gly Lys Arg
            260                 265                 270

Tyr Leu Leu Val Leu Asp Asp Val Trp Asn Glu Asn Pro Asn Gln Leu
        275                 280                 285

Arg Xaa Xaa Xaa Xaa Phe Phe Met Gly Gly Gln Arg Gly Asn Trp Ile
290                 295                 300

Val Val Thr Thr Arg Ser His Glu Thr Thr Arg Ile Ile Arg Asp Gly
305                 310                 315                 320

Pro Leu His Lys Leu Gln Gly Leu Ser Glu Glu Asn Ser Trp Arg Leu
                325                 330                 335

Phe Val Arg Trp Thr Phe Gly Ser Val Gln Pro Lys Phe Pro Asn Asp
            340                 345                 350

Phe Val Met Ile Ala Arg Asp Ile Val Asp Lys Cys Ala Arg Asn Pro
        355                 360                 365

Leu Ala Ile Arg Val Val Gly Ser Leu Leu Cys Gly Gln Asp Lys Ser
370                 375                 380

Lys Trp Leu Ser Phe His Glu Ile Cys Leu Ala Asn Ile Arg Lys Ser
385                 390                 395                 400

His Asn Asp Ile Met Leu Ile Leu Asn Leu Ser Tyr His His Leu Glu
                405                 410                 415

Pro Pro Ile Arg Arg Cys Phe Ser Tyr Cys Ala Met Phe Pro Lys Asp
            420                 425                 430

Phe Leu Ile Gly Lys Lys Thr Leu Ile Asn Leu Trp Met Ala Gln Gly
        435                 440                 445

Tyr Ile Val Pro Leu Asp Lys Asp Gln Ser Ile Asp Asp Ala Ser Glu
        450                 455                 460

Glu Tyr Ile Ser Ile Leu Leu Gln Arg Cys Phe Phe Glu Asn Ile Gly
465                 470                 475                 480

Thr Glu Lys Asp Tyr Val Ile Lys Ile His Asp Leu Met His Asp Ile
                485                 490                 495

Ala Gln Asn Val Met Gly Lys Glu Leu Cys Thr Thr Lys Asn Ile Ser
            500                 505                 510

Gly Ser Leu Asp Lys Asn Val Arg His Leu Ser Leu Ala Arg Thr Ser
        515                 520                 525

Phe Ala Arg Tyr Ser Phe Asn Ala Thr His Ile Arg Ser Tyr Phe Tyr
        530                 535                 540

Ala Gly Tyr Trp Cys Gln Asp Ala Glu Ile Asn Gln Phe Ser Val Glu
545                 550                 555                 560
```

```
Ala Leu Val Pro Asn Cys Leu Cys Leu Arg Ala Leu Asp Leu Ala Trp
                565                 570                 575

Ser Lys Ile Lys Ser Val Pro Asp Ser Ile Gly Gly Leu Leu His Leu
            580                 585                 590

Arg Tyr Leu Asp Leu Ser Tyr Asn Glu Asp Leu Glu Val Leu Pro Asn
        595                 600                 605

Ser Ile Ala Lys Leu Tyr Asn Leu Gln Thr Leu Gln Leu Lys Gly Cys
    610                 615                 620

Lys Arg Leu Glu Gly Leu Pro Lys His Leu Ser Arg Leu Val Lys Leu
625                 630                 635                 640

Gln Thr Leu Asp Ile Tyr Gly Cys Asn Asn Val Thr Tyr Met Pro Lys
                645                 650                 655

Gly Met Gly Lys Met Thr Cys Leu His Thr Leu Ser Lys Phe Ile Val
            660                 665                 670

Gly Gly Glu Gly Ser Cys Ser Ser Trp Lys Gln Trp Phe Asp Gly Gln
        675                 680                 685

Glu Asp Leu Lys Ala Leu Asn Asn Leu Lys Gly His Leu Glu Ile Gln
    690                 695                 700

Ile Arg Trp Pro Glu Asn Thr Thr Asp Ala Val Lys Glu Asp Val Lys
705                 710                 715                 720

Arg Glu Gly Leu Tyr Leu Asn His
                725

<210> SEQ ID NO 16
<211> LENGTH: 728
<212> TYPE: PRT
<213> ORGANISM: Beta vulgaris
<220> FEATURE:
<221> NAME/KEY: MOD_RES
<222> LOCATION: (291)..(291)
<223> OTHER INFORMATION: Any amino acid

<400> SEQUENCE: 16

Met Asp Val Val Gly Thr Ala Leu Ser Ala Ala Gln Ser Leu Phe Ala
1               5                   10                  15

Ala Leu Gln Ser Ser Glu Leu Lys Glu Ile Leu Ser Ile Phe Gly Tyr
            20                  25                  30

Lys Ser Gln Leu Asp Asp Leu Gln Arg Thr Val Ser Thr Ile Asn Ala
        35                  40                  45

Val Phe Arg Asp Ala Glu Thr Lys Gln Glu Leu Thr His Glu Ala Gln
    50                  55                  60

His Trp Leu Glu Glu Leu Lys Asp Ala Val Phe Glu Ala Asp Asp Leu
65                  70                  75                  80

Phe Asp Glu Phe Val Thr Leu Ala Glu Gln Lys Gln Leu Val Glu Ala
                85                  90                  95

Gly Gly Ser Leu Ser Lys Lys Met Arg Gln Phe Phe Ser Asp Ser Asn
            100                 105                 110

Pro Leu Gly Ile Ala Tyr Arg Met Ser Arg Gly Val Lys Lys Ile Lys
        115                 120                 125

Lys Lys Leu Asp Ala Ile Ala Tyr Asn His Gln Phe Ser Phe Lys Ile
    130                 135                 140

Asp Leu Glu Pro Ile Lys Glu Arg Arg Leu Glu Thr Gly Ser Val Val
145                 150                 155                 160

Asn Ala Gly Asp Ile Ile Gly Arg Glu Asp Asp Leu Glu Lys Ile Val
                165                 170                 175

Gly Leu Leu Leu Asp Ser Asn Ile Gln Arg Asp Val Ser Phe Leu Thr
```

```
              180                 185                 190
Ile Val Gly Met Gly Gly Leu Gly Lys Thr Ala Leu Ala Gln Leu Val
            195                 200                 205

Tyr Asn Asp Pro Arg Val Arg Thr Ala Phe Pro Leu Arg Cys Trp Asn
        210                 215                 220

Cys Val Ser Asp Gln Asp Gln Lys Lys Leu Asp Val Lys Glu Ile Leu
225                 230                 235                 240

Gly Lys Ile Leu Ser Thr Ala Thr Gly Lys Asn His Glu Gly Ser Thr
                245                 250                 255

Met Asp His Val Gln Thr Gln Leu Gln Glu Gln Leu Cys Gly Lys Arg
            260                 265                 270

Tyr Leu Leu Val Leu Asp Asp Val Trp Asn Glu Asn Pro Asn Gln Leu
        275                 280                 285

Arg Asp Xaa Val Glu Phe Phe Met Gly Gly Gln Arg Gly Asn Trp Ile
    290                 295                 300

Val Val Thr Thr Arg Ser His Glu Thr Thr Arg Ile Ile Arg Asp Gly
305                 310                 315                 320

Pro Leu His Lys Leu Gln Gly Leu Ser Glu Glu Asn Ser Trp Arg Leu
                325                 330                 335

Phe Val Arg Trp Thr Phe Gly Ser Val Gln Pro Lys Phe Pro Asn Asp
            340                 345                 350

Phe Val Met Ile Ala Arg Asp Ile Val Asp Lys Cys Ala Arg Asn Pro
        355                 360                 365

Leu Ala Ile Arg Val Val Gly Ser Leu Leu Cys Gly Gln Asp Lys Ser
    370                 375                 380

Lys Trp Leu Ser Phe His Glu Ile Cys Leu Ala Asn Ile Arg Lys Ser
385                 390                 395                 400

His Asn Asp Ile Met Leu Ile Leu Asn Leu Ser Tyr His His Leu Glu
                405                 410                 415

Pro Pro Ile Arg Arg Cys Phe Ser Tyr Cys Ala Met Phe Pro Lys Asp
            420                 425                 430

Phe Leu Ile Gly Lys Lys Thr Leu Ile Asn Leu Trp Met Ala Gln Gly
        435                 440                 445

Tyr Ile Val Pro Leu Asp Lys Asp Gln Ser Ile Asp Asp Ala Ser Glu
    450                 455                 460

Glu Tyr Ile Ser Ile Leu Leu Gln Arg Cys Phe Phe Glu Asn Ile Gly
465                 470                 475                 480

Thr Glu Lys Asp Tyr Val Ile Lys Ile His Asp Leu Met His Asp Ile
                485                 490                 495

Ala Gln Asn Val Met Gly Lys Glu Leu Cys Thr Thr Lys Asn Ile Ser
            500                 505                 510

Gly Ser Leu Asp Lys Asn Val Arg His Leu Ser Leu Ala Arg Thr Ser
        515                 520                 525

Phe Ala Arg Tyr Ser Phe Asn Ala Thr His Ile Arg Ser Tyr Phe Tyr
    530                 535                 540

Ala Gly Tyr Trp Cys Gln Asp Ala Glu Ile Asn Gln Phe Ser Val Glu
545                 550                 555                 560

Ala Leu Val Pro Asn Cys Leu Cys Leu Arg Ala Leu Asp Leu Ala Trp
                565                 570                 575

Ser Lys Ile Lys Ser Val Pro Asp Ser Ile Gly Gly Leu Leu His Leu
            580                 585                 590

Arg Tyr Leu Asp Leu Ser Tyr Asn Glu Asp Leu Glu Val Leu Pro Asn
        595                 600                 605
```

Ser Ile Ala Lys Leu Tyr Asn Leu Gln Thr Leu Gln Leu Lys Gly Cys
610                 615                 620

Lys Arg Leu Glu Gly Leu Pro Lys His Leu Ser Arg Leu Val Lys Leu
625                 630                 635                 640

Gln Thr Leu Asp Ile Tyr Gly Cys Asn Asn Val Thr Tyr Met Pro Lys
                645                 650                 655

Gly Met Gly Lys Met Thr Cys Leu His Thr Leu Ser Lys Phe Ile Val
                660                 665                 670

Gly Gly Glu Gly Ser Cys Ser Ser Trp Lys Gln Trp Phe Asp Gly Gln
            675                 680                 685

Glu Asp Leu Lys Ala Leu Asn Asn Leu Lys Gly His Leu Glu Ile Gln
            690                 695                 700

Ile Arg Trp Pro Glu Asn Thr Thr Asp Ala Val Lys Glu Asp Val Lys
705                 710                 715                 720

Arg Glu Gly Leu Tyr Leu Asn His
                725

<210> SEQ ID NO 17
<211> LENGTH: 885
<212> TYPE: PRT
<213> ORGANISM: Beta vulgaris

<400> SEQUENCE: 17

Met Asp Val Val Gly Thr Ala Leu Ser Ala Ala Gln Ser Leu Phe Ala
1               5                   10                  15

Ala Leu Gln Ser Ser Glu Leu Lys Glu Ile Leu Ser Ile Phe Gly Tyr
                20                  25                  30

Lys Ser Gln Leu Asp Asp Leu Gln Arg Thr Val Ser Thr Ile Asn Ala
            35                  40                  45

Val Phe Arg Asp Ala Glu Thr Lys Gln Glu Leu Thr His Glu Ala Gln
50                  55                  60

His Trp Leu Glu Glu Leu Lys Asp Ala Val Phe Glu Ala Asp Asp Leu
65                  70                  75                  80

Phe Asp Glu Phe Val Thr Leu Ala Glu Gln Lys Gln Leu Val Glu Ala
                85                  90                  95

Gly Gly Ser Leu Ser Lys Lys Met Arg Gln Phe Phe Ser Asp Ser Asn
                100                 105                 110

Pro Leu Gly Ile Ala Tyr Arg Met Ser Arg Gly Val Lys Lys Ile Lys
            115                 120                 125

Lys Lys Leu Asp Ala Ile Ala Tyr Asn His Gln Phe Ser Phe Lys Ile
130                 135                 140

Asp Leu Glu Pro Ile Lys Glu Arg Arg Leu Glu Thr Gly Ser Val Val
145                 150                 155                 160

Asn Ala Gly Asp Ile Ile Gly Arg Glu Asp Asp Leu Glu Lys Ile Val
                165                 170                 175

Gly Leu Leu Leu Asp Ser Asn Ile Gln Arg Asp Val Ser Phe Leu Thr
                180                 185                 190

Ile Val Gly Met Gly Gly Leu Gly Lys Thr Ala Leu Ala Gln Leu Val
            195                 200                 205

Tyr Asn Asp Pro Arg Val Arg Thr Ala Phe Pro Leu Arg Cys Trp Asn
            210                 215                 220

Cys Val Ser Asp Gln Asp Gln Lys Leu Asp Val Lys Glu Ile Leu
225                 230                 235                 240

Gly Lys Ile Leu Ser Thr Ala Thr Gly Lys Asn His Glu Gly Ser Thr

-continued

```
            245                 250                 255
Met Asp His Val Gln Thr Gln Leu Arg Glu Gln Leu Cys Gly Lys Arg
                260                 265                 270

Tyr Leu Leu Val Leu Asp Asp Val Trp Asn Glu Asn Pro Asn Gln Leu
            275                 280                 285

Arg Tyr Leu Val Glu Phe Phe Met Gly Gly Gln Arg Gly Asn Trp Ile
        290                 295                 300

Val Val Thr Thr Arg Ser His Glu Thr Ala Arg Ile Ile Arg Asp Gly
305                 310                 315                 320

Pro Leu His Lys Leu Gln Gly Leu Ser Glu Glu Asn Ser Trp Arg Leu
                325                 330                 335

Phe Val Arg Trp Thr Phe Gly Ser Val Gln Pro Lys Phe Pro Asn Asp
            340                 345                 350

Phe Val Met Ile Ala Arg Asp Ile Val Asp Lys Cys Ala Arg Asn Pro
        355                 360                 365

Leu Ala Ile Arg Val Val Gly Ser Leu Leu Cys Gly Gln Asp Lys Ser
    370                 375                 380

Lys Trp Leu Ser Phe His Glu Ile Cys Leu Ala Asn Ile Arg Lys Ser
385                 390                 395                 400

His Asn Asp Ile Met Pro Ile Leu Asn Leu Ser Tyr His His Leu Glu
                405                 410                 415

Pro Pro Ile Arg Arg Cys Phe Ser Tyr Cys Ala Met Phe Pro Lys Asp
            420                 425                 430

Phe Leu Ile Gly Lys Lys Thr Leu Ile Asn Leu Trp Met Ala Gln Gly
        435                 440                 445

Tyr Ile Val Pro Leu Asp Lys Asp Gln Ser Ile Asp Asp Ala Ser Glu
    450                 455                 460

Glu Tyr Ile Ser Ile Leu Leu Gln Arg Cys Phe Phe Glu Asn Ile Gly
465                 470                 475                 480

Thr Glu Lys Asp Tyr Val Ile Lys Ile His Asp Leu Met His Asp Ile
                485                 490                 495

Ala Gln Asn Val Met Gly Lys Glu Leu Cys Thr Thr Lys Asn Ile Ser
            500                 505                 510

Gly Ser Leu Asp Lys Asn Val Arg His Leu Ser Leu Ala Arg Thr Ser
        515                 520                 525

Phe Ala Arg Tyr Ser Phe Asn Ala Thr His Ile Arg Ser Tyr Phe Tyr
    530                 535                 540

Ala Gly Tyr Trp Cys Gln Asp Ala Glu Ile Asn Gln Phe Ser Val Glu
545                 550                 555                 560

Ala Leu Val Pro Asn Cys Leu Cys Leu Arg Ala Leu Asp Leu Ala Trp
                565                 570                 575

Ser Lys Ile Lys Ser Val Pro Asp Ser Ile Gly Gly Leu Leu His Leu
            580                 585                 590

Arg Tyr Leu Asp Leu Ser Tyr Asn Glu Asp Leu Glu Val Leu Pro Asn
        595                 600                 605

Ser Ile Ala Lys Leu Tyr Asn Leu Gln Thr Leu Gln Leu Lys Gly Cys
    610                 615                 620

Lys Arg Leu Glu Gly Leu Pro Lys His Leu Ser Arg Leu Val Lys Leu
625                 630                 635                 640

Gln Thr Leu Asp Ile Tyr Gly Cys Asn Asn Val Thr Tyr Met Pro Lys
                645                 650                 655

Gly Met Gly Lys Met Thr Cys Leu His Thr Leu Ser Lys Phe Ile Val
            660                 665                 670
```

```
Gly Gly Glu Gly Ser Cys Ser Ser Trp Lys Gln Trp Phe Asp Gly Gln
            675                 680                 685

Glu Asp Leu Lys Ala Leu Asn Asn Leu Lys Gly His Leu Glu Ile Gln
        690                 695                 700

Ile Arg Trp Pro Glu Asn Thr Thr Asp Ala Val Lys Glu Asp Val Lys
705                 710                 715                 720

Arg Glu Gly Leu Tyr Leu Asn His Lys Glu His Leu Asn His Ile Val
                725                 730                 735

Val Asp Phe Arg Cys Glu Gly Gly Arg Met Asp Asp Glu Glu
            740                 745                 750

Ala Arg Arg Leu Met Glu Glu Leu Arg Pro His Pro Tyr Leu Glu Asn
            755                 760                 765

Leu Ala Val Lys Ala Tyr Tyr Gly Ala Lys Met Pro Gly Trp Ala Thr
        770                 775                 780

Leu Leu Pro Asn Leu Thr Glu Leu Tyr Leu Ser Asp Cys Gly Glu Ser
785                 790                 795                 800

Glu Cys Leu Pro Cys Met Gly Asn Leu Asp Cys Leu Lys Val Leu Arg
                805                 810                 815

Leu Ser His Leu Ala Lys Leu Glu Tyr Ile Glu Glu Asp Ser Thr Ser
                820                 825                 830

Ala Asn Phe Ser Phe Arg Pro Gly Pro Glu Ser Ala Gly Leu Ser Leu
            835                 840                 845

Tyr Phe Pro Ser Leu Glu Leu Leu Glu Leu Lys Arg Leu His Lys Leu
        850                 855                 860

Lys Gly Trp Arg Arg Arg Glu Gly Leu Gly Asp Asp His Gln Pro Phe
865                 870                 875                 880

Asn Glu Ser Ser Ser
                885

<210> SEQ ID NO 18
<211> LENGTH: 738
<212> TYPE: PRT
<213> ORGANISM: Beta vulgaris

<400> SEQUENCE: 18

Met Asp Val Val Gly Thr Ala Leu Ser Ala Ala Gln Ser Leu Phe Ala
1               5                   10                  15

Ala Leu Gln Ser Ser Glu Leu Lys Glu Ile Leu Ser Ile Phe Gly Tyr
            20                  25                  30

Lys Ser Gln Leu Asp Asp Leu Gln Arg Thr Val Ser Thr Ile Asn Ala
        35                  40                  45

Val Phe Arg Asp Ala Glu Thr Lys Gln Glu Leu Thr His Glu Ala Gln
    50                  55                  60

His Trp Leu Glu Glu Leu Lys Asp Ala Val Phe Glu Ala Asp Leu
65                  70                  75                  80

Phe Asp Glu Phe Val Thr Leu Ala Glu Gln Lys Gln Leu Val Glu Ala
                85                  90                  95

Gly Gly Ser Leu Ser Lys Lys Met Arg Gln Phe Phe Ser Asp Ser Asn
            100                 105                 110

Pro Leu Gly Ile Ala Tyr Arg Met Ser Arg Gly Val Lys Lys Ile Lys
        115                 120                 125

Lys Lys Leu Asp Ala Ile Ala Tyr Asn His Gln Phe Ser Phe Lys Ile
    130                 135                 140

Asp Leu Glu Pro Ile Lys Glu Arg Arg Leu Glu Thr Gly Ser Val Val
```

```
145                 150                 155                 160
Asn Ala Gly Asp Ile Ile Gly Arg Glu Asp Asp Leu Glu Lys Ile Val
                165                 170                 175
Gly Leu Leu Leu Asp Ser Asn Ile Gln Arg Asp Val Ser Phe Leu Thr
                180                 185                 190
Ile Val Gly Met Gly Gly Leu Gly Lys Thr Ala Leu Ala Gln Leu Val
                195                 200                 205
Tyr Asn Asp Pro Arg Val Arg Thr Ala Phe Pro Leu Arg Cys Trp Asn
                210                 215                 220
Cys Val Ser Asp Gln Asp Gln Lys Lys Leu Asp Val Lys Glu Ile Leu
225                 230                 235                 240
Gly Lys Ile Leu Ser Thr Ala Thr Gly Lys Asn His Glu Gly Ser Thr
                245                 250                 255
Met Asp His Val Gln Thr Gln Leu Arg Glu Gln Leu Cys Gly Lys Arg
                260                 265                 270
Tyr Leu Leu Val Leu Asp Asp Val Trp Asn Glu Asn Pro Asn Gln Leu
                275                 280                 285
Arg Tyr Leu Val Glu Phe Phe Met Gly Gly Arg Gly Asn Trp Ile
                290                 295                 300
Val Val Thr Thr Arg Ser His Glu Thr Ala Arg Ile Ile Arg Asp Gly
305                 310                 315                 320
Pro Leu His Lys Leu Gln Gly Leu Ser Glu Glu Asn Ser Trp Arg Leu
                325                 330                 335
Phe Val Arg Trp Thr Phe Gly Ser Val Gln Pro Lys Phe Pro Asn Asp
                340                 345                 350
Phe Val Met Ile Ala Arg Asp Ile Val Asp Lys Cys Ala Arg Asn Pro
                355                 360                 365
Leu Ala Ile Arg Val Val Gly Ser Leu Leu Cys Gly Gln Asp Lys Ser
                370                 375                 380
Lys Trp Leu Ser Phe His Glu Ile Cys Leu Ala Asn Ile Arg Lys Ser
385                 390                 395                 400
His Asn Asp Ile Met Pro Ile Leu Asn Leu Ser Tyr His His Leu Glu
                405                 410                 415
Pro Pro Ile Arg Arg Cys Phe Ser Tyr Cys Ala Met Phe Pro Lys Asp
                420                 425                 430
Phe Leu Ile Gly Lys Lys Thr Leu Ile Asn Leu Trp Met Ala Gln Gly
                435                 440                 445
Tyr Ile Val Pro Leu Asp Lys Asp Gln Ser Ile Asp Asp Ala Ser Glu
                450                 455                 460
Glu Tyr Ile Ser Ile Leu Leu Gln Arg Cys Phe Phe Glu Asn Ile Gly
465                 470                 475                 480
Thr Glu Lys Asp Tyr Val Ile Lys Ile His Asp Leu Met His Asp Ile
                485                 490                 495
Ala Gln Asn Val Met Gly Lys Glu Leu Cys Thr Thr Lys Asn Ile Ser
                500                 505                 510
Gly Ser Leu Asp Lys Asn Val Arg His Leu Ser Leu Ala Arg Thr Ser
                515                 520                 525
Phe Ala Arg Tyr Ser Phe Asn Ala Thr His Ile Arg Ser Tyr Phe Tyr
                530                 535                 540
Ala Gly Tyr Trp Cys Gln Asp Ala Glu Ile Asn Gln Phe Ser Val Glu
545                 550                 555                 560
Ala Leu Val Pro Asn Cys Leu Cys Leu Arg Ala Leu Asp Leu Ala Trp
                565                 570                 575
```

Ser Lys Ile Lys Ser Val Pro Asp Ser Ile Gly Gly Leu Leu His Leu
                580                 585                 590

Arg Tyr Leu Asp Leu Ser Tyr Asn Glu Asp Leu Glu Val Leu Pro Asn
                595                 600                 605

Ser Ile Ala Lys Leu Tyr Asn Leu Gln Thr Leu Gln Leu Lys Gly Cys
610                 615                 620

Lys Arg Leu Glu Gly Leu Pro Lys His Leu Ser Arg Leu Val Lys Leu
625                 630                 635                 640

Gln Thr Leu Asp Ile Tyr Gly Cys Asn Asn Val Thr Tyr Met Pro Lys
                645                 650                 655

Gly Met Gly Lys Met Thr Cys Leu His Thr Leu Ser Lys Phe Ile Val
                660                 665                 670

Gly Gly Glu Gly Ser Cys Ser Ser Trp Lys Gln Trp Phe Asp Gly Gln
                675                 680                 685

Glu Asp Leu Lys Ala Leu Asn Asn Leu Lys Gly His Leu Glu Ile Gln
                690                 695                 700

Ile Arg Trp Pro Glu Asn Thr Thr Asp Ala Val Lys Glu Asp Val Lys
705                 710                 715                 720

Arg Glu Gly Leu Tyr Leu Asn His Lys Glu His Leu Asn His Ile Val
                725                 730                 735

Val Asp

<210> SEQ ID NO 19
<211> LENGTH: 738
<212> TYPE: PRT
<213> ORGANISM: Beta vulgaris
<220> FEATURE:
<221> NAME/KEY: MOD_RES
<222> LOCATION: (289)..(293)
<223> OTHER INFORMATION: Any amino acid

<400> SEQUENCE: 19

Met Asp Val Val Gly Thr Ala Leu Ser Ala Ala Gln Ser Leu Phe Ala
1               5                   10                  15

Ala Leu Gln Ser Ser Glu Leu Lys Glu Ile Leu Ser Ile Phe Gly Tyr
                20                  25                  30

Lys Ser Gln Leu Asp Asp Leu Gln Arg Thr Val Ser Thr Ile Asn Ala
                35                  40                  45

Val Phe Arg Asp Ala Glu Thr Lys Gln Glu Leu Thr His Glu Ala Gln
                50                  55                  60

His Trp Leu Glu Glu Leu Lys Asp Ala Val Phe Glu Ala Asp Leu
65                  70                  75                  80

Phe Asp Glu Phe Val Thr Leu Ala Glu Gln Lys Gln Leu Val Glu Ala
                85                  90                  95

Gly Gly Ser Leu Ser Lys Lys Met Arg Gln Phe Phe Ser Asp Ser Asn
                100                 105                 110

Pro Leu Gly Ile Ala Tyr Arg Met Ser Arg Gly Val Lys Lys Ile Lys
                115                 120                 125

Lys Lys Leu Asp Ala Ile Ala Tyr Asn His Gln Phe Ser Phe Lys Ile
130                 135                 140

Asp Leu Glu Pro Ile Lys Glu Arg Arg Leu Thr Gly Ser Val Val
145                 150                 155                 160

Asn Ala Gly Asp Ile Ile Gly Arg Glu Asp Asp Leu Glu Lys Ile Val
                165                 170                 175

Gly Leu Leu Leu Asp Ser Asn Ile Gln Arg Asp Val Ser Phe Leu Thr

```
            180                 185                 190
Ile Val Gly Met Gly Gly Leu Gly Lys Thr Ala Leu Ala Gln Leu Val
            195                 200                 205
Tyr Asn Asp Pro Arg Val Arg Thr Ala Phe Pro Leu Arg Cys Trp Asn
            210                 215                 220
Cys Val Ser Asp Gln Asp Gln Lys Lys Leu Asp Val Lys Glu Ile Leu
225                 230                 235                 240
Gly Lys Ile Leu Ser Thr Ala Thr Gly Lys Asn His Glu Gly Ser Thr
            245                 250                 255
Met Asp His Val Gln Thr Gln Leu Arg Glu Gln Leu Cys Gly Lys Arg
            260                 265                 270
Tyr Leu Leu Val Leu Asp Asp Val Trp Asn Glu Asn Pro Asn Gln Leu
            275                 280                 285
Xaa Xaa Xaa Xaa Xaa Phe Phe Met Gly Gly Gln Arg Gly Asn Trp Ile
            290                 295                 300
Val Val Thr Thr Arg Ser His Glu Thr Ala Arg Ile Ile Arg Asp Gly
305                 310                 315                 320
Pro Leu His Lys Leu Gln Gly Leu Ser Glu Glu Asn Ser Trp Arg Leu
            325                 330                 335
Phe Val Arg Trp Thr Phe Gly Ser Val Gln Pro Lys Phe Pro Asn Asp
            340                 345                 350
Phe Val Met Ile Ala Arg Asp Ile Val Asp Lys Cys Ala Arg Asn Pro
            355                 360                 365
Leu Ala Ile Arg Val Val Gly Ser Leu Leu Cys Gly Gln Asp Lys Ser
            370                 375                 380
Lys Trp Leu Ser Phe His Glu Ile Cys Leu Ala Asn Ile Arg Lys Ser
385                 390                 395                 400
His Asn Asp Ile Met Pro Ile Leu Asn Leu Ser Tyr His His Leu Glu
            405                 410                 415
Pro Pro Ile Arg Arg Cys Phe Ser Tyr Cys Ala Met Phe Pro Lys Asp
            420                 425                 430
Phe Leu Ile Gly Lys Lys Thr Leu Ile Asn Leu Trp Met Ala Gln Gly
            435                 440                 445
Tyr Ile Val Pro Leu Asp Lys Asp Gln Ser Ile Asp Asp Ala Ser Glu
            450                 455                 460
Glu Tyr Ile Ser Ile Leu Leu Gln Arg Cys Phe Phe Glu Asn Ile Gly
465                 470                 475                 480
Thr Glu Lys Asp Tyr Val Ile Lys Ile His Asp Leu Met His Asp Ile
            485                 490                 495
Ala Gln Asn Val Met Gly Lys Glu Leu Cys Thr Thr Lys Asn Ile Ser
            500                 505                 510
Gly Ser Leu Asp Lys Asn Val Arg His Leu Ser Leu Ala Arg Thr Ser
            515                 520                 525
Phe Ala Arg Tyr Ser Phe Asn Ala Thr His Ile Arg Ser Tyr Phe Tyr
            530                 535                 540
Ala Gly Tyr Trp Cys Gln Asp Ala Glu Ile Asn Gln Phe Ser Val Glu
545                 550                 555                 560
Ala Leu Val Pro Asn Cys Leu Cys Leu Arg Ala Leu Asp Leu Ala Trp
            565                 570                 575
Ser Lys Ile Lys Ser Val Pro Asp Ser Ile Gly Gly Leu Leu His Leu
            580                 585                 590
Arg Tyr Leu Asp Leu Ser Tyr Asn Glu Asp Leu Glu Val Leu Pro Asn
            595                 600                 605
```

```
Ser Ile Ala Lys Leu Tyr Asn Leu Gln Thr Leu Gln Leu Lys Gly Cys
        610                 615                 620

Lys Arg Leu Glu Gly Leu Pro Lys His Leu Ser Arg Leu Val Lys Leu
625                 630                 635                 640

Gln Thr Leu Asp Ile Tyr Gly Cys Asn Asn Val Thr Tyr Met Pro Lys
                645                 650                 655

Gly Met Gly Lys Met Thr Cys Leu His Thr Leu Ser Lys Phe Ile Val
                660                 665                 670

Gly Gly Glu Gly Ser Cys Ser Ser Trp Lys Gln Trp Phe Asp Gly Gln
            675                 680                 685

Glu Asp Leu Lys Ala Leu Asn Asn Leu Lys Gly His Leu Glu Ile Gln
        690                 695                 700

Ile Arg Trp Pro Glu Asn Thr Thr Asp Ala Val Lys Glu Asp Val Lys
705                 710                 715                 720

Arg Glu Gly Leu Tyr Leu Asn His Lys Glu His Leu Asn His Ile Val
                725                 730                 735

Val Asp

<210> SEQ ID NO 20
<211> LENGTH: 183
<212> TYPE: PRT
<213> ORGANISM: Beta vulgaris

<400> SEQUENCE: 20

Ser Thr Ile Asn Ala Val Phe Arg Asp Ala Glu Thr Lys Gln Glu Leu
1               5                   10                  15

Thr His Glu Ala Gln His Trp Leu Glu Glu Leu Lys Asp Ala Val Phe
            20                  25                  30

Glu Ala Asp Asp Leu Phe Asp Glu Phe Val Thr Leu Ala Glu Gln Lys
        35                  40                  45

Gln Leu Val Glu Ala Gly Gly Ser Leu Ser Lys Lys Met Arg Gln Phe
    50                  55                  60

Phe Ser Asp Ser Asn Pro Leu Gly Ile Ala Tyr Arg Met Ser Arg Gly
65                  70                  75                  80

Val Lys Lys Ile Lys Lys Leu Asp Ala Ile Ala Tyr Asn His Gln
                85                  90                  95

Phe Ser Phe Lys Ile Asp Leu Glu Pro Ile Lys Glu Arg Arg Leu Glu
            100                 105                 110

Thr Gly Ser Val Val Asn Ala Gly Asp Ile Ile Gly Arg Glu Asp Asp
        115                 120                 125

Leu Glu Lys Ile Val Gly Leu Leu Asp Ser Asn Ile Gln Arg Asp
    130                 135                 140

Val Ser Phe Leu Thr Ile Val Gly Met Gly Gly Leu Gly Lys Thr Ala
145                 150                 155                 160

Leu Ala Gln Leu Val Tyr Asn Asp Pro Arg Val Arg Thr Ala Phe Pro
                165                 170                 175

Leu Arg Cys Trp Asn Cys Leu
            180

<210> SEQ ID NO 21
<211> LENGTH: 738
<212> TYPE: PRT
<213> ORGANISM: Beta vulgaris

<400> SEQUENCE: 21
```

-continued

```
Met Asp Val Val Gly Thr Ala Leu Ser Ala Ala Gln Ser Leu Phe Ala
1               5                   10                  15

Ala Leu Gln Ser Ser Glu Leu Lys Glu Ile Leu Ser Ile Phe Gly Tyr
            20                  25                  30

Lys Ser Gln Leu Asp Asp Leu Gln Arg Thr Val Ser Thr Ile Asn Ala
            35                  40                  45

Val Phe Arg Asp Ala Glu Thr Lys Gln Glu Leu Thr His Glu Ala Gln
50                  55                  60

His Trp Leu Glu Glu Leu Lys Asp Ala Val Phe Glu Ala Asp Asp Leu
65                  70                  75                  80

Phe Asp Glu Phe Val Thr Leu Ala Glu Gln Lys Gln Leu Val Glu Ala
            85                  90                  95

Gly Gly Ser Leu Ser Lys Lys Met Arg Gln Phe Phe Ser Asp Ser Asn
            100                 105                 110

Pro Leu Gly Ile Ala Tyr Arg Met Ser Arg Gly Val Lys Lys Ile Lys
            115                 120                 125

Lys Lys Leu Asp Ala Ile Ala Tyr Asn His Gln Phe Ser Phe Lys Ile
            130                 135                 140

Asp Leu Glu Pro Ile Lys Glu Arg Arg Leu Glu Thr Gly Ser Val Val
145                 150                 155                 160

Asn Ala Gly Asp Ile Ile Gly Arg Glu Asp Asp Leu Glu Lys Ile Val
            165                 170                 175

Gly Leu Leu Leu Asp Ser Asn Ile Gln Arg Asp Val Ser Phe Leu Thr
            180                 185                 190

Ile Val Gly Met Gly Gly Leu Gly Lys Thr Ala Leu Ala Gln Leu Val
            195                 200                 205

Tyr Asn Asp Pro Arg Val Arg Thr Ala Phe Pro Leu Arg Cys Trp Asn
            210                 215                 220

Cys Val Ser Asp Gln Asp Gln Lys Lys Leu Asp Val Lys Glu Ile Leu
225                 230                 235                 240

Gly Lys Ile Leu Ser Thr Ala Thr Gly Lys Asn His Glu Gly Ser Thr
            245                 250                 255

Met Asp His Val Gln Thr Gln Leu Arg Glu Gln Leu Cys Gly Lys Arg
            260                 265                 270

Tyr Leu Leu Val Leu Asp Asp Val Trp Asn Glu Asn Pro Asn Gln Leu
            275                 280                 285

Arg Ile Leu Val Glu Phe Phe Met Gly Gly Gln Arg Gly Asn Trp Ile
            290                 295                 300

Val Val Thr Thr Arg Ser His Glu Thr Ala Arg Ile Ile Arg Asp Gly
305                 310                 315                 320

Pro Leu His Lys Leu Gln Gly Leu Ser Glu Glu Asn Ser Trp Arg Leu
            325                 330                 335

Phe Val Arg Trp Thr Phe Gly Ser Val Gln Pro Lys Phe Pro Asn Asp
            340                 345                 350

Phe Val Met Ile Ala Arg Asp Ile Val Asp Lys Cys Ala Arg Asn Pro
            355                 360                 365

Leu Ala Ile Arg Val Val Gly Ser Leu Leu Cys Gly Gln Asp Lys Ser
            370                 375                 380

Lys Trp Leu Ser Phe His Glu Ile Cys Leu Ala Asn Ile Arg Lys Ser
385                 390                 395                 400

His Asn Asp Ile Met Pro Ile Leu Asn Leu Ser Tyr His His Leu Glu
            405                 410                 415

Pro Pro Ile Arg Arg Cys Phe Ser Tyr Cys Ala Met Phe Pro Lys Asp
```

```
                    420                 425                 430
Phe Leu Ile Gly Lys Lys Thr Leu Ile Asn Leu Trp Met Ala Gln Gly
                435                 440                 445
Tyr Ile Val Pro Leu Asp Lys Asp Gln Ser Ile Asp Asp Ala Ser Glu
450                 455                 460
Glu Tyr Ile Ser Ile Leu Leu Gln Arg Cys Phe Glu Asn Ile Gly
465                 470                 475                 480
Thr Glu Lys Asp Tyr Val Ile Lys Ile His Asp Leu Met His Asp Ile
                485                 490                 495
Ala Gln Asn Val Met Gly Lys Glu Leu Cys Thr Thr Lys Asn Ile Ser
                500                 505                 510
Gly Ser Leu Asp Lys Asn Val Arg His Leu Ser Leu Ala Arg Thr Ser
                515                 520                 525
Phe Ala Arg Tyr Ser Phe Asn Ala Thr His Ile Arg Ser Tyr Phe Tyr
                530                 535                 540
Ala Gly Tyr Trp Cys Gln Asp Ala Glu Ile Asn Gln Phe Ser Val Glu
545                 550                 555                 560
Ala Leu Val Pro Asn Cys Leu Cys Leu Arg Ala Leu Asp Leu Ala Trp
                565                 570                 575
Ser Lys Ile Lys Ser Val Pro Asp Ser Ile Gly Gly Leu Leu His Leu
                580                 585                 590
Arg Tyr Leu Asp Leu Ser Tyr Asn Glu Asp Leu Glu Val Leu Pro Asn
                595                 600                 605
Ser Ile Ala Lys Leu Tyr Asn Leu Gln Thr Leu Gln Leu Lys Gly Cys
                610                 615                 620
Lys Arg Leu Glu Gly Leu Pro Lys His Leu Ser Arg Leu Val Lys Leu
625                 630                 635                 640
Gln Thr Leu Asp Ile Tyr Gly Cys Asn Asn Val Thr Tyr Met Pro Lys
                645                 650                 655
Gly Met Gly Lys Met Thr Cys Leu His Thr Leu Ser Lys Phe Ile Val
                660                 665                 670
Gly Gly Glu Gly Ser Cys Ser Ser Trp Lys Gln Trp Phe Asp Gly Gln
                675                 680                 685
Glu Asp Leu Lys Ala Leu Asn Asn Leu Lys Gly His Leu Glu Ile Gln
                690                 695                 700
Ile Arg Trp Pro Glu Asn Thr Thr Asp Ala Val Lys Glu Asp Val Lys
705                 710                 715                 720
Arg Glu Gly Leu Tyr Leu Asn His Lys Glu His Leu Asn His Ile Val
                725                 730                 735
Val Asp

<210> SEQ ID NO 22
<211> LENGTH: 738
<212> TYPE: PRT
<213> ORGANISM: Beta vulgaris
<220> FEATURE:
<221> NAME/KEY: MOD_RES
<222> LOCATION: (290)..(293)
<223> OTHER INFORMATION: Any amino acid

<400> SEQUENCE: 22

Met Asp Val Val Gly Thr Ala Leu Ser Ala Ala Gln Ser Leu Phe Ala
1               5                   10                  15
Ala Leu Gln Ser Ser Glu Leu Lys Glu Ile Leu Ser Ile Phe Gly Tyr
                20                  25                  30
```

```
Lys Ser Gln Leu Asp Asp Leu Gln Arg Thr Val Ser Thr Ile Asn Ala
         35                  40                  45

Val Phe Arg Asp Ala Glu Thr Lys Gln Glu Leu Thr His Glu Ala Gln
 50                  55                  60

His Trp Leu Glu Glu Leu Lys Asp Ala Val Phe Glu Ala Asp Asp Leu
 65                  70                  75                  80

Phe Asp Glu Phe Val Thr Leu Ala Glu Gln Lys Gln Leu Val Glu Ala
                 85                  90                  95

Gly Gly Ser Leu Ser Lys Lys Met Arg Gln Phe Ser Asp Ser Asn
            100                 105                 110

Pro Leu Gly Ile Ala Tyr Arg Met Ser Arg Gly Val Lys Lys Ile Lys
            115                 120                 125

Lys Lys Leu Asp Ala Ile Ala Tyr Asn His Gln Phe Ser Phe Lys Ile
130                 135                 140

Asp Leu Glu Pro Ile Lys Glu Arg Arg Leu Glu Thr Gly Ser Val Val
145                 150                 155                 160

Asn Ala Gly Asp Ile Ile Gly Arg Glu Asp Asp Leu Glu Lys Ile Val
                165                 170                 175

Gly Leu Leu Leu Asp Ser Asn Ile Gln Arg Asp Val Ser Phe Leu Thr
            180                 185                 190

Ile Val Gly Met Gly Gly Leu Gly Lys Thr Ala Leu Ala Gln Leu Val
        195                 200                 205

Tyr Asn Asp Pro Arg Val Arg Thr Ala Phe Pro Leu Arg Cys Trp Asn
210                 215                 220

Cys Val Ser Asp Gln Asp Gln Lys Lys Leu Asp Val Lys Glu Ile Leu
225                 230                 235                 240

Gly Lys Ile Leu Ser Thr Ala Thr Gly Lys Asn His Glu Gly Ser Thr
                245                 250                 255

Met Asp His Val Gln Thr Gln Leu Arg Glu Gln Leu Cys Gly Lys Arg
            260                 265                 270

Tyr Leu Leu Val Leu Asp Asp Val Trp Asn Glu Asn Pro Asn Gln Leu
        275                 280                 285

Arg Xaa Xaa Xaa Xaa Phe Phe Met Gly Gly Gln Arg Gly Asn Trp Ile
290                 295                 300

Val Val Thr Thr Arg Ser His Glu Thr Ala Arg Ile Ile Arg Asp Gly
305                 310                 315                 320

Pro Leu His Lys Leu Gln Gly Leu Ser Glu Glu Asn Ser Trp Arg Leu
                325                 330                 335

Phe Val Arg Trp Thr Phe Gly Ser Val Gln Pro Lys Phe Pro Asn Asp
            340                 345                 350

Phe Val Met Ile Ala Arg Asp Ile Val Asp Lys Cys Ala Arg Asn Pro
        355                 360                 365

Leu Ala Ile Arg Val Val Gly Ser Leu Leu Cys Gly Gln Asp Lys Ser
370                 375                 380

Lys Trp Leu Ser Phe His Glu Ile Cys Leu Ala Asn Ile Arg Lys Ser
385                 390                 395                 400

His Asn Asp Ile Met Pro Ile Leu Asn Leu Ser Tyr His His Leu Glu
                405                 410                 415

Pro Pro Ile Arg Arg Cys Phe Ser Tyr Cys Ala Met Phe Pro Lys Asp
            420                 425                 430

Phe Leu Ile Gly Lys Lys Thr Leu Ile Asn Leu Trp Met Ala Gln Gly
        435                 440                 445

Tyr Ile Val Pro Leu Asp Lys Asp Gln Ser Ile Asp Asp Ala Ser Glu
```

```
                450                 455                 460
Glu Tyr Ile Ser Ile Leu Leu Gln Arg Cys Phe Phe Glu Asn Ile Gly
465                 470                 475                 480

Thr Glu Lys Asp Tyr Val Ile Lys Ile His Asp Leu Met His Asp Ile
                485                 490                 495

Ala Gln Asn Val Met Gly Lys Glu Leu Cys Thr Thr Lys Asn Ile Ser
                500                 505                 510

Gly Ser Leu Asp Lys Asn Val Arg His Leu Ser Leu Ala Arg Thr Ser
                515                 520                 525

Phe Ala Arg Tyr Ser Phe Asn Ala Thr His Ile Arg Ser Tyr Phe Tyr
                530                 535                 540

Ala Gly Tyr Trp Cys Gln Asp Ala Glu Ile Asn Gln Phe Ser Val Glu
545                 550                 555                 560

Ala Leu Val Pro Asn Cys Leu Cys Leu Arg Ala Leu Asp Leu Ala Trp
                565                 570                 575

Ser Lys Ile Lys Ser Val Pro Asp Ser Ile Gly Gly Leu Leu His Leu
                580                 585                 590

Arg Tyr Leu Asp Leu Ser Tyr Asn Glu Asp Leu Glu Val Leu Pro Asn
                595                 600                 605

Ser Ile Ala Lys Leu Tyr Asn Leu Gln Thr Leu Gln Leu Lys Gly Cys
610                 615                 620

Lys Arg Leu Glu Gly Leu Pro Lys His Leu Ser Arg Leu Val Lys Leu
625                 630                 635                 640

Gln Thr Leu Asp Ile Tyr Gly Cys Asn Asn Val Thr Tyr Met Pro Lys
                645                 650                 655

Gly Met Gly Lys Met Thr Cys Leu His Thr Leu Ser Lys Phe Ile Val
                660                 665                 670

Gly Gly Glu Gly Ser Cys Ser Ser Trp Lys Gln Trp Phe Asp Gly Gln
                675                 680                 685

Glu Asp Leu Lys Ala Leu Asn Asn Leu Lys Gly His Leu Glu Ile Gln
                690                 695                 700

Ile Arg Trp Pro Glu Asn Thr Thr Asp Ala Val Lys Glu Asp Val Lys
705                 710                 715                 720

Arg Glu Gly Leu Tyr Leu Asn His Lys Glu His Leu Asn His Ile Val
                725                 730                 735

Val Asp

<210> SEQ ID NO 23
<211> LENGTH: 738
<212> TYPE: PRT
<213> ORGANISM: Beta vulgaris
<220> FEATURE:
<221> NAME/KEY: MOD_RES
<222> LOCATION: (290)..(291)
<223> OTHER INFORMATION: Any amino acid

<400> SEQUENCE: 23

Met Asp Val Val Gly Thr Ala Leu Ser Ala Gln Ser Leu Phe Ala
1               5                   10                  15

Ala Leu Gln Ser Ser Glu Leu Lys Glu Ile Leu Ser Ile Phe Gly Tyr
                20                  25                  30

Lys Ser Gln Leu Asp Asp Leu Gln Arg Thr Val Ser Thr Ile Asn Ala
            35                  40                  45

Val Phe Arg Asp Ala Glu Thr Lys Gln Glu Leu Thr His Glu Ala Gln
        50                  55                  60
```

```
His Trp Leu Glu Glu Leu Lys Asp Ala Val Phe Glu Ala Asp Asp Leu
 65                  70                  75                  80

Phe Asp Glu Phe Val Thr Leu Ala Glu Gln Lys Gln Leu Val Glu Ala
                 85                  90                  95

Gly Gly Ser Leu Ser Lys Lys Met Arg Gln Phe Phe Ser Asp Ser Asn
            100                 105                 110

Pro Leu Gly Ile Ala Tyr Arg Met Ser Arg Gly Val Lys Lys Ile Lys
        115                 120                 125

Lys Lys Leu Asp Ala Ile Ala Tyr Asn His Gln Phe Ser Phe Lys Ile
130                 135                 140

Asp Leu Glu Pro Ile Lys Glu Arg Arg Leu Glu Thr Gly Ser Val Val
145                 150                 155                 160

Asn Ala Gly Asp Ile Ile Gly Arg Glu Asp Asp Leu Glu Lys Ile Val
                165                 170                 175

Gly Leu Leu Leu Asp Ser Asn Ile Gln Arg Asp Val Ser Phe Leu Thr
            180                 185                 190

Ile Val Gly Met Gly Gly Leu Gly Lys Thr Ala Leu Ala Gln Leu Val
        195                 200                 205

Tyr Asn Asp Pro Arg Val Arg Thr Ala Phe Pro Leu Arg Cys Trp Asn
210                 215                 220

Cys Val Ser Asp Gln Asp Gln Lys Leu Asp Val Lys Glu Ile Leu
225                 230                 235                 240

Gly Lys Ile Leu Ser Thr Ala Thr Gly Lys Asn His Glu Gly Ser Thr
                245                 250                 255

Met Asp His Val Gln Thr Gln Leu Arg Glu Gln Leu Cys Gly Lys Arg
            260                 265                 270

Tyr Leu Leu Val Leu Asp Asp Val Trp Asn Glu Asn Pro Asn Gln Leu
        275                 280                 285

Arg Xaa Xaa Val Glu Phe Phe Met Gly Gly Gln Arg Gly Asn Trp Ile
290                 295                 300

Val Val Thr Thr Arg Ser His Glu Thr Ala Arg Ile Ile Arg Asp Gly
305                 310                 315                 320

Pro Leu His Lys Leu Gln Gly Leu Ser Glu Glu Asn Ser Trp Arg Leu
                325                 330                 335

Phe Val Arg Trp Thr Phe Gly Ser Val Gln Pro Lys Phe Pro Asn Asp
            340                 345                 350

Phe Val Met Ile Ala Arg Asp Ile Val Asp Lys Cys Ala Arg Asn Pro
        355                 360                 365

Leu Ala Ile Arg Val Val Gly Ser Leu Leu Cys Gly Gln Asp Lys Ser
370                 375                 380

Lys Trp Leu Ser Phe His Glu Ile Cys Leu Ala Asn Ile Arg Lys Ser
385                 390                 395                 400

His Asn Asp Ile Met Pro Ile Leu Asn Leu Ser Tyr His His Leu Glu
                405                 410                 415

Pro Pro Ile Arg Arg Cys Phe Ser Tyr Cys Ala Met Phe Pro Lys Asp
            420                 425                 430

Phe Leu Ile Gly Lys Lys Thr Leu Ile Asn Leu Trp Met Ala Gln Gly
        435                 440                 445

Tyr Ile Val Pro Leu Asp Lys Asp Gln Ser Ile Asp Asp Ala Ser Glu
450                 455                 460

Glu Tyr Ile Ser Ile Leu Leu Gln Arg Cys Phe Phe Glu Asn Ile Gly
465                 470                 475                 480

Thr Glu Lys Asp Tyr Val Ile Lys Ile His Asp Leu Met His Asp Ile
```

```
                    485                 490                 495
Ala Gln Asn Val Met Gly Lys Glu Leu Cys Thr Thr Lys Asn Ile Ser
                500                 505                 510

Gly Ser Leu Asp Lys Asn Val Arg His Leu Ser Leu Ala Arg Thr Ser
            515                 520                 525

Phe Ala Arg Tyr Ser Phe Asn Ala Thr His Ile Arg Ser Tyr Phe Tyr
530                 535                 540

Ala Gly Tyr Trp Cys Gln Asp Ala Glu Ile Asn Gln Phe Ser Val Glu
545                 550                 555                 560

Ala Leu Val Pro Asn Cys Leu Cys Leu Arg Ala Leu Asp Leu Ala Trp
                565                 570                 575

Ser Lys Ile Lys Ser Val Pro Asp Ser Ile Gly Gly Leu Leu His Leu
            580                 585                 590

Arg Tyr Leu Asp Leu Ser Tyr Asn Glu Asp Leu Glu Val Leu Pro Asn
        595                 600                 605

Ser Ile Ala Lys Leu Tyr Asn Leu Gln Thr Leu Gln Leu Lys Gly Cys
    610                 615                 620

Lys Arg Leu Glu Gly Leu Pro Lys His Leu Ser Arg Leu Val Lys Leu
625                 630                 635                 640

Gln Thr Leu Asp Ile Tyr Gly Cys Asn Asn Val Thr Tyr Met Pro Lys
                645                 650                 655

Gly Met Gly Lys Met Thr Cys Leu His Thr Leu Ser Lys Phe Ile Val
            660                 665                 670

Gly Gly Glu Gly Ser Cys Ser Ser Trp Lys Gln Trp Phe Asp Gly Gln
        675                 680                 685

Glu Asp Leu Lys Ala Leu Asn Asn Leu Lys Gly His Leu Glu Ile Gln
    690                 695                 700

Ile Arg Trp Pro Glu Asn Thr Thr Asp Ala Val Lys Glu Asp Val Lys
705                 710                 715                 720

Arg Glu Gly Leu Tyr Leu Asn His Lys Glu His Leu Asn His Ile Val
                725                 730                 735

Val Asp

<210> SEQ ID NO 24
<211> LENGTH: 738
<212> TYPE: PRT
<213> ORGANISM: Beta vulgaris

<400> SEQUENCE: 24

Met Asp Val Val Gly Thr Ala Leu Ser Ala Ala Gln Ser Leu Phe Ala
1               5                   10                  15

Ala Leu Gln Ser Ser Glu Leu Lys Glu Ile Leu Ser Ile Phe Gly Tyr
                20                  25                  30

Lys Ser Gln Leu Asp Asp Leu Gln Arg Thr Val Ser Thr Ile Asn Ala
            35                  40                  45

Val Phe Arg Asp Ala Glu Thr Lys Gln Glu Leu Thr His Glu Ala Gln
        50                  55                  60

His Trp Leu Glu Glu Leu Lys Asp Ala Val Phe Glu Ala Asp Leu
65                  70                  75                  80

Phe Asp Glu Phe Val Thr Leu Ala Glu Gln Lys Gln Leu Val Glu Ala
                85                  90                  95

Gly Gly Ser Leu Ser Lys Lys Met Arg Gln Phe Phe Ser Asp Ser Asn
            100                 105                 110

Pro Leu Gly Ile Ala Tyr Arg Met Ser Arg Gly Val Lys Lys Ile Lys
```

```
            115                 120                 125
Lys Lys Leu Asp Ala Ile Ala Tyr Asn His Gln Phe Ser Phe Lys Ile
            130                 135                 140
Asp Leu Glu Pro Ile Lys Glu Arg Arg Leu Glu Thr Gly Ser Val Val
145                 150                 155                 160
Asn Ala Gly Asp Ile Ile Gly Arg Glu Asp Leu Glu Lys Ile Val
            165                 170                 175
Gly Leu Leu Leu Asp Ser Asn Ile Gln Arg Asp Val Ser Phe Leu Thr
            180                 185                 190
Ile Val Gly Met Gly Gly Leu Gly Lys Thr Ala Leu Ala Gln Leu Val
            195                 200                 205
Tyr Asn Asp Pro Arg Val Arg Thr Ala Phe Pro Leu Arg Cys Trp Asn
            210                 215                 220
Cys Val Ser Asp Gln Asp Gln Lys Lys Leu Asp Val Lys Glu Ile Leu
225                 230                 235                 240
Gly Lys Ile Leu Ser Thr Ala Thr Gly Lys Asn His Glu Gly Ser Thr
            245                 250                 255
Met Asp His Val Gln Thr Gln Leu Gln Glu Gln Leu Cys Gly Lys Arg
            260                 265                 270
Tyr Leu Leu Val Leu Asp Asp Val Trp Asn Glu Asn Pro Asn Gln Leu
            275                 280                 285
Arg Asp Leu Val Glu Phe Phe Met Gly Gly Gln Arg Gly Asn Trp Ile
            290                 295                 300
Val Val Thr Thr Arg Ser His Glu Thr Thr Arg Ile Ile Arg Asp Gly
305                 310                 315                 320
Pro Leu His Lys Leu Gln Gly Leu Ser Glu Glu Asn Ser Trp Arg Leu
            325                 330                 335
Phe Val Arg Trp Thr Phe Gly Ser Val Gln Pro Lys Phe Pro Asn Asp
            340                 345                 350
Phe Val Met Ile Ala Arg Asp Ile Val Asp Lys Cys Ala Arg Asn Pro
            355                 360                 365
Leu Ala Ile Arg Val Val Gly Ser Leu Leu Cys Gly Gln Asp Lys Ser
            370                 375                 380
Lys Trp Leu Ser Phe His Glu Ile Cys Leu Ala Asn Ile Arg Lys Ser
385                 390                 395                 400
His Asn Asp Ile Met Leu Ile Leu Asn Leu Ser Tyr His His Leu Glu
            405                 410                 415
Pro Pro Ile Arg Arg Cys Phe Ser Tyr Cys Ala Met Phe Pro Lys Asp
            420                 425                 430
Phe Leu Ile Gly Lys Lys Thr Leu Ile Asn Leu Trp Met Ala Gln Gly
            435                 440                 445
Tyr Ile Val Pro Leu Asp Lys Asp Gln Ser Ile Asp Asp Ala Ser Glu
            450                 455                 460
Glu Tyr Ile Ser Ile Leu Leu Gln Arg Cys Phe Phe Glu Asn Ile Gly
465                 470                 475                 480
Thr Glu Lys Asp Tyr Val Ile Lys Ile His Asp Leu Met His Asp Ile
            485                 490                 495
Ala Gln Asn Val Met Gly Lys Glu Leu Cys Thr Thr Lys Asn Ile Ser
            500                 505                 510
Gly Ser Leu Asp Lys Asn Val Arg His Leu Ser Leu Ala Arg Thr Ser
            515                 520                 525
Phe Ala Arg Tyr Ser Phe Asn Ala Thr His Ile Arg Ser Tyr Phe Tyr
            530                 535                 540
```

```
Ala Gly Tyr Trp Cys Gln Asp Ala Glu Ile Asn Gln Phe Ser Val Glu
545                 550                 555                 560

Ala Leu Val Pro Asn Cys Leu Cys Leu Arg Ala Leu Asp Leu Ala Trp
                565                 570                 575

Ser Lys Ile Lys Ser Val Pro Asp Ser Ile Gly Gly Leu Leu His Leu
            580                 585                 590

Arg Tyr Leu Asp Leu Ser Tyr Asn Glu Asp Leu Glu Val Leu Pro Asn
        595                 600                 605

Ser Ile Ala Lys Leu Tyr Asn Leu Gln Thr Leu Gln Leu Lys Gly Cys
    610                 615                 620

Lys Arg Leu Glu Gly Leu Pro Lys His Leu Ser Arg Leu Val Lys Leu
625                 630                 635                 640

Gln Thr Leu Asp Ile Tyr Gly Cys Asn Asn Val Thr Tyr Met Pro Lys
                645                 650                 655

Gly Met Gly Lys Met Thr Cys Leu His Thr Leu Ser Lys Phe Ile Val
            660                 665                 670

Gly Gly Glu Gly Ser Cys Ser Ser Trp Lys Gln Trp Phe Asp Gly Gln
        675                 680                 685

Glu Asp Leu Lys Ala Leu Asn Asn Leu Lys Gly His Leu Glu Ile Gln
    690                 695                 700

Ile Arg Trp Pro Glu Asn Thr Thr Asp Ala Val Lys Glu Asp Val Lys
705                 710                 715                 720

Arg Glu Gly Leu Tyr Leu Asn His Lys Glu His Leu Asn His Ile Val
                725                 730                 735

Val Asp

<210> SEQ ID NO 25
<211> LENGTH: 737
<212> TYPE: PRT
<213> ORGANISM: Beta vulgaris

<400> SEQUENCE: 25

Met Asp Val Val Gly Thr Ala Leu Ser Ala Ala Gln Ser Leu Phe Ala
1               5                   10                  15

Ala Leu Gln Ser Ser Glu Leu Lys Glu Ile Leu Ser Ile Phe Gly Tyr
                20                  25                  30

Lys Ser Gln Leu Asp Asp Leu Gln Arg Thr Val Ser Thr Ile Asn Ala
            35                  40                  45

Val Phe Arg Asp Ala Glu Thr Lys Gln Glu Leu Thr His Glu Ala Gln
        50                  55                  60

His Trp Leu Glu Glu Leu Lys Asp Ala Val Phe Glu Ala Asp Asp Leu
65                  70                  75                  80

Phe Asp Glu Phe Val Thr Leu Ala Glu Gln Lys Gln Leu Val Glu Ala
                85                  90                  95

Gly Gly Ser Leu Ser Lys Lys Met Arg Gln Phe Phe Ser Asp Ser Asn
            100                 105                 110

Pro Leu Gly Ile Ala Tyr Arg Met Ser Arg Gly Leu Lys Lys Ile Lys
        115                 120                 125

Lys Lys Leu Asp Ala Ile Ala Tyr Asn His Gln Phe Ser Phe Lys Ile
    130                 135                 140

Asp Leu Glu Pro Ile Lys Glu Arg Arg Leu Glu Thr Gly Ser Val Val
145                 150                 155                 160

Asn Ala Gly Asp Ile Ile Gly Arg Glu Asp Asp Leu Glu Lys Ile Val
                165                 170                 175
```

```
Gly Leu Leu Leu Asp Ser Asn Ile Gln Arg Asp Met Ser Phe Leu Thr
            180                 185                 190

Ile Val Gly Met Gly Gly Leu Gly Lys Thr Ala Leu Ala Gln Leu Val
            195                 200                 205

Tyr Asn Asp Pro Arg Val Arg Thr Ala Phe Pro Leu Arg Cys Trp Asn
            210                 215                 220

Cys Val Phe Asp Gln Asp Gln Lys Gln Leu Asp Val Lys Glu Ile Leu
225                 230                 235                 240

Gly Lys Ile Leu Ser Thr Ala Thr Gly Lys Asn His Glu Gly Ser Thr
                245                 250                 255

Met Asp Gln Val Gln Thr Gln Leu Arg Glu Leu Cys Gly Lys Arg Tyr
            260                 265                 270

Leu Leu Val Leu Asp Asp Val Trp Asn Glu Asn Pro Asn Gln Leu Arg
            275                 280                 285

Asp Leu Val Glu Phe Phe Met Gly Gly Gln Arg Gly Asn Trp Ile Val
            290                 295                 300

Val Thr Thr Arg Ser His Glu Thr Ala Arg Ile Ile Arg Asp Gly Pro
305                 310                 315                 320

Leu His Lys Leu Gln Gly Leu Ser Glu Glu Asn Ser Trp Arg Leu Phe
                325                 330                 335

Val Arg Trp Thr Phe Gly Ser Val Gln Pro Lys Phe Pro Asn Asp Phe
            340                 345                 350

Val Met Ile Ala Arg Asp Ile Val Asp Lys Cys Ala Arg Asn Pro Leu
            355                 360                 365

Ala Ile Arg Val Val Gly Ser Leu Leu Cys Gly Gln Asp Lys Ser Lys
            370                 375                 380

Trp Leu Ser Phe His Glu Ile Cys Leu Ala Asn Ile Arg Lys Ser His
385                 390                 395                 400

Asn Asp Ile Met Pro Ile Leu Asn Leu Ser Tyr His His Leu Glu Pro
                405                 410                 415

Pro Ile Arg Arg Cys Phe Ser Tyr Cys Val Val Phe Pro Lys Asp Phe
            420                 425                 430

Leu Ile Gly Lys Lys Thr Leu Ile Asn Leu Trp Met Ala Gln Gly Tyr
            435                 440                 445

Ile Val Pro Leu Asp Lys Asp Gln Ser Ile Asp Ala Ser Glu Glu
450                 455                 460

Tyr Ile Ser Ile Leu Leu Gln Arg Cys Phe Phe Glu Asn Ile Gly Thr
465                 470                 475                 480

Glu Lys Asp Asp Val Ile Lys Ile His Asp Leu Met His Asp Ile Ala
                485                 490                 495

Gln Asn Val Met Gly Lys Glu Leu Cys Thr Thr Lys Asn Ile Ser Gly
            500                 505                 510

Ser Leu Asp Lys Asn Val Arg His Leu Ser Leu Ala Arg Thr Ser Phe
            515                 520                 525

Ala Arg Tyr Ser Phe Asn Ala Thr His Ile Arg Ser Tyr Phe Tyr Ala
            530                 535                 540

Gly Tyr Trp Cys Gln Asn Ala Glu Ile Asn Gln Phe Ser Val Glu Ala
545                 550                 555                 560

Leu Val Pro Asn Cys Leu Cys Leu Arg Ala Leu Asp Leu Ala Trp Ser
                565                 570                 575

Lys Ile Lys Ser Val Pro Asp Ser Ile Gly Gly Leu Leu His Leu Arg
            580                 585                 590
```

-continued

```
Tyr Leu Asp Ile Ser Tyr Asn Glu Asp Leu Glu Val Leu Pro Asn Ser
            595                 600                 605

Ile Ala Lys Leu Tyr Asn Leu Gln Thr Leu Gln Leu Lys Gly Cys Lys
610                 615                 620

Arg Leu Glu Gly Leu Pro Lys His Leu Ser Arg Leu Val Lys Leu Gln
625                 630                 635                 640

Thr Leu Asp Ile Tyr Gly Cys Asn Asn Val Thr Tyr Met Pro Lys Gly
            645                 650                 655

Met Gly Lys Met Thr Cys Leu His Thr Leu Ser Lys Phe Ile Val Gly
            660                 665                 670

Gly Glu Gly Ser Cys Ser Ser Trp Lys Gln Trp Phe Asp Gly Leu Glu
            675                 680                 685

Asp Leu Lys Ala Leu Asn Asn Leu Lys Gly His Leu Glu Ile Gln Ile
            690                 695                 700

Arg Trp Pro Glu Asn Thr Thr Asp Val Val Lys Glu Asp Val Lys Arg
705                 710                 715                 720

Glu Gly Leu Tyr Leu Asn His Lys Glu His Leu Asn His Ile Val Val
            725                 730                 735

Asp

<210> SEQ ID NO 26
<211> LENGTH: 738
<212> TYPE: PRT
<213> ORGANISM: Beta vulgaris
<220> FEATURE:
<221> NAME/KEY: MOD_RES
<222> LOCATION: (297)..(325)
<223> OTHER INFORMATION: Any amino acid

<400> SEQUENCE: 26

Met Asp Val Val Gly Thr Ala Leu Ser Ala Ala Gln Ser Leu Phe Ala
1               5                   10                  15

Ala Leu Gln Ser Ser Glu Leu Lys Glu Ile Leu Ser Ile Phe Gly Tyr
            20                  25                  30

Lys Ser Gln Leu Asp Asp Leu Gln Arg Thr Val Ser Thr Ile Asn Ala
        35                  40                  45

Val Phe Arg Asp Ala Glu Thr Lys Gln Glu Leu Thr His Glu Ala Gln
    50                  55                  60

His Trp Leu Glu Glu Leu Lys Asp Ala Val Phe Glu Ala Asp Asp Leu
65                  70                  75                  80

Phe Asp Glu Phe Val Thr Leu Ala Glu Gln Lys Gln Leu Val Glu Ala
                85                  90                  95

Gly Gly Ser Leu Ser Lys Lys Met Arg Gln Phe Phe Ser Asp Ser Asn
            100                 105                 110

Pro Leu Gly Ile Ala Tyr Arg Met Ser Arg Gly Val Lys Lys Ile Lys
        115                 120                 125

Lys Lys Leu Asp Ala Ile Ala Tyr Asn His Gln Phe Ser Phe Lys Ile
130                 135                 140

Asp Leu Glu Pro Ile Lys Glu Arg Arg Leu Glu Thr Gly Ser Val Val
145                 150                 155                 160

Asn Ala Gly Asp Ile Ile Gly Arg Glu Asp Leu Glu Lys Ile Val
                165                 170                 175

Gly Leu Leu Leu Asp Ser Asn Ile Gln Arg Asp Val Ser Phe Leu Thr
            180                 185                 190

Ile Val Gly Met Gly Gly Leu Gly Lys Thr Ala Leu Ala Gln Leu Val
        195                 200                 205
```

```
Tyr Asn Asp Pro Arg Val Arg Thr Ala Phe Pro Leu Arg Cys Trp Asn
    210                 215                 220

Cys Val Ser Asp Gln Asp Gln Lys Lys Leu Asp Val Lys Glu Ile Leu
225                 230                 235                 240

Gly Lys Ile Leu Ser Thr Ala Thr Gly Lys Asn His Glu Gly Ser Thr
                245                 250                 255

Met Asp His Val Gln Thr Gln Leu Arg Glu Gln Leu Cys Gly Lys Arg
            260                 265                 270

Tyr Leu Leu Val Leu Asp Asp Val Trp Asn Glu Asn Pro Asn Gln Leu
        275                 280                 285

Arg Ile Leu Val Glu Phe Phe Met Xaa Xaa Xaa Xaa Xaa Xaa Xaa Xaa
    290                 295                 300

Xaa Xaa Xaa Xaa Xaa Xaa Xaa Xaa Xaa Xaa Xaa Xaa Xaa Xaa Xaa Xaa
305                 310                 315                 320

Xaa Xaa Xaa Xaa Xaa Gln Gly Leu Ser Glu Glu Asn Ser Trp Arg Leu
                325                 330                 335

Phe Val Arg Trp Thr Phe Gly Ser Val Gln Pro Lys Phe Pro Asn Asp
            340                 345                 350

Phe Val Met Ile Ala Arg Asp Ile Val Asp Lys Cys Ala Arg Asn Pro
        355                 360                 365

Leu Ala Ile Arg Val Val Gly Ser Leu Leu Cys Gly Gln Asp Lys Ser
    370                 375                 380

Lys Trp Leu Ser Phe His Glu Ile Cys Leu Ala Asn Ile Arg Lys Ser
385                 390                 395                 400

His Asn Asp Ile Met Pro Ile Leu Asn Leu Ser Tyr His His Leu Glu
                405                 410                 415

Pro Pro Ile Arg Arg Cys Phe Ser Tyr Cys Ala Met Phe Pro Lys Asp
            420                 425                 430

Phe Leu Ile Gly Lys Lys Thr Leu Ile Asn Leu Trp Met Ala Gln Gly
        435                 440                 445

Tyr Ile Val Pro Leu Asp Lys Asp Gln Ser Ile Asp Asp Ala Ser Glu
    450                 455                 460

Glu Tyr Ile Ser Ile Leu Leu Gln Arg Cys Phe Phe Glu Asn Ile Gly
465                 470                 475                 480

Thr Glu Lys Asp Tyr Val Ile Lys Ile His Asp Leu Met His Asp Ile
                485                 490                 495

Ala Gln Asn Val Met Gly Lys Glu Leu Cys Thr Thr Lys Asn Ile Ser
            500                 505                 510

Gly Ser Leu Asp Lys Asn Val Arg His Leu Ser Leu Ala Arg Thr Ser
        515                 520                 525

Phe Ala Arg Tyr Ser Phe Asn Ala Thr His Ile Arg Ser Tyr Phe Tyr
    530                 535                 540

Ala Gly Tyr Trp Cys Gln Asp Ala Glu Ile Asn Gln Phe Ser Val Glu
545                 550                 555                 560

Ala Leu Val Pro Asn Cys Leu Cys Leu Arg Ala Leu Asp Leu Ala Trp
                565                 570                 575

Ser Lys Ile Lys Ser Val Pro Asp Ser Ile Gly Gly Leu Leu His Leu
            580                 585                 590

Arg Tyr Leu Asp Leu Ser Tyr Asn Glu Asp Leu Glu Val Leu Pro Asn
        595                 600                 605

Ser Ile Ala Lys Leu Tyr Asn Leu Gln Thr Leu Gln Leu Lys Gly Cys
    610                 615                 620
```

-continued

```
Lys Arg Leu Glu Gly Leu Pro Lys His Leu Ser Arg Leu Val Lys Leu
625                 630                 635                 640

Gln Thr Leu Asp Ile Tyr Gly Cys Asn Asn Val Thr Tyr Met Pro Lys
            645                 650                 655

Gly Met Gly Lys Met Thr Cys Leu His Thr Leu Ser Lys Phe Ile Val
            660                 665                 670

Gly Gly Glu Gly Ser Cys Ser Ser Trp Lys Gln Trp Phe Asp Gly Gln
            675                 680                 685

Glu Asp Leu Lys Ala Leu Asn Asn Leu Lys Gly His Leu Glu Ile Gln
            690                 695                 700

Ile Arg Trp Pro Glu Asn Thr Thr Asp Ala Val Lys Glu Asp Val Lys
705                 710                 715                 720

Arg Glu Gly Leu Tyr Leu Asn His Lys Glu His Leu Asn His Ile Val
                725                 730                 735

Val Asp

<210> SEQ ID NO 27
<211> LENGTH: 738
<212> TYPE: PRT
<213> ORGANISM: Beta vulgaris
<220> FEATURE:
<221> NAME/KEY: MOD_RES
<222> LOCATION: (544)..(544)
<223> OTHER INFORMATION: Any amino acid

<400> SEQUENCE: 27

Met Asp Val Val Gly Thr Ala Leu Ser Ala Ala Gln Ser Leu Phe Ala
1               5                   10                  15

Ala Leu Gln Ser Ser Glu Leu Lys Glu Ile Leu Ser Ile Phe Gly Tyr
                20                  25                  30

Lys Ser Gln Leu Asp Asp Leu Gln Arg Thr Val Ser Thr Ile Asn Ala
            35                  40                  45

Val Phe Arg Asp Ala Glu Thr Lys Gln Glu Leu Thr His Glu Ala Gln
    50                  55                  60

His Trp Leu Glu Glu Leu Lys Asp Ala Val Phe Glu Ala Asp Asp Leu
65                  70                  75                  80

Phe Asp Glu Phe Val Thr Leu Ala Glu Gln Lys Gln Leu Val Glu Ala
                85                  90                  95

Gly Gly Ser Leu Ser Lys Lys Met Arg Gln Phe Phe Ser Asp Ser Asn
            100                 105                 110

Pro Leu Gly Ile Ala Tyr Arg Met Ser Arg Gly Val Lys Lys Ile Lys
        115                 120                 125

Lys Lys Leu Asp Ala Ile Ala Tyr Asn His Gln Phe Ser Phe Lys Ile
130                 135                 140

Asp Leu Glu Pro Ile Lys Glu Arg Arg Leu Glu Thr Gly Ser Val Val
145                 150                 155                 160

Asn Ala Gly Asp Ile Ile Gly Arg Glu Asp Asp Leu Glu Lys Ile Val
                165                 170                 175

Gly Leu Leu Leu Asp Ser Asn Ile Gln Arg Asp Val Ser Phe Leu Thr
            180                 185                 190

Ile Val Gly Met Gly Gly Leu Gly Lys Thr Ala Leu Ala Gln Leu Val
        195                 200                 205

Tyr Asn Asp Pro Arg Val Arg Thr Ala Phe Pro Leu Arg Cys Trp Asn
    210                 215                 220

Cys Val Ser Asp Gln Asp Gln Lys Lys Leu Asp Val Lys Glu Ile Leu
225                 230                 235                 240
```

Gly Lys Ile Leu Ser Thr Ala Thr Gly Lys Asn His Glu Gly Ser Thr
            245                 250                 255

Met Asp His Val Gln Thr Gln Leu Arg Glu Gln Leu Cys Gly Lys Arg
        260                 265                 270

Tyr Leu Leu Val Leu Asp Asp Val Trp Asn Glu Asn Pro Asn Gln Leu
        275                 280                 285

Arg Asp Leu Val Glu Phe Phe Met Gly Gly Gln Arg Gly Asn Trp Ile
        290                 295                 300

Val Val Thr Thr Arg Ser His Glu Thr Ala Arg Ile Ile Arg Asp Gly
305                 310                 315                 320

Pro Leu His Lys Leu Gln Gly Leu Ser Glu Glu Asn Ser Trp Arg Leu
                325                 330                 335

Phe Val Arg Trp Thr Phe Gly Ser Val Gln Pro Lys Phe Pro Asn Asp
            340                 345                 350

Phe Val Met Ile Ala Arg Asp Ile Val Asp Lys Cys Ala Arg Asn Pro
            355                 360                 365

Leu Ala Ile Arg Val Val Gly Ser Leu Leu Cys Gly Gln Asp Lys Ser
        370                 375                 380

Lys Trp Leu Ser Phe His Glu Ile Cys Leu Ala Asn Ile Arg Lys Ser
385                 390                 395                 400

His Asn Asp Ile Met Pro Ile Leu Asn Leu Ser Tyr His His Leu Glu
                405                 410                 415

Pro Pro Ile Arg Arg Cys Phe Ser Tyr Cys Ala Met Phe Pro Lys Asp
            420                 425                 430

Phe Leu Ile Gly Lys Lys Thr Leu Ile Asn Leu Trp Met Ala Gln Gly
            435                 440                 445

Tyr Ile Val Pro Leu Asp Lys Asp Gln Ser Ile Asp Asp Ala Ser Glu
        450                 455                 460

Glu Tyr Ile Ser Ile Leu Leu Gln Arg Cys Phe Phe Glu Asn Ile Gly
465                 470                 475                 480

Thr Glu Lys Asp Tyr Val Ile Lys Ile His Asp Leu Met His Asp Ile
                485                 490                 495

Ala Gln Asn Val Met Gly Lys Glu Leu Cys Thr Thr Lys Asn Ile Ser
            500                 505                 510

Gly Ser Leu Asp Lys Asn Val Arg His Leu Ser Leu Ala Arg Thr Ser
        515                 520                 525

Phe Ala Arg Tyr Ser Phe Asn Ala Thr His Ile Arg Ser Tyr Phe Xaa
        530                 535                 540

Ala Gly Tyr Trp Cys Gln Asp Ala Glu Ile Asn Gln Phe Ser Val Glu
545                 550                 555                 560

Ala Leu Val Pro Asn Cys Leu Cys Leu Arg Ala Leu Asp Leu Ala Trp
                565                 570                 575

Ser Lys Ile Lys Ser Val Pro Asp Ser Ile Gly Gly Leu Leu His Leu
            580                 585                 590

Arg Tyr Leu Asp Leu Ser Tyr Asn Glu Asp Leu Glu Val Leu Pro Asn
        595                 600                 605

Ser Ile Ala Lys Leu Tyr Asn Leu Gln Thr Leu Gln Leu Lys Gly Cys
        610                 615                 620

Lys Arg Leu Glu Gly Leu Pro Lys His Leu Ser Arg Leu Val Lys Leu
625                 630                 635                 640

Gln Thr Leu Asp Ile Tyr Gly Cys Asn Asn Val Thr Tyr Met Pro Lys
                645                 650                 655

```
Gly Met Gly Lys Met Thr Cys Leu His Thr Leu Ser Lys Phe Ile Val
            660                 665                 670

Gly Gly Glu Gly Ser Cys Ser Ser Trp Lys Gln Trp Phe Asp Gly Gln
        675                 680                 685

Glu Asp Leu Lys Ala Leu Asn Asn Leu Lys Gly His Leu Glu Ile Gln
    690                 695                 700

Ile Arg Trp Pro Glu Asn Thr Thr Asp Ala Val Lys Glu Asp Val Lys
705                 710                 715                 720

Arg Glu Gly Leu Tyr Leu Asn His Lys Glu His Leu Asn His Ile Val
                725                 730                 735

Val Asp

<210> SEQ ID NO 28
<211> LENGTH: 728
<212> TYPE: PRT
<213> ORGANISM: Beta vulgaris
<220> FEATURE:
<221> NAME/KEY: MOD_RES
<222> LOCATION: (298)..(544)
<223> OTHER INFORMATION: Any amino acid

<400> SEQUENCE: 28

Met Asp Val Val Gly Ser Ala Leu Ser Ala Ala Gln Ser Leu Phe Ala
1               5                   10                  15

Ala Leu Gln Ser Ser Glu Leu Lys Glu Ile Leu Ser Ile Phe Gly Tyr
            20                  25                  30

Lys Ser Gln Leu Asp Asp Leu Gln Arg Ile Val Ser Thr Ile Asn Ala
        35                  40                  45

Val Phe Arg Asp Ala Glu Thr Lys Gln Glu Leu Thr His Glu Ala Gln
50                  55                  60

His Trp Leu Glu Glu Leu Lys Asp Ala Val Phe Glu Ala Asp Asp Leu
65                  70                  75                  80

Phe Asp Glu Phe Val Thr Leu Ala Glu Gln Lys Gln Leu Val Glu Ala
                85                  90                  95

Gly Gly Ser Leu Ser Lys Lys Met Arg Gln Phe Phe Ser Asp Ser Asn
            100                 105                 110

Pro Leu Gly Ile Ala Tyr Lys Met Ser Gln Gly Val Lys Lys Ile Lys
        115                 120                 125

Lys Lys Leu Asp Val Ile Ala Tyr Asn His Gln Phe Ser Phe Lys Ile
    130                 135                 140

Asp Leu Glu Pro Ile Lys Glu Arg Arg Leu Glu Thr Gly Ser Val Val
145                 150                 155                 160

Asn Ala Gly Asp Ile Ile Gly Arg Glu Asp Asp Leu Glu Lys Ile Val
                165                 170                 175

Gly Leu Phe Leu Asp Ser Asn Ile Gln Arg Asp Val Ser Phe Leu Thr
            180                 185                 190

Ile Val Gly Met Gly Gly Leu Gly Lys Thr Ala Leu Ala Gln Leu Val
        195                 200                 205

Tyr Asn Asp Pro Arg Val Arg Thr Ala Phe Pro Leu Arg Cys Trp Asn
    210                 215                 220

Cys Val Ser Asp Gln Asp Gln Asn Gln Leu Asp Val Lys Glu Ile Leu
225                 230                 235                 240

Gly Lys Ile Leu Ser Thr Ala Thr Gly Lys Asn His Lys Gly Ser Thr
                245                 250                 255

Met Asp Gln Val Gln Thr Gln Leu Arg Glu Gln Leu Cys Gly Lys Arg
            260                 265                 270
```

```
Tyr Leu Leu Val Leu Asp Asp Val Trp Asn Glu Asn Pro Asn Gln Leu
            275                 280                 285

Arg Asp Leu Val Glu Phe Phe Met Gly Xaa Xaa Xaa Xaa Xaa Xaa Xaa
    290                 295                 300

Xaa Xaa Xaa Xaa Xaa Xaa Xaa Xaa Xaa Xaa Xaa Xaa Xaa Xaa Xaa Xaa
305                 310                 315                 320

Xaa Xaa Xaa Xaa Xaa Xaa Xaa Xaa Xaa Xaa Xaa Xaa Xaa Xaa Xaa Xaa
                325                 330                 335

Xaa Xaa Xaa Xaa Xaa Xaa Xaa Xaa Xaa Xaa Xaa Xaa Xaa Xaa Xaa Xaa
            340                 345                 350

Xaa Xaa Xaa Xaa Xaa Xaa Xaa Xaa Xaa Xaa Xaa Xaa Xaa Xaa Xaa Xaa
        355                 360                 365

Xaa Xaa Xaa Xaa Xaa Xaa Xaa Xaa Xaa Xaa Xaa Xaa Xaa Xaa Xaa Xaa
    370                 375                 380

Xaa Xaa Xaa Xaa Xaa Xaa Xaa Xaa Xaa Xaa Xaa Xaa Xaa Xaa Xaa Xaa
385                 390                 395                 400

Xaa Xaa Xaa Xaa Xaa Xaa Xaa Xaa Xaa Xaa Xaa Xaa Xaa Xaa Xaa Xaa
                405                 410                 415

Xaa Xaa Xaa Xaa Xaa Xaa Xaa Xaa Xaa Xaa Xaa Xaa Xaa Xaa Xaa Xaa
            420                 425                 430

Xaa Xaa Xaa Xaa Xaa Xaa Xaa Xaa Xaa Xaa Xaa Xaa Xaa Xaa Xaa Xaa
        435                 440                 445

Xaa Xaa Xaa Xaa Xaa Xaa Xaa Xaa Xaa Xaa Xaa Xaa Xaa Xaa Xaa Xaa
    450                 455                 460

Xaa Xaa Xaa Xaa Xaa Xaa Xaa Xaa Xaa Xaa Xaa Xaa Xaa Xaa Xaa Xaa
465                 470                 475                 480

Xaa Xaa Xaa Xaa Xaa Xaa Xaa Xaa Xaa Xaa Xaa Xaa Xaa Xaa Xaa Xaa
                485                 490                 495

Xaa Xaa Xaa Xaa Xaa Xaa Xaa Xaa Xaa Xaa Xaa Xaa Xaa Xaa Xaa Xaa
            500                 505                 510

Xaa Xaa Xaa Xaa Xaa Xaa Xaa Xaa Xaa Xaa Xaa Xaa Xaa Xaa Xaa Xaa
        515                 520                 525

Xaa Xaa Xaa Xaa Xaa Xaa Xaa Xaa Xaa Xaa Xaa Xaa Xaa Xaa Xaa Xaa
    530                 535                 540

Ala Gly Tyr Trp Cys Gln Glu Ser Glu Ile Asn Gln Phe Ser Val Glu
545                 550                 555                 560

Ala Leu Val Pro Asn Cys Leu Cys Leu Arg Ala Leu Asp Leu Ala Trp
                565                 570                 575

Ser Lys Ile Lys Ser Leu Pro Asp Ser Ile Gly Gly Leu Leu His Leu
            580                 585                 590

Arg Tyr Leu Asp Leu Ser Tyr Asn Glu Asp Leu Glu Val Leu Pro Asn
        595                 600                 605

Ser Ile Ala Lys Leu Tyr Asn Leu Gln Thr Leu Gln Leu Lys Gly Cys
    610                 615                 620

Lys Arg Leu Glu Gly Leu Pro Lys His Leu Ser Arg Leu Val Lys Leu
625                 630                 635                 640

Gln Thr Leu Asp Ile Tyr Gly Cys Asn Asn Val Thr Tyr Met Pro Lys
                645                 650                 655

Gly Met Gly Lys Met Thr Cys Leu His Thr Leu Ser Lys Phe Ile Val
            660                 665                 670

Gly Gly Glu Gly Ser Cys Ser Ser Trp Lys Lys Arg Phe Asp Gly Leu
        675                 680                 685
```

```
Glu Asp Leu Lys Ala Leu Asn Asn Leu Lys Gly His Leu Glu Ile Gln
    690                 695                 700
Ile Arg Trp Pro Glu Asn Thr Thr Asp Ala Val Lys Glu Asp Val Lys
705                 710                 715                 720
Arg Glu Gly Leu Tyr Leu Asn His
                725

<210> SEQ ID NO 29
<211> LENGTH: 738
<212> TYPE: PRT
<213> ORGANISM: Beta vulgaris
<220> FEATURE:
<221> NAME/KEY: MOD_RES
<222> LOCATION: (290)..(361)
<223> OTHER INFORMATION: Any amino acid
<220> FEATURE:
<221> NAME/KEY: MOD_RES
<222> LOCATION: (392)..(392)
<223> OTHER INFORMATION: Any amino acid
<220> FEATURE:
<221> NAME/KEY: MOD_RES
<222> LOCATION: (471)..(471)
<223> OTHER INFORMATION: Any amino acid
<220> FEATURE:
<221> NAME/KEY: MOD_RES
<222> LOCATION: (525)..(564)
<223> OTHER INFORMATION: Any amino acid

<400> SEQUENCE: 29

Met Asp Val Val Gly Ser Ala Leu Ser Ala Ala Gln Ser Leu Phe Ala
1               5                   10                  15

Ala Leu Gln Ser Ser Glu Leu Lys Glu Ile Leu Ser Ile Phe Gly Tyr
                20                  25                  30

Lys Ser Gln Leu Asp Asp Leu Gln Arg Ile Val Ser Thr Ile Asn Ala
            35                  40                  45

Val Phe Arg Asp Ala Glu Thr Lys Gln Glu Leu Thr His Glu Ala Gln
    50                  55                  60

His Trp Leu Glu Glu Leu Lys Asp Ala Val Phe Glu Ala Asp Asp Leu
65                  70                  75                  80

Phe Asp Glu Phe Val Thr Leu Ala Glu Gln Lys Gln Leu Val Glu Ala
                85                  90                  95

Gly Gly Ser Leu Ser Lys Lys Met Arg Gln Phe Phe Ser Asp Ser Asn
                100                 105                 110

Pro Leu Gly Ile Ala Tyr Lys Met Ser Gln Gly Val Lys Lys Ile Lys
            115                 120                 125

Lys Lys Leu Asp Val Ile Ala Tyr Asn His Gln Phe Ser Phe Lys Ile
130                 135                 140

Asp Leu Glu Pro Ile Lys Glu Arg Arg Leu Glu Thr Gly Ser Val Val
145                 150                 155                 160

Asn Ala Gly Asp Ile Ile Gly Arg Glu Asp Asp Leu Glu Lys Ile Val
                165                 170                 175

Gly Leu Phe Leu Asp Ser Asn Ile Gln Arg Asp Val Ser Phe Leu Thr
            180                 185                 190

Ile Val Gly Met Gly Gly Leu Gly Lys Thr Ala Leu Ala Gln Leu Val
        195                 200                 205

Tyr Asn Asp Pro Arg Val Arg Thr Ala Phe Pro Leu Arg Cys Trp Asn
    210                 215                 220

Cys Val Ser Asp Gln Asp Gln Asn Gln Leu Asp Val Lys Glu Ile Leu
225                 230                 235                 240

Gly Lys Ile Leu Ser Thr Ala Thr Gly Lys Asn His Lys Gly Ser Thr
```

```
            245                 250                 255
Met Asp Gln Val Gln Thr Gln Leu Arg Glu Gln Leu Cys Gly Lys Arg
            260                 265                 270

Tyr Leu Leu Val Leu Asp Asp Val Trp Asn Glu Asn Pro Asn Gln Leu
        275                 280                 285

Arg Xaa Xaa Xaa Xaa Xaa Xaa Xaa Xaa Xaa Xaa Xaa Xaa Xaa Xaa Xaa
    290                 295                 300

Xaa Xaa Xaa Xaa Xaa Xaa Xaa Xaa Xaa Xaa Xaa Xaa Xaa Xaa Xaa Xaa
305                 310                 315                 320

Xaa Xaa Xaa Xaa Xaa Xaa Xaa Xaa Xaa Xaa Xaa Xaa Xaa Xaa Xaa Xaa
            325                 330                 335

Xaa Xaa Xaa Xaa Xaa Xaa Xaa Xaa Xaa Xaa Xaa Xaa Xaa Xaa Xaa Xaa
            340                 345                 350

Xaa Xaa Xaa Xaa Xaa Xaa Xaa Xaa Asp Lys Cys Ala Arg Asn Pro
            355                 360                 365

Leu Ala Ile Arg Val Val Gly Ser Leu Leu Cys Gly Gln Asp Lys Ser
        370                 375                 380

Lys Trp Leu Ser Phe His Glu Xaa Cys Leu Ala Asn Ile Arg Lys Ser
385                 390                 395                 400

His Asn Asp Ile Met Pro Ile Leu Asn Leu Ser Tyr His His Leu Glu
                405                 410                 415

Pro Pro Ile Arg Arg Cys Phe Ser Tyr Cys Ala Val Phe Pro Lys Asp
            420                 425                 430

Phe Leu Ile Gly Lys Lys Thr Leu Ile Asn Leu Trp Met Ala Gln Gly
            435                 440                 445

Tyr Ile Val Pro Leu Asp Lys Asp Gln Ser Ile Asp Asp Ala Ser Glu
    450                 455                 460

Glu Tyr Ile Ser Ile Leu Xaa Gln Arg Cys Phe Phe Glu Asn Ile Gly
465                 470                 475                 480

Thr Glu Lys Asp Asp Val Ile Lys Ile His Asp Leu Met His Asp Ile
                485                 490                 495

Ala Gln Asn Val Met Gly Lys Glu Leu Cys Thr Thr Lys Asn Ile Ser
            500                 505                 510

Gly Ser Leu Asp Lys Asn Val Arg His Leu Ser Leu Xaa Xaa Xaa Xaa
        515                 520                 525

Xaa Xaa Xaa Xaa Xaa Xaa Xaa Xaa Xaa Xaa Xaa Xaa Xaa Xaa Xaa Xaa
    530                 535                 540

Xaa Xaa Xaa Xaa Xaa Xaa Xaa Xaa Xaa Xaa Xaa Xaa Xaa Xaa Xaa Xaa
545                 550                 555                 560

Xaa Xaa Xaa Xaa Asn Cys Leu Cys Leu Arg Ala Leu Asp Leu Ala Trp
            565                 570                 575

Ser Lys Ile Lys Ser Leu Pro Asp Ser Ile Gly Gly Leu Leu His Leu
        580                 585                 590

Arg Tyr Leu Asp Leu Ser Tyr Asn Glu Asp Leu Glu Val Leu Pro Asn
            595                 600                 605

Ser Ile Ala Lys Leu Tyr Asn Leu Gln Thr Leu Gln Leu Lys Gly Cys
    610                 615                 620

Lys Arg Leu Glu Gly Leu Pro Lys His Leu Ser Arg Leu Val Lys Leu
625                 630                 635                 640

Gln Thr Leu Asp Ile Tyr Gly Cys Asn Asn Val Thr Tyr Met Pro Lys
                645                 650                 655

Gly Met Gly Lys Met Thr Cys Leu His Thr Leu Ser Lys Phe Ile Val
            660                 665                 670
```

Gly Gly Glu Gly Ser Cys Ser Ser Trp Lys Lys Arg Phe Asp Gly Leu
            675                 680                 685

Glu Asp Leu Lys Ala Leu Asn Asn Leu Lys Gly His Leu Glu Ile Gln
        690                 695                 700

Ile Arg Trp Pro Glu Asn Thr Thr Asp Ala Val Lys Glu Asp Val Lys
705                 710                 715                 720

Arg Glu Gly Leu Tyr Leu Asn His Lys Glu His Leu Asn His Ile Val
                725                 730                 735

Val Asp

<210> SEQ ID NO 30
<211> LENGTH: 895
<212> TYPE: PRT
<213> ORGANISM: Beta vulgaris

<400> SEQUENCE: 30

Met Glu Arg Val Val Tyr Arg Trp Asn Thr Ala Gly His Leu Trp Pro
1               5                   10                  15

Thr Asn Gln Lys Leu Ile Leu Ile Pro Tyr Ala Leu Gln Ser Ser Glu
            20                  25                  30

Leu Lys Glu Ile Leu Ser Ile Phe Gly Tyr Lys Ser Gln Leu Asp Asp
        35                  40                  45

Leu Gln Arg Thr Val Ser Thr Ile Asn Ala Val Phe Arg Asp Ala Glu
50                  55                  60

Thr Lys Gln Glu Leu Thr His Glu Ala Gln His Trp Leu Glu Glu Leu
65                  70                  75                  80

Lys Asp Ala Val Phe Glu Ala Asp Asp Leu Phe Asp Glu Phe Val Thr
                85                  90                  95

Leu Ala Glu Gln Lys Gln Leu Val Glu Ala Gly Gly Ser Leu Ser Lys
            100                 105                 110

Lys Met Arg Gln Phe Phe Ser Asp Ser Asn Pro Leu Gly Ile Ala Tyr
        115                 120                 125

Arg Met Ser Arg Gly Val Lys Lys Ile Lys Lys Lys Leu Asp Ala Ile
130                 135                 140

Ala Tyr Asn His Gln Phe Ser Phe Lys Ile Asp Leu Glu Pro Ile Lys
145                 150                 155                 160

Glu Arg Arg Leu Glu Thr Gly Ser Val Val Asn Ala Gly Asp Ile Ile
                165                 170                 175

Gly Arg Glu Asp Asp Leu Glu Lys Ile Val Gly Leu Leu Asp Ser
            180                 185                 190

Asn Ile Gln Arg Asp Val Ser Phe Leu Thr Ile Val Gly Met Gly Gly
        195                 200                 205

Leu Gly Lys Thr Ala Leu Ala Gln Leu Val Tyr Asn Asp Pro Arg Val
210                 215                 220

Arg Thr Ala Phe Pro Leu Arg Cys Trp Asn Cys Val Ser Asp Gln Asp
225                 230                 235                 240

Gln Lys Lys Leu Asp Val Lys Glu Ile Leu Gly Lys Ile Leu Ser Thr
                245                 250                 255

Ala Thr Gly Lys Asn His Glu Gly Ser Thr Met Asp His Val Gln Thr
            260                 265                 270

Gln Leu Arg Glu Gln Leu Cys Gly Lys Arg Tyr Leu Leu Val Leu Asp
        275                 280                 285

Asp Val Trp Asn Glu Asn Pro Asn Gln Leu Arg Tyr Leu Val Glu Phe
290                 295                 300

```
Phe Met Gly Gly Gln Arg Gly Asn Trp Ile Val Val Thr Thr Arg Ser
305                 310                 315                 320

His Glu Thr Ala Arg Ile Ile Arg Asp Gly Pro Leu His Lys Leu Gln
                325                 330                 335

Gly Leu Ser Glu Glu Asn Ser Trp Arg Leu Phe Val Arg Trp Thr Phe
            340                 345                 350

Gly Ser Val Gln Pro Lys Phe Pro Asn Asp Phe Val Met Ile Ala Arg
        355                 360                 365

Asp Ile Val Asp Lys Cys Ala Arg Asn Pro Leu Ala Ile Arg Val Val
370                 375                 380

Gly Ser Leu Leu Cys Gly Gln Asp Lys Ser Lys Trp Leu Ser Phe His
385                 390                 395                 400

Glu Ile Cys Leu Ala Asn Ile Arg Lys Ser His Asn Asp Ile Met Pro
                405                 410                 415

Ile Leu Asn Leu Ser Tyr His His Leu Glu Pro Pro Ile Arg Arg Cys
            420                 425                 430

Phe Ser Tyr Cys Ala Met Phe Pro Lys Asp Phe Leu Ile Gly Lys Lys
        435                 440                 445

Thr Leu Ile Asn Leu Trp Met Ala Gln Gly Tyr Ile Val Pro Leu Asp
450                 455                 460

Lys Asp Gln Ser Ile Asp Asp Ala Ser Glu Glu Tyr Ile Ser Ile Leu
465                 470                 475                 480

Leu Gln Arg Cys Phe Phe Glu Asn Ile Gly Thr Glu Lys Asp Tyr Val
                485                 490                 495

Ile Lys Ile His Asp Leu Met His Asp Ile Ala Gln Asn Val Met Gly
            500                 505                 510

Lys Glu Leu Cys Thr Thr Lys Asn Ile Ser Gly Ser Leu Asp Lys Asn
        515                 520                 525

Val Arg His Leu Ser Leu Ala Arg Thr Ser Phe Ala Arg Tyr Ser Phe
530                 535                 540

Asn Ala Thr His Ile Arg Ser Tyr Phe Tyr Ala Gly Tyr Trp Cys Gln
545                 550                 555                 560

Asp Ala Glu Ile Asn Gln Phe Ser Val Glu Ala Leu Val Pro Asn Cys
                565                 570                 575

Leu Cys Leu Arg Ala Leu Asp Leu Ala Trp Ser Lys Ile Lys Ser Val
            580                 585                 590

Pro Asp Ser Ile Gly Gly Leu Leu His Leu Arg Tyr Leu Asp Leu Ser
        595                 600                 605

Tyr Asn Glu Asp Leu Glu Val Leu Pro Asn Ser Ile Ala Lys Leu Tyr
610                 615                 620

Asn Leu Gln Thr Leu Gln Leu Lys Gly Cys Lys Arg Leu Glu Gly Leu
625                 630                 635                 640

Pro Lys His Leu Ser Arg Leu Val Lys Leu Gln Thr Leu Asp Ile Tyr
                645                 650                 655

Gly Cys Asn Asn Val Thr Tyr Met Pro Lys Gly Met Gly Lys Met Thr
            660                 665                 670

Cys Leu His Thr Leu Ser Lys Phe Ile Val Gly Gly Glu Gly Ser Cys
        675                 680                 685

Ser Ser Trp Lys Gln Trp Phe Asp Gly Gln Glu Asp Leu Lys Ala Leu
690                 695                 700

Asn Asn Leu Lys Gly His Leu Glu Ile Gln Ile Arg Trp Pro Glu Asn
705                 710                 715                 720
```

-continued

```
Thr Thr Asp Ala Val Lys Glu Asp Val Lys Arg Glu Gly Leu Tyr Leu
            725                 730                 735

Asn His Lys Glu His Leu Asn His Ile Val Val Asp Phe Arg Cys Glu
            740                 745                 750

Glu Gly Gly Gly Arg Met Asp Asp Glu Glu Ala Arg Arg Leu Met Glu
            755                 760                 765

Glu Leu Arg Pro His Pro Tyr Leu Glu Asn Leu Ala Val Lys Ala Tyr
            770                 775                 780

Tyr Gly Ala Lys Met Pro Gly Trp Ala Thr Leu Pro Asn Leu Thr
785                 790                 795                 800

Glu Leu Tyr Leu Ser Asp Cys Gly Glu Ser Glu Cys Leu Pro Cys Met
            805                 810                 815

Gly Asn Leu Asp Cys Leu Lys Val Leu Arg Leu Ser His Leu Ala Lys
            820                 825                 830

Leu Glu Tyr Ile Glu Glu Asp Ser Thr Ser Ala Asn Phe Ser Phe Arg
            835                 840                 845

Pro Gly Pro Glu Ser Ala Gly Leu Ser Leu Tyr Phe Pro Ser Leu Glu
            850                 855                 860

Leu Leu Glu Leu Lys Arg Leu His Lys Leu Lys Gly Trp Arg Arg Arg
865                 870                 875                 880

Glu Gly Leu Gly Asp Asp His Gln Pro Phe Asn Glu Ser Ser Ser
            885                 890                 895

<210> SEQ ID NO 31
<211> LENGTH: 752
<212> TYPE: PRT
<213> ORGANISM: Beta vulgaris
<220> FEATURE:
<221> NAME/KEY: MOD_RES
<222> LOCATION: (304)..(307)
<223> OTHER INFORMATION: Any amino acid
<220> FEATURE:
<221> NAME/KEY: MOD_RES
<222> LOCATION: (569)..(569)
<223> OTHER INFORMATION: Any amino acid

<400> SEQUENCE: 31

Met Glu Arg Val Val Tyr Arg Trp Asn Thr Ala Glu Thr Ala Gly His
1               5                   10                  15

Leu Trp Pro Thr Asn Pro Lys Leu Ile Leu Ile Pro Tyr Ser Ala Leu
            20                  25                  30

Gln Ser Ser Glu Leu Lys Glu Ile Leu Ser Ile Phe Gly Tyr Lys Ser
            35                  40                  45

Gln Leu Asp Asp Leu Gln Arg Thr Val Ser Thr Ile Asn Ala Val Phe
        50                  55                  60

Arg Asp Ala Glu Thr Lys Gln Glu Leu Thr His Glu Ala Gln His Trp
65                  70                  75                  80

Leu Glu Glu Leu Lys Asp Ala Val Phe Glu Ala Asp Leu Phe Asp
            85                  90                  95

Glu Phe Val Thr Leu Ala Glu Gln Lys Gln Leu Val Glu Ala Gly Gly
            100                 105                 110

Ser Leu Ser Lys Lys Met Arg Gln Phe Phe Ser Asp Ser Asn Pro Leu
            115                 120                 125

Gly Ile Ala Tyr Arg Met Ser Arg Gly Val Lys Lys Ile Lys Lys Lys
            130                 135                 140

Leu Asp Ala Ile Ala Tyr Asn His Gln Phe Ser Phe Lys Ile Asp Leu
145                 150                 155                 160
```

```
Glu Pro Ile Lys Glu Arg Arg Leu Glu Thr Gly Ser Val Val Asn Ala
            165                 170                 175

Gly Asp Ile Ile Gly Arg Glu Asp Leu Glu Lys Ile Val Gly Leu
        180                 185                 190

Leu Leu Asp Ser Asn Ile Gln Arg Asp Val Ser Phe Leu Thr Ile Val
            195                 200                 205

Gly Met Gly Gly Leu Gly Lys Thr Ala Leu Ala Gln Leu Val Tyr Asn
        210                 215                 220

Asp Pro Arg Val Arg Thr Ala Phe Pro Leu Arg Cys Trp Asn Cys Val
225                 230                 235                 240

Ser Asp Gln Asp Gln Lys Lys Leu Asp Val Lys Glu Ile Leu Gly Lys
            245                 250                 255

Ile Leu Ser Thr Ala Thr Gly Lys Asn His Glu Gly Ser Thr Met Asp
            260                 265                 270

His Val Gln Thr Gln Leu Gln Glu Gln Leu Cys Gly Lys Arg Tyr Leu
            275                 280                 285

Leu Val Leu Asp Asp Val Trp Asn Glu Asn Pro Asn Gln Leu Arg Xaa
        290                 295                 300

Xaa Xaa Xaa Phe Phe Met Gly Gly Gln Arg Gly Asn Trp Ile Val Val
305                 310                 315                 320

Thr Thr Arg Ser His Glu Thr Thr Arg Ile Ile Arg Asp Gly Pro Leu
            325                 330                 335

His Lys Leu Gln Gly Leu Ser Glu Glu Asn Ser Trp Arg Leu Phe Val
            340                 345                 350

Arg Trp Thr Phe Gly Ser Val Gln Pro Lys Phe Pro Asn Asp Phe Val
        355                 360                 365

Met Ile Ala Arg Asp Ile Val Asp Lys Cys Ala Arg Asn Pro Leu Ala
370                 375                 380

Ile Arg Val Val Gly Ser Leu Leu Cys Gly Gln Asp Lys Ser Lys Trp
385                 390                 395                 400

Leu Ser Phe His Glu Ile Cys Leu Ala Asn Ile Arg Lys Ser His Asn
            405                 410                 415

Asp Ile Met Leu Ile Leu Asn Leu Ser Tyr His His Leu Glu Pro Pro
            420                 425                 430

Ile Arg Arg Cys Phe Ser Tyr Cys Ala Met Phe Pro Lys Asp Phe Leu
            435                 440                 445

Ile Gly Lys Lys Thr Leu Ile Asn Leu Trp Met Ala Gln Gly Tyr Ile
            450                 455                 460

Val Pro Leu Asp Lys Asp Gln Ser Ile Asp Asp Ala Ser Glu Glu Tyr
465                 470                 475                 480

Ile Ser Ile Leu Leu Gln Arg Cys Phe Phe Glu Asn Ile Gly Thr Glu
            485                 490                 495

Lys Asp Tyr Val Ile Lys Ile His Asp Leu Met His Asp Ile Ala Gln
            500                 505                 510

Asn Val Met Gly Lys Glu Leu Cys Thr Thr Lys Asn Ile Ser Gly Ser
            515                 520                 525

Leu Asp Lys Asn Val Arg His Leu Ser Leu Ala Arg Thr Ser Phe Ala
        530                 535                 540

Arg Tyr Ser Phe Asn Ala Thr His Ile Arg Ser Tyr Phe Tyr Ala Gly
545                 550                 555                 560

Tyr Trp Cys Gln Asp Ala Glu Ile Xaa Gln Phe Ser Val Glu Ala Leu
            565                 570                 575

Val Pro Asn Cys Leu Cys Leu Arg Ala Leu Asp Leu Ala Trp Ser Lys
```

```
                580              585              590
Ile Lys Ser Val Pro Asp Ser Ile Gly Gly Leu Leu His Leu Arg Tyr
            595              600              605

Leu Asp Leu Ser Tyr Asn Glu Asp Leu Glu Val Leu Pro Asn Ser Ile
        610              615              620

Ala Lys Leu Tyr Asn Leu Gln Thr Leu Gln Leu Lys Gly Cys Lys Arg
625              630              635              640

Leu Glu Gly Leu Pro Lys His Leu Ser Arg Leu Val Lys Leu Gln Thr
                645              650              655

Leu Asp Ile Tyr Gly Cys Asn Asn Val Thr Tyr Met Pro Lys Gly Met
            660              665              670

Gly Lys Met Thr Cys Leu His Thr Leu Ser Lys Phe Ile Val Gly Gly
        675              680              685

Glu Gly Ser Cys Ser Ser Trp Lys Gln Trp Phe Asp Gly Gln Glu Asp
    690              695              700

Leu Lys Ala Leu Asn Asn Leu Lys Gly His Leu Glu Ile Gln Ile Arg
705              710              715              720

Trp Pro Glu Asn Thr Thr Asp Ala Val Lys Glu Asp Val Lys Arg Glu
                725              730              735

Gly Leu Tyr Leu Asn His Lys Glu His Leu Asn His Ile Val Val Asp
            740              745              750
```

<210> SEQ ID NO 32
<211> LENGTH: 752
<212> TYPE: PRT
<213> ORGANISM: Beta vulgaris

<400> SEQUENCE: 32

```
Met Glu Arg Val Val Tyr Arg Trp Asn Thr Ala Glu Thr Ala Gly His
1               5                  10                  15

Leu Trp Pro Thr Asn Pro Lys Leu Ile Leu Ile Pro Tyr Ser Ala Leu
            20                  25                  30

Gln Ser Ser Glu Leu Lys Glu Ile Leu Ser Ile Phe Gly Tyr Lys Ser
        35                  40                  45

Gln Leu Asp Asp Leu Gln Arg Thr Val Ser Thr Ile Asn Ala Val Phe
    50                  55                  60

Arg Asp Ala Glu Thr Lys Gln Glu Leu Thr His Glu Ala Gln His Trp
65                  70                  75                  80

Leu Glu Glu Leu Lys Asp Ala Val Phe Glu Ala Asp Leu Phe Asp
                85                  90                  95

Glu Phe Val Thr Leu Ala Glu Gln Lys Gln Leu Val Glu Ala Gly Gly
            100                 105                 110

Ser Leu Ser Lys Lys Met Arg Gln Phe Phe Ser Asp Ser Asn Pro Leu
        115                 120                 125

Gly Ile Ala Tyr Arg Met Ser Arg Gly Val Lys Lys Ile Lys Lys Lys
    130                 135                 140

Leu Asp Ala Ile Ala Tyr Asn His Gln Phe Ser Phe Lys Ile Asp Leu
145                 150                 155                 160

Glu Pro Ile Lys Glu Arg Arg Leu Glu Thr Gly Ser Val Val Asn Ala
                165                 170                 175

Gly Asp Ile Ile Gly Arg Glu Asp Asp Leu Glu Lys Ile Val Gly Leu
            180                 185                 190

Leu Leu Asp Ser Asn Ile Gln Arg Asp Val Ser Phe Leu Thr Ile Val
        195                 200                 205
```

```
Gly Met Gly Gly Leu Gly Lys Thr Ala Leu Ala Gln Leu Val Tyr Asn
    210             215                 220
Asp Pro Arg Val Arg Thr Ala Phe Pro Leu Arg Cys Trp Asn Cys Val
225             230                 235                 240
Ser Asp Gln Asp Gln Lys Lys Leu Asp Val Lys Glu Ile Leu Gly Lys
                245                 250                 255
Ile Leu Ser Thr Ala Thr Gly Lys Asn His Glu Gly Ser Thr Met Asp
            260                 265                 270
His Val Gln Thr Gln Leu Gln Glu Gln Leu Cys Gly Lys Arg Tyr Leu
        275                 280                 285
Leu Val Leu Asp Asp Val Trp Asn Glu Asn Pro Asn Gln Leu Arg Asp
    290                 295                 300
Leu Gly Lys Phe Phe Met Gly Gln Arg Gly Asn Trp Ile Val Val
305             310                 315                 320
Thr Thr Arg Ser His Glu Thr Thr Arg Ile Ile Arg Asp Gly Pro Leu
                325                 330                 335
His Lys Leu Gln Gly Leu Ser Glu Glu Asn Ser Trp Arg Leu Phe Val
            340                 345                 350
Arg Trp Thr Phe Gly Ser Val Gln Pro Lys Phe Pro Asn Asp Phe Val
        355                 360                 365
Met Ile Ala Arg Asp Ile Val Asp Lys Cys Ala Arg Asn Pro Leu Ala
    370                 375                 380
Ile Arg Val Val Gly Ser Leu Leu Cys Gly Gln Asp Lys Ser Lys Trp
385             390                 395                 400
Leu Ser Phe His Glu Ile Cys Leu Ala Asn Ile Arg Lys Ser His Asn
                405                 410                 415
Asp Ile Met Leu Ile Leu Asn Leu Ser Tyr His His Leu Glu Pro Pro
            420                 425                 430
Ile Arg Arg Cys Phe Ser Tyr Cys Ala Met Phe Pro Lys Asp Phe Leu
        435                 440                 445
Ile Gly Lys Lys Thr Leu Ile Asn Leu Trp Met Ala Gln Gly Tyr Ile
    450                 455                 460
Val Pro Leu Asp Lys Asp Gln Ser Ile Asp Asp Ala Ser Glu Glu Tyr
465             470                 475                 480
Ile Ser Ile Leu Leu Gln Arg Cys Phe Phe Glu Asn Ile Gly Thr Glu
                485                 490                 495
Lys Asp Tyr Val Ile Lys Ile His Asp Leu Met His Asp Ile Ala Gln
            500                 505                 510
Asn Val Met Gly Lys Glu Leu Cys Thr Thr Lys Asn Ile Ser Gly Ser
        515                 520                 525
Leu Asp Lys Asn Val Arg His Leu Ser Leu Ala Arg Thr Ser Phe Ala
    530                 535                 540
Arg Tyr Ser Phe Asn Ala Thr His Ile Arg Ser Tyr Phe Tyr Ala Gly
545             550                 555                 560
Tyr Trp Cys Gln Asp Ala Glu Ile Asn Gln Phe Ser Val Glu Ala Leu
                565                 570                 575
Val Pro Asn Cys Leu Cys Leu Arg Ala Leu Asp Leu Ala Trp Ser Lys
            580                 585                 590
Ile Lys Ser Val Pro Asp Ser Ile Gly Gly Leu Leu His Leu Arg Tyr
        595                 600                 605
Leu Asp Leu Ser Tyr Asn Glu Asp Leu Glu Val Leu Pro Asn Ser Ile
    610                 615                 620
Ala Lys Leu Tyr Asn Leu Gln Thr Leu Gln Leu Lys Gly Cys Lys Arg
```

```
625                 630                 635                 640
Leu Glu Gly Leu Pro Lys His Leu Ser Arg Leu Val Lys Leu Gln Thr
                645                 650                 655

Leu Asp Ile Tyr Gly Cys Asn Asn Val Thr Tyr Met Pro Lys Gly Met
                660                 665                 670

Gly Lys Met Thr Cys Leu His Thr Leu Ser Lys Phe Ile Val Gly Gly
                675                 680                 685

Glu Gly Ser Cys Ser Ser Trp Lys Gln Trp Phe Asp Gly Gln Glu Asp
                690                 695                 700

Leu Lys Ala Leu Asn Asn Leu Lys Gly His Leu Glu Ile Gln Ile Arg
705                 710                 715                 720

Trp Pro Glu Asn Thr Thr Asp Ala Val Lys Glu Asp Val Lys Arg Glu
                725                 730                 735

Gly Leu Tyr Leu Asn His Lys Glu His Leu Asn His Ile Val Val Asp
                740                 745                 750
```

<210> SEQ ID NO 33
<211> LENGTH: 752
<212> TYPE: PRT
<213> ORGANISM: Beta vulgaris
<220> FEATURE:
<221> NAME/KEY: MOD_RES
<222> LOCATION: (305)..(305)
<223> OTHER INFORMATION: Any amino acid

<400> SEQUENCE: 33

```
Met Glu Arg Val Val Tyr Arg Trp Asn Thr Ala Glu Thr Ala Gly His
1               5                   10                  15

Leu Trp Pro Thr Asn Pro Lys Leu Ile Leu Ile Pro Tyr Ser Ala Leu
                20                  25                  30

Gln Ser Ser Glu Leu Lys Glu Ile Leu Ser Ile Phe Gly Tyr Lys Ser
                35                  40                  45

Gln Leu Asp Asp Leu Gln Arg Thr Val Ser Thr Ile Asn Ala Val Phe
        50                  55                  60

Arg Asp Ala Glu Thr Lys Gln Glu Leu Thr His Glu Ala Gln His Trp
65                  70                  75                  80

Leu Glu Glu Leu Lys Asp Ala Val Phe Glu Ala Asp Leu Phe Asp
                85                  90                  95

Glu Phe Val Thr Leu Ala Glu Gln Lys Gln Leu Val Glu Ala Gly Gly
                100                 105                 110

Ser Leu Ser Lys Lys Met Arg Gln Phe Phe Ser Asp Ser Asn Pro Leu
                115                 120                 125

Gly Ile Ala Tyr Arg Met Ser Arg Gly Val Lys Lys Ile Lys Lys Lys
        130                 135                 140

Leu Asp Ala Ile Ala Tyr Asn His Gln Phe Ser Phe Lys Ile Asp Leu
145                 150                 155                 160

Glu Pro Ile Lys Glu Arg Arg Leu Glu Thr Gly Ser Val Val Asn Ala
                165                 170                 175

Gly Asp Ile Ile Gly Arg Glu Asp Leu Glu Lys Ile Val Gly Leu
                180                 185                 190

Leu Leu Asp Ser Asn Ile Gln Arg Asp Val Ser Phe Leu Thr Ile Val
                195                 200                 205

Gly Met Gly Gly Leu Gly Lys Thr Ala Leu Ala Gln Leu Val Tyr Asn
        210                 215                 220

Asp Pro Arg Val Arg Thr Ala Phe Pro Leu Arg Cys Trp Asn Cys Val
225                 230                 235                 240
```

-continued

```
Ser Asp Gln Asp Gln Lys Lys Leu Asp Val Lys Glu Ile Leu Gly Lys
            245                 250                 255

Ile Leu Ser Thr Ala Thr Gly Lys Asn His Glu Gly Ser Thr Met Asp
        260                 265                 270

His Val Gln Thr Gln Leu Gln Glu Gln Leu Cys Gly Lys Arg Tyr Leu
    275                 280                 285

Leu Val Leu Asp Asp Val Trp Asn Glu Asn Pro Asn Gln Leu Arg Asp
290                 295                 300

Xaa Val Glu Phe Phe Met Gly Gly Gln Arg Gly Asn Trp Ile Val Val
305                 310                 315                 320

Thr Thr Arg Ser His Glu Thr Thr Arg Ile Ile Arg Asp Gly Pro Leu
            325                 330                 335

His Lys Leu Gln Gly Leu Ser Glu Glu Asn Ser Trp Arg Leu Phe Val
        340                 345                 350

Arg Trp Thr Phe Gly Ser Val Gln Pro Lys Phe Pro Asn Asp Phe Val
    355                 360                 365

Met Ile Ala Arg Asp Ile Val Asp Lys Cys Ala Arg Asn Pro Leu Ala
370                 375                 380

Ile Arg Val Val Gly Ser Leu Cys Gly Gln Asp Lys Ser Lys Trp
385                 390                 395                 400

Leu Ser Phe His Glu Ile Cys Leu Ala Asn Ile Arg Lys Ser His Asn
            405                 410                 415

Asp Ile Met Leu Ile Leu Asn Leu Ser Tyr His His Leu Glu Pro Pro
        420                 425                 430

Ile Arg Arg Cys Phe Ser Tyr Cys Ala Met Phe Pro Lys Asp Phe Leu
    435                 440                 445

Ile Gly Lys Lys Thr Leu Ile Asn Leu Trp Met Ala Gln Gly Tyr Ile
450                 455                 460

Val Pro Leu Asp Lys Asp Gln Ser Ile Asp Asp Ala Ser Glu Glu Tyr
465                 470                 475                 480

Ile Ser Ile Leu Leu Gln Arg Cys Phe Phe Glu Asn Ile Gly Thr Glu
            485                 490                 495

Lys Asp Tyr Val Ile Lys Ile His Asp Leu Met His Asp Ile Ala Gln
        500                 505                 510

Asn Val Met Gly Lys Glu Leu Cys Thr Thr Lys Asn Ile Ser Gly Ser
    515                 520                 525

Leu Asp Lys Asn Val Arg His Leu Ser Leu Ala Arg Thr Ser Phe Ala
530                 535                 540

Arg Tyr Ser Phe Asn Ala Thr His Ile Arg Ser Tyr Phe Tyr Ala Gly
545                 550                 555                 560

Tyr Trp Cys Gln Asp Ala Glu Ile Asn Gln Phe Ser Val Glu Ala Leu
            565                 570                 575

Val Pro Asn Cys Leu Cys Leu Arg Ala Leu Asp Leu Ala Trp Ser Lys
        580                 585                 590

Ile Lys Ser Val Pro Asp Ser Ile Gly Gly Leu Leu His Leu Arg Tyr
    595                 600                 605

Leu Asp Leu Ser Tyr Asn Glu Asp Leu Glu Val Leu Pro Asn Ser Ile
610                 615                 620

Ala Lys Leu Tyr Asn Leu Gln Thr Leu Gln Leu Lys Gly Cys Lys Arg
625                 630                 635                 640

Leu Glu Gly Leu Pro Lys His Leu Ser Arg Leu Val Lys Leu Gln Thr
            645                 650                 655
```

```
Leu Asp Ile Tyr Gly Cys Asn Asn Val Thr Tyr Met Pro Lys Gly Met
            660                 665                 670

Gly Lys Met Thr Cys Leu His Thr Leu Ser Lys Phe Ile Val Gly Gly
        675                 680                 685

Glu Gly Ser Cys Ser Ser Trp Lys Gln Trp Phe Asp Gly Gln Glu Asp
    690                 695                 700

Leu Lys Ala Leu Asn Asn Leu Lys Gly His Leu Glu Ile Gln Ile Arg
705                 710                 715                 720

Trp Pro Glu Asn Thr Thr Asp Ala Val Lys Asp Val Lys Arg Glu
                725                 730                 735

Gly Leu Tyr Leu Asn His Lys Glu His Leu Asn His Ile Val Val Asp
        740                 745                 750

<210> SEQ ID NO 34
<211> LENGTH: 742
<212> TYPE: PRT
<213> ORGANISM: Beta vulgaris
<220> FEATURE:
<221> NAME/KEY: MOD_RES
<222> LOCATION: (303)..(307)
<223> OTHER INFORMATION: Any amino acid
<220> FEATURE:
<221> NAME/KEY: MOD_RES
<222> LOCATION: (558)..(558)
<223> OTHER INFORMATION: Any amino acid

<400> SEQUENCE: 34

Met Glu Arg Val Val Tyr Arg Trp Asn Thr Ala Glu Thr Ala Gly His
1               5                   10                  15

Leu Trp Pro Thr Asn Pro Lys Leu Ile Leu Ile Pro Tyr Ser Ala Leu
            20                  25                  30

Gln Ser Ser Glu Leu Lys Glu Ile Leu Ser Ile Phe Gly Tyr Lys Ser
        35                  40                  45

Gln Leu Asp Asp Leu Gln Arg Thr Val Ser Thr Ile Asn Ala Val Phe
    50                  55                  60

Arg Asp Ala Glu Thr Lys Gln Glu Leu Thr His Glu Ala Gln His Trp
65                  70                  75                  80

Leu Glu Glu Leu Lys Asp Ala Val Phe Glu Ala Asp Asp Leu Phe Asp
                85                  90                  95

Glu Phe Val Thr Leu Ala Glu Gln Lys Gln Leu Val Glu Ala Gly Gly
            100                 105                 110

Ser Leu Ser Lys Lys Met Arg Gln Phe Phe Ser Asp Ser Asn Pro Leu
        115                 120                 125

Gly Ile Ala Tyr Arg Met Ser Arg Gly Val Lys Lys Ile Lys Lys Lys
    130                 135                 140

Leu Asp Ala Ile Ala Tyr Asn His Gln Phe Ser Phe Lys Ile Asp Leu
145                 150                 155                 160

Glu Pro Ile Lys Glu Arg Arg Leu Glu Thr Gly Ser Val Val Asn Ala
                165                 170                 175

Gly Asp Ile Ile Gly Arg Glu Asp Leu Glu Lys Ile Val Gly Leu
            180                 185                 190

Leu Leu Asp Ser Asn Ile Gln Arg Asp Val Ser Phe Leu Thr Ile Val
        195                 200                 205

Gly Met Gly Gly Leu Gly Lys Thr Ala Leu Ala Gln Leu Val Tyr Asn
    210                 215                 220

Asp Pro Arg Val Arg Thr Ala Phe Pro Leu Arg Cys Trp Asn Cys Val
225                 230                 235                 240
```

```
Ser Asp Gln Asp Gln Lys Lys Leu Asp Val Lys Glu Ile Leu Gly Lys
                245                 250                 255

Ile Leu Ser Thr Ala Thr Gly Lys Asn His Glu Gly Ser Thr Met Asp
            260                 265                 270

His Val Gln Thr Gln Leu Gln Glu Gln Leu Cys Gly Lys Arg Tyr Leu
        275                 280                 285

Leu Val Leu Asp Asp Val Trp Asn Glu Asn Pro Asn Gln Leu Xaa Xaa
    290                 295                 300

Xaa Xaa Xaa Phe Phe Met Gly Gly Gln Arg Gly Asn Trp Ile Val Val
305                 310                 315                 320

Thr Thr Arg Ser His Glu Thr Thr Arg Ile Ile Arg Asp Gly Pro Leu
                325                 330                 335

His Lys Leu Gln Gly Leu Ser Glu Glu Asn Ser Trp Arg Leu Phe Val
            340                 345                 350

Arg Trp Thr Phe Gly Ser Val Gln Pro Lys Phe Pro Asn Asp Phe Val
        355                 360                 365

Met Ile Ala Arg Asp Ile Val Asp Lys Cys Ala Arg Asn Pro Leu Ala
    370                 375                 380

Ile Arg Val Val Gly Ser Leu Leu Cys Gly Gln Asp Lys Ser Lys Trp
385                 390                 395                 400

Leu Ser Phe His Glu Ile Cys Leu Ala Asn Ile Arg Lys Ser His Asn
                405                 410                 415

Asp Ile Met Leu Ile Leu Asn Leu Ser Tyr His His Leu Glu Pro Pro
            420                 425                 430

Ile Arg Arg Cys Phe Ser Tyr Cys Ala Met Phe Pro Lys Asp Phe Leu
        435                 440                 445

Ile Gly Lys Lys Thr Leu Ile Asn Leu Trp Met Ala Gln Gly Tyr Ile
    450                 455                 460

Val Pro Leu Asp Lys Asp Gln Ser Ile Asp Asp Ala Ser Glu Glu Tyr
465                 470                 475                 480

Ile Ser Ile Leu Leu Gln Arg Cys Phe Phe Glu Asn Ile Gly Thr Glu
                485                 490                 495

Lys Asp Tyr Val Ile Lys Ile His Asp Leu Met His Asp Ile Ala Gln
            500                 505                 510

Asn Val Met Gly Lys Glu Leu Cys Thr Thr Lys Asn Ile Ser Gly Ser
        515                 520                 525

Leu Asp Lys Asn Val Arg His Leu Ser Leu Ala Arg Thr Ser Phe Ala
    530                 535                 540

Arg Tyr Ser Phe Asn Ala Thr His Ile Arg Ser Tyr Phe Xaa Ala Gly
545                 550                 555                 560

Tyr Trp Cys Gln Asp Ala Glu Ile Asn Gln Phe Ser Val Glu Ala Leu
                565                 570                 575

Val Pro Asn Cys Leu Cys Leu Arg Ala Leu Asp Leu Ala Trp Ser Lys
            580                 585                 590

Ile Lys Ser Val Pro Asp Ser Ile Gly Gly Leu Leu His Leu Arg Tyr
        595                 600                 605

Leu Asp Leu Ser Tyr Asn Glu Asp Leu Glu Val Leu Pro Asn Ser Ile
    610                 615                 620

Ala Lys Leu Tyr Asn Leu Gln Thr Leu Gln Leu Lys Gly Cys Lys Arg
625                 630                 635                 640

Leu Glu Gly Leu Pro Lys His Leu Ser Arg Leu Val Lys Leu Gln Thr
                645                 650                 655

Leu Asp Ile Tyr Gly Cys Asn Asn Val Thr Tyr Met Pro Lys Gly Met
```

```
                    660                 665                 670
Gly Lys Met Thr Cys Leu His Thr Leu Ser Lys Phe Ile Val Gly Gly
                675                 680                 685

Glu Gly Ser Cys Ser Ser Trp Lys Gln Trp Phe Asp Gly Gln Glu Asp
            690                 695                 700

Leu Lys Ala Leu Asn Asn Leu Lys Gly His Leu Glu Ile Gln Ile Arg
705                 710                 715                 720

Trp Pro Glu Asn Thr Thr Asp Ala Val Lys Glu Asp Val Lys Arg Glu
                725                 730                 735

Gly Leu Tyr Leu Asn His
            740

<210> SEQ ID NO 35
<211> LENGTH: 738
<212> TYPE: PRT
<213> ORGANISM: Beta vulgaris
<220> FEATURE:
<221> NAME/KEY: MOD_RES
<222> LOCATION: (302)..(302)
<223> OTHER INFORMATION: Any amino acid

<400> SEQUENCE: 35

Met Glu Arg Val Val Tyr Arg Trp Asn Thr Ala Gly His Leu Trp Pro
1               5                   10                  15

Thr Asn Gln Lys Leu Ile Leu Ile Pro Tyr Ser Ala Leu Gln Ser Ser
                20                  25                  30

Glu Leu Lys Glu Ile Leu Ser Ile Phe Gly Tyr Lys Ser Gln Leu Asp
            35                  40                  45

Asp Leu Gln Arg Thr Val Ser Thr Ile Asn Ala Val Phe Arg Asp Ala
        50                  55                  60

Glu Thr Lys Gln Glu Leu Thr His Glu Ala Gln His Trp Leu Glu Glu
65                  70                  75                  80

Leu Lys Asp Ala Val Phe Glu Ala Asp Asp Leu Phe Asp Glu Phe Val
                85                  90                  95

Thr Leu Ala Glu Gln Lys Gln Leu Val Glu Ala Gly Gly Ser Leu Ser
            100                 105                 110

Lys Lys Met Arg Gln Phe Phe Ser Asp Ser Asn Pro Leu Gly Ile Ala
        115                 120                 125

Tyr Arg Met Ser Arg Gly Val Lys Lys Ile Lys Lys Lys Leu Asp Ala
    130                 135                 140

Ile Ala Tyr Asn His Gln Phe Ser Phe Lys Ile Asp Leu Glu Pro Ile
145                 150                 155                 160

Lys Glu Arg Arg Leu Glu Thr Gly Ser Val Val Asn Ala Gly Asp Ile
                165                 170                 175

Ile Gly Arg Glu Asp Asp Leu Glu Lys Ile Val Gly Leu Leu Leu Asp
            180                 185                 190

Ser Asn Ile Gln Arg Asp Val Ser Phe Leu Thr Ile Val Gly Met Gly
        195                 200                 205

Gly Leu Gly Lys Thr Ala Leu Ala Gln Leu Val Tyr Asn Asp Pro Arg
    210                 215                 220

Val Arg Thr Ala Phe Pro Leu Arg Cys Trp Asn Cys Val Ser Asp Gln
225                 230                 235                 240

Asp Gln Lys Lys Leu Asp Val Lys Glu Ile Leu Gly Lys Ile Leu Ser
                245                 250                 255

Thr Ala Thr Gly Lys Asn His Glu Gly Ser Thr Met Asp His Val Gln
            260                 265                 270
```

```
Thr Gln Leu Arg Glu Gln Leu Cys Gly Lys Arg Tyr Leu Val Leu
        275                 280                 285

Asp Asp Val Trp Asn Glu Asn Pro Asn Gln Leu Arg Ile Xaa Val Glu
    290                 295                 300

Phe Phe Met Gly Gly Gln Arg Gly Asn Trp Ile Val Val Thr Thr Arg
305                 310                 315                 320

Ser His Glu Thr Ala Arg Ile Ile Arg Asp Gly Pro Leu His Lys Leu
                325                 330                 335

Gln Gly Leu Ser Glu Glu Asn Ser Trp Arg Leu Phe Val Arg Trp Thr
                340                 345                 350

Phe Gly Ser Val Gln Pro Lys Phe Pro Asn Asp Phe Val Met Ile Ala
            355                 360                 365

Arg Asp Ile Val Asp Lys Cys Ala Arg Asn Pro Leu Ala Ile Arg Val
        370                 375                 380

Val Gly Ser Leu Leu Cys Gly Gln Asp Lys Ser Lys Trp Leu Ser Phe
385                 390                 395                 400

His Glu Ile Cys Leu Ala Asn Ile Arg Lys Ser His Asn Asp Ile Met
                405                 410                 415

Pro Ile Leu Asn Leu Ser Tyr His His Leu Glu Pro Pro Ile Arg Arg
                420                 425                 430

Cys Phe Ser Tyr Cys Ala Met Phe Pro Lys Asp Phe Leu Ile Gly Lys
            435                 440                 445

Lys Thr Leu Ile Asn Leu Trp Met Ala Gln Gly Tyr Ile Val Pro Leu
        450                 455                 460

Asp Lys Asp Gln Ser Ile Asp Asp Ala Ser Glu Tyr Ile Ser Ile
465                 470                 475                 480

Leu Leu Gln Arg Cys Phe Phe Glu Asn Ile Gly Thr Glu Lys Asp Tyr
                485                 490                 495

Val Ile Lys Ile His Asp Leu Met His Asp Ile Ala Gln Asn Val Met
                500                 505                 510

Gly Lys Glu Leu Cys Thr Thr Lys Asn Ile Ser Gly Ser Leu Asp Lys
        515                 520                 525

Asn Val Arg His Leu Ser Leu Ala Arg Thr Ser Phe Ala Arg Tyr Ser
    530                 535                 540

Phe Asn Ala Thr His Ile Arg Ser Tyr Phe Tyr Ala Gly Tyr Trp Cys
545                 550                 555                 560

Gln Asp Ala Glu Ile Asn Gln Phe Ser Val Glu Ala Leu Val Pro Asn
                565                 570                 575

Cys Leu Cys Leu Arg Ala Leu Asp Leu Ala Trp Ser Lys Ile Lys Ser
                580                 585                 590

Val Pro Asp Ser Ile Gly Gly Leu Leu His Leu Arg Tyr Leu Asp Leu
        595                 600                 605

Ser Tyr Asn Glu Asp Leu Glu Val Leu Pro Asn Ser Ile Ala Lys Leu
    610                 615                 620

Tyr Asn Leu Gln Thr Leu Gln Leu Lys Gly Cys Lys Arg Leu Glu Gly
625                 630                 635                 640

Leu Pro Lys His Leu Ser Arg Leu Val Lys Leu Gln Thr Leu Asp Ile
                645                 650                 655

Tyr Gly Cys Asn Asn Val Thr Tyr Met Pro Lys Gly Met Gly Lys Met
                660                 665                 670

Thr Cys Leu His Thr Leu Ser Lys Phe Ile Val Gly Gly Glu Gly Ser
                675                 680                 685
```

```
Cys Ser Ser Trp Lys Gln Trp Phe Asp Gly Gln Glu Asp Leu Lys Ala
    690             695                 700

Leu Asn Asn Leu Lys Gly His Leu Glu Ile Gln Ile Arg Trp Pro Glu
705                 710                 715                 720

Asn Thr Thr Asp Ala Val Lys Glu Asp Val Lys Arg Glu Gly Leu Tyr
                725                 730                 735

Leu Asn
```

```
<210> SEQ ID NO 36
<211> LENGTH: 183
<212> TYPE: PRT
<213> ORGANISM: Beta vulgaris

<400> SEQUENCE: 36
```

```
Ser Thr Ile Asn Ala Val Phe Arg Asp Ala Glu Thr Lys Gln Glu Leu
1               5                   10                  15

Thr His Glu Ala Gln His Trp Leu Glu Glu Leu Lys Asp Ala Val Phe
                20                  25                  30

Glu Ala Asp Asp Leu Phe Asp Glu Phe Val Thr Leu Ala Glu Gln Lys
            35                  40                  45

Gln Leu Val Glu Ala Gly Gly Ser Leu Ser Lys Lys Met Arg Gln Phe
    50                  55                  60

Phe Ser Asp Ser Asn Pro Leu Gly Ile Ala Tyr Arg Met Ser Arg Gly
65                  70                  75                  80

Val Lys Lys Ile Lys Lys Leu Asp Ala Ile Ala Tyr Asn His Gln
                85                  90                  95

Phe Ser Phe Lys Ile Asp Leu Glu Pro Ile Lys Glu Arg Arg Leu Glu
                100                 105                 110

Thr Gly Ser Val Val Asn Ala Gly Asp Ile Ile Gly Arg Glu Asp Asp
            115                 120                 125

Leu Glu Lys Ile Val Gly Leu Leu Asp Ser Asn Ile Gln Arg Asp
    130                 135                 140

Val Ser Phe Leu Thr Ile Val Gly Met Gly Gly Leu Gly Lys Thr Ala
145                 150                 155                 160

Leu Ala Gln Leu Val Tyr Asn Asp Pro Arg Val Arg Thr Ala Phe Pro
                165                 170                 175

Leu Arg Cys Trp Asn Cys Leu
            180
```

```
<210> SEQ ID NO 37
<211> LENGTH: 742
<212> TYPE: PRT
<213> ORGANISM: Beta vulgaris
<220> FEATURE:
<221> NAME/KEY: MOD_RES
<222> LOCATION: (304)..(307)
<223> OTHER INFORMATION: Any amino acid

<400> SEQUENCE: 37
```

```
Met Glu Arg Val Val Tyr Arg Trp Asn Thr Ala Glu Thr Ala Gly His
1               5                   10                  15

Leu Trp Pro Thr Asn Pro Lys Leu Ile Leu Ile Pro Tyr Ser Ala Leu
                20                  25                  30

Gln Ser Ser Glu Leu Lys Glu Ile Leu Ser Ile Phe Gly Tyr Lys Ser
            35                  40                  45

Gln Leu Asp Asp Leu Gln Arg Thr Val Ser Thr Ile Asn Ala Val Phe
    50                  55                  60
```

```
Arg Asp Ala Glu Thr Lys Gln Glu Leu Thr His Glu Ala Gln His Trp
 65                  70                  75                  80

Leu Glu Glu Leu Lys Asp Ala Val Phe Glu Ala Asp Asp Leu Phe Asp
                 85                  90                  95

Glu Phe Val Thr Leu Ala Glu Gln Lys Gln Leu Val Glu Ala Gly Gly
            100                 105                 110

Ser Leu Ser Lys Lys Met Arg Gln Phe Phe Ser Asp Ser Asn Pro Leu
        115                 120                 125

Gly Ile Ala Tyr Arg Met Ser Arg Gly Val Lys Lys Ile Lys Lys Lys
    130                 135                 140

Leu Asp Ala Ile Ala Tyr Asn His Gln Phe Ser Phe Lys Ile Asp Leu
145                 150                 155                 160

Glu Pro Ile Lys Glu Arg Arg Leu Glu Thr Gly Ser Val Val Asn Ala
                165                 170                 175

Gly Asp Ile Ile Gly Arg Glu Asp Asp Leu Glu Lys Ile Val Gly Leu
            180                 185                 190

Leu Leu Asp Ser Asn Ile Gln Arg Asp Val Ser Phe Leu Thr Ile Val
        195                 200                 205

Gly Met Gly Gly Leu Gly Lys Thr Ala Leu Ala Gln Leu Val Tyr Asn
    210                 215                 220

Asp Pro Arg Val Arg Thr Ala Phe Pro Leu Arg Cys Trp Asn Cys Val
225                 230                 235                 240

Ser Asp Gln Asp Gln Lys Lys Leu Asp Val Lys Glu Ile Leu Gly Lys
                245                 250                 255

Ile Leu Ser Thr Ala Thr Gly Lys Asn His Glu Gly Ser Thr Met Asp
            260                 265                 270

His Val Gln Thr Gln Leu Gln Glu Gln Leu Cys Gly Lys Arg Tyr Leu
        275                 280                 285

Leu Val Leu Asp Asp Val Trp Asn Glu Asn Pro Asn Gln Leu Arg Xaa
    290                 295                 300

Xaa Xaa Xaa Phe Phe Met Gly Gly Gln Arg Gly Asn Trp Ile Val Val
305                 310                 315                 320

Thr Thr Arg Ser His Glu Thr Thr Arg Ile Ile Arg Asp Gly Pro Leu
                325                 330                 335

His Lys Leu Gln Gly Leu Ser Glu Glu Asn Ser Trp Arg Leu Phe Val
            340                 345                 350

Arg Trp Thr Phe Gly Ser Val Gln Pro Lys Phe Pro Asn Asp Phe Val
        355                 360                 365

Met Ile Ala Arg Asp Ile Val Asp Lys Cys Ala Arg Asn Pro Leu Ala
    370                 375                 380

Ile Arg Val Val Gly Ser Leu Cys Gly Gln Asp Lys Ser Lys Trp
385                 390                 395                 400

Leu Ser Phe His Glu Ile Cys Leu Ala Asn Ile Arg Lys Ser His Asn
                405                 410                 415

Asp Ile Met Leu Ile Leu Asn Leu Ser Tyr His His Leu Glu Pro Pro
            420                 425                 430

Ile Arg Arg Cys Phe Ser Tyr Cys Ala Met Phe Pro Lys Asp Phe Leu
        435                 440                 445

Ile Gly Lys Lys Thr Leu Ile Asn Leu Trp Met Ala Gln Gly Tyr Ile
    450                 455                 460

Val Pro Leu Asp Lys Asp Gln Ser Ile Asp Asp Ala Ser Glu Glu Tyr
465                 470                 475                 480

Ile Ser Ile Leu Leu Gln Arg Cys Phe Phe Glu Asn Ile Gly Thr Glu
```

```
                    485                 490                 495
Lys Asp Tyr Val Ile Lys Ile His Asp Leu Met His Asp Ile Ala Gln
                500                 505                 510

Asn Val Met Gly Lys Glu Leu Cys Thr Thr Lys Asn Ile Ser Gly Ser
            515                 520                 525

Leu Asp Lys Asn Val Arg His Leu Ser Leu Ala Arg Thr Ser Phe Ala
        530                 535                 540

Arg Tyr Ser Phe Asn Ala Thr His Ile Arg Ser Tyr Phe Tyr Ala Gly
545                 550                 555                 560

Tyr Trp Cys Gln Asp Ala Glu Ile Asn Gln Phe Ser Val Glu Ala Leu
                565                 570                 575

Val Pro Asn Cys Leu Cys Leu Arg Ala Leu Asp Leu Ala Trp Ser Lys
            580                 585                 590

Ile Lys Ser Val Pro Asp Ser Ile Gly Gly Leu Leu His Leu Arg Tyr
        595                 600                 605

Leu Asp Leu Ser Tyr Asn Glu Asp Leu Glu Val Leu Pro Asn Ser Ile
610                 615                 620

Ala Lys Leu Tyr Asn Leu Gln Thr Leu Gln Leu Lys Gly Cys Lys Arg
625                 630                 635                 640

Leu Glu Gly Leu Pro Lys His Leu Ser Arg Leu Val Lys Leu Gln Thr
                645                 650                 655

Leu Asp Ile Tyr Gly Cys Asn Asn Val Thr Tyr Met Pro Lys Gly Met
            660                 665                 670

Gly Lys Met Thr Cys Leu His Thr Leu Ser Lys Phe Ile Val Gly Gly
        675                 680                 685

Glu Gly Ser Cys Ser Ser Trp Lys Gln Trp Phe Asp Gly Gln Glu Asp
690                 695                 700

Leu Lys Ala Leu Asn Asn Leu Lys Gly His Leu Glu Ile Gln Ile Arg
705                 710                 715                 720

Trp Pro Glu Asn Thr Thr Asp Ala Val Lys Glu Asp Val Lys Arg Glu
                725                 730                 735

Gly Leu Tyr Leu Asn His
            740

<210> SEQ ID NO 38
<211> LENGTH: 742
<212> TYPE: PRT
<213> ORGANISM: Beta vulgaris
<220> FEATURE:
<221> NAME/KEY: MOD_RES
<222> LOCATION: (305)..(305)
<223> OTHER INFORMATION: Any amino acid

<400> SEQUENCE: 38

Met Glu Arg Val Val Tyr Arg Trp Asn Thr Ala Glu Thr Ala Gly His
1               5                   10                  15

Leu Trp Pro Thr Asn Pro Lys Leu Ile Leu Ile Pro Tyr Ser Ala Leu
            20                  25                  30

Gln Ser Ser Glu Leu Lys Glu Ile Leu Ser Ile Phe Gly Tyr Lys Ser
        35                  40                  45

Gln Leu Asp Asp Leu Gln Arg Thr Val Ser Thr Ile Asn Ala Val Phe
    50                  55                  60

Arg Asp Ala Glu Thr Lys Gln Glu Leu Thr His Glu Ala Gln His Trp
65                  70                  75                  80

Leu Glu Glu Leu Lys Asp Ala Val Phe Glu Ala Asp Asp Leu Phe Asp
                85                  90                  95
```

```
Glu Phe Val Thr Leu Ala Glu Gln Lys Gln Leu Val Glu Ala Gly Gly
                100                 105                 110

Ser Leu Ser Lys Lys Met Arg Gln Phe Phe Ser Asp Ser Asn Pro Leu
            115                 120                 125

Gly Ile Ala Tyr Arg Met Ser Arg Gly Val Lys Ile Lys Lys
        130                 135                 140

Leu Asp Ala Ile Ala Tyr Asn His Gln Phe Ser Phe Lys Ile Asp Leu
145                 150                 155                 160

Glu Pro Ile Lys Glu Arg Arg Leu Glu Thr Gly Ser Val Val Asn Ala
                165                 170                 175

Gly Asp Ile Ile Gly Arg Glu Asp Leu Glu Lys Ile Val Gly Leu
        180                 185                 190

Leu Leu Asp Ser Asn Ile Gln Arg Asp Val Ser Phe Leu Thr Ile Val
            195                 200                 205

Gly Met Gly Gly Leu Gly Lys Thr Ala Leu Ala Gln Leu Val Tyr Asn
        210                 215                 220

Asp Pro Arg Val Arg Thr Ala Phe Pro Leu Arg Cys Trp Asn Cys Val
225                 230                 235                 240

Ser Asp Gln Asp Gln Lys Lys Leu Asp Val Lys Glu Ile Leu Gly Lys
                245                 250                 255

Ile Leu Ser Thr Ala Thr Gly Lys Asn His Glu Gly Ser Thr Met Asp
        260                 265                 270

His Val Gln Thr Gln Leu Gln Glu Gln Leu Cys Gly Lys Arg Tyr Leu
            275                 280                 285

Leu Val Leu Asp Asp Val Trp Asn Glu Asn Pro Gln Leu Arg Asp
        290                 295                 300

Xaa Val Glu Phe Phe Met Gly Gly Gln Arg Gly Asn Trp Ile Val Val
305                 310                 315                 320

Thr Thr Arg Ser His Glu Thr Thr Arg Ile Ile Arg Asp Gly Pro Leu
                325                 330                 335

His Lys Leu Gln Gly Leu Ser Glu Glu Asn Ser Trp Arg Leu Phe Val
            340                 345                 350

Arg Trp Thr Phe Gly Ser Val Gln Pro Lys Phe Pro Asn Asp Phe Val
        355                 360                 365

Met Ile Ala Arg Asp Ile Val Asp Lys Cys Ala Arg Asn Pro Leu Ala
        370                 375                 380

Ile Arg Val Val Gly Ser Leu Leu Cys Gly Gln Asp Lys Ser Lys Trp
385                 390                 395                 400

Leu Ser Phe His Glu Ile Cys Leu Ala Asn Ile Arg Lys Ser His Asn
                405                 410                 415

Asp Ile Met Leu Ile Leu Asn Leu Ser Tyr His His Leu Glu Pro Pro
            420                 425                 430

Ile Arg Arg Cys Phe Ser Tyr Cys Ala Met Phe Pro Lys Asp Phe Leu
        435                 440                 445

Ile Gly Lys Lys Thr Leu Ile Asn Leu Trp Met Ala Gln Gly Tyr Ile
        450                 455                 460

Val Pro Leu Asp Lys Asp Gln Ser Ile Asp Asp Ala Ser Glu Glu Tyr
465                 470                 475                 480

Ile Ser Ile Leu Leu Gln Arg Cys Phe Phe Glu Asn Ile Gly Thr Glu
                485                 490                 495

Lys Asp Tyr Val Ile Lys Ile His Asp Leu Met His Asp Ile Ala Gln
        500                 505                 510
```

```
Asn Val Met Gly Lys Glu Leu Cys Thr Thr Lys Asn Ile Ser Gly Ser
            515                 520                 525

Leu Asp Lys Asn Val Arg His Leu Ser Leu Ala Arg Thr Ser Phe Ala
530                 535                 540

Arg Tyr Ser Phe Asn Ala Thr His Ile Arg Ser Tyr Phe Tyr Ala Gly
545                 550                 555                 560

Tyr Trp Cys Gln Asp Ala Glu Ile Asn Gln Phe Ser Val Glu Ala Leu
                565                 570                 575

Val Pro Asn Cys Leu Cys Leu Arg Ala Leu Asp Leu Ala Trp Ser Lys
                580                 585                 590

Ile Lys Ser Val Pro Asp Ser Ile Gly Gly Leu Leu His Leu Arg Tyr
            595                 600                 605

Leu Asp Leu Ser Tyr Asn Glu Asp Leu Glu Val Leu Pro Asn Ser Ile
610                 615                 620

Ala Lys Leu Tyr Asn Leu Gln Thr Leu Gln Leu Lys Gly Cys Lys Arg
625                 630                 635                 640

Leu Glu Gly Leu Pro Lys His Leu Ser Arg Leu Val Lys Leu Gln Thr
                645                 650                 655

Leu Asp Ile Tyr Gly Cys Asn Asn Val Thr Tyr Met Pro Lys Gly Met
                660                 665                 670

Gly Lys Met Thr Cys Leu His Thr Leu Ser Lys Phe Ile Val Gly Gly
            675                 680                 685

Glu Gly Ser Cys Ser Ser Trp Lys Gln Trp Phe Asp Gly Gln Glu Asp
            690                 695                 700

Leu Lys Ala Leu Asn Asn Leu Lys Gly His Leu Glu Ile Gln Ile Arg
705                 710                 715                 720

Trp Pro Glu Asn Thr Thr Asp Ala Val Lys Glu Asp Val Lys Arg Glu
                725                 730                 735

Gly Leu Tyr Leu Asn His
                740

<210> SEQ ID NO 39
<211> LENGTH: 895
<212> TYPE: PRT
<213> ORGANISM: Beta vulgaris

<400> SEQUENCE: 39

Met Glu Arg Val Val Tyr Arg Trp Asn Thr Ala Gly His Leu Trp Pro
1               5                   10                  15

Thr Asn Gln Lys Leu Ile Leu Ile Pro Tyr Ala Leu Gln Ser Ser Glu
            20                  25                  30

Leu Lys Glu Ile Leu Ser Ile Phe Gly Tyr Lys Ser Gln Leu Asp Asp
        35                  40                  45

Leu Gln Arg Thr Val Ser Thr Ile Asn Ala Val Phe Arg Asp Ala Glu
    50                  55                  60

Thr Lys Gln Glu Leu Thr His Glu Ala Gln His Trp Leu Glu Glu Leu
65                  70                  75                  80

Lys Asp Ala Val Phe Glu Ala Asp Asp Leu Phe Asp Glu Phe Val Thr
                85                  90                  95

Leu Ala Glu Gln Lys Gln Leu Val Glu Ala Gly Gly Ser Leu Ser Lys
            100                 105                 110

Lys Met Arg Gln Phe Phe Ser Asp Ser Asn Pro Leu Gly Ile Ala Tyr
        115                 120                 125

Arg Met Ser Arg Gly Val Lys Lys Ile Lys Lys Lys Leu Asp Ala Ile
    130                 135                 140
```

```
Ala Tyr Asn His Gln Phe Ser Phe Lys Ile Asp Leu Glu Pro Ile Lys
145                 150                 155                 160

Glu Arg Arg Leu Glu Thr Gly Ser Val Val Asn Ala Gly Asp Ile Ile
            165                 170                 175

Gly Arg Glu Asp Asp Leu Glu Lys Ile Val Gly Leu Leu Asp Ser
        180                 185                 190

Asn Ile Gln Arg Asp Val Ser Phe Leu Thr Ile Val Gly Met Gly Gly
            195                 200                 205

Leu Gly Lys Thr Ala Leu Ala Gln Leu Val Tyr Asn Asp Pro Arg Val
    210                 215                 220

Arg Thr Ala Phe Pro Leu Arg Cys Trp Asn Cys Val Ser Asp Gln Asp
225                 230                 235                 240

Gln Lys Lys Leu Asp Val Lys Glu Ile Leu Gly Lys Ile Leu Ser Thr
                245                 250                 255

Ala Thr Gly Lys Asn His Glu Gly Ser Thr Met Asp His Val Gln Thr
            260                 265                 270

Gln Leu Arg Glu Gln Leu Cys Gly Lys Arg Tyr Leu Leu Val Leu Asp
        275                 280                 285

Asp Val Trp Asn Glu Asn Pro Asn Gln Leu Arg Tyr Leu Val Glu Phe
    290                 295                 300

Phe Met Gly Gly Gln Arg Gly Asn Trp Ile Val Val Thr Thr Arg Ser
305                 310                 315                 320

His Glu Thr Ala Arg Ile Ile Arg Asp Gly Pro Leu His Lys Leu Gln
                325                 330                 335

Gly Leu Ser Glu Glu Asn Ser Trp Arg Leu Phe Val Arg Trp Thr Phe
            340                 345                 350

Gly Ser Val Gln Pro Lys Phe Pro Asn Asp Phe Val Met Ile Ala Arg
        355                 360                 365

Asp Ile Val Asp Lys Cys Ala Arg Asn Pro Leu Ala Ile Arg Val Val
    370                 375                 380

Gly Ser Leu Leu Cys Gly Gln Asp Lys Ser Lys Trp Leu Ser Phe His
385                 390                 395                 400

Glu Ile Cys Leu Ala Asn Ile Arg Lys Ser His Asn Asp Ile Met Pro
                405                 410                 415

Ile Leu Asn Leu Ser Tyr His His Leu Glu Pro Pro Ile Arg Arg Cys
            420                 425                 430

Phe Ser Tyr Cys Ala Met Phe Pro Lys Asp Phe Leu Ile Gly Lys Lys
        435                 440                 445

Thr Leu Ile Asn Leu Trp Met Ala Gln Gly Tyr Ile Val Pro Leu Asp
    450                 455                 460

Lys Asp Gln Ser Ile Asp Asp Ala Ser Glu Glu Tyr Ile Ser Ile Leu
465                 470                 475                 480

Leu Gln Arg Cys Phe Phe Glu Asn Ile Gly Thr Glu Lys Asp Tyr Val
                485                 490                 495

Ile Lys Ile His Asp Leu Met His Asp Ile Ala Gln Asn Val Met Gly
            500                 505                 510

Lys Glu Leu Cys Thr Thr Lys Asn Ile Ser Gly Ser Leu Asp Lys Asn
        515                 520                 525

Val Arg His Leu Ser Leu Ala Arg Thr Ser Phe Ala Arg Tyr Ser Phe
    530                 535                 540

Asn Ala Thr His Ile Arg Ser Tyr Phe Tyr Ala Gly Tyr Trp Cys Gln
545                 550                 555                 560
```

```
Asp Ala Glu Ile Asn Gln Phe Ser Val Glu Ala Leu Val Pro Asn Cys
            565                 570                 575

Leu Cys Leu Arg Ala Leu Asp Leu Ala Trp Ser Lys Ile Lys Ser Val
        580                 585                 590

Pro Asp Ser Ile Gly Gly Leu Leu His Leu Arg Tyr Leu Asp Leu Ser
        595                 600                 605

Tyr Asn Glu Asp Leu Glu Val Leu Pro Asn Ser Ile Ala Lys Leu Tyr
610                 615                 620

Asn Leu Gln Thr Leu Gln Leu Lys Gly Cys Arg Leu Glu Gly Leu
625                 630                 635                 640

Pro Lys His Leu Ser Arg Leu Val Lys Leu Gln Thr Leu Asp Ile Tyr
                645                 650                 655

Gly Cys Asn Asn Val Thr Tyr Met Pro Lys Gly Met Gly Lys Met Thr
                660                 665                 670

Cys Leu His Thr Leu Ser Lys Phe Ile Val Gly Gly Glu Gly Ser Cys
                675                 680                 685

Ser Ser Trp Lys Gln Trp Phe Asp Gly Gln Glu Asp Leu Lys Ala Leu
            690                 695                 700

Asn Asn Leu Lys Gly His Leu Glu Ile Gln Ile Arg Trp Pro Glu Asn
705                 710                 715                 720

Thr Thr Asp Ala Val Lys Glu Asp Val Lys Arg Glu Gly Leu Tyr Leu
                725                 730                 735

Asn His Lys Glu His Leu Asn His Ile Val Val Asp Phe Arg Cys Glu
                740                 745                 750

Glu Gly Gly Gly Arg Met Asp Asp Glu Glu Ala Arg Arg Leu Met Glu
            755                 760                 765

Glu Leu Arg Pro His Pro Tyr Leu Glu Asn Leu Ala Val Lys Ala Tyr
770                 775                 780

Tyr Gly Ala Lys Met Pro Gly Trp Ala Thr Leu Leu Pro Asn Leu Thr
785                 790                 795                 800

Glu Leu Tyr Leu Ser Asp Cys Gly Glu Ser Cys Leu Pro Cys Met
                805                 810                 815

Gly Asn Leu Asp Cys Leu Lys Val Leu Arg Leu Ser His Leu Ala Lys
                820                 825                 830

Leu Glu Tyr Ile Glu Glu Asp Ser Thr Ser Ala Asn Phe Ser Phe Arg
            835                 840                 845

Pro Gly Pro Glu Ser Ala Gly Leu Ser Leu Tyr Phe Pro Ser Leu Glu
        850                 855                 860

Leu Leu Glu Leu Lys Arg Leu His Lys Leu Lys Gly Trp Arg Arg Arg
865                 870                 875                 880

Glu Gly Leu Gly Asp Asp His Gln Pro Phe Asn Glu Ser Ser Ser
                885                 890                 895

<210> SEQ ID NO 40
<211> LENGTH: 749
<212> TYPE: PRT
<213> ORGANISM: Beta vulgaris

<400> SEQUENCE: 40

Met Glu Arg Val Val Tyr Arg Trp Asn Thr Ala Gly His Leu Trp Pro
1               5                   10                  15

Thr Asn Gln Lys Leu Ile Leu Ile Pro Tyr Ser Ala Leu Gln Ser Ser
                20                  25                  30

Glu Leu Lys Glu Ile Leu Ser Ile Phe Gly Tyr Lys Ser Gln Leu Asp
            35                  40                  45
```

```
Asp Leu Gln Arg Thr Val Ser Thr Ile Asn Ala Val Phe Arg Asp Ala
 50                  55                  60
Glu Thr Lys Gln Glu Leu Thr His Glu Ala Gln His Trp Leu Glu Glu
 65                  70                  75                  80
Leu Lys Asp Ala Val Phe Glu Ala Asp Asp Leu Phe Asp Glu Phe Val
                 85                  90                  95
Thr Leu Ala Glu Gln Lys Gln Leu Val Glu Ala Gly Gly Ser Leu Ser
                100                 105                 110
Lys Lys Met Arg Gln Phe Phe Ser Asp Ser Asn Pro Leu Gly Ile Ala
                115                 120                 125
Tyr Arg Met Ser Arg Gly Val Lys Lys Ile Lys Lys Leu Asp Ala
                130                 135                 140
Ile Ala Tyr Asn His Gln Phe Ser Phe Lys Ile Asp Leu Glu Pro Ile
145                 150                 155                 160
Lys Glu Arg Arg Leu Glu Thr Gly Ser Val Val Asn Ala Gly Asp Ile
                165                 170                 175
Ile Gly Arg Glu Asp Asp Leu Glu Lys Ile Val Gly Leu Leu Leu Asp
                180                 185                 190
Ser Asn Ile Gln Arg Asp Val Ser Phe Leu Thr Ile Val Gly Met Gly
                195                 200                 205
Gly Leu Gly Lys Thr Ala Leu Ala Gln Leu Val Tyr Asn Asp Pro Arg
                210                 215                 220
Val Arg Thr Ala Phe Pro Leu Arg Cys Trp Asn Cys Val Ser Asp Gln
225                 230                 235                 240
Asp Gln Lys Lys Leu Asp Val Lys Glu Ile Leu Gly Lys Ile Leu Ser
                245                 250                 255
Thr Ala Thr Gly Lys Asn His Glu Gly Ser Thr Met Asp His Val Gln
                260                 265                 270
Thr Gln Leu Arg Glu Gln Leu Cys Gly Lys Arg Tyr Leu Leu Val Leu
                275                 280                 285
Asp Asp Val Trp Asn Glu Asn Pro Asn Gln Leu Arg Tyr Leu Val Glu
                290                 295                 300
Phe Phe Met Gly Gly Gln Arg Gly Asn Trp Ile Val Val Thr Thr Arg
305                 310                 315                 320
Ser His Glu Thr Ala Arg Ile Ile Arg Asp Gly Pro Leu His Lys Leu
                325                 330                 335
Gln Gly Leu Ser Glu Glu Asn Ser Trp Arg Leu Phe Val Arg Trp Thr
                340                 345                 350
Phe Gly Ser Val Gln Pro Lys Phe Pro Asn Asp Phe Val Met Ile Ala
                355                 360                 365
Arg Asp Ile Val Asp Lys Cys Ala Arg Asn Pro Leu Ala Ile Arg Val
                370                 375                 380
Val Gly Ser Leu Leu Cys Gly Gln Asp Lys Ser Lys Trp Leu Ser Phe
385                 390                 395                 400
His Glu Ile Cys Leu Ala Asn Ile Arg Lys Ser His Asn Asp Ile Met
                405                 410                 415
Pro Ile Leu Asn Leu Ser Tyr His His Leu Glu Pro Pro Ile Arg Arg
                420                 425                 430
Cys Phe Ser Tyr Cys Ala Met Phe Pro Lys Asp Phe Leu Ile Gly Lys
                435                 440                 445
Lys Thr Leu Ile Asn Leu Trp Met Ala Gln Gly Tyr Ile Val Pro Leu
                450                 455                 460
```

-continued

```
Asp Lys Asp Gln Ser Ile Asp Asp Ala Ser Glu Glu Tyr Ile Ser Ile
465                 470                 475                 480

Leu Leu Gln Arg Cys Phe Phe Glu Asn Ile Gly Thr Glu Lys Asp Tyr
            485                 490                 495

Val Ile Lys Ile His Asp Leu Met His Asp Ile Ala Gln Asn Val Met
        500                 505                 510

Gly Lys Glu Leu Cys Thr Thr Lys Asn Ile Ser Gly Ser Leu Asp Lys
    515                 520                 525

Asn Val Arg His Leu Ser Leu Ala Arg Thr Ser Phe Ala Arg Tyr Ser
530                 535                 540

Phe Asn Ala Thr His Ile Arg Ser Tyr Phe Tyr Ala Gly Tyr Trp Cys
545                 550                 555                 560

Gln Asp Ala Glu Ile Asn Gln Phe Ser Val Glu Ala Leu Val Pro Asn
                565                 570                 575

Cys Leu Cys Leu Arg Ala Leu Asp Leu Ala Trp Ser Lys Ile Lys Ser
            580                 585                 590

Val Pro Asp Ser Ile Gly Gly Leu Leu His Leu Arg Tyr Leu Asp Leu
        595                 600                 605

Ser Tyr Asn Glu Asp Leu Glu Val Leu Pro Asn Ser Ile Ala Lys Leu
    610                 615                 620

Tyr Asn Leu Gln Thr Leu Gln Leu Lys Gly Cys Lys Arg Leu Glu Gly
625                 630                 635                 640

Leu Pro Lys His Leu Ser Arg Leu Val Lys Leu Gln Thr Leu Asp Ile
                645                 650                 655

Tyr Gly Cys Asn Asn Val Thr Tyr Met Pro Lys Gly Met Gly Lys Met
            660                 665                 670

Thr Cys Leu His Thr Leu Ser Lys Phe Ile Val Gly Gly Glu Gly Ser
        675                 680                 685

Cys Ser Ser Trp Lys Gln Trp Phe Asp Gly Gln Glu Asp Leu Lys Ala
    690                 695                 700

Leu Asn Asn Leu Lys Gly His Leu Glu Ile Gln Ile Arg Trp Pro Glu
705                 710                 715                 720

Asn Thr Thr Asp Ala Val Lys Glu Asp Val Lys Arg Glu Gly Leu Tyr
                725                 730                 735

Leu Asn His Lys Glu His Leu Asn His Ile Val Val Asp
            740                 745
```

<210> SEQ ID NO 41
<211> LENGTH: 749
<212> TYPE: PRT
<213> ORGANISM: Beta vulgaris
<220> FEATURE:
<221> NAME/KEY: MOD_RES
<222> LOCATION: (300)..(304)
<223> OTHER INFORMATION: Any amino acid

<400> SEQUENCE: 41

```
Met Glu Arg Val Val Tyr Arg Trp Asn Thr Ala Gly His Leu Trp Pro
1               5                   10                  15

Thr Asn Gln Lys Leu Ile Leu Ile Pro Tyr Ser Ala Leu Gln Ser Ser
            20                  25                  30

Glu Leu Lys Glu Ile Leu Ser Ile Phe Gly Tyr Lys Ser Gln Leu Asp
        35                  40                  45

Asp Leu Gln Arg Thr Val Ser Thr Ile Asn Ala Val Phe Arg Asp Ala
    50                  55                  60

Glu Thr Lys Gln Glu Leu Thr His Glu Ala Gln His Trp Leu Glu Glu
```

```
                65                  70                  75                  80
Leu Lys Asp Ala Val Phe Glu Ala Asp Leu Phe Asp Glu Phe Val
                    85                  90                  95

Thr Leu Ala Glu Gln Lys Gln Leu Val Glu Ala Gly Gly Ser Leu Ser
                100                 105                 110

Lys Lys Met Arg Gln Phe Phe Ser Asp Ser Asn Pro Leu Gly Ile Ala
                115                 120                 125

Tyr Arg Met Ser Arg Gly Val Lys Lys Ile Lys Lys Leu Asp Ala
    130                 135                 140

Ile Ala Tyr Asn His Gln Phe Ser Phe Lys Ile Asp Leu Glu Pro Ile
145                 150                 155                 160

Lys Glu Arg Arg Leu Glu Thr Gly Ser Val Val Asn Ala Gly Asp Ile
                165                 170                 175

Ile Gly Arg Glu Asp Asp Leu Glu Lys Ile Val Gly Leu Leu Asp
                180                 185                 190

Ser Asn Ile Gln Arg Asp Val Ser Phe Leu Thr Ile Val Gly Met Gly
    195                 200                 205

Gly Leu Gly Lys Thr Ala Leu Ala Gln Leu Val Tyr Asn Asp Pro Arg
    210                 215                 220

Val Arg Thr Ala Phe Pro Leu Arg Cys Trp Asn Cys Val Ser Asp Gln
225                 230                 235                 240

Asp Gln Lys Lys Leu Asp Val Lys Glu Ile Leu Gly Lys Ile Leu Ser
                245                 250                 255

Thr Ala Thr Gly Lys Asn His Glu Gly Ser Thr Met Asp His Val Gln
                260                 265                 270

Thr Gln Leu Arg Glu Gln Leu Cys Gly Lys Arg Tyr Leu Leu Val Leu
    275                 280                 285

Asp Asp Val Trp Asn Glu Asn Pro Asn Gln Leu Xaa Xaa Xaa Xaa Xaa
    290                 295                 300

Phe Phe Met Gly Gly Gln Arg Gly Asn Trp Ile Val Val Thr Thr Arg
305                 310                 315                 320

Ser His Glu Thr Ala Arg Ile Ile Arg Asp Gly Pro Leu His Lys Leu
                325                 330                 335

Gln Gly Leu Ser Glu Glu Asn Ser Trp Arg Leu Phe Val Arg Trp Thr
                340                 345                 350

Phe Gly Ser Val Gln Pro Lys Phe Pro Asn Asp Phe Val Met Ile Ala
    355                 360                 365

Arg Asp Ile Val Asp Lys Cys Ala Arg Asn Pro Leu Ala Ile Arg Val
370                 375                 380

Val Gly Ser Leu Leu Cys Gly Gln Asp Lys Ser Lys Trp Leu Ser Phe
385                 390                 395                 400

His Glu Ile Cys Leu Ala Asn Ile Arg Lys Ser His Asn Asp Ile Met
                405                 410                 415

Pro Ile Leu Asn Leu Ser Tyr His His Leu Glu Pro Pro Ile Arg Arg
                420                 425                 430

Cys Phe Ser Tyr Cys Ala Met Phe Pro Lys Asp Phe Leu Ile Gly Lys
    435                 440                 445

Lys Thr Leu Ile Asn Leu Trp Met Ala Gln Gly Tyr Ile Val Pro Leu
    450                 455                 460

Asp Lys Asp Gln Ser Ile Asp Asp Ala Ser Glu Glu Tyr Ile Ser Ile
465                 470                 475                 480

Leu Leu Gln Arg Cys Phe Phe Glu Asn Ile Gly Thr Glu Lys Asp Tyr
                485                 490                 495
```

```
Val Ile Lys Ile His Asp Leu Met His Asp Ile Ala Gln Asn Val Met
            500                 505                 510
Gly Lys Glu Leu Cys Thr Thr Lys Asn Ile Ser Gly Ser Leu Asp Lys
        515                 520                 525
Asn Val Arg His Leu Ser Leu Ala Arg Thr Ser Phe Ala Arg Tyr Ser
    530                 535                 540
Phe Asn Ala Thr His Ile Arg Ser Tyr Phe Ala Gly Tyr Trp Cys
545                 550                 555                 560
Gln Asp Ala Glu Ile Asn Gln Phe Ser Val Glu Ala Leu Val Pro Asn
                565                 570                 575
Cys Leu Cys Leu Arg Ala Leu Asp Leu Ala Trp Ser Lys Ile Lys Ser
            580                 585                 590
Val Pro Asp Ser Ile Gly Gly Leu Leu His Leu Arg Tyr Leu Asp Leu
        595                 600                 605
Ser Tyr Asn Glu Asp Leu Glu Val Leu Pro Asn Ser Ile Ala Lys Leu
    610                 615                 620
Tyr Asn Leu Gln Thr Leu Gln Leu Lys Gly Cys Lys Arg Leu Glu Gly
625                 630                 635                 640
Leu Pro Lys His Leu Ser Arg Leu Val Lys Leu Gln Thr Leu Asp Ile
                645                 650                 655
Tyr Gly Cys Asn Asn Val Thr Tyr Met Pro Lys Gly Met Gly Lys Met
            660                 665                 670
Thr Cys Leu His Thr Leu Ser Lys Phe Ile Val Gly Glu Gly Ser
        675                 680                 685
Cys Ser Ser Trp Lys Gln Trp Phe Asp Gly Gln Asp Leu Lys Ala
    690                 695                 700
Leu Asn Asn Leu Lys Gly His Leu Glu Ile Gln Ile Arg Trp Pro Glu
705                 710                 715                 720
Asn Thr Thr Asp Ala Val Lys Glu Asp Val Lys Arg Glu Gly Leu Tyr
                725                 730                 735
Leu Asn His Lys Glu His Leu Asn His Ile Val Val Asp
            740                 745

<210> SEQ ID NO 42
<211> LENGTH: 183
<212> TYPE: PRT
<213> ORGANISM: Beta vulgaris

<400> SEQUENCE: 42

Ser Thr Ile Asn Ala Val Phe Arg Asp Ala Glu Thr Lys Gln Glu Leu
1               5                   10                  15
Thr His Glu Ala Gln His Trp Leu Glu Glu Leu Lys Asp Ala Val Phe
            20                  25                  30
Glu Ala Asp Asp Leu Phe Asp Glu Phe Val Thr Leu Ala Glu Gln Lys
        35                  40                  45
Gln Leu Val Glu Ala Gly Gly Ser Leu Ser Lys Met Arg Gln Phe
    50                  55                  60
Phe Ser Asp Ser Asn Pro Leu Gly Ile Ala Tyr Arg Met Ser Arg Gly
65                  70                  75                  80
Val Lys Lys Ile Lys Lys Lys Leu Asp Ala Ile Ala Tyr Asn His Gln
                85                  90                  95
Phe Ser Phe Lys Ile Asp Leu Glu Pro Ile Lys Glu Arg Arg Leu Glu
            100                 105                 110
Thr Gly Ser Val Val Asn Ala Gly Asp Ile Ile Gly Arg Glu Asp Asp
```

```
                115                 120                 125
Leu Glu Lys Ile Val Gly Leu Leu Asp Ser Asn Ile Gln Arg Asp
    130                 135                 140

Val Ser Phe Leu Thr Ile Val Gly Met Gly Gly Leu Gly Lys Thr Ala
145                 150                 155                 160

Leu Ala Gln Leu Val Tyr Asn Asp Pro Arg Val Arg Thr Ala Phe Pro
                165                 170                 175

Leu Arg Cys Trp Asn Cys Leu
                180

<210> SEQ ID NO 43
<211> LENGTH: 749
<212> TYPE: PRT
<213> ORGANISM: Beta vulgaris

<400> SEQUENCE: 43

Met Glu Arg Val Val Tyr Arg Trp Asn Thr Ala Gly His Leu Trp Pro
1               5                   10                  15

Thr Asn Gln Lys Leu Ile Leu Ile Pro Tyr Ser Ala Leu Gln Ser Ser
                20                  25                  30

Glu Leu Lys Glu Ile Leu Ser Ile Phe Gly Tyr Lys Ser Gln Leu Asp
            35                  40                  45

Asp Leu Gln Arg Thr Val Ser Thr Ile Asn Ala Val Phe Arg Asp Ala
        50                  55                  60

Glu Thr Lys Gln Glu Leu Thr His Glu Ala Gln His Trp Leu Glu Glu
65                  70                  75                  80

Leu Lys Asp Ala Val Phe Glu Ala Asp Leu Phe Asp Glu Phe Val
                85                  90                  95

Thr Leu Ala Glu Gln Lys Gln Leu Val Glu Ala Gly Gly Ser Leu Ser
                100                 105                 110

Lys Lys Met Arg Gln Phe Phe Ser Asp Ser Asn Pro Leu Gly Ile Ala
            115                 120                 125

Tyr Arg Met Ser Arg Gly Val Lys Lys Ile Lys Lys Lys Leu Asp Ala
        130                 135                 140

Ile Ala Tyr Asn His Gln Phe Ser Phe Lys Ile Asp Leu Glu Pro Ile
145                 150                 155                 160

Lys Glu Arg Arg Leu Glu Thr Gly Ser Val Val Asn Ala Gly Asp Ile
                165                 170                 175

Ile Gly Arg Glu Asp Asp Leu Glu Lys Ile Val Gly Leu Leu Leu Asp
            180                 185                 190

Ser Asn Ile Gln Arg Asp Val Ser Phe Leu Thr Ile Val Gly Met Gly
        195                 200                 205

Gly Leu Gly Lys Thr Ala Leu Ala Gln Leu Val Tyr Asn Asp Pro Arg
    210                 215                 220

Val Arg Thr Ala Phe Pro Leu Arg Cys Trp Asn Cys Val Ser Asp Gln
225                 230                 235                 240

Asp Gln Lys Lys Leu Asp Val Lys Glu Ile Leu Gly Lys Ile Leu Ser
                245                 250                 255

Thr Ala Thr Gly Lys Asn His Glu Gly Ser Thr Met Asp His Val Gln
            260                 265                 270

Thr Gln Leu Arg Glu Gln Leu Cys Gly Lys Arg Tyr Leu Leu Val Leu
        275                 280                 285

Asp Asp Val Trp Asn Glu Asn Pro Asn Gln Leu Arg Ile Leu Val Glu
    290                 295                 300
```

```
Phe Phe Met Gly Gly Gln Arg Gly Asn Trp Ile Val Thr Thr Arg
305                 310                 315                 320

Ser His Glu Thr Ala Arg Ile Ile Arg Asp Gly Pro Leu His Lys Leu
            325                 330                 335

Gln Gly Leu Ser Glu Glu Asn Ser Trp Arg Leu Phe Val Arg Trp Thr
                340                 345                 350

Phe Gly Ser Val Gln Pro Lys Phe Pro Asn Asp Phe Val Met Ile Ala
            355                 360                 365

Arg Asp Ile Val Asp Lys Cys Ala Arg Asn Pro Leu Ala Ile Arg Val
370                 375                 380

Val Gly Ser Leu Leu Cys Gly Gln Asp Lys Ser Lys Trp Leu Ser Phe
385                 390                 395                 400

His Glu Ile Cys Leu Ala Asn Ile Arg Lys Ser His Asn Asp Ile Met
            405                 410                 415

Pro Ile Leu Asn Leu Ser Tyr His His Leu Glu Pro Pro Ile Arg Arg
            420                 425                 430

Cys Phe Ser Tyr Cys Ala Met Phe Pro Lys Asp Phe Leu Ile Gly Lys
            435                 440                 445

Lys Thr Leu Ile Asn Leu Trp Met Ala Gln Gly Tyr Ile Val Pro Leu
450                 455                 460

Asp Lys Asp Gln Ser Ile Asp Asp Ala Ser Glu Glu Tyr Ile Ser Ile
465                 470                 475                 480

Leu Leu Gln Arg Cys Phe Phe Glu Asn Ile Gly Thr Glu Lys Asp Tyr
                485                 490                 495

Val Ile Lys Ile His Asp Leu Met His Asp Ile Ala Gln Asn Val Met
            500                 505                 510

Gly Lys Glu Leu Cys Thr Thr Lys Asn Ile Ser Gly Ser Leu Asp Lys
            515                 520                 525

Asn Val Arg His Leu Ser Leu Ala Arg Thr Ser Phe Ala Arg Tyr Ser
530                 535                 540

Phe Asn Ala Thr His Ile Arg Ser Tyr Phe Tyr Ala Gly Tyr Trp Cys
545                 550                 555                 560

Gln Asp Ala Glu Ile Asn Gln Phe Ser Val Glu Ala Leu Val Pro Asn
                565                 570                 575

Cys Leu Cys Leu Arg Ala Leu Asp Leu Ala Trp Ser Lys Ile Lys Ser
            580                 585                 590

Val Pro Asp Ser Ile Gly Gly Leu His Leu Arg Tyr Leu Asp Leu
            595                 600                 605

Ser Tyr Asn Glu Asp Leu Glu Val Leu Pro Asn Ser Ile Ala Lys Leu
610                 615                 620

Tyr Asn Leu Gln Thr Leu Gln Leu Lys Gly Cys Lys Arg Leu Glu Gly
625                 630                 635                 640

Leu Pro Lys His Leu Ser Arg Leu Val Lys Leu Gln Thr Leu Asp Ile
            645                 650                 655

Tyr Gly Cys Asn Asn Val Thr Tyr Met Pro Lys Gly Met Gly Lys Met
            660                 665                 670

Thr Cys Leu His Thr Leu Ser Lys Phe Ile Val Gly Gly Glu Gly Ser
            675                 680                 685

Cys Ser Ser Trp Lys Gln Trp Phe Asp Gly Gln Glu Asp Leu Lys Ala
            690                 695                 700

Leu Asn Asn Leu Lys Gly His Leu Glu Ile Gln Ile Arg Trp Pro Glu
705                 710                 715                 720

Asn Thr Thr Asp Ala Val Lys Glu Asp Val Lys Arg Glu Gly Leu Tyr
```

```
                    725                 730                 735

Leu Asn His Lys Glu His Leu Asn His Ile Val Val Asp
                740                 745

<210> SEQ ID NO 44
<211> LENGTH: 749
<212> TYPE: PRT
<213> ORGANISM: Beta vulgaris
<220> FEATURE:
<221> NAME/KEY: MOD_RES
<222> LOCATION: (301)..(304)
<223> OTHER INFORMATION: Any amino acid

<400> SEQUENCE: 44

Met Glu Arg Val Val Tyr Arg Trp Asn Thr Ala Gly His Leu Trp Pro
1               5                   10                  15

Thr Asn Gln Lys Leu Ile Leu Ile Pro Tyr Ser Ala Leu Gln Ser Ser
            20                  25                  30

Glu Leu Lys Glu Ile Leu Ser Ile Phe Gly Tyr Lys Ser Gln Leu Asp
        35                  40                  45

Asp Leu Gln Arg Thr Val Ser Thr Ile Asn Ala Val Phe Arg Asp Ala
    50                  55                  60

Glu Thr Lys Gln Glu Leu Thr His Glu Ala Gln His Trp Leu Glu Glu
65                  70                  75                  80

Leu Lys Asp Ala Val Phe Glu Ala Asp Leu Phe Asp Glu Phe Val
                85                  90                  95

Thr Leu Ala Glu Gln Lys Gln Leu Val Glu Ala Gly Gly Ser Leu Ser
            100                 105                 110

Lys Lys Met Arg Gln Phe Phe Ser Asp Ser Asn Pro Leu Gly Ile Ala
        115                 120                 125

Tyr Arg Met Ser Arg Gly Val Lys Lys Ile Lys Lys Leu Asp Ala
    130                 135                 140

Ile Ala Tyr Asn His Gln Phe Ser Phe Lys Ile Asp Leu Glu Pro Ile
145                 150                 155                 160

Lys Glu Arg Arg Leu Glu Thr Gly Ser Val Val Asn Ala Gly Asp Ile
                165                 170                 175

Ile Gly Arg Glu Asp Asp Leu Glu Lys Ile Val Gly Leu Leu Leu Asp
            180                 185                 190

Ser Asn Ile Gln Arg Asp Val Ser Phe Leu Thr Ile Val Gly Met Gly
        195                 200                 205

Gly Leu Gly Lys Thr Ala Leu Ala Gln Leu Val Tyr Asn Asp Pro Arg
    210                 215                 220

Val Arg Thr Ala Phe Pro Leu Arg Cys Trp Asn Cys Val Ser Asp Gln
225                 230                 235                 240

Asp Gln Lys Lys Leu Asp Val Lys Glu Ile Leu Gly Lys Ile Leu Ser
                245                 250                 255

Thr Ala Thr Gly Lys Asn His Glu Gly Ser Thr Met Asp His Val Gln
            260                 265                 270

Thr Gln Leu Arg Glu Gln Leu Cys Gly Lys Arg Tyr Leu Leu Val Leu
        275                 280                 285

Asp Asp Val Trp Asn Glu Asn Pro Asn Gln Leu Arg Xaa Xaa Xaa Xaa
    290                 295                 300

Phe Phe Met Gly Gly Gln Arg Gly Asn Trp Ile Val Val Thr Thr Arg
305                 310                 315                 320

Ser His Glu Thr Ala Arg Ile Ile Arg Asp Gly Pro Leu His Lys Leu
                325                 330                 335
```

```
Gln Gly Leu Ser Glu Glu Asn Ser Trp Arg Leu Phe Val Arg Trp Thr
            340                 345                 350

Phe Gly Ser Val Gln Pro Lys Phe Pro Asn Asp Phe Val Met Ile Ala
            355                 360                 365

Arg Asp Ile Val Asp Lys Cys Ala Arg Asn Pro Leu Ala Ile Arg Val
        370                 375                 380

Val Gly Ser Leu Leu Cys Gly Gln Asp Lys Ser Lys Trp Leu Ser Phe
385                 390                 395                 400

His Glu Ile Cys Leu Ala Asn Ile Arg Lys Ser His Asn Asp Ile Met
                405                 410                 415

Pro Ile Leu Asn Leu Ser Tyr His His Leu Glu Pro Ile Arg Arg
            420                 425                 430

Cys Phe Ser Tyr Cys Ala Met Phe Pro Lys Asp Phe Leu Ile Gly Lys
            435                 440                 445

Lys Thr Leu Ile Asn Leu Trp Met Ala Gln Gly Tyr Ile Val Pro Leu
            450                 455                 460

Asp Lys Asp Gln Ser Ile Asp Asp Ala Ser Glu Glu Tyr Ile Ser Ile
465                 470                 475                 480

Leu Leu Gln Arg Cys Phe Phe Glu Asn Ile Gly Thr Glu Lys Asp Tyr
                485                 490                 495

Val Ile Lys Ile His Asp Leu Met His Asp Ile Ala Gln Asn Val Met
            500                 505                 510

Gly Lys Glu Leu Cys Thr Thr Lys Asn Ile Ser Gly Ser Leu Asp Lys
        515                 520                 525

Asn Val Arg His Leu Ser Leu Ala Arg Thr Ser Phe Ala Arg Tyr Ser
        530                 535                 540

Phe Asn Ala Thr His Ile Arg Ser Tyr Phe Tyr Ala Gly Tyr Trp Cys
545                 550                 555                 560

Gln Asp Ala Glu Ile Asn Gln Phe Ser Val Glu Ala Leu Val Pro Asn
                565                 570                 575

Cys Leu Cys Leu Arg Ala Leu Asp Leu Ala Trp Ser Lys Ile Lys Ser
            580                 585                 590

Val Pro Asp Ser Ile Gly Gly Leu Leu His Leu Arg Tyr Leu Asp Leu
        595                 600                 605

Ser Tyr Asn Glu Asp Leu Glu Val Leu Pro Asn Ser Ile Ala Lys Leu
        610                 615                 620

Tyr Asn Leu Gln Thr Leu Gln Leu Lys Gly Cys Lys Arg Leu Glu Gly
625                 630                 635                 640

Leu Pro Lys His Leu Ser Arg Leu Val Lys Leu Gln Thr Leu Asp Ile
                645                 650                 655

Tyr Gly Cys Asn Asn Val Thr Tyr Met Pro Lys Gly Met Gly Lys Met
            660                 665                 670

Thr Cys Leu His Thr Leu Ser Lys Phe Ile Val Gly Gly Glu Gly Ser
        675                 680                 685

Cys Ser Ser Trp Lys Gln Trp Phe Asp Gly Gln Glu Asp Leu Lys Ala
        690                 695                 700

Leu Asn Asn Leu Lys Gly His Leu Glu Ile Gln Ile Arg Trp Pro Glu
705                 710                 715                 720

Asn Thr Thr Asp Ala Val Lys Glu Asp Val Lys Arg Glu Gly Leu Tyr
                725                 730                 735

Leu Asn His Lys Glu His Leu Asn His Ile Val Val Asp
            740                 745
```

<210> SEQ ID NO 45
<211> LENGTH: 749
<212> TYPE: PRT
<213> ORGANISM: Beta vulgaris
<220> FEATURE:
<221> NAME/KEY: MOD_RES
<222> LOCATION: (301)..(302)
<223> OTHER INFORMATION: Any amino acid

<400> SEQUENCE: 45

```
Met Glu Arg Val Val Tyr Arg Trp Asn Thr Ala Gly His Leu Trp Pro
1               5                   10                  15

Thr Asn Gln Lys Leu Ile Leu Ile Pro Tyr Ser Ala Leu Gln Ser Ser
            20                  25                  30

Glu Leu Lys Glu Ile Leu Ser Ile Phe Gly Tyr Lys Ser Gln Leu Asp
        35                  40                  45

Asp Leu Gln Arg Thr Val Ser Thr Ile Asn Ala Val Phe Arg Asp Ala
    50                  55                  60

Glu Thr Lys Gln Glu Leu Thr His Glu Ala Gln His Trp Leu Glu Glu
65                  70                  75                  80

Leu Lys Asp Ala Val Phe Glu Ala Asp Asp Leu Phe Asp Glu Phe Val
                85                  90                  95

Thr Leu Ala Glu Gln Lys Gln Leu Val Glu Ala Gly Gly Ser Leu Ser
            100                 105                 110

Lys Lys Met Arg Gln Phe Phe Ser Asp Ser Asn Pro Leu Gly Ile Ala
        115                 120                 125

Tyr Arg Met Ser Arg Gly Val Lys Lys Ile Lys Lys Lys Leu Asp Ala
    130                 135                 140

Ile Ala Tyr Asn His Gln Phe Ser Phe Lys Ile Asp Leu Glu Pro Ile
145                 150                 155                 160

Lys Glu Arg Arg Leu Glu Thr Gly Ser Val Val Asn Ala Gly Asp Ile
                165                 170                 175

Ile Gly Arg Glu Asp Asp Leu Glu Lys Ile Val Gly Leu Leu Leu Asp
            180                 185                 190

Ser Asn Ile Gln Arg Asp Val Ser Phe Leu Thr Ile Val Gly Met Gly
        195                 200                 205

Gly Leu Gly Lys Thr Ala Leu Ala Gln Leu Val Tyr Asn Asp Pro Arg
    210                 215                 220

Val Arg Thr Ala Phe Pro Leu Arg Cys Trp Asn Cys Val Ser Asp Gln
225                 230                 235                 240

Asp Gln Lys Lys Leu Asp Val Lys Glu Ile Leu Gly Lys Ile Leu Ser
                245                 250                 255

Thr Ala Thr Gly Lys Asn His Glu Gly Ser Thr Met Asp His Val Gln
            260                 265                 270

Thr Gln Leu Arg Glu Gln Leu Cys Gly Lys Arg Tyr Leu Leu Val Leu
        275                 280                 285

Asp Asp Val Trp Asn Glu Asn Pro Asn Gln Leu Arg Xaa Xaa Val Glu
    290                 295                 300

Phe Phe Met Gly Gly Gln Arg Gly Asn Trp Ile Val Val Thr Thr Arg
305                 310                 315                 320

Ser His Glu Thr Ala Arg Ile Ile Arg Asp Gly Pro Leu His Lys Leu
                325                 330                 335

Gln Gly Leu Ser Glu Glu Asn Ser Trp Arg Leu Phe Val Arg Trp Thr
            340                 345                 350

Phe Gly Ser Val Gln Pro Lys Phe Pro Asn Asp Phe Val Met Ile Ala
```

```
            355                 360                 365
Arg Asp Ile Val Asp Lys Cys Ala Arg Asn Pro Leu Ala Ile Arg Val
370                 375                 380

Val Gly Ser Leu Leu Cys Gly Gln Asp Lys Ser Lys Trp Leu Ser Phe
385                 390                 395                 400

His Glu Ile Cys Leu Ala Asn Ile Arg Lys Ser His Asn Asp Ile Met
                405                 410                 415

Pro Ile Leu Asn Leu Ser Tyr His His Leu Glu Pro Pro Ile Arg Arg
            420                 425                 430

Cys Phe Ser Tyr Cys Ala Met Phe Pro Lys Asp Phe Leu Ile Gly Lys
        435                 440                 445

Lys Thr Leu Ile Asn Leu Trp Met Ala Gln Gly Tyr Ile Val Pro Leu
    450                 455                 460

Asp Lys Asp Gln Ser Ile Asp Asp Ala Ser Glu Glu Tyr Ile Ser Ile
465                 470                 475                 480

Leu Leu Gln Arg Cys Phe Phe Glu Asn Ile Gly Thr Glu Lys Asp Tyr
                485                 490                 495

Val Ile Lys Ile His Asp Leu Met His Asp Ile Ala Gln Asn Val Met
            500                 505                 510

Gly Lys Glu Leu Cys Thr Thr Lys Asn Ile Ser Gly Ser Leu Asp Lys
        515                 520                 525

Asn Val Arg His Leu Ser Leu Ala Arg Thr Ser Phe Ala Arg Tyr Ser
530                 535                 540

Phe Asn Ala Thr His Ile Arg Ser Tyr Phe Tyr Ala Gly Tyr Trp Cys
545                 550                 555                 560

Gln Asp Ala Glu Ile Asn Gln Phe Ser Val Glu Ala Leu Val Pro Asn
                565                 570                 575

Cys Leu Cys Leu Arg Ala Leu Asp Leu Ala Trp Ser Lys Ile Lys Ser
            580                 585                 590

Val Pro Asp Ser Ile Gly Gly Leu Leu His Leu Arg Tyr Leu Asp Leu
        595                 600                 605

Ser Tyr Asn Glu Asp Leu Glu Val Leu Pro Asn Ser Ile Ala Lys Leu
    610                 615                 620

Tyr Asn Leu Gln Thr Leu Gln Leu Lys Gly Cys Lys Arg Leu Glu Gly
625                 630                 635                 640

Leu Pro Lys His Leu Ser Arg Leu Val Lys Leu Gln Thr Leu Asp Ile
                645                 650                 655

Tyr Gly Cys Asn Asn Val Thr Tyr Met Pro Lys Gly Met Gly Lys Met
            660                 665                 670

Thr Cys Leu His Thr Leu Ser Lys Phe Ile Val Gly Glu Gly Ser
        675                 680                 685

Cys Ser Ser Trp Lys Gln Trp Phe Asp Gly Gln Glu Asp Leu Lys Ala
    690                 695                 700

Leu Asn Asn Leu Lys Gly His Leu Glu Ile Gln Ile Arg Trp Pro Glu
705                 710                 715                 720

Asn Thr Thr Asp Ala Val Lys Glu Asp Val Lys Arg Glu Gly Leu Tyr
                725                 730                 735

Leu Asn His Lys Glu His Leu Asn His Ile Val Val Asp
            740                 745

<210> SEQ ID NO 46
<211> LENGTH: 752
<212> TYPE: PRT
<213> ORGANISM: Beta vulgaris
```

<400> SEQUENCE: 46

```
Met Glu Arg Val Val Tyr Arg Trp Asn Thr Ala Glu Thr Ala Gly His
1               5                   10                  15

Leu Trp Pro Thr Asn Pro Lys Leu Ile Leu Ile Pro Tyr Ser Ala Leu
            20                  25                  30

Gln Ser Ser Glu Leu Lys Glu Ile Leu Ser Ile Phe Gly Tyr Lys Ser
        35                  40                  45

Gln Leu Asp Asp Leu Gln Arg Thr Val Ser Thr Ile Asn Ala Val Phe
    50                  55                  60

Arg Asp Ala Glu Thr Lys Gln Glu Leu Thr His Glu Ala Gln His Trp
65                  70                  75                  80

Leu Glu Glu Leu Lys Asp Ala Val Phe Glu Ala Asp Asp Leu Phe Asp
                85                  90                  95

Glu Phe Val Thr Leu Ala Glu Gln Lys Gln Leu Val Glu Ala Gly Gly
            100                 105                 110

Ser Leu Ser Lys Lys Met Arg Gln Phe Ser Asp Ser Asn Pro Leu
        115                 120                 125

Gly Ile Ala Tyr Arg Met Ser Arg Gly Val Lys Lys Ile Lys Lys Lys
    130                 135                 140

Leu Asp Ala Ile Ala Tyr Asn His Gln Phe Ser Phe Lys Ile Asp Leu
145                 150                 155                 160

Glu Pro Ile Lys Glu Arg Arg Leu Glu Thr Gly Ser Val Val Asn Ala
                165                 170                 175

Gly Asp Ile Ile Gly Arg Glu Asp Leu Glu Lys Ile Val Gly Leu
            180                 185                 190

Leu Leu Asp Ser Asn Ile Gln Arg Asp Val Ser Phe Leu Thr Ile Val
        195                 200                 205

Gly Met Gly Gly Leu Gly Lys Thr Ala Leu Ala Gln Leu Val Tyr Asn
    210                 215                 220

Asp Pro Arg Val Arg Thr Ala Phe Pro Leu Arg Cys Trp Asn Cys Val
225                 230                 235                 240

Ser Asp Gln Asp Gln Lys Lys Leu Asp Val Lys Glu Ile Leu Gly Lys
                245                 250                 255

Ile Leu Ser Thr Ala Thr Gly Lys Asn His Glu Gly Ser Thr Met Asp
            260                 265                 270

His Val Gln Thr Gln Leu Gln Glu Gln Leu Cys Gly Lys Arg Tyr Leu
        275                 280                 285

Leu Val Leu Asp Asp Val Trp Asn Glu Asn Pro Asn Gln Leu Arg Asp
    290                 295                 300

Leu Val Glu Phe Phe Met Gly Gly Gln Arg Gly Asn Trp Ile Val Val
305                 310                 315                 320

Thr Thr Arg Ser His Glu Thr Thr Arg Ile Ile Arg Asp Gly Pro Leu
                325                 330                 335

His Lys Leu Gln Gly Leu Ser Glu Glu Asn Ser Trp Arg Leu Phe Val
            340                 345                 350

Arg Trp Thr Phe Gly Ser Val Gln Pro Lys Phe Pro Asn Asp Phe Val
        355                 360                 365

Met Ile Ala Arg Asp Ile Val Asp Lys Cys Ala Arg Asn Pro Leu Ala
    370                 375                 380

Ile Arg Val Val Gly Ser Leu Leu Cys Gly Gln Asp Lys Ser Lys Trp
385                 390                 395                 400

Leu Ser Phe His Glu Ile Cys Leu Ala Asn Ile Arg Lys Ser His Asn
```

```
            405                 410                 415
Asp Ile Met Leu Ile Leu Asn Leu Ser Tyr His His Leu Glu Pro Pro
        420                 425                 430

Ile Arg Arg Cys Phe Ser Tyr Cys Ala Met Phe Pro Lys Asp Phe Leu
        435                 440                 445

Ile Gly Lys Lys Thr Leu Ile Asn Leu Trp Met Ala Gln Gly Tyr Ile
        450                 455                 460

Val Pro Leu Asp Lys Asp Gln Ser Ile Asp Asp Ala Ser Glu Glu Tyr
465                 470                 475                 480

Ile Ser Ile Leu Leu Gln Arg Cys Phe Phe Glu Asn Ile Gly Thr Glu
                485                 490                 495

Lys Asp Tyr Val Ile Lys Ile His Asp Leu Met His Asp Ile Ala Gln
                500                 505                 510

Asn Val Met Gly Lys Glu Leu Cys Thr Thr Lys Asn Ile Ser Gly Ser
                515                 520                 525

Leu Asp Lys Asn Val Arg His Leu Ser Leu Ala Arg Thr Ser Phe Ala
        530                 535                 540

Arg Tyr Ser Phe Asn Ala Thr His Ile Arg Ser Tyr Phe Tyr Ala Gly
545                 550                 555                 560

Tyr Trp Cys Gln Asp Ala Glu Ile Asn Gln Phe Ser Val Glu Ala Leu
                565                 570                 575

Val Pro Asn Cys Leu Cys Leu Arg Ala Leu Asp Leu Ala Trp Ser Lys
                580                 585                 590

Ile Lys Ser Val Pro Asp Ser Ile Gly Gly Leu Leu His Leu Arg Tyr
                595                 600                 605

Leu Asp Leu Ser Tyr Asn Glu Asp Leu Glu Val Leu Pro Asn Ser Ile
        610                 615                 620

Ala Lys Leu Tyr Asn Leu Gln Thr Leu Gln Leu Lys Gly Cys Lys Arg
625                 630                 635                 640

Leu Glu Gly Leu Pro Lys His Leu Ser Arg Leu Val Lys Leu Gln Thr
                645                 650                 655

Leu Asp Ile Tyr Gly Cys Asn Asn Val Thr Tyr Met Pro Lys Gly Met
                660                 665                 670

Gly Lys Met Thr Cys Leu His Thr Leu Ser Lys Phe Ile Val Gly Gly
        675                 680                 685

Glu Gly Ser Cys Ser Ser Trp Lys Gln Trp Phe Asp Gly Gln Glu Asp
        690                 695                 700

Leu Lys Ala Leu Asn Asn Leu Lys Gly His Leu Glu Ile Gln Ile Arg
705                 710                 715                 720

Trp Pro Glu Asn Thr Thr Asp Ala Val Lys Glu Asp Val Lys Arg Glu
                725                 730                 735

Gly Leu Tyr Leu Asn His Lys Glu His Leu Asn His Ile Val Val Asp
        740                 745                 750

<210> SEQ ID NO 47
<211> LENGTH: 751
<212> TYPE: PRT
<213> ORGANISM: Beta vulgaris

<400> SEQUENCE: 47

Met Glu Arg Val Val Tyr Arg Trp Asn Thr Ala Glu Thr Ala Gly His
1               5                   10                  15

Leu Trp Pro Thr Asn Pro Lys Leu Ile Leu Ile Pro Tyr Ser Ala Leu
            20                  25                  30
```

-continued

```
Gln Ser Ser Glu Leu Lys Glu Ile Leu Ser Ile Phe Gly Tyr Lys Ser
             35                  40                  45

Gln Leu Asp Asp Leu Gln Arg Thr Val Ser Thr Ile Asn Ala Val Phe
 50                  55                  60

Arg Asp Ala Glu Thr Lys Gln Glu Leu Thr His Glu Ala Gln His Trp
 65                  70                  75                  80

Leu Glu Glu Leu Lys Asp Ala Val Phe Glu Ala Asp Leu Phe Asp
                 85                  90                  95

Glu Phe Val Thr Leu Ala Glu Gln Lys Gln Leu Val Glu Ala Gly Gly
             100                 105                 110

Ser Leu Ser Lys Lys Met Arg Gln Phe Phe Ser Asp Ser Asn Pro Leu
             115                 120                 125

Gly Ile Ala Tyr Arg Met Ser Arg Gly Leu Lys Lys Ile Lys Lys Lys
         130                 135                 140

Leu Asp Ala Ile Ala Tyr Asn His Gln Phe Ser Phe Lys Ile Asp Leu
145                 150                 155                 160

Glu Pro Ile Lys Glu Arg Arg Leu Glu Thr Gly Ser Val Val Asn Ala
                 165                 170                 175

Gly Asp Ile Ile Gly Arg Glu Asp Leu Glu Lys Ile Val Gly Leu
             180                 185                 190

Leu Leu Asp Ser Asn Ile Gln Arg Asp Met Ser Phe Leu Thr Ile Val
         195                 200                 205

Gly Met Gly Gly Leu Gly Lys Thr Ala Leu Ala Gln Leu Val Tyr Asn
     210                 215                 220

Asp Pro Arg Val Arg Thr Ala Phe Pro Leu Arg Cys Trp Asn Cys Val
225                 230                 235                 240

Phe Asp Gln Asp Gln Lys Gln Leu Asp Val Lys Glu Ile Leu Gly Lys
                 245                 250                 255

Ile Leu Ser Thr Ala Thr Gly Lys Asn His Glu Gly Ser Thr Met Asp
             260                 265                 270

Gln Val Gln Thr Gln Leu Arg Glu Leu Cys Gly Lys Arg Tyr Leu Leu
         275                 280                 285

Val Leu Asp Asp Val Trp Asn Glu Asn Pro Asn Gln Leu Arg Asp Leu
     290                 295                 300

Val Glu Phe Phe Met Gly Gly Gln Arg Gly Asn Trp Ile Val Val Thr
305                 310                 315                 320

Thr Arg Ser His Glu Thr Ala Arg Ile Ile Arg Asp Gly Pro Leu His
                 325                 330                 335

Lys Leu Gln Gly Leu Ser Glu Glu Asn Ser Trp Arg Leu Phe Val Arg
             340                 345                 350

Trp Thr Phe Gly Ser Val Gln Pro Lys Phe Pro Asn Asp Phe Val Met
         355                 360                 365

Ile Ala Arg Asp Ile Val Asp Lys Cys Ala Arg Asn Pro Leu Ala Ile
     370                 375                 380

Arg Val Val Gly Ser Leu Leu Cys Gly Gln Asp Lys Ser Lys Trp Leu
385                 390                 395                 400

Ser Phe His Glu Ile Cys Leu Ala Asn Ile Arg Lys Ser His Asn Asp
                 405                 410                 415

Ile Met Pro Ile Leu Asn Leu Ser Tyr His His Leu Glu Pro Pro Ile
             420                 425                 430

Arg Arg Cys Phe Ser Tyr Cys Val Val Phe Pro Lys Asp Phe Leu Ile
         435                 440                 445

Gly Lys Lys Thr Leu Ile Asn Leu Trp Met Ala Gln Gly Tyr Ile Val
```

450                 455                 460
Pro Leu Asp Lys Asp Gln Ser Ile Asp Asp Ala Ser Glu Glu Tyr Ile
465                 470                 475                 480

Ser Ile Leu Leu Gln Arg Cys Phe Phe Glu Asn Ile Gly Thr Glu Lys
                485                 490                 495

Asp Asp Val Ile Lys Ile His Asp Leu Met His Asp Ile Ala Gln Asn
            500                 505                 510

Val Met Gly Lys Glu Leu Cys Thr Thr Lys Asn Ile Ser Gly Ser Leu
        515                 520                 525

Asp Lys Asn Val Arg His Leu Ser Leu Ala Arg Thr Ser Phe Ala Arg
    530                 535                 540

Tyr Ser Phe Asn Ala Thr His Ile Arg Ser Tyr Phe Tyr Ala Gly Tyr
545                 550                 555                 560

Trp Cys Gln Asn Ala Glu Ile Asn Gln Phe Ser Val Glu Ala Leu Val
                565                 570                 575

Pro Asn Cys Leu Cys Leu Arg Ala Leu Asp Leu Ala Trp Ser Lys Ile
            580                 585                 590

Lys Ser Val Pro Asp Ser Ile Gly Gly Leu Leu His Leu Arg Tyr Leu
        595                 600                 605

Asp Ile Ser Tyr Asn Glu Asp Leu Glu Val Leu Pro Asn Ser Ile Ala
    610                 615                 620

Lys Leu Tyr Asn Leu Gln Thr Leu Gln Leu Lys Gly Cys Lys Arg Leu
625                 630                 635                 640

Glu Gly Leu Pro Lys His Leu Ser Arg Leu Val Lys Leu Gln Thr Leu
                645                 650                 655

Asp Ile Tyr Gly Cys Asn Asn Val Thr Tyr Met Pro Lys Gly Met Gly
            660                 665                 670

Lys Met Thr Cys Leu His Thr Leu Ser Lys Phe Ile Val Gly Gly Glu
        675                 680                 685

Gly Ser Cys Ser Ser Trp Lys Gln Trp Phe Asp Gly Leu Glu Asp Leu
    690                 695                 700

Lys Ala Leu Asn Asn Leu Lys Gly His Leu Glu Ile Gln Ile Arg Trp
705                 710                 715                 720

Pro Glu Asn Thr Thr Asp Val Val Lys Glu Asp Val Lys Arg Glu Gly
                725                 730                 735

Leu Tyr Leu Asn His Lys Glu His Leu Asn His Ile Val Val Asp
            740                 745                 750

<210> SEQ ID NO 48
<211> LENGTH: 749
<212> TYPE: PRT
<213> ORGANISM: Beta vulgaris
<220> FEATURE:
<221> NAME/KEY: MOD_RES
<222> LOCATION: (308)..(336)
<223> OTHER INFORMATION: Any amino acid

<400> SEQUENCE: 48

Met Glu Arg Val Val Tyr Arg Trp Asn Thr Ala Gly His Leu Trp Pro
1               5                   10                  15

Thr Asn Gln Lys Leu Ile Leu Ile Pro Tyr Ser Ala Leu Gln Ser Ser
            20                  25                  30

Glu Leu Lys Glu Ile Leu Ser Ile Phe Gly Tyr Lys Ser Gln Leu Asp
        35                  40                  45

Asp Leu Gln Arg Thr Val Ser Thr Ile Asn Ala Val Phe Arg Asp Ala
    50                  55                  60

```
Glu Thr Lys Gln Glu Leu Thr His Glu Ala Gln His Trp Leu Glu Glu
 65                  70                  75                  80

Leu Lys Asp Ala Val Phe Glu Ala Asp Asp Leu Phe Asp Glu Phe Val
                 85                  90                  95

Thr Leu Ala Glu Gln Lys Gln Leu Val Glu Ala Gly Gly Ser Leu Ser
            100                 105                 110

Lys Lys Met Arg Gln Phe Phe Ser Asp Ser Asn Pro Leu Gly Ile Ala
        115                 120                 125

Tyr Arg Met Ser Arg Gly Val Lys Lys Ile Lys Lys Leu Asp Ala
130                 135                 140

Ile Ala Tyr Asn His Gln Phe Ser Phe Lys Ile Asp Leu Glu Pro Ile
145                 150                 155                 160

Lys Glu Arg Arg Leu Glu Thr Gly Ser Val Val Asn Ala Gly Asp Ile
                165                 170                 175

Ile Gly Arg Glu Asp Asp Leu Glu Lys Ile Val Gly Leu Leu Leu Asp
            180                 185                 190

Ser Asn Ile Gln Arg Asp Val Ser Phe Leu Thr Ile Val Gly Met Gly
        195                 200                 205

Gly Leu Gly Lys Thr Ala Leu Ala Gln Leu Val Tyr Asn Asp Pro Arg
210                 215                 220

Val Arg Thr Ala Phe Pro Leu Arg Cys Trp Asn Cys Val Ser Asp Gln
225                 230                 235                 240

Asp Gln Lys Lys Leu Asp Val Lys Glu Ile Leu Gly Lys Ile Leu Ser
                245                 250                 255

Thr Ala Thr Gly Lys Asn His Glu Gly Ser Thr Met Asp His Val Gln
            260                 265                 270

Thr Gln Leu Arg Glu Gln Leu Cys Gly Lys Arg Tyr Leu Leu Val Leu
        275                 280                 285

Asp Asp Val Trp Asn Glu Asn Pro Asn Gln Leu Arg Ile Leu Val Glu
290                 295                 300

Phe Phe Met Xaa Xaa Xaa Xaa Xaa Xaa Xaa Xaa Xaa Xaa Xaa Xaa Xaa
305                 310                 315                 320

Xaa Xaa Xaa Xaa Xaa Xaa Xaa Xaa Xaa Xaa Xaa Xaa Xaa Xaa Xaa Xaa
                325                 330                 335

Gln Gly Leu Ser Glu Glu Asn Ser Trp Arg Leu Phe Val Arg Trp Thr
            340                 345                 350

Phe Gly Ser Val Gln Pro Lys Phe Pro Asn Asp Phe Val Met Ile Ala
        355                 360                 365

Arg Asp Ile Val Asp Lys Cys Ala Arg Asn Pro Leu Ala Ile Arg Val
370                 375                 380

Val Gly Ser Leu Leu Cys Gly Gln Asp Lys Ser Lys Trp Leu Ser Phe
385                 390                 395                 400

His Glu Ile Cys Leu Ala Asn Ile Arg Lys Ser His Asn Asp Ile Met
                405                 410                 415

Pro Ile Leu Asn Leu Ser Tyr His His Leu Glu Pro Pro Ile Arg Arg
            420                 425                 430

Cys Phe Ser Tyr Cys Ala Met Phe Pro Lys Asp Phe Leu Ile Gly Lys
        435                 440                 445

Lys Thr Leu Ile Asn Leu Trp Met Ala Gln Gly Tyr Ile Val Pro Leu
450                 455                 460

Asp Lys Asp Gln Ser Ile Asp Asp Ala Ser Glu Glu Tyr Ile Ser Ile
465                 470                 475                 480
```

-continued

Leu Leu Gln Arg Cys Phe Phe Glu Asn Ile Gly Thr Glu Lys Asp Tyr
                485                 490                 495

Val Ile Lys Ile His Asp Leu Met His Asp Ile Ala Gln Asn Val Met
            500                 505                 510

Gly Lys Glu Leu Cys Thr Thr Lys Asn Ile Ser Gly Ser Leu Asp Lys
        515                 520                 525

Asn Val Arg His Leu Ser Leu Ala Arg Thr Ser Phe Ala Arg Tyr Ser
    530                 535                 540

Phe Asn Ala Thr His Ile Arg Ser Tyr Phe Tyr Ala Gly Tyr Trp Cys
545                 550                 555                 560

Gln Asp Ala Glu Ile Asn Gln Phe Ser Val Glu Ala Leu Val Pro Asn
                565                 570                 575

Cys Leu Cys Leu Arg Ala Leu Asp Leu Ala Trp Ser Lys Ile Lys Ser
            580                 585                 590

Val Pro Asp Ser Ile Gly Gly Leu Leu His Leu Arg Tyr Leu Asp Leu
        595                 600                 605

Ser Tyr Asn Glu Asp Leu Glu Val Leu Pro Asn Ser Ile Ala Lys Leu
    610                 615                 620

Tyr Asn Leu Gln Thr Leu Gln Leu Lys Gly Cys Lys Arg Leu Glu Gly
625                 630                 635                 640

Leu Pro Lys His Leu Ser Arg Leu Val Lys Leu Gln Thr Leu Asp Ile
                645                 650                 655

Tyr Gly Cys Asn Asn Val Thr Tyr Met Pro Lys Gly Met Gly Lys Met
            660                 665                 670

Thr Cys Leu His Thr Leu Ser Lys Phe Ile Val Gly Gly Gly Ser
        675                 680                 685

Cys Ser Ser Trp Lys Gln Trp Phe Asp Gly Gln Glu Asp Leu Lys Ala
690                 695                 700

Leu Asn Asn Leu Lys Gly His Leu Glu Ile Gln Ile Arg Trp Pro Glu
705                 710                 715                 720

Asn Thr Thr Asp Ala Val Lys Glu Asp Val Lys Arg Glu Gly Leu Tyr
                725                 730                 735

Leu Asn His Lys Glu His Leu Asn His Ile Val Val Asp
            740                 745

<210> SEQ ID NO 49
<211> LENGTH: 749
<212> TYPE: PRT
<213> ORGANISM: Beta vulgaris
<220> FEATURE:
<221> NAME/KEY: MOD_RES
<222> LOCATION: (555)..(555)
<223> OTHER INFORMATION: Any amino acid

<400> SEQUENCE: 49

Met Glu Arg Val Val Tyr Arg Trp Asn Thr Ala Gly His Leu Trp Pro
1               5                   10                  15

Thr Asn Gln Lys Leu Ile Leu Ile Pro Tyr Ser Ala Leu Gln Ser Ser
            20                  25                  30

Glu Leu Lys Glu Ile Leu Ser Ile Phe Gly Tyr Lys Ser Gln Leu Asp
        35                  40                  45

Asp Leu Gln Arg Thr Val Ser Thr Ile Asn Ala Val Phe Arg Asp Ala
    50                  55                  60

Glu Thr Lys Gln Glu Leu Thr His Glu Ala Gln His Trp Leu Glu Glu
65                  70                  75                  80

Leu Lys Asp Ala Val Phe Glu Ala Asp Asp Leu Phe Asp Glu Phe Val

```
                85                 90                 95
Thr Leu Ala Glu Gln Lys Gln Leu Val Glu Ala Gly Gly Ser Leu Ser
            100                 105                 110

Lys Lys Met Arg Gln Phe Phe Ser Asp Ser Asn Pro Leu Gly Ile Ala
            115                 120                 125

Tyr Arg Met Ser Arg Gly Val Lys Ile Lys Lys Leu Asp Ala
            130                 135                 140

Ile Ala Tyr Asn His Gln Phe Ser Phe Lys Ile Asp Leu Glu Pro Ile
145                 150                 155                 160

Lys Glu Arg Arg Leu Glu Thr Gly Ser Val Val Asn Ala Gly Asp Ile
                165                 170                 175

Ile Gly Arg Glu Asp Asp Leu Glu Lys Ile Val Gly Leu Leu Leu Asp
                180                 185                 190

Ser Asn Ile Gln Arg Asp Val Ser Phe Leu Thr Ile Val Gly Met Gly
                195                 200                 205

Gly Leu Gly Lys Thr Ala Leu Ala Gln Leu Val Tyr Asn Asp Pro Arg
            210                 215                 220

Val Arg Thr Ala Phe Pro Leu Arg Cys Trp Asn Cys Val Ser Asp Gln
225                 230                 235                 240

Asp Gln Lys Lys Leu Asp Val Lys Glu Ile Leu Gly Lys Ile Leu Ser
                245                 250                 255

Thr Ala Thr Gly Lys Asn His Glu Gly Ser Thr Met Asp His Val Gln
                260                 265                 270

Thr Gln Leu Arg Glu Gln Leu Cys Gly Lys Arg Tyr Leu Leu Val Leu
            275                 280                 285

Asp Asp Val Trp Asn Glu Asn Pro Asn Gln Leu Arg Asp Leu Val Glu
            290                 295                 300

Phe Phe Met Gly Gly Gln Arg Gly Asn Trp Ile Val Val Thr Thr Arg
305                 310                 315                 320

Ser His Glu Thr Ala Arg Ile Ile Arg Asp Gly Pro Leu His Lys Leu
                325                 330                 335

Gln Gly Leu Ser Glu Glu Asn Ser Trp Arg Leu Phe Val Arg Trp Thr
            340                 345                 350

Phe Gly Ser Val Gln Pro Lys Phe Pro Asn Asp Phe Val Met Ile Ala
            355                 360                 365

Arg Asp Ile Val Asp Lys Cys Ala Arg Asn Pro Leu Ala Ile Arg Val
            370                 375                 380

Val Gly Ser Leu Leu Cys Gly Gln Asp Lys Ser Lys Trp Leu Ser Phe
385                 390                 395                 400

His Glu Ile Cys Leu Ala Asn Ile Arg Lys Ser His Asn Asp Ile Met
                405                 410                 415

Pro Ile Leu Asn Leu Ser Tyr His His Leu Glu Pro Pro Ile Arg Arg
            420                 425                 430

Cys Phe Ser Tyr Cys Ala Met Phe Pro Lys Asp Phe Leu Ile Gly Lys
            435                 440                 445

Lys Thr Leu Ile Asn Leu Trp Met Ala Gln Gly Tyr Ile Val Pro Leu
            450                 455                 460

Asp Lys Asp Gln Ser Ile Asp Asp Ala Ser Glu Glu Tyr Ile Ser Ile
465                 470                 475                 480

Leu Leu Gln Arg Cys Phe Phe Glu Asn Ile Gly Thr Glu Lys Asp Tyr
                485                 490                 495

Val Ile Lys Ile His Asp Leu Met His Asp Ile Ala Gln Asn Val Met
                500                 505                 510
```

```
Gly Lys Glu Leu Cys Thr Thr Lys Asn Ile Ser Gly Ser Leu Asp Lys
            515                 520                 525

Asn Val Arg His Leu Ser Leu Ala Arg Thr Ser Phe Ala Arg Tyr Ser
    530                 535                 540

Phe Asn Ala Thr His Ile Arg Ser Tyr Phe Xaa Ala Gly Tyr Trp Cys
545                 550                 555                 560

Gln Asp Ala Glu Ile Asn Gln Phe Ser Val Glu Ala Leu Val Pro Asn
                565                 570                 575

Cys Leu Cys Leu Arg Ala Leu Asp Leu Ala Trp Ser Lys Ile Lys Ser
                580                 585                 590

Val Pro Asp Ser Ile Gly Gly Leu Leu His Leu Arg Tyr Leu Asp Leu
                595                 600                 605

Ser Tyr Asn Glu Asp Leu Glu Val Leu Pro Asn Ser Ile Ala Lys Leu
                610                 615                 620

Tyr Asn Leu Gln Thr Leu Gln Leu Lys Gly Cys Lys Arg Leu Glu Gly
625                 630                 635                 640

Leu Pro Lys His Leu Ser Arg Leu Val Lys Leu Gln Thr Leu Asp Ile
                645                 650                 655

Tyr Gly Cys Asn Asn Val Thr Tyr Met Pro Lys Gly Met Gly Lys Met
                660                 665                 670

Thr Cys Leu His Thr Leu Ser Lys Phe Ile Val Gly Gly Glu Gly Ser
                675                 680                 685

Cys Ser Ser Trp Lys Gln Trp Phe Asp Gly Gln Glu Asp Leu Lys Ala
690                 695                 700

Leu Asn Asn Leu Lys Gly His Leu Glu Ile Gln Ile Arg Trp Pro Glu
705                 710                 715                 720

Asn Thr Thr Asp Ala Val Lys Glu Asp Val Lys Arg Glu Gly Leu Tyr
                725                 730                 735

Leu Asn His Lys Glu His Leu Asn His Ile Val Val Asp
                740                 745

<210> SEQ ID NO 50
<211> LENGTH: 712
<212> TYPE: PRT
<213> ORGANISM: Beta vulgaris
<220> FEATURE:
<221> NAME/KEY: MOD_RES
<222> LOCATION: (282)..(528)
<223> OTHER INFORMATION: Any amino acid

<400> SEQUENCE: 50

Ala Leu Gln Ser Ser Glu Leu Lys Glu Ile Leu Ser Ile Phe Gly Tyr
1               5                   10                  15

Lys Ser Gln Leu Asp Asp Leu Gln Arg Ile Val Ser Thr Ile Asn Ala
                20                  25                  30

Val Phe Arg Asp Ala Glu Thr Lys Gln Glu Leu Thr His Glu Ala Gln
                35                  40                  45

His Trp Leu Glu Glu Leu Lys Asp Ala Val Phe Glu Ala Asp Asp Leu
            50                  55                  60

Phe Asp Glu Phe Val Thr Leu Ala Glu Gln Lys Gln Leu Val Glu Ala
65              70                  75                  80

Gly Gly Ser Leu Ser Lys Lys Met Arg Gln Phe Phe Ser Asp Ser Asn
                85                  90                  95

Pro Leu Gly Ile Ala Tyr Lys Met Ser Gln Gly Val Lys Lys Ile Lys
                100                 105                 110
```

```
Lys Lys Leu Asp Val Ile Ala Tyr Asn His Gln Phe Ser Phe Lys Ile
            115                 120                 125

Asp Leu Glu Pro Ile Lys Glu Arg Arg Leu Glu Thr Gly Ser Val Val
130                 135                 140

Asn Ala Gly Asp Ile Ile Gly Arg Glu Asp Leu Glu Lys Ile Val
145                 150                 155                 160

Gly Leu Phe Leu Asp Ser Asn Ile Gln Arg Asp Val Ser Phe Leu Thr
                    165                 170                 175

Ile Val Gly Met Gly Gly Leu Gly Lys Thr Ala Leu Ala Gln Leu Val
                180                 185                 190

Tyr Asn Asp Pro Arg Val Arg Thr Ala Phe Pro Leu Arg Cys Trp Asn
                195                 200                 205

Cys Val Ser Asp Gln Asp Gln Asn Gln Leu Asp Val Lys Glu Ile Leu
            210                 215                 220

Gly Lys Ile Leu Ser Thr Ala Thr Gly Lys Asn His Lys Gly Ser Thr
225                 230                 235                 240

Met Asp Gln Val Gln Thr Gln Leu Arg Glu Gln Leu Cys Gly Lys Arg
                245                 250                 255

Tyr Leu Leu Val Leu Asp Asp Val Trp Asn Glu Asn Pro Asn Gln Leu
                260                 265                 270

Arg Asp Leu Val Glu Phe Phe Met Gly Xaa Xaa Xaa Xaa Xaa Xaa
                275                 280                 285

Xaa Xaa Xaa Xaa Xaa Xaa Xaa Xaa Xaa Xaa Xaa Xaa Xaa Xaa Xaa
        290                 295                 300

Xaa Xaa Xaa Xaa Xaa Xaa Xaa Xaa Xaa Xaa Xaa Xaa Xaa Xaa Xaa Xaa
305                 310                 315                 320

Xaa Xaa Xaa Xaa Xaa Xaa Xaa Xaa Xaa Xaa Xaa Xaa Xaa Xaa Xaa
            325                 330                 335

Xaa Xaa Xaa Xaa Xaa Xaa Xaa Xaa Xaa Xaa Xaa Xaa Xaa Xaa Xaa
            340                 345                 350

Xaa Xaa Xaa Xaa Xaa Xaa Xaa Xaa Xaa Xaa Xaa Xaa Xaa Xaa Xaa
        355                 360                 365

Xaa Xaa Xaa Xaa Xaa Xaa Xaa Xaa Xaa Xaa Xaa Xaa Xaa Xaa Xaa
        370                 375                 380

Xaa Xaa Xaa Xaa Xaa Xaa Xaa Xaa Xaa Xaa Xaa Xaa Xaa Xaa Xaa Xaa
385                 390                 395                 400

Xaa Xaa Xaa Xaa Xaa Xaa Xaa Xaa Xaa Xaa Xaa Xaa Xaa Xaa Xaa
            405                 410                 415

Xaa Xaa Xaa Xaa Xaa Xaa Xaa Xaa Xaa Xaa Xaa Xaa Xaa Xaa Xaa
            420                 425                 430

Xaa Xaa Xaa Xaa Xaa Xaa Xaa Xaa Xaa Xaa Xaa Xaa Xaa Xaa Xaa
            435                 440                 445

Xaa Xaa Xaa Xaa Xaa Xaa Xaa Xaa Xaa Xaa Xaa Xaa Xaa Xaa Xaa
        450                 455                 460

Xaa Xaa Xaa Xaa Xaa Xaa Xaa Xaa Xaa Xaa Xaa Xaa Xaa Xaa Xaa Xaa
465                 470                 475                 480

Xaa Xaa Xaa Xaa Xaa Xaa Xaa Xaa Xaa Xaa Xaa Xaa Xaa Xaa Xaa
            485                 490                 495

Xaa Xaa Xaa Xaa Xaa Xaa Xaa Xaa Xaa Xaa Xaa Xaa Xaa Xaa Xaa
            500                 505                 510

Xaa Xaa Xaa Xaa Xaa Xaa Xaa Xaa Xaa Xaa Xaa Xaa Xaa Xaa Xaa
        515                 520                 525

Ala Gly Tyr Trp Cys Gln Glu Ser Glu Ile Asn Gln Phe Ser Val Glu
```

```
                530             535             540
Ala Leu Val Pro Asn Cys Leu Cys Leu Arg Ala Leu Asp Leu Ala Trp
545                 550                 555                 560

Ser Lys Ile Lys Ser Leu Pro Asp Ser Ile Gly Gly Leu Leu His Leu
                565                 570                 575

Arg Tyr Leu Asp Leu Ser Tyr Asn Glu Asp Leu Glu Val Leu Pro Asn
                580                 585                 590

Ser Ile Ala Lys Leu Tyr Asn Leu Gln Thr Leu Gln Leu Lys Gly Cys
                595                 600                 605

Lys Arg Leu Glu Gly Leu Pro Lys His Leu Ser Arg Leu Val Lys Leu
610                 615                 620

Gln Thr Leu Asp Ile Tyr Gly Cys Asn Asn Val Thr Tyr Met Pro Lys
625                 630                 635                 640

Gly Met Gly Lys Met Thr Cys Leu His Thr Leu Ser Lys Phe Ile Val
                645                 650                 655

Gly Gly Glu Gly Ser Cys Ser Ser Trp Lys Lys Arg Phe Asp Gly Leu
                660                 665                 670

Glu Asp Leu Lys Ala Leu Asn Asn Leu Lys Gly His Leu Glu Ile Gln
                675                 680                 685

Ile Arg Trp Pro Glu Asn Thr Thr Asp Ala Val Lys Glu Asp Val Lys
690                 695                 700

Arg Glu Gly Leu Tyr Leu Asn His
705                 710

<210> SEQ ID NO 51
<211> LENGTH: 722
<212> TYPE: PRT
<213> ORGANISM: Beta vulgaris
<220> FEATURE:
<221> NAME/KEY: MOD_RES
<222> LOCATION: (274)..(345)
<223> OTHER INFORMATION: Any amino acid
<220> FEATURE:
<221> NAME/KEY: MOD_RES
<222> LOCATION: (376)..(376)
<223> OTHER INFORMATION: Any amino acid
<220> FEATURE:
<221> NAME/KEY: MOD_RES
<222> LOCATION: (455)..(455)
<223> OTHER INFORMATION: Any amino acid
<220> FEATURE:
<221> NAME/KEY: MOD_RES
<222> LOCATION: (509)..(548)
<223> OTHER INFORMATION: Any amino acid

<400> SEQUENCE: 51

Ala Leu Gln Ser Ser Glu Leu Lys Glu Ile Leu Ser Ile Phe Gly Tyr
1               5                   10                  15

Lys Ser Gln Leu Asp Asp Leu Gln Arg Ile Val Ser Thr Ile Asn Ala
                20                  25                  30

Val Phe Arg Asp Ala Glu Thr Lys Gln Glu Leu Thr His Glu Ala Gln
                35                  40                  45

His Trp Leu Glu Glu Leu Lys Asp Ala Val Phe Glu Ala Asp Asp Leu
50                  55                  60

Phe Asp Glu Phe Val Thr Leu Ala Glu Gln Lys Gln Leu Val Glu Ala
65                  70                  75                  80

Gly Gly Ser Leu Ser Lys Lys Met Arg Gln Phe Phe Ser Asp Ser Asn
                85                  90                  95

Pro Leu Gly Ile Ala Tyr Lys Met Ser Gln Gly Val Lys Lys Ile Lys
                100                 105                 110
```

```
Lys Lys Leu Asp Val Ile Ala Tyr Asn His Gln Phe Ser Lys Ile
        115                 120                 125

Asp Leu Glu Pro Ile Lys Glu Arg Arg Leu Glu Thr Gly Ser Val Val
130                 135                 140

Asn Ala Gly Asp Ile Ile Gly Arg Glu Asp Asp Leu Glu Lys Ile Val
145                 150                 155                 160

Gly Leu Phe Leu Asp Ser Asn Ile Gln Arg Asp Val Ser Phe Leu Thr
                165                 170                 175

Ile Val Gly Met Gly Gly Leu Gly Lys Thr Ala Leu Ala Gln Leu Val
                180                 185                 190

Tyr Asn Asp Pro Arg Val Arg Thr Ala Phe Pro Leu Arg Cys Trp Asn
            195                 200                 205

Cys Val Ser Asp Gln Asp Gln Asn Gln Leu Asp Val Lys Glu Ile Leu
210                 215                 220

Gly Lys Ile Leu Ser Thr Ala Thr Gly Lys Asn His Lys Gly Ser Thr
225                 230                 235                 240

Met Asp Gln Val Gln Thr Gln Leu Arg Glu Gln Leu Cys Gly Lys Arg
                245                 250                 255

Tyr Leu Leu Val Leu Asp Asp Val Trp Asn Glu Asn Pro Asn Gln Leu
            260                 265                 270

Arg Xaa Xaa Xaa Xaa Xaa Xaa Xaa Xaa Xaa Xaa Xaa Xaa Xaa Xaa
        275                 280                 285

Xaa Xaa Xaa Xaa Xaa Xaa Xaa Xaa Xaa Xaa Xaa Xaa Xaa Xaa Xaa Xaa
        290                 295                 300

Xaa Xaa Xaa Xaa Xaa Xaa Xaa Xaa Xaa Xaa Xaa Xaa Xaa Xaa Xaa Xaa
305                 310                 315                 320

Xaa Xaa Xaa Xaa Xaa Xaa Xaa Xaa Xaa Xaa Xaa Xaa Xaa Xaa Xaa
                325                 330                 335

Xaa Xaa Xaa Xaa Xaa Xaa Xaa Xaa Xaa Asp Lys Cys Ala Arg Asn Pro
            340                 345                 350

Leu Ala Ile Arg Val Val Gly Ser Leu Leu Cys Gly Gln Asp Lys Ser
            355                 360                 365

Lys Trp Leu Ser Phe His Glu Xaa Cys Leu Ala Asn Ile Arg Lys Ser
370                 375                 380

His Asn Asp Ile Met Pro Ile Leu Asn Leu Ser Tyr His His Leu Glu
385                 390                 395                 400

Pro Pro Ile Arg Arg Cys Phe Ser Tyr Cys Ala Val Phe Pro Lys Asp
                405                 410                 415

Phe Leu Ile Gly Lys Lys Thr Leu Ile Asn Leu Trp Met Ala Gln Gly
            420                 425                 430

Tyr Ile Val Pro Leu Asp Lys Asp Gln Ser Ile Asp Asp Ala Ser Glu
            435                 440                 445

Glu Tyr Ile Ser Ile Leu Xaa Gln Arg Cys Phe Phe Glu Asn Ile Gly
450                 455                 460

Thr Glu Lys Asp Asp Val Ile Lys Ile His Asp Leu Met His Asp Ile
465                 470                 475                 480

Ala Gln Asn Val Met Gly Lys Glu Leu Cys Thr Thr Lys Asn Ile Ser
                485                 490                 495

Gly Ser Leu Asp Lys Asn Val Arg His Leu Ser Leu Xaa Xaa Xaa Xaa
            500                 505                 510

Xaa Xaa Xaa Xaa Xaa Xaa Xaa Xaa Xaa Xaa Xaa Xaa Xaa Xaa Xaa
        515                 520                 525
```

```
Xaa Xaa Xaa Xaa Xaa Xaa Xaa Xaa Xaa Xaa Xaa Xaa
    530                 535                 540

Xaa Xaa Xaa Xaa Asn Cys Leu Cys Leu Arg Ala Leu Asp Leu Ala Trp
545                 550                 555                 560

Ser Lys Ile Lys Ser Leu Pro Asp Ser Ile Gly Gly Leu Leu His Leu
                565                 570                 575

Arg Tyr Leu Asp Leu Ser Tyr Asn Glu Asp Leu Glu Val Leu Pro Asn
            580                 585                 590

Ser Ile Ala Lys Leu Tyr Asn Leu Gln Thr Leu Gln Leu Lys Gly Cys
        595                 600                 605

Lys Arg Leu Glu Gly Leu Pro Lys His Leu Ser Arg Leu Val Lys Leu
    610                 615                 620

Gln Thr Leu Asp Ile Tyr Gly Cys Asn Asn Val Thr Tyr Met Pro Lys
625                 630                 635                 640

Gly Met Gly Lys Met Thr Cys Leu His Thr Leu Ser Lys Phe Ile Val
                645                 650                 655

Gly Gly Glu Gly Ser Cys Ser Ser Trp Lys Lys Arg Phe Asp Gly Leu
            660                 665                 670

Glu Asp Leu Lys Ala Leu Asn Asn Leu Lys Gly His Leu Glu Ile Gln
        675                 680                 685

Ile Arg Trp Pro Glu Asn Thr Thr Asp Ala Val Lys Glu Asp Val Lys
    690                 695                 700

Arg Glu Gly Leu Tyr Leu Asn His Lys Glu His Leu Asn His Ile Val
705                 710                 715                 720

Val Asp

<210> SEQ ID NO 52
<211> LENGTH: 4658
<212> TYPE: DNA
<213> ORGANISM: Beta vulgaris
<220> FEATURE:
<221> NAME/KEY: modified_base
<222> LOCATION: (461)..(485)
<223> OTHER INFORMATION: a, c, t, g, unknown or other
<220> FEATURE:
<221> NAME/KEY: modified_base
<222> LOCATION: (608)..(638)
<223> OTHER INFORMATION: a, c, t, g, unknown or other
<220> FEATURE:
<221> NAME/KEY: modified_base
<222> LOCATION: (650)..(696)
<223> OTHER INFORMATION: a, c, t, g, unknown or other
<220> FEATURE:
<221> NAME/KEY: modified_base
<222> LOCATION: (701)..(704)
<223> OTHER INFORMATION: a, c, t, g, unknown or other
<220> FEATURE:
<221> NAME/KEY: modified_base
<222> LOCATION: (1114)..(1122)
<223> OTHER INFORMATION: a, c, t, g, unknown or other
<220> FEATURE:
<221> NAME/KEY: modified_base
<222> LOCATION: (1180)..(1181)
<223> OTHER INFORMATION: a, c, t, g, unknown or other
<220> FEATURE:
<221> NAME/KEY: modified_base
<222> LOCATION: (1877)..(1878)
<223> OTHER INFORMATION: a, c, t, g, unknown or other
<220> FEATURE:
<221> NAME/KEY: modified_base
<222> LOCATION: (2193)..(2193)
<223> OTHER INFORMATION: a, c, t, g, unknown or other

<400> SEQUENCE: 52
caaatcttct ggcatcaatg gcggtgttgc cgttcatcaw tttaacatca atggaggtaa    60
```

```
gagtcatgtt ttttcaacaa tataaaactt atatgatttt tctgttttc cccgtatctt      120
gtttgagatt gtgattatta agagagtcaa gtctcacaat attcgaaagt ctacgtaatc      180
cacctcaaat tgacgaagaa aacaagcagg aaaggattaa gtaagttcgt ggaaccayta      240
gaattaattt tcaaatatag ctctacctaa tatatggcct acttttaatt ttaaataaga      300
agaaggtaat gtgattagaa acaaattggt cttaaattat tcattaagct taataatgca      360
taaactttat caagtgctat cttcttttca gggccgtctt gaagatttk ggkcccrgtt      420
ctattatgaa aattgrgccc ctaaatttat asaaaataaa nnnnnnnnnn nnnnnnnnn      480
nnnnngatgg aaggttagag yyctaaagat agaaagttga aaatctaamt ataaatcatt      540
gacaaattta ttaagggtga gaaacaaggg tgttttcttc aaatatgaag caaaattttc      600
aaaataannn nnnnnnnnn nnnnnnnnnn nnnnnnnnta taattttggn nnnnnnnnn      660
nnnnnnnnnn nnnnnnnnnn nnnnnnnnnn nnnnncttc nnnntttgat acaattttts      720
agcgacatga ttgtcgattg atgcttatat tattgtatac tcgatccata ttgtttaaga      780
tgaattgttt gtctttgatg gtctccaatg catattttgt atwmttagga attytaatta      840
tgtactatta gtasayatyg agaygaatac araatygcca taatgaagta tgattatttt      900
arttatatac tttctccgtt ccaaatatat aartgtaaca cttgtgtact ttatgcgtac      960
taatgcataa yaacgtgcac tctccygtgt ttaattatat acttttttgag agaagtgwta     1020
cattggggac catgggactg tgtataattt gaccgcaaaa tygaagtgty gcatttgatt     1080
gaaaayggag arrgtagtat atagrtggaa cacnnnnnnn nntgctgrtc atctttggcc     1140
aacaaaccma aaattgatat taatccyytw wtymrgkywn ntttcatctt tttgacacaa     1200
aatggatgtt gtaggcwctg cgctatctgc tgcccaatct ctgtttgcag ccctgcaaag     1260
ttctgagctc aaagagatcc tctcgatctt tggctacaaa tcccaacttg atgacctcca     1320
acgcaytgtm tctaccatca aygctgtatt ccgtgatgct gagaccaaac aggagctcac     1380
tcatgaagca carcattggc tcgaggaact caaggatgct gtctttgaag cagatgatct     1440
gttcgacgag tttgtcactc ttgccgagca gaagcaactt gtagaggctg gtggcagtct     1500
ttccaaaaag atgcgccaat tcttttctga ttccaacccc cttggcatyg cttatargat     1560
gtcacraggg gttaagaaga tcaagaagaa gttggatgyt atygcttaca atcatcaatt     1620
tagctttaag attgatcttg agcctataaa agagagaagg ctcgagactg ttctgtcgt     1680
gaacgcaggt gatatcattg aagagagga tgacttggag aagatcgtag gtttgttkct     1740
tgattctaac atccagcgtg atgtgtcttt ccttackatw gtgggaatgg gagggttggg     1800
taaaactgct cttgcccaac tcgtgtacaa tgatccaagg gtcagaactg cttttccatt     1860
gagatgttgg aattgtnnct ctgatcaaga tcaaaakmaa ctagatgtga aagaaatttt     1920
gggtaagatt ctgtctacag ctactggtaa gaatcayrag ggttcaacca tggatcakgt     1980
gcaaaccyaa ctacrrgaac aactatgtgg caagagatac ttgcttgttt tggatgatgt     2040
atggaatgag aatcctaatc aattgcgtdw yytkgkwraa ttcttcatgg gaggtcaaag     2100
gggaaattgg attstggtaa ctacgcgttc gcaygagaca rcgagaatta taagagatgg     2160
tccattgcac aagctscaag gtttgtctga rrnaaaacty ttggcgttta tytgtaaggt     2220
ggaccttcgg atcagtgcaa ccaaaattcc ctaatgactt tgtcatgatt gcacgagata     2280
tagtygacaa atgtgctcga aaccctytgg ctataagakt ggtaggaagt cttttgtgtg     2340
gtcaagacaa gagtaagtgg ctttcatttc atgagatmtg tttagccaac attagaaaga     2400
```

```
gycataatga tatcatgcya atactgaacc taagttacca tcatcttgaa cctccaatca    2460
kgagatgctt tagttattgt gcartgtttc caaaggattt ccttataggg aagaagacgt    2520
tgataaacct ttggatggca caaggttata ttgttccatt agacaaagat caaagcatag    2580
atgaygctag tgaggaatac atatcaattt tgytgcagag atgttttttc gaaaacatcg    2640
gaacagaaaa agatkatgtt attaagatac atgatctcat gcatgatatt gctcaaaatg    2700
tcatggggaa ggagctttgt acgacaaaaa acattagtgg cagcttggat aaaaatgttc    2760
gccatctatc tcttgccaga actagttttg caagatactc tttyaatgca actcatattc    2820
gctccyattt ctrtgctggc tactggtgtc aggawkctga gataamccag ttytcagttg    2880
aggcattagt accaaaytgt ttgtgcctaa gggcattgka cctsgcttgg tcgaagataa    2940
aaagtktacc agactcratt ggtggattgt tgcatttgag gtacttagat ctttcrtata    3000
asgaagatyt ggaagtactt ccgaactcaa ttgcyaaact atataatctr caaaccttac    3060
aattgaaggg ttgcaagaga ttggaagggt taycaaaaca tttgagcagg ctggttaagc    3120
ttcaaacttt rgatatatat ggttgcaaya atgtaactta tatgcccaaa ggcatgggta    3180
agatgacttg ccttcacact ctcagtaagt ttatagtggg tggagaaggg arttgttcaa    3240
gttggaagma ayggtttgat gggcwggaag atctcaaggc tctcaacaac ctaaagggtc    3300
atctggraat ccaaatcagg tggcccgaaa atactacaga tgctgtcaag gaagatgtta    3360
agagggaagg attatacytg aatcataagg aacatctcaa tcacattgtg ttgatttca    3420 gatgtgagga gggtggtgga agaatggatg atgaggaagc aagaagattg atggaagagy    3480
tgcggccaca tccttatctt gaaaatttgg ctgtgaaagc ataytatggt gygaaaaygc    3540
ctgrttgggy aacccttcty ccaaatctta cagagctttw tctttytgat tgtggggaay    3600
yggagwrcct tccatgcmtg ggaaacttgg wtydtctraa mgtyctccgr ctttcgcatt    3660
tggcraaatt ggagtayatt gragaagata gcwcatcagc tmwtttcagk tktaggcctg    3720
gaccrgaaag tgcaggacta tcattatact tcccctccct tgaackcctt gagttgaagc    3780
rtttgyryaa gttaaaagga tggaggagar gggaagggtt aggagatgat caccagcctt    3840
ttaatgaaag cagcagcaat aagtcattga gaatagaaag atgcccattg ctgacattta    3900
tgccgctgtg tcccaagaca gaaaaacdgc atttagttgt atttaatgaa ygactccgga    3960
tagtgcatac taaaggagat gagaatttct atgctccatt acattcatca tcatctgatc    4020
ctgaaaaccc gaggagcact attcccattc ccatgttaag agaggtatac ataaacaatg    4080
tggcatggct aaattcgctg cctatggagg cttttaggtg tctcactcat atgacaataa    4140
aaaacgacaa ggtagagagt ttgggagaag ttggggaggt gtttcggagc trctcatctt    4200
ctttgcgatc cttgaatatc acaggttgct ccaacttaag aagtgtttct ggagggctgg    4260
agcatctcac trcttttggag atkttagaaa tatacgacac ccataagctg agtctwtcag    4320
aagacccaga aggtgttgtg ccatggaaat cccttcatca ctccctcagc tacttgmaat    4380
tgatgaatct cccwcagctg gtcaacctgc ctgattcgat gcagttcttg gyctccctcc    4440 aaacccttc aatggtgcat tgcagtaaac tggaatcagt gccagattgg atgcccmgac    4500
tcacttcyct caggaagctt atggtttcat tctgttccgc acatctggag agaagatgyc    4560
aaaatccaac tggggtggac tggcctaaca ttcaacacat ccctscatt gatgtcacct    4620 ctagccgtcc taagttttta gtgttgccgt atgaatag                          4658
```